(12) United States Patent
Aktoudianakis et al.

(10) Patent No.: US 9,255,089 B2
(45) Date of Patent: Feb. 9, 2016

(54) BENZIMIDAZOLONE DERIVATIVES AS BROMODOMAIN INHIBITORS

(71) Applicant: Gilead Sciences, Inc., Foster City, CA (US)

(72) Inventors: Evangelos Aktoudianakis, San Mateo, CA (US); Gregory Chin, San Francisco, CA (US); Britton Kenneth Corkey, Redwood City, CA (US); Jinfa Du, Redwood City, CA (US); Kristyna Elbel, South San Francisco, CA (US); Robert H. Jiang, Cupertino, CA (US); Tetsuya Kobayashi, Pleasanton, CA (US); Ruben Martinez, San Diego, CA (US); Samuel E. Metobo, Newark, CA (US); Michael R. Mish, Foster City, CA (US); Sophie Shevick, San Francisco, CA (US); David Sperandio, Palo Alto, CA (US); Hai Yang, San Mateo, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 23 days.

(21) Appl. No.: 14/227,736

(22) Filed: Mar. 27, 2014

(65) Prior Publication Data
US 2014/0296246 A1    Oct. 2, 2014

Related U.S. Application Data

(60) Provisional application No. 61/805,995, filed on Mar. 28, 2013, provisional application No. 61/860,230, filed on Jul. 30, 2013.

(51) Int. Cl.
*C07D 413/14* (2006.01)
*C07D 413/04* (2006.01)
*C07D 417/14* (2006.01)

(52) U.S. Cl.
CPC ............ *C07D 413/14* (2013.01); *C07D 413/04* (2013.01); *C07D 417/14* (2013.01)

(58) Field of Classification Search
None
See application file for complete search history.

(56) References Cited

U.S. PATENT DOCUMENTS

| | | |
|---|---|---|
| 6,162,804 A | 12/2000 | Bilodeau et al. |
| 2007/0275984 A1 | 11/2007 | Imogai et al. |
| 2009/0176778 A1 | 7/2009 | Schmitz et al. |
| 2010/0204265 A1 | 8/2010 | Baskaran et al. |
| 2012/0121540 A1 | 5/2012 | Schmitz et al. |
| 2012/0232074 A1 | 9/2012 | Bouillot et al. |
| 2014/0187533 A1 | 7/2014 | Pajouhesh et al. |

FOREIGN PATENT DOCUMENTS

WO    WO-2004/098494 A2    11/2004

OTHER PUBLICATIONS

Hay et al, J. Am. Chem. Soc. 2014, 136, 9308-9319.*
Bamborogh, P. et al. (2012) "Fragment-Based Discovery of Bromodomain Inhibitors Part 2: Optimization of Phenylisoxazole Sulfonamides", J. Med. Chem., 56: 587-596.
Chun-Wa, C. et al. (2012) "Fragment-Based Discovery of Bromodomain Inhibitors Part 1: Inhibitor Binding Modes and Implications for Lead Discovery", J. Med. Chem., 55: 576-586.
Hewings, D.S. et al. (2011) "3,5-Dimethylisoxazoles Act as Acetyl-Lysine-Mimetic Bromodomain Ligands" J. Med. Chem., 54: 6761-6770.
Mirguet, O. et al. (2013) "Discovery of Epigenetic Regulator I-BET762: Lead Optimization to Afford a Clinical Candidate Inhibitor of the BET Bromodomains", J. Med. Chem., 56: 7501-7515.

* cited by examiner

*Primary Examiner* — Kamal Saeed

(57) ABSTRACT

This application relates to chemical compounds which may act as inhibitors of, or which may otherwise modulate the activity of, a bromodomain-containing protein, including bromodomain-containing protein 4 (BRD4), and to compositions and formulations containing such compounds, and methods of using and making such compounds. Compounds include compounds of Formula (I)

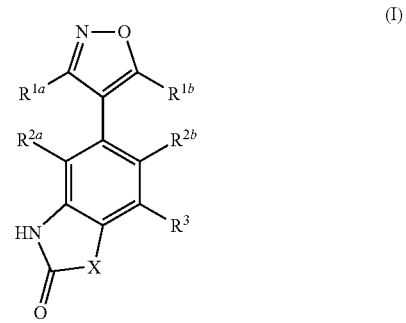

wherein $R^{1a}$, $R^{1b}$, $R^{2a}$, $R^{2b}$, $R^3$, and X are described herein.

19 Claims, No Drawings

BENZIMIDAZOLONE DERIVATIVES AS BROMODOMAIN INHIBITORS

This application claims the benefits of U.S. Provisional Application 61/805,995, filed on Mar. 28, 2013, and U.S. Provisional Application 61/860,230, filed on Jul. 30, 2013, both of which are incorporated herein by reference in their entireties.

FIELD

This application relates to chemical compounds which may inhibit or otherwise modulate the activity of a bromodomain-containing protein, including bromodomain-containing protein 4 (BRD4), and to compositions and formulations containing such compounds, and methods of using and making such compounds.

BACKGROUND

The bromodomain and extraterminal (BET) family of proteins (BET proteins) are readers of the epigenetic code that couple acetylation of lysine residues on histones to changes in chromatin structure and gene expression. The BET family includes BRD2, BRD3, BRD4, and BRDT, all of which are widely expressed across diverse tissues, with the exception of the BRDT, whose expression is restricted to the testes. See Wu, S. Y. & Chiang, C. M., *J. Biol. Chem.*, 282: 13141-13145 (2007). Each BET family member contains tandem bromodomains in the N-terminal regions that specifically bind acetylated lysine residues in histones H3 and H4. Id. Once bound to histones, BET proteins recruit protein complexes that modulate gene transcription either directly, such as transcriptional activators or repressors, or indirectly such as chromatin remodeling complexes. BRD4 is the most well studied member of the BET family and is known to preferentially recognize tetra-acelyated histone H4 epigenetic marks. See Filippakopoulos, P., et al., *Cell*, 149: 214-231 (2012). BRD4 recruits the p-TEFb complex to nucleosomes, which in turn phosphorylates the C-terminal tail of RNA polymerase II and increases the transcriptional elongation of neighboring genes. See Yang, Z., et al., *Mol. Cell Biol.*, 28: 967-976 (2008); Urano, E., et al., FEBS Lett., 582: 4053-4058 (2008).

The epigenetic code, including histone acetylation, is highly perturbed in many pathological disease states, resulting in the aberrant expression of genes that control cell fate, cell differentiation, cell survival, and inflammatory processes. See, e.g., Cohen, I., et al., Genes Cancer, 2: 631-647 (2011); Brooks, W. H., et al., J. Autoimmun., 34: J207-219 (2010); Wierda, R. J., et al., J. Cell Mol. Med., 14: 1225-1240 (2010); Shirodkar, A. V. & Marsden, P. A., Curr. Opin. Cardiol., 26: 209-215 (2011); Villeneuve, L. M., et al., Clin. Exp. Pharmacol. Physiol., 38: 401-409 (2011). BET proteins including BRD4 have been identified as important mediators of altered gene expression profiles found in numerous diseases including cancer, diabetes, obesity, atherosclerosis, cardiovascular and renal disorders, and viral infection. See Muller, S., et al., Expert Rev. Mol. Med., 13: e29 (2011); Zhou, M., et al., J. Virol., 83: 1036-1044 (2009); Chung, C. W., et al., J. Med. Chem., 54: 3827-3838 (2011). For example, MYC has been implicated in the majority of human cancers and BET proteins have been identified as regulatory factors of c-Myc; inhibition of BET, including BRD4, has been shown to downregulate MYC transcription. See Delmore, J. E., et al. Cell, 146, 904-17 (2011); Lovén, J. et al., Cell, 153, 320-34 (2013). Inhibitors and modulators of BET proteins, including BRD4, are therefore needed.

SUMMARY

One aspect provides for a compound of Formula (I)

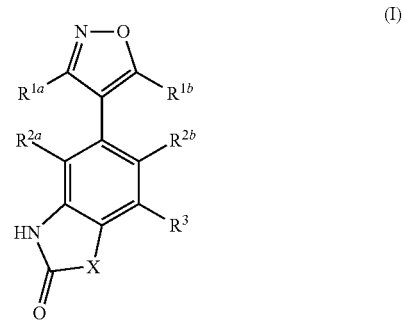

wherein
$R^{1a}$ and $R^{1b}$ are each independently $C_1$-$C_6$ alkyl, $C_1$-$C_6$ alkoxy, $C_1$-$C_6$ haloalkyl, $C_1$-$C_6$ haloalkoxy, $C_1$-$C_6$ hydroxyalkyl, $C_3$-$C_6$ cycloalkyl, or $CH_2$—$C_3$-$C_6$ cycloalkyl;
$R^{2a}$ and $R^{2b}$ are each independently H or halogen;
$R^3$ is
  $C_5$-$C_{10}$ aryl, $C_5$-$C_{10}$ heteroaryl, or $C_5$-$C_{10}$ heteroarylalkyl, each of which is optionally substituted with from 1 to 5 $R^{20}$ groups; or
  —$S(O)_2NHR^4$,
    wherein $R^4$ is $C_1$-$C_6$ alkyl or $C_3$-$C_7$ cycloalkyl, each of which is optionally substituted with from 1 to 5 $R^{20}$ groups; or
  a moiety of the formula

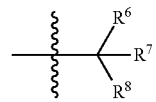

wherein
  $R^6$ is H, OH, or halogen; and $R^7$ and $R^8$ are each independently $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, $C_5$-$C_{12}$ aryl, $C_5$-$C_{12}$ heteroaryl, or $C_5$-$C_{12}$ heteroarylalkyl, each of which is optionally substituted with from 1 to 5 $R^{20}$ groups; or
  $R^6$ is H, $C_1$-$C_6$ alkyl, $C_2$-$C_6$ alkenyl, $C_2$-$C_6$ alkynyl, $C_3$-$C_6$ cycloalkyl, phenyl, naphthyl, or $C_3$-$C_{12}$ heteroaryl; and $R^7$ and $R^8$ together form a $C_1$-$C_6$ alkylidene group having a double bond with the carbon to which each of $R^6$, $R^7$, and $R^8$ are bound wherein each of the $C_1$-$C_6$ alkyl, $C_2$-$C_6$ alkenyl, $C_2$-$C_6$ alkynyl, —$C_3$-$C_6$ cycloalkyl, phenyl, naphthyl, or $C_3$-$C_{12}$ heteroaryl groups is optionally substituted with from 1 to 5 $R^{20}$ groups;
X is N-Q, or O;
Q is H, $C_1$-$C_3$ alkyl, $C_1$-$C_3$ haloalkyl, benzyl or substituted benzyl;
each $R^{20}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, wherein each $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl is optionally substituted with from one to five halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$;

each R$^a$ and R$^b$ is independently H; or C$_1$-C$_6$ alkyl, C$_3$-C$_6$ cycloalkyl, C$_1$-C$_6$ heteroalkyl, C$_3$-C$_6$ heterocyclic, C$_5$-C$_{12}$ aryl, C$_5$-C$_{12}$ heteroaryl, each of which is optionally substituted with from one to five R$^{21}$; or R$^a$ and R$^b$ together with the atoms to which they are attached form a heterocycle, and;

each R$^{21}$ is independently C$_1$-C$_6$ alkyl, C$_3$-C$_6$ cycloalkyl, C$_1$-C$_6$ heteroalkyl, C$_3$-C$_6$ heterocyclic, C$_5$-C$_{12}$ aryl, C$_5$-C$_{12}$ heteroaryl, or halogen;

or a pharmaceutically acceptable salt thereof.

Another aspect provides for a compound selected from the group consisting the title compounds listed in Examples 1 to 201.

Another aspect provides for a pharmaceutical composition comprising a compound of Formula (I), or a pharmaceutically acceptable salt thereof, and a pharmaceutically acceptable carrier.

Another aspect provides for a use of a compound of Formula (I), or a pharmaceutically acceptable salt thereof, in therapy. Another aspect provides for a method of treating a subject having a disease or condition responsive to the inhibition of a bromodomain-containing protein, comprising administering a therapeutically effective amount of a compound of Formula (I), or a pharmaceutically acceptable salt thereof. In some aspects, the bromodomain-containing protein is BRD4. In some aspects, the disease or condition is an autoimmune disease, an inflammatory disease, a neurodegenerative disease, a cancer, a cardiovascular disorder, a renal disorder, a viral infection, or obesity. In certain embodiments, the disease or condition is chosen from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), acute rejection of transplanted organs, lymphomas, multiple myelomas, leukemias, neoplasms and solid tumors. In some aspects the disease or condition is a solid tumor of the colon, rectum, prostate, lung, pancreas, liver, kidney, cervix, stomach, ovaries, breast, skin, brain, meninges, or central nervous system (including a neuroblastoma or a glioblastoma). In some aspects, the disease or condition is a lymphoma. In some aspects, the disease or condition is a B-cell lymphoma. In some aspects, the disease or condition is Burkitt's lymphoma. In some aspects, the disease or condition is diffuse large B-cell lymphoma. In some aspects, the disease or condition is multiple myeloma. In some aspects the disease or condition is a carcinoma. In some aspects the disease or condition is NUT midline cardinoma. In some aspects the subject is a human.

Another aspect provides for a method of downregulating or decreasing MYC transcription in a subject, comprising administering to the subject a compound of Formula (I). Another aspect provides for a method of treating a disease or condition in a subject in which activation of MYC is implicated, comprising administering to the subject a compound of Formula (I).

In some aspects, the compound is administered intravenously, intramuscularly, parenterally, nasally, or orally. In one aspect, the compound is administered orally.

Also provided is a method of inhibiting a bromodomain in a subject, comprising providing to the subject a therapeutically effective amount of a compound of Formula (I) or a pharmaceutically or a pharmaceutically acceptable salt thereof acceptable salt thereof. Also provided is a method of inhibiting a bromodomain in a cell, comprising providing to the cell a compound of Formula (I). It is understood that providing to the cell may be accomplished by administering the compound to the subject. Also provided is a method of inhibiting a bromodomain, comprising contacting the bromodomain with a compound of Formula (I), or a pharmaceutically acceptable salt thereof.

Also provided is the use of a compound of Formula (I), or a pharmaceutically acceptable salt thereof, in the manufacture of a medicament for the treatment of a disease or condition responsive to bromodomain inhibition.

Also provided are kits that include a compound of Formula (I), or a pharmaceutically acceptable salt thereof. In one aspect, the kit further includes instructions for use. In one aspect, a kit includes a compound of Formula (I), or a pharmaceutically acceptable salt thereof, and instructions for use of the compounds in the treatment of the diseases or conditions described above.

Also provided are articles of manufacture that include a compound of Formula (I), or a pharmaceutically acceptable salt thereof. In one embodiment, the container may be a vial, jar, ampoule, preloaded syringe, or an intravenous bag.

DETAILED DESCRIPTION

Described herein are compounds of Formula (I), which include compounds of Formulae (Ia) and (Ib), compositions and formulations containing such compounds, and methods of using and making such compounds.

One aspect of the current disclosure relates to compounds of Formula (I)

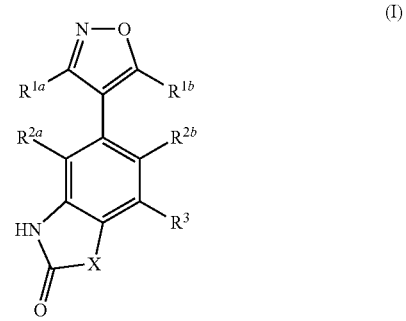

(I)

wherein
R$^{1a}$ and R$^{1b}$ are each independently C$_1$-C$_6$ alkyl, C$_1$-C$_6$ alkoxy, C$_1$-C$_6$ haloalkyl, C$_1$-C$_6$ haloalkoxy, C$_1$-C$_6$ hydroxyalkyl, C$_3$-C$_6$ cycloalkyl, or CH$_2$—C$_3$-C$_6$ cycloalkyl;
R$^{2a}$ and R$^{2b}$ are each independently H or halogen;
R$^3$ is
C$_5$-C$_{10}$ aryl, C$_5$-C$_{10}$ heteroaryl, or C$_5$-C$_{10}$ heteroarylalkyl, each of which is optionally substituted with from 1 to 5 R$^{20}$ groups; or
—S(O)$_2$NHR$^4$,
wherein R$^4$ is C$_1$-C$_6$ alkyl or C$_3$-C$_7$ cycloalkyl, each of which is optionally substituted with from 1 to 5 R$^{20}$ groups; or
a moiety of the formula

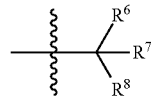

wherein
R$^6$ is H, OH, or halogen; and R$^7$ and R$^8$ are each independently C$_1$-C$_6$ alkyl, C$_2$-C$_6$ alkenyl, C$_2$-C$_6$ alkynyl, $C_3$-$C_6$ cycloalkyl, $C_1$-$C_6$ heteroalkyl, $C_5$-$C_{12}$ aryl, $C_5$-$C_{12}$ heteroaryl, or $C_5$-$C_{12}$ heteroarylalkyl, each of which is optionally substituted with from 1 to 5 $R^{20}$ groups; or $R^6$ is H, $C_1$-$C_6$ alkyl, $C_2$-$C_6$ alkenyl, $C_2$-$C_6$ alkynyl, $C_3$-$C_6$ cycloalkyl, phenyl, naphthyl, or $C_3$-$C_{12}$ heteroaryl; and $R^7$ and $R^8$ together form a $C_1$-$C_6$ alkylidene group having a double bond with the carbon to which each of $R^6$, $R^7$, and $R^8$ are bound wherein each of the $C_1$-$C_6$ alkyl, $C_2$-$C_6$ alkenyl, $C_2$-$C_6$ alkynyl, —$C_3$-$C_6$ cycloalkyl, phenyl, naphthyl, or $C_3$-$C_{12}$ heteroaryl groups is optionally substituted with from 1 to 5 $R^{20}$ groups;

X is N-Q, or O;

Q is H, $C_1$-$C_3$ alkyl, $C_1$-$C_3$ haloalkyl, benzyl or substituted benzyl;

each $R^{20}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, wherein each $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$;

each $R^a$ and $R^b$ is independently H; or $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, each of which is optionally substituted with from one to five $R^{21}$; or $R^a$ and $R^b$ together with the atoms to which they are attached form a heterocycle, and;

each $R^{21}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, or halogen;

or a pharmaceutically acceptable salt thereof.

One subset of compounds of Formula (I) relates to compounds of Formula (Ia)

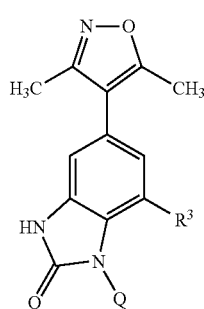

(Ia)

wherein $R^3$ is $C_5$-$C_{10}$ aryl, $C_5$-$C_{10}$ heteroaryl, or $C_5$-$C_{10}$ heteroarylalkyl, each of which is optionally substituted with from 1 to 5 $R^{20}$ groups; or

—$S(O)_2NHR^4$, wherein $R^4$ is $C_1$-$C_6$ alkyl or $C_3$-$C_7$ cycloalkyl, each of which is optionally substituted with from 1 to 5 $R^{20}$ groups; or a moiety of the formula

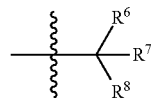

wherein $R^6$ is H, OH, or halogen; and $R^7$ and $R^8$ are each independently $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, $C_5$-$C_{12}$ aryl, $C_5$-$C_{12}$ heteroaryl, or $C_5$-$C_{12}$ heteroarylalkyl, each of which is optionally substituted with from 1 to 5 $R^{20}$ groups; or $R^6$ is H, $C_1$-$C_6$ alkyl, $C_2$-$C_6$ alkenyl, $C_2$-$C_6$ alkynyl, $C_3$-$C_6$ cycloalkyl, phenyl, naphthyl, or $C_3$-$C_{12}$ heteroaryl; and $R^7$ and $R^8$ together form a $C_1$-$C_6$ alkylidene group having a double bond with the carbon to which each of $R^6$, $R^7$, and $R^8$ are bound wherein each of the $C_1$-$C_6$ alkyl, $C_2$-$C_6$ alkenyl, $C_2$-$C_6$ alkynyl, —$C_3$-$C_6$ cycloalkyl, phenyl, naphthyl, or $C_3$-$C_{12}$ heteroaryl groups is optionally substituted with from 1 to 5 $R^{20}$ groups;

Q is H, $C_1$-$C_3$ alkyl, $C_1$-$C_3$ haloalkyl, benzyl or substituted benzyl;

each $R^{20}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, wherein each $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$;

each $R^a$ and $R^b$ is independently H; or $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, each of which is optionally substituted with from one to five $R^{21}$; or $R^a$ and $R^b$ together with the atoms to which they are attached form a heterocycle, and;

each $R^{21}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, or halogen;

or a pharmaceutically acceptable salt thereof.

Another subset of compounds of Formula (I) relates to compounds of Formula (Ib)

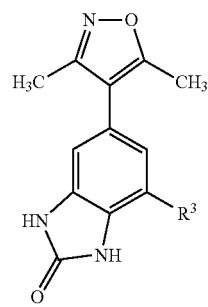

(Ib)

wherein
R³ is
C₅-C₁₀ aryl, C₅-C₁₀ heteroaryl, or C₅-C₁₀ heteroarylalkyl, each of which is optionally substituted with from 1 to 5 R²⁰ groups; or
—S(O)₂NHR⁴,
wherein R⁴ is C₁-C₆ alkyl or C₃-C₇ cycloalkyl, each of which is optionally substituted with from 1 to 5 R²⁰ groups; or
a moiety of the formula

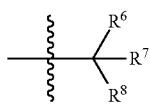

wherein
R⁶ is H, OH, or halogen; and R⁷ and R⁸ are each independently C₁-C₆ alkyl, C₂-C₆ alkenyl, C₂-C₆ alkynyl, C₃-C₆ cycloalkyl, C₁-C₆ heteroalkyl, C₅-C₁₂ aryl, C₅-C₁₂ heteroaryl, or C₅-C₁₂ heteroarylalkyl, each of which is optionally substituted with from 1 to 5 R²⁰ groups; or
R⁶ is H, C₁-C₆ alkyl, C₂-C₆ alkenyl, C₂-C₆ alkynyl, C₃-C₆ cycloalkyl, phenyl, naphthyl, or C₃-C₁₂ heteroaryl; and R⁷ and R⁸ together form a C₁-C₆ alkylidene group having a double bond with the carbon to which each of R⁶, R⁷, and R⁸ are bound wherein each of the C₁-C₆ alkyl, C₂-C₆ alkenyl, C₂-C₆ alkynyl, —C₃-C₆ cycloalkyl, phenyl, naphthyl, or C₃-C₁₂ heteroaryl groups is optionally substituted with from 1 to 5 R²⁰ groups;
each R²⁰ is independently C₁-C₆ alkyl, C₃-C₆ cycloalkyl, C₁-C₆ heteroalkyl, C₃-C₆ heterocyclic, C₅-C₁₂ aryl, C₅-C₁₂ heteroaryl, halogen, oxo, —OR^a, —C(O)R^a, —C(O)OR^a, —C(O)NR^aR^b, —OC(O)NR^aR^b, —NR^aR^b, —NR^aC(O)R^b, —NR^aC(O)OR^b, —S(O)₀₋₂R^a, —S(O)₂NR^aR^b, —NR^aS(O)₂R^b, —N₃, —CN, or —NO₂, wherein each C₁-C₆ alkyl, C₃-C₆ cycloalkyl, C₁-C₆ heteroalkyl, C₃-C₆ heterocyclic, C₅-C₁₂ aryl, C₅-C₁₂ heteroaryl is optionally substituted with from one to five halogen, oxo, —OR^a, —C(O)R^a, —C(O)OR^a, —C(O)NR^aR^b, —OC(O)NR^aR^b, —NR^aR^b, —NR^aC(O)R^b, —NR^aC(O)OR^b, —S(O)₀₋₂R^a, —S(O)₂NR^aR^b, —NR^aS(O)₂R^b, —N₃, —CN, or —NO₂;
each R^a and R^b is independently H; or C₁-C₆ alkyl, C₃-C₆ cycloalkyl, C₁-C₆ heteroalkyl, C₃-C₆ heterocyclic, C₅-C₁₂ aryl, C₅-C₁₂ heteroaryl, each of which is optionally substituted with from one to five R²¹; or R^a and R^b together with the atoms to which they are attached form a heterocycle, and;
each R²¹ is independently C₁-C₆ alkyl, C₃-C₆ cycloalkyl, C₁-C₆ heteroalkyl, C₃-C₆ heterocyclic, C₅-C₁₂ aryl, C₅-C₁₂ heteroaryl, or halogen;
or a pharmaceutically acceptable salt thereof.

In some compounds of Formula (I), R^{1a} and R^{1b} are each independently C₁-C₆ alkyl. In some compounds of Formula (I), R^{1a} and R^{1b} are each independently methyl, ethyl, or propyl. In some compounds of Formula (I), R^{1a} and R^{1b} are different. In some compounds of Formula (I), R^{1a} and R^{1b} are the same. In some compounds of Formula (I), R^{1a} and R^{1b} are both methyl.

In some compounds of Formula (I), R^{2a} and R^{2b} are both H. In some compounds of Formula (I), R^{2a} and R^{2b} are both halo.

In some compounds of Formula (I), one of R^{2a} and R^{2b} is H and the other is halo. In some compounds of Formula (I), the halo is —F or —Cl.

In some compound of Formula (I), X is N-Q.

In some compounds of Formula (I) or (Ia), Q is H, C₁-C₃ alkyl, or C₁-C₃ haloalkyl.

In some compounds of Formula (I), (Ia) or (Ib), R³ is C₅-C₁₀ aryl, C₅-C₁₀ heteroaryl, or C₅-C₁₀ heteroarylalkyl, each of which is optionally substituted with from 1 to 5 R²⁰ groups.

In some compounds of Formula (I), (Ia) or (Ib), R³ is phenyl, oxetanyl, tetrahydrofuranyl, furanyl, tetrahydrothiophenyl, thiophenyl, pyrrolyl, pyrrolinyl, pyrrolidinyl, dioxolanayl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridinyl, piperidinyl, dioxanyl, morpholinyl, thiomorpholinyl, pyridazinyl, pyrimidinyl, pyrazinyl, piperazinyl, triazinyl, indolizinyl, indolyl, isoindolyl, indolinyl, chromenyl, benzofuranyl, benzothiophenyl, dihydrobenzothiophenyl, indazolyl, benzimidazolyl, benzothiazolyl, benzoxazolyl, imidazo[1,2-a]pyridinyl, purinyl, quinolinyl, quinolizinyl, isoquinolinyl, cinnolinyl, phthalazinyl, quinazolinyl, quinoxalinyl, indenyl, naphthalenyl, or azulenyl, each of which is optionally substituted with from 1 to 5 R²⁰ groups.

In some compounds of Formula (I), (Ia) or (Ib), R³ is a moiety of the formula

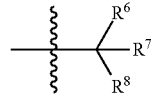

wherein R⁶ is H, OH, or halogen; and R⁷ and R⁸ are each independently C₁-C₆ alkyl, C₂-C₆ alkenyl, C₂-C₆ alkynyl, C₃-C₆ cycloalkyl, C₁-C₆ heteroalkyl, C₅-C₁₂ aryl, C₅-C₁₂ heteroaryl, or C₅-C₁₂ heteroarylalkyl, each of which is optionally substituted with from 1 to 5 R²⁰ groups. In some compounds, R⁶ is OH. In some compounds, R⁷ and R⁸ are each independently C₁-C₆ alkyl, C₃-C₆ cycloalkyl, C₁-C₆ heteroalkyl, C₅-C₁₂ aryl, C₅-C₁₂ heteroaryl, or C₅-C₁₂ heteroarylalkyl, each of which is optionally substituted with from 1 to 5 R²⁰ groups. In some compounds of Formula (I), (Ia) or (Ib), R⁷ and R⁸ are each independently C₁-C₆ alkyl, C₆ aryl or C₆ heteroaryl, each of which is optionally substituted with from 1 to 5 R²⁰ groups. In some compounds, R⁷ and R⁸ are each independently C₆ aryl or C₆ heteroaryl (e.g. a pyridyl), each of which is optionally substituted with from 1 to 5 R²⁰ groups. In some compounds of Formula (I), (Ia) or (Ib), R⁷ and R⁸ are each independently C₁-C₆ alkyl, each of which is optionally substituted with from 1 to 5 R²⁰ groups.

Other non-limiting examples of R³ include the following:

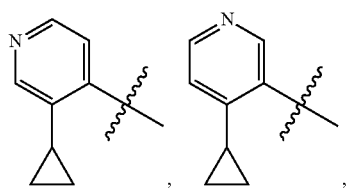

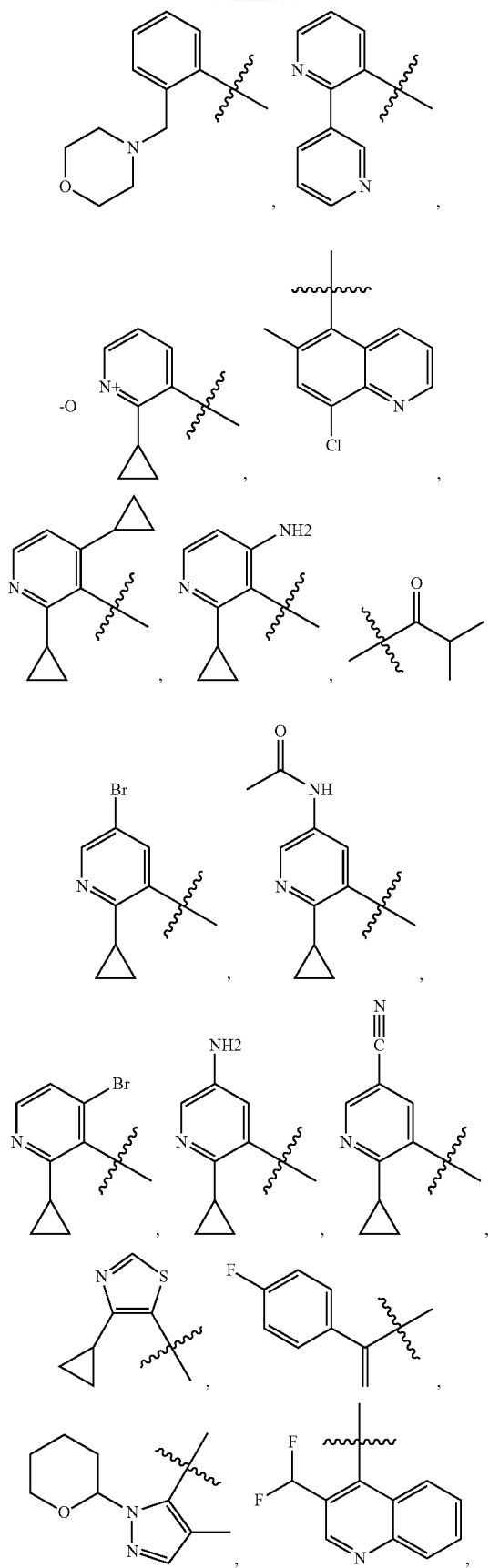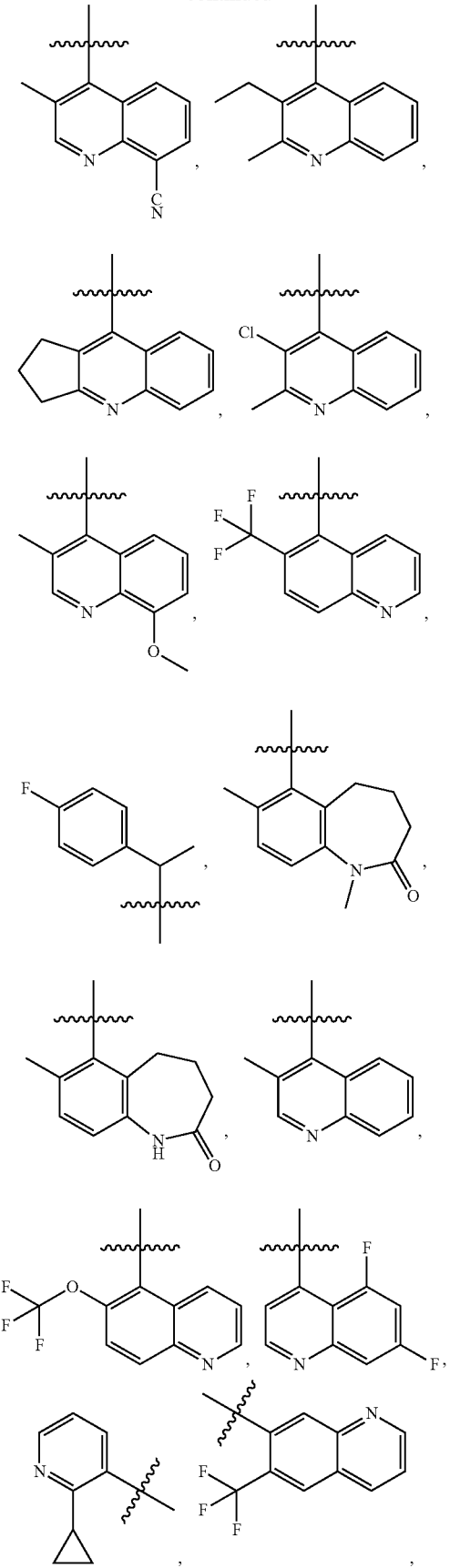

-continued
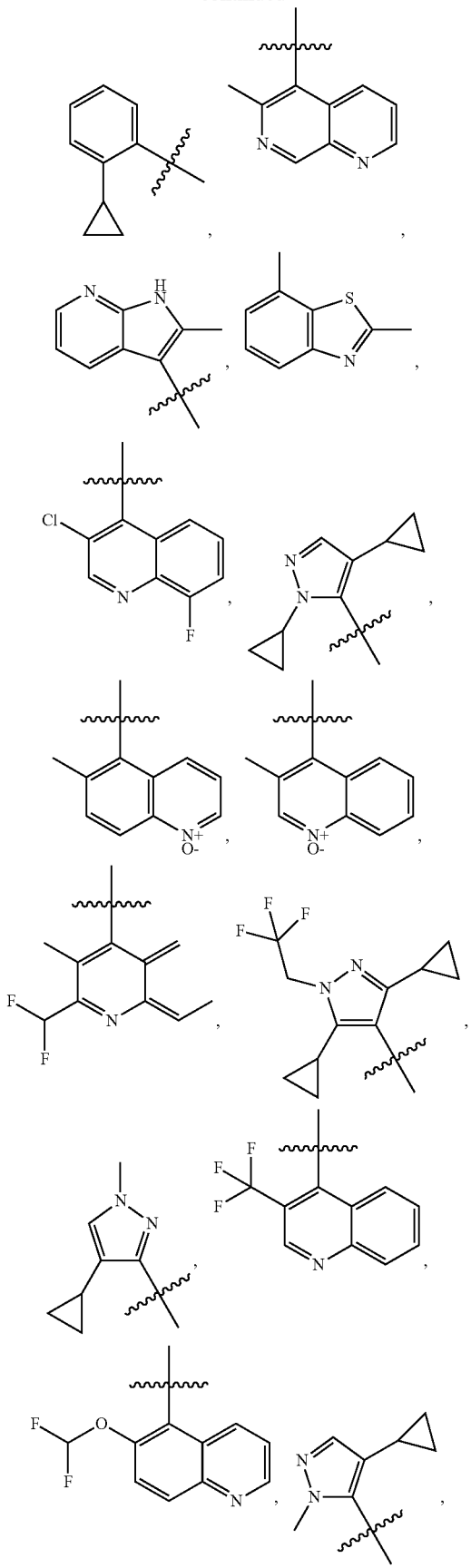
-continued
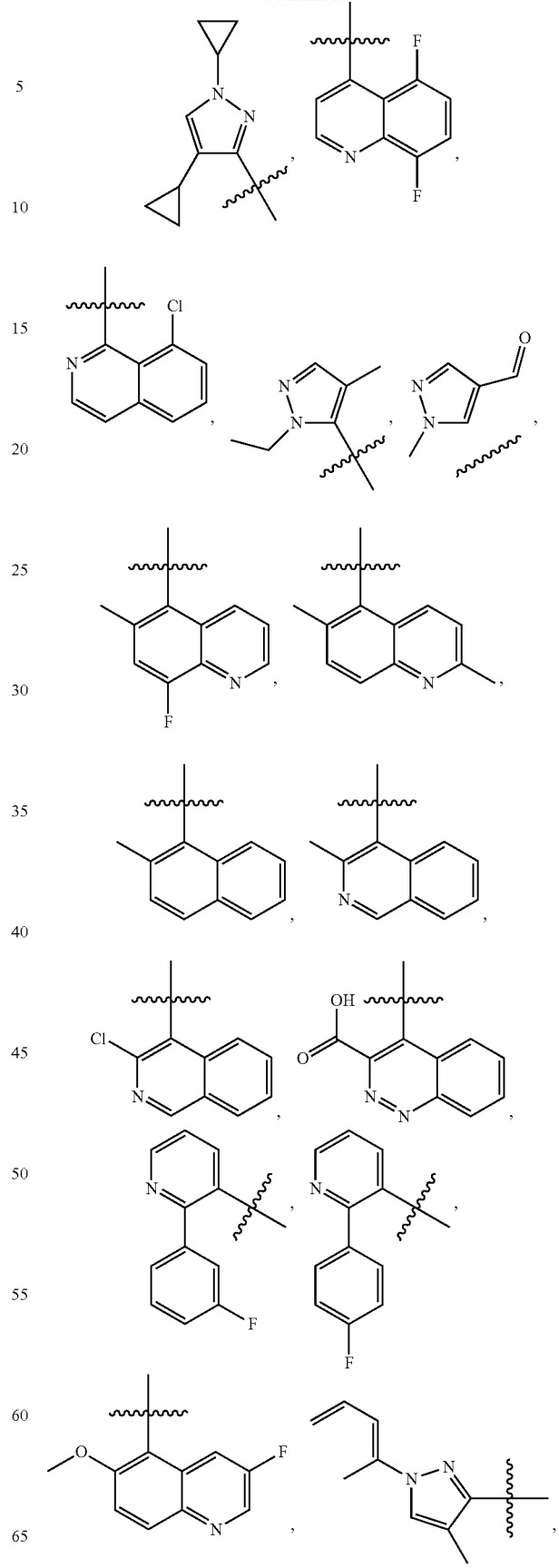

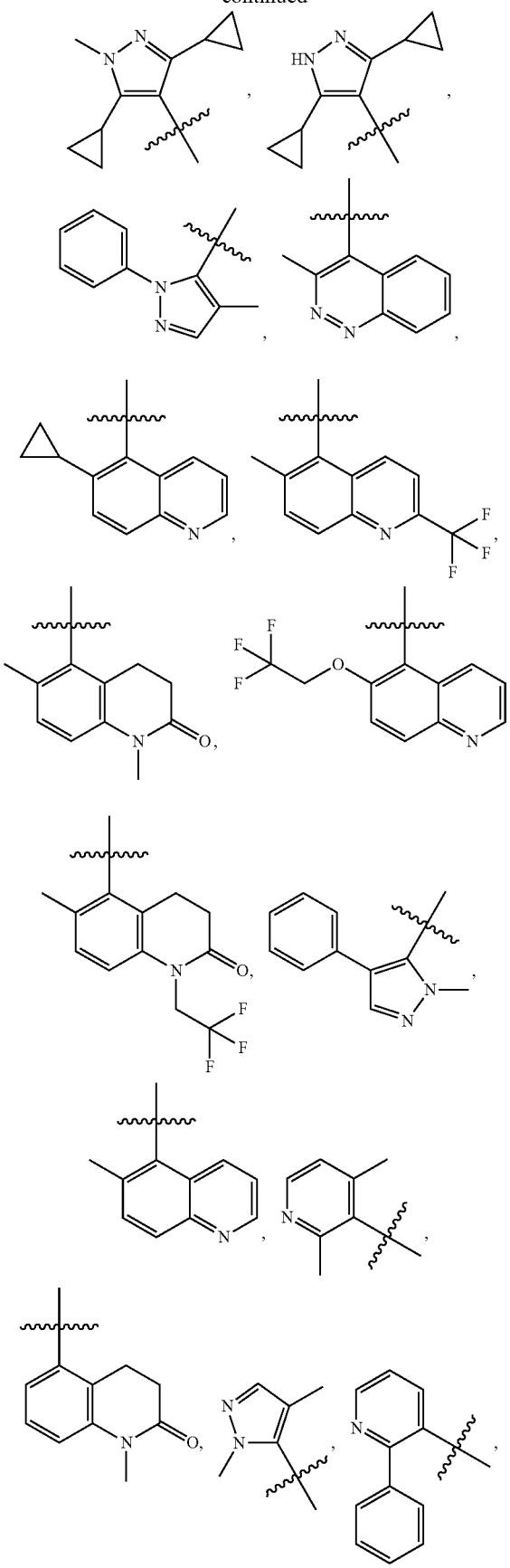
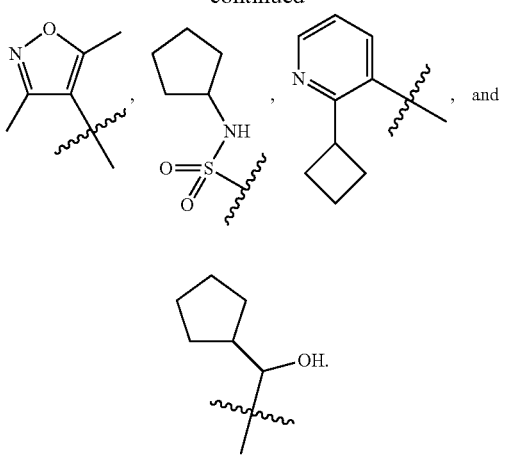
Additional non-limiting examples of R³ include the following:
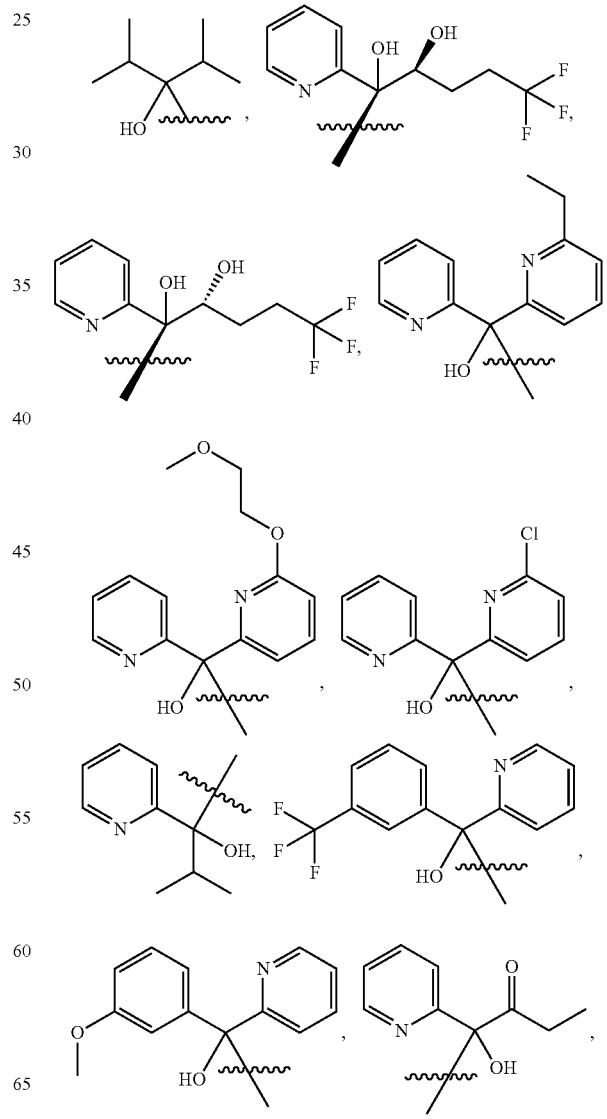

-continued
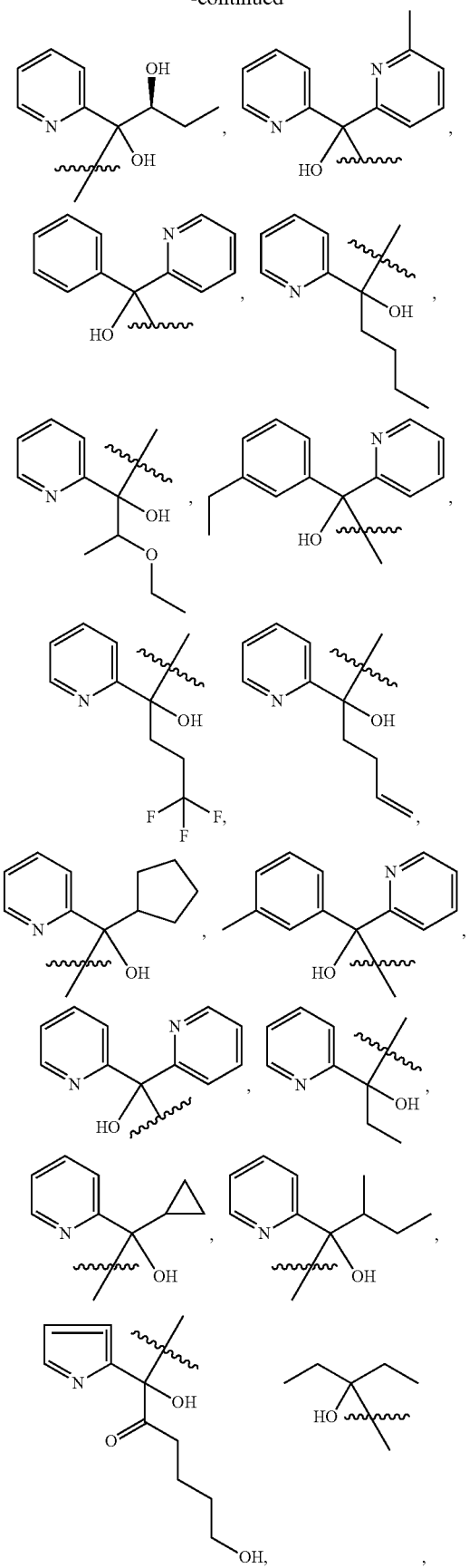
-continued
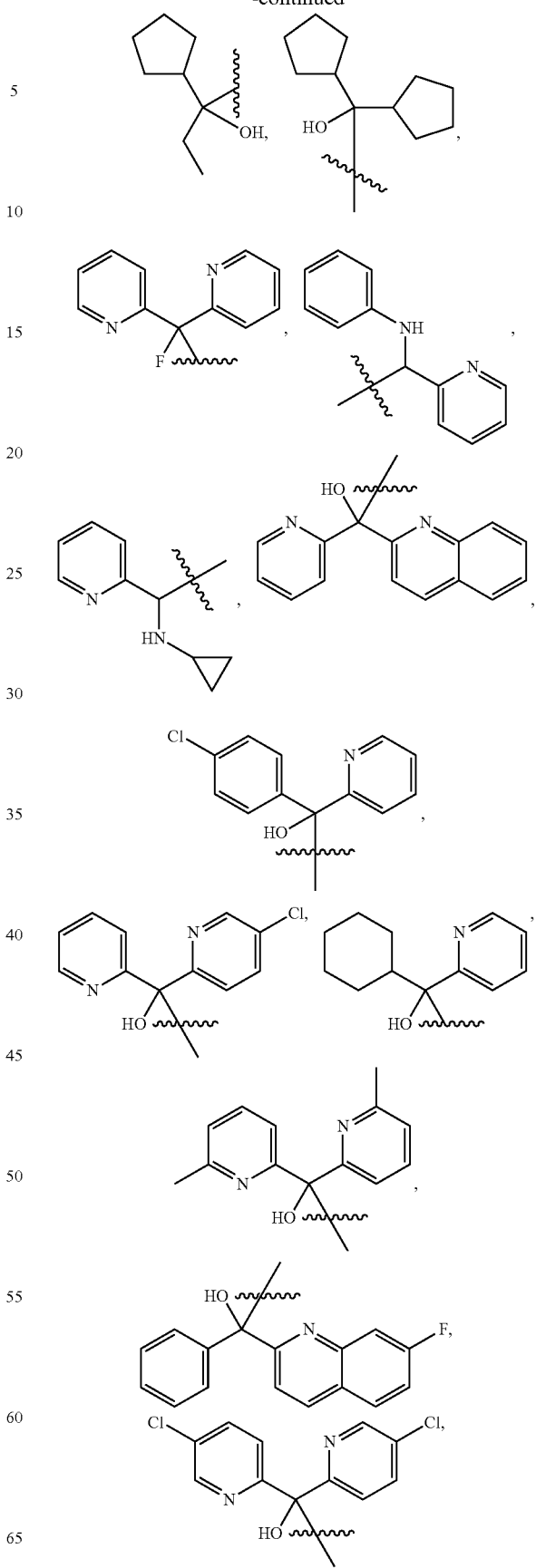

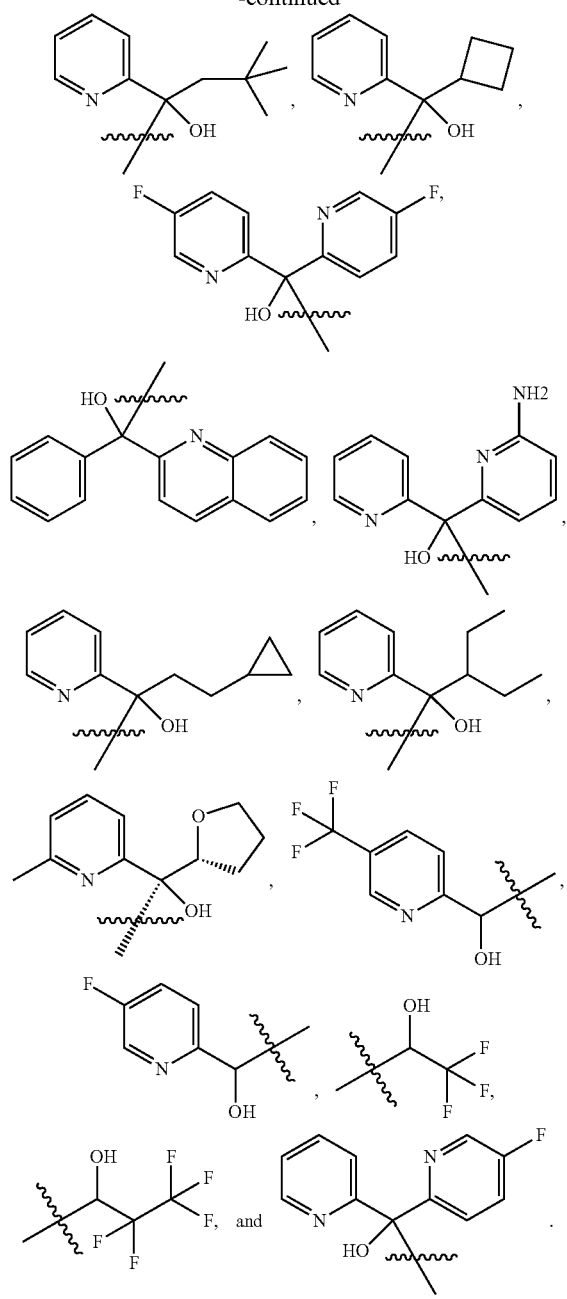
In another aspect, the compound of Formula (I) may be any of the following compounds:
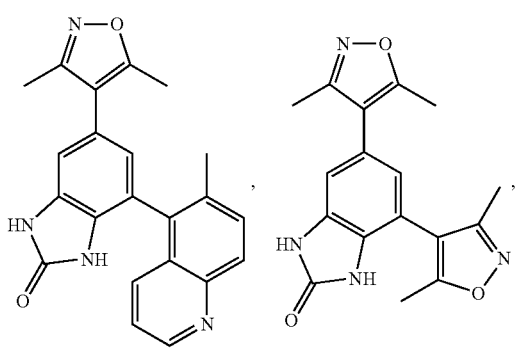
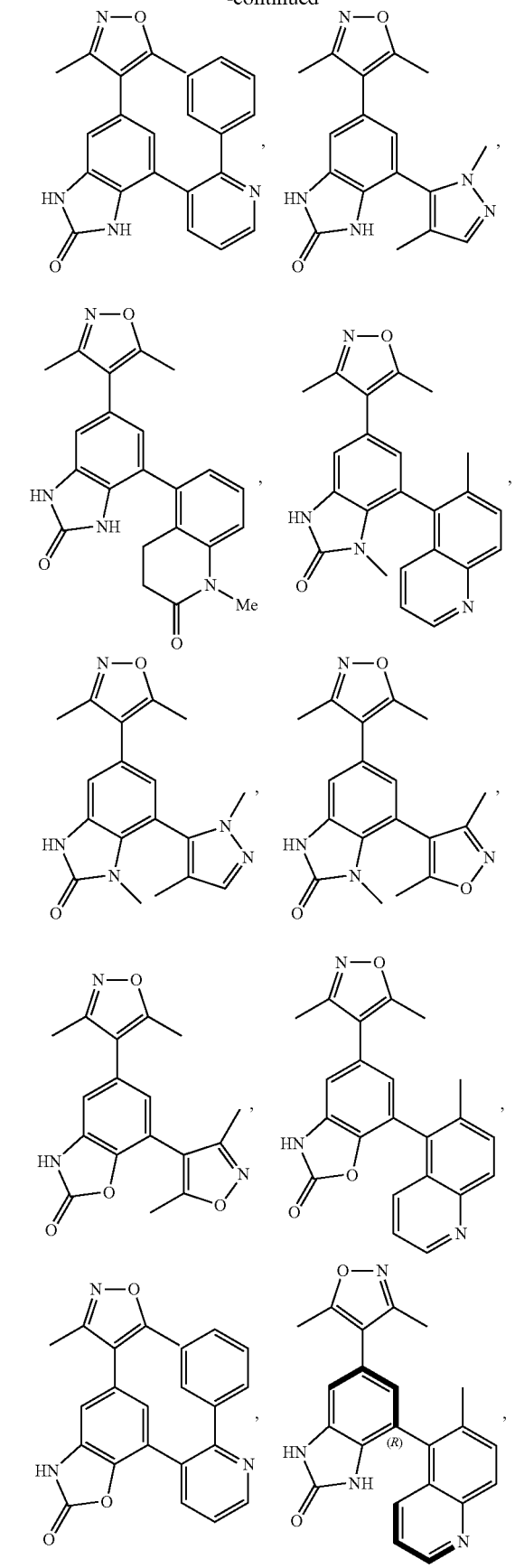

-continued
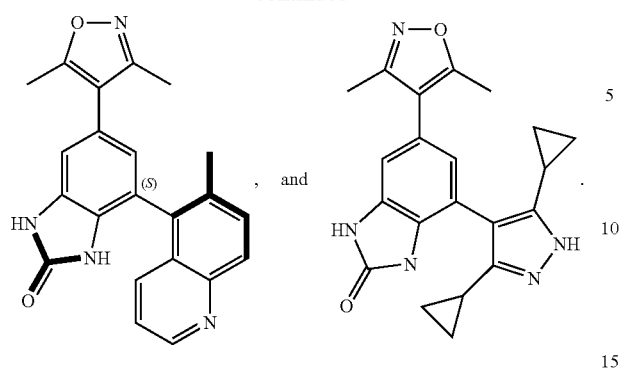, and 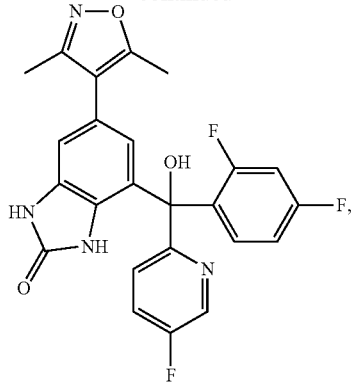.
In another aspect, the compound of Formula (I) may be any of the following compounds:
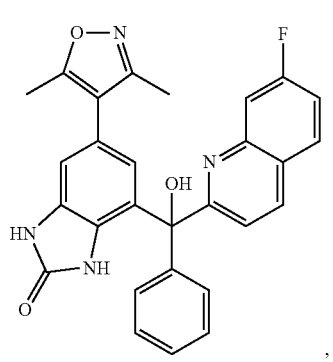,
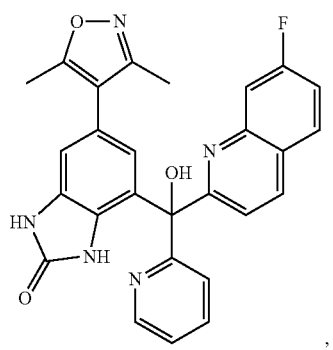,
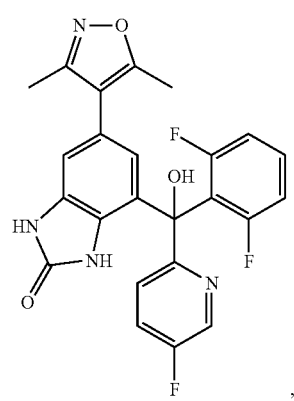,
-continued
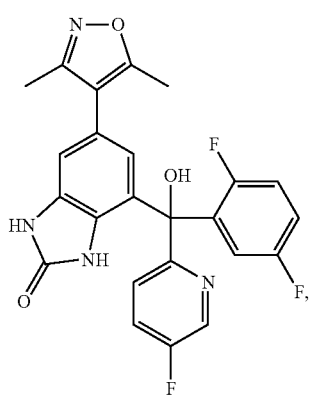,
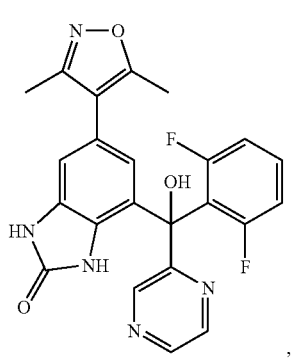,
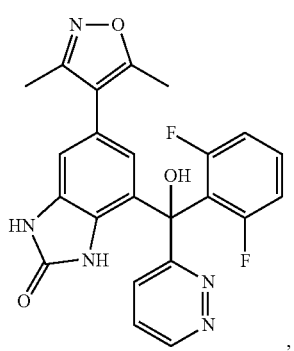, -continued
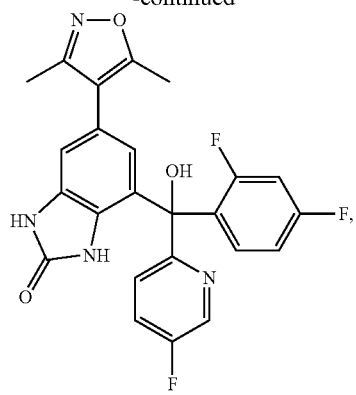
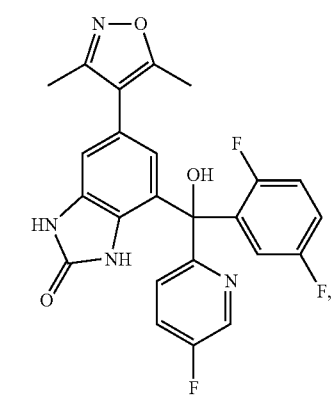
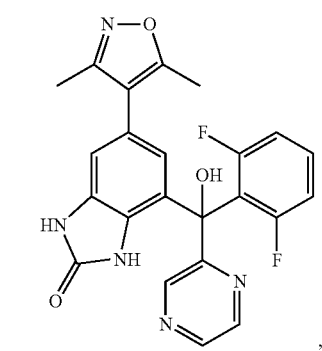
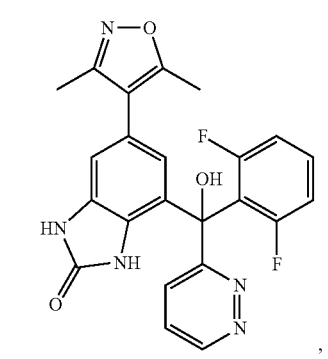
-continued
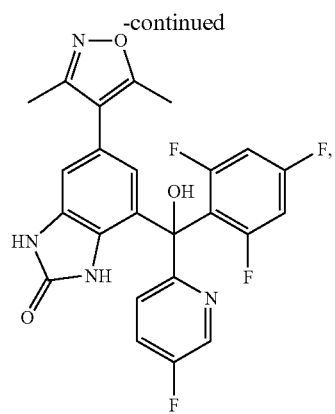
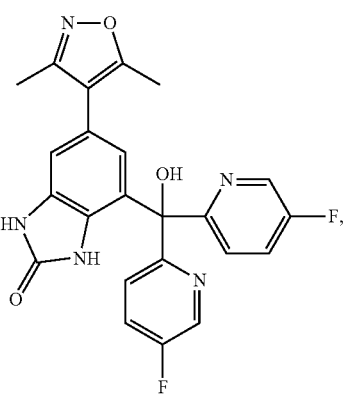
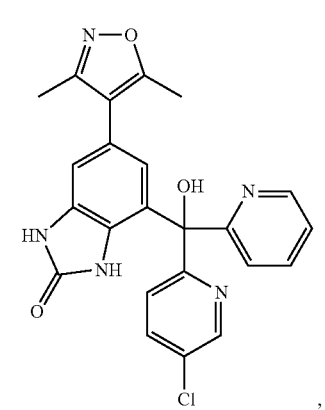
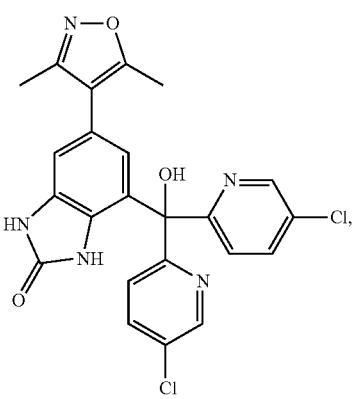

-continued

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written. For instance, the group "—$SO_2CH_2$—" is equivalent to "—$CH_2SO_2$—" and both may be connected in either direction. The prefix "$C_{u-v}$" indicates that the following group has from u to v carbon atoms, one or more of which, in certain groups (e.g. heteroalkyl, heteroaryl, heteroarylalkyl, etc.), may be replaced with one or more heteroatoms or heteroatomic groups. For example, "$C_{1-6}$ alkyl" indicates that the alkyl group has from 1 to 6 carbon atoms.

Also, certain commonly used alternative chemical names may or may not be used. For example, a divalent group such as a divalent "alkyl" group, a divalent "aryl" group, etc., may also be referred to as an "alkylene" group or an "alkylenyl" group, an "arylene" group or an "arylenyl" group, respectively.

"Alkyl" refers to any group derived from a linear or branched saturated hydrocarbon. Alkyl groups include, but are not limited to, methyl, ethyl, propyls such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, decyls, and the like. Unless otherwise specified, an alkyl group has from 1 to about 10 carbon atoms, for example from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to about 10 carbon atoms, for example from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡CH), propargyl (—$CH_2$C≡CH), (E)-pent-3-en-1-ynyl, and the like. Unless otherwise specified, an alkynyl group has from 2 to about 10 carbon atoms, for example from 2 to 10 carbon atoms, for example from 2 to 6 carbon atoms, for example from 2 to 4 carbon atoms.

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like.

"Arylalkyl" (also "aralkyl") refers to any combination of one or more aryl groups and one or more alkyl groups. Arylalkyl groups include, but are not limited to, those groups derived from benzyl, tolyl, dimethylphenyl, 2-phenylethan-1-yl, 2-naphthylmethyl, phenylmethylbenzyl, 1,2,3,4-tetrahydronapthyl, and the like. An arylalkyl group comprises from 6 to about 30 carbon atoms, for example the alkyl group can comprise from 1 to about 10 carbon atoms and the aryl group can comprise from 5 to about 20 carbon atoms.

"Cycloalkyl" refers to a cyclic alkyl group. A cycloalkyl group can have one or more cyclic rings and includes fused and bridged groups. Examples include, but are not limited to, cyclopropyl, cyclobutyl, cyclopentyl, cyclohexyl, adamantyl, methylcycloproyl (cyclopropylmethyl), ethylcyclopropyl, and the like.

"Halo" and "halogen" refer to fluoro, chloro, bromo and iodo.

"Haloalkyl" refers to an alkyl wherein one or more hydrogen atoms are each replaced by a halogen. Examples include, but are not limited to, —$CH_2Cl$, —$CH_2F$, —$CH_2Br$, —CFClBr, —$CH_2CH_2Cl$, —$CH_2CH_2F$, —$CF_3$, —$CH_2CF_3$, —$CH_2CCl_3$, and the like, as well as alkyl groups such as perfluoroalkyl in which all hydrogen atoms are replaced by fluorine atoms.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, —$P(O)_2$—, —S(O)—, —$S(O)_2$—, and the like, where R is H, alkyl, aryl, cycloalkyl, heteroalkyl, heteroaryl or cycloheteroalkyl. The term "heteroalkyl" includes heterocycloalkyl (a cyclic heteroalkyl group), alkyl-heterocycloalkyl (a linear or branched C1-C6 alkyl group attached to a cyclic heteroalkyl group), and the like. Heteroalkyl groups include, but are not limited to, —$OCH_3$, —$CH_2OCH_3$, —$SCH_3$, —$CH_2SCH_3$, —$NRCH_3$, —$CH_2NRCH_3$, and the like, where R is hydrogen, alkyl, aryl, arylalkyl, heteroalkyl, or heteroaryl, each of which may be optionally substituted. A heteroalkyl group comprises from 1 to about 10 carbon and hetero atoms, e.g., from 1 to 6 carbon and hetero atoms.

"Heteroaryl" refers to an aryl group in which one or more of the carbon atoms (and any associated hydrogen atoms) are each independently replaced with the same or different heteroatom or heteroatomic group, as defined above. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroarylalkyl" refers to an arylalkyl group in which one or more carbon atoms (and any associated hydrogen atoms) are independently replaced with the same or different heteroatoms or heteratomic groups, as defined above. Heteroarylalkyl groups include, but are not limited to, groups derived from heteroaryl groups with alkyl substituents (e.g. methylpyridines, ethylthiophenes, methylthiazoles, dimethylisoxazoles, etc.), hydrogenated heteroaryl groups (dihydroquinolines, e.g. 3,4-dihydroquinoline, dihydroisoquinolines, e.g. 1,2-dihydroisoquinoline, dihydroimidazole, tetrahydroimidazole, etc.), indoline, isoindoline, isoindolones (e.g. isoindolin-1-one), isatin, dihydrophthalazine, quinolinone, spiro[cyclopropane-1,1'-isoindolin]-3'-one, and the like.

"Heterocycle," "heterocyclic," and "heterocyclyl" refer to a single saturated or partially unsaturated non-aromatic ring or a non-aromatic multiple-ring system with at least one heteroatom or heteroatomic group, as defined above. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like.

The term "pharmaceutically acceptable" with respect to a substance refers to that substance which is generally regarded as safe and suitable for use without undue toxicity, irritation, allergic response, and the like, commensurate with a reasonable benefit/risk ratio.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

"Treating" and "treatment" of a disease include the following:
(1) preventing or reducing the risk of developing the disease, i.e., causing the clinical symptoms of the disease not to develop in a subject that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

"Effective amount" refers to an amount that may be effective to elicit the desired biological, clinical, or medical response, including the amount of a compound that, when administered to a subject for treating a disease, is sufficient to effect such treatment. The effective amount will vary depending on the compound, the disease and its severity and the age, weight, etc., of the subject to be treated. The effective amount can include a range of amounts.

It understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged.

Provided are also compounds in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Compounds of a given formula described herein encompasses the compound disclosed and all pharmaceutically acceptable salts, stereoisomers, tautomers, solvates, and deuterated forms thereof, unless otherwise specified.

The pharmaceutical compositions of compounds of Formula (I) (including compounds of Formulae (Ia) and (Ib)) may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula (I), or a pharmaceutically acceptable salt, ester, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula (I), or a pharmaceutically acceptable salt, ester, prodrug, or solvate thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 250 mg, or about 300 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 500 mg of an active ingredient.

Frequency of dosage may also vary depending on the compound used and the particular disease or condition treated. In some embodiments, for example, for the treatment of an autoimmune and/or inflammatory disease, a dosage regimen of 4 times daily or less is used. In some embodiments, a dosage regimen of 1 or 2 times daily is used. It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease in the subject undergoing therapy.

For preparing solid compositions such as tablets, the principal active ingredient may be mixed with a pharmaceutical excipient to form a solid preformulation composition containing a homogeneous mixture of a compound of Formula (I), or a pharmaceutically acceptable salt, ester, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Kits that include a compound of Formula (I), or a pharmaceutically acceptable salt, thereof, and suitable packaging are provided. In one embodiment, a kit further includes instructions for use. In one aspect, a kit includes a compound of Formula (I), or a pharmaceutically acceptable salt thereof, and instructions for use of the compounds in the treatment of the diseases or conditions described herein.

Articles of manufacture that include a compound of Formula (I), or a pharmaceutically acceptable salt thereof, in a suitable container are provided. The container may be a vial, jar, ampoule, preloaded syringe, and intravenous bag.

Compounds of Formula (I) may be combined with one or more additional anti-cancer or anti-inflammatory agents, including any of the following. Various kinase inhibitors are being used and are being developed to treat various cancers. For example, the activation of the phosphatidylinositol 3-kinase (PI3K) pathway is observed in human cancer, and agents inhibiting PI3K are being investigated or developed as potential anti-cancer drugs and for the use in anti-cancer therapies. Additional kinase inhibitors include inhibitors of spleen tyrosine kinase (Syk) and Janus kinase (JAK). Other agents inhibiting related pathways are also of interest as anti-cancer or anti-inflammatory agents, including agents inhibiting the Ras/Raf/MEK/ERK pathway and the PI3K/PTEN/Akt/mTOR pathway. As described herein, such inhibitors include agents that inhibit all subclasses of a target (e.g. PI3K alpha, beta, delta and gamma), agents that inhibit primarily one subclass, and agents that inhibit a subset of all subclasses. Compounds of Formula (I) may also be combined with one or more additional anti-cancer or anti-inflammatory agents including inhibitors or antagonists of lysyl oxidase-like 2 (LOXL2), and inhibitors or antagonists of adenosine A2B receptor.

In various aspects, compounds of Formula (I) may be combined with one or more kinase inhibitors. Examples of kinase inhibitors include PI3K inhibitors, Syk inhibitors and JAK inhibitors.

Examples of PI3K inhibitors include Compound A, Compound B, and Compound C:

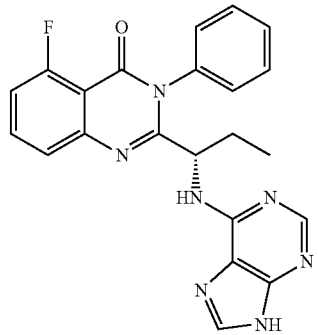
(Compound A)

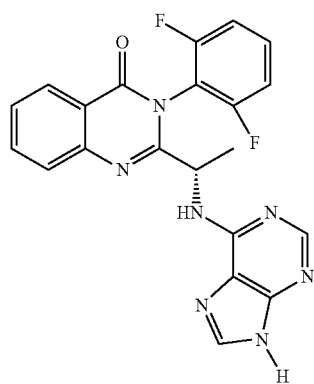
(Compound B)

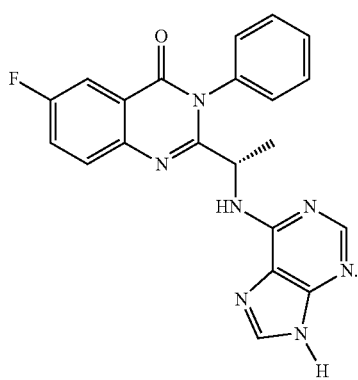
(Compound C)

Additional examples of PI3K inhibitors include XL147, BKM120, GDC-0941, BAY80-6946, PX-866, CH5132799, XL756, BEZ235, and GDC-0980.

Inhibitors of mTOR include OSI-027, AZD2014, and CC-223.

Inhibitors of AKT include MK-2206, GDC-0068 and GSK795.

Examples of Syk inhibitors include compound D:

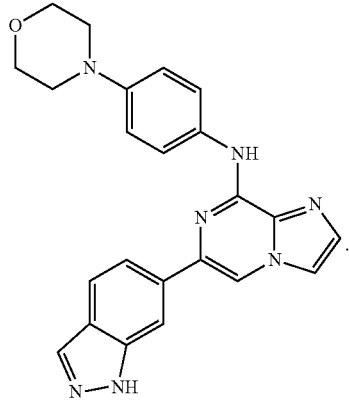
(Compound D)

Additional Syk inhibitors include R788 (fostamatinib), R-406 (tamatinib), and PRT062607.

Examples of JAK inhibitors include Compound E:

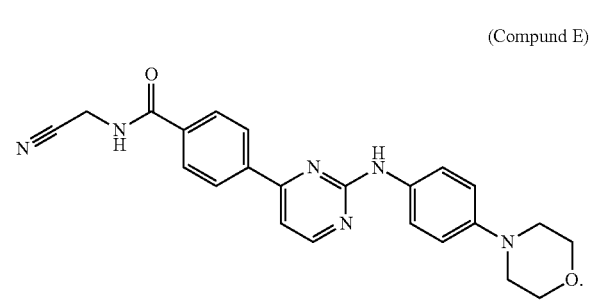 [SMILES: N#CCNC(=O)c1ccc(-c2ccnc(Nc3ccc(N4CCOCC4)cc3)n2)cc1]
(Compound E)

Additional JAK inhibitors include Ruxolitinib, Tofacitinib, Baricitinib, CYT387, Lestaurtinib, Pacritinib, and TG101348.

In other aspects, compounds of Formula (I) may be combined with one or more inhibitors or modulators (e.g. antagonists) of LOXL2, adenosine A2B receptor, MMP-9, ASK1, BTK, mTOR, HDAC, and MEK.

In other aspects, compounds of Formula (I) may be combined with one or more components of CHOP therapy (cyclophosphamide, Adriamycin, Vincristine, Prednisolone).

In other aspects, compounds of Formula (I) may be combined with one or more of ribavirin and interferon.

In other aspects, compounds of Formula (I) may be combined with one or more agents that activate or reactivate latent human immunodeficiency virus (HIV). For example, compounds of Formula (I) may be combined with a histone deacetylase (HDAC) inhibitor (listed above) or a protein kinase C (PKC) activator. For example, compounds of Formula (I) may be combined with romidepsin or panobinostat.

EXAMPLES

General Methods

Synthesis of certain compounds, and intermediates used to prepare compounds, is detailed in the following sections. Compound numbers are listed for convenience.

All operations involving moisture and/or oxygen sensitive materials were conducted under an atmosphere of dry nitrogen in pre-dried glassware. Unless noted otherwise, materials were obtained from commercially available sources and used without further purification.

Flash chromatography was performed on an Isco Combiflash Companion using RediSep Rf silica gel cartridges by Teledyne Isco. Thin layer chromatography was performed using precoated plates purchased from E. Merck (silica gel 60 PF254, 0.25 mm) and spots were visualized with long-wave ultraviolet light followed by an appropriate staining reagent.

Nuclear magnetic resonance ("NMR") spectra were recorded on a Varian 400 MHz resonance spectrometer. 1H NMR chemical shifts are given in parts per million (δ) downfield from tetramethylsilane ("TMS") using TMS or the residual solvent signal (CHCl3=δ7.24, DMSO=δ2.50) as internal standard. 1H NMR information is tabulated in the following format: multiplicity (s, singlet; d, doublet; t, triplet; q, quartet; m, multiplet), coupling constant(s) (J) in Hertz, number of protons. The prefix app is occasionally applied in cases where the true signal multiplicity was unresolved and br indicates the signal in question was broadened.

The compounds were named using ChemBioDraw Ultra Version 12.0.

LCMS analysis was performed using a PE SCIEX API 2000 spectrometer with a Phenomenex Luna 5 micron C18 column.

Preparatory HPLC was performed on a Gilson HPLC 215 liquid handler with a Phenomenex column (Gemini 10☐, C18, 110A) and a UV/VIS 156 detector.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. The methods or features described in various Examples may be combined or adapted in various ways to provide additional ways of making the compounds described herein.

Methods for obtaining the novel compounds described herein will be apparent to those of ordinary skill in the art, procedures described in, for example, the reaction schemes and examples below, and in the references cited herein.

EXAMPLES

Methods for obtaining the novel compounds described herein will be apparent to those of ordinary skill in the art, with suitable procedures being described, for example, in the reaction schemes and examples below, and in the references cited herein.

Scheme 1

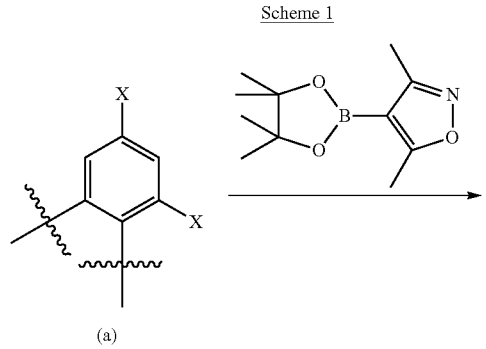

(a)

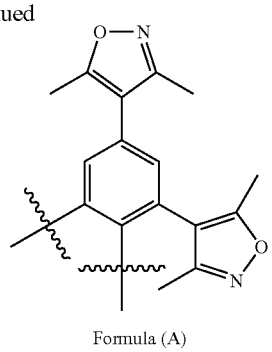

Formula (A)

The compound of Formula (1-a) can be prepared by Suzuki coupling of a compound of commercially available compound of Formula (a) to commercially available isoxazole boronic acid ester shown above in the presence of a base. Substituents X in compound (a) may be any appropriate leaving group (e.g., Cl, Br, I, OTf). Suitable catalysts may include palladium catalysts, such as (1,3-bis(2,6-diisopropylphenyl)imidazolidene)(3-chloropyridyl) palladium(II) dichloride (Peppsi-iPr). Suitable bases may include, for example, cesium carbonate or 1,8-diazobicycloundec-7-ene. Suitable solvents may include a combination of organic solvents and water, including, for example, 1,4-dioxane, THF, dimethoxyethane or dimethylformamide and water. The reaction is carried out in an appropriate solvent under nitrogen, at an elevated temperature of about 70° C. to 150° C., for about 30 seconds to 5 hours. When the reaction is substantially complete, the reaction is allowed to cool to room temperature. The reaction mixture can be partitioned between an aqueous phase and an organic phase. The aqueous phase is discarded, and the organic phase concentrated under reduced pressure, and the residue is purified by reverse phase high-performance liquid chromatography, eluting with an appropriate solvent mixture such as acetonitrile and water, to isolate compounds of Formula (A).

Another exemplary method of preparing compounds of Formula (B) is shown in Reaction Scheme No. 2.

Scheme 2

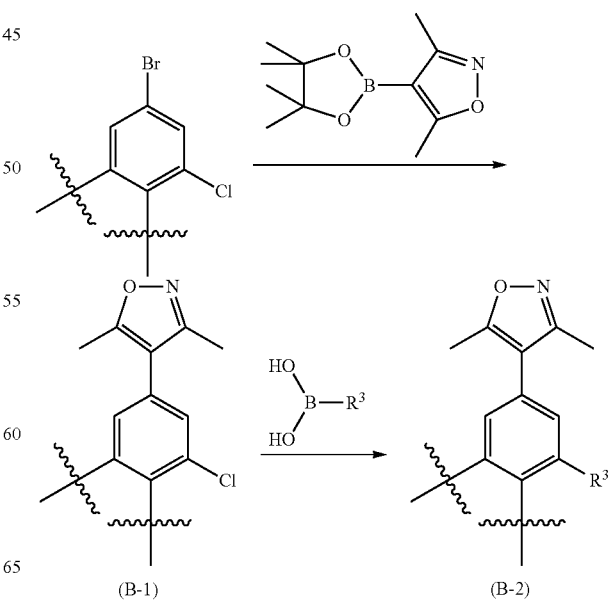

(B-1)    (B-2)

Step 1—Preparation of Formula (B-1)

The compound of Formula (B-1) can be prepared by Suzuki coupling of a compound of commercially available compound chloro-bromo substituted aromatic heterocycle which may bear an additional heteroaryl ring as shown above as two variable attachment bonds to commercially available isoxazole boronic acid ester shown above in the presence of a base. Suitable catalysts may include palladium catalysts, such as [1,1'-Bis(diphenylphosphino) ferrocene]dichloropalladium(II). Suitable bases may include, for example, cesium carbonate or 1,8-diazobicycloundec-7-ene. Suitable solvents may include a combination of organic solvents and water, including, for example, 1,4-dioxane, THF, dimethoxyethane or dimethylformamide and water. The reaction is carried out in an appropriate solvent under nitrogen, at an elevated temperature of about 70° C. to 150° C., for about 30 seconds to 5 hours. When the reaction is substantially complete, the reaction is allowed to cool to room temperature. The reaction mixture can be partitioned between an aqueous phase and an organic phase. The aqueous phase is discarded, and the organic phase concentrated under reduced pressure, and the residue is purified by reverse phase high-performance liquid chromatography, eluting with an appropriate solvent mixture such as acetonitrile and water, to isolate compounds of Formula (B-1). The compound of Formula (B-1) may also be purified by other conventional means, such as silica gel chromatography.

Step 2—Preparation of Formula (B-2)

The compound of Formula (B-2) can be prepared by Suzuki coupling of a compound of Formula (B-1) to commercially available boronic acid derivatives bearing substituent $R^3$ as defined in the specification for compounds of Formula (I). Suitable catalysts may include palladium catalysts, such as (1,3-bis(2,6-diisopropylphenyl)imidazolidene)(3-chloropyridyl) palladium(II) dichloride (Peppsi-iPr). Suitable bases may include, for example, cesium carbonate or 1,8-diazobicycloundec-7-ene. Suitable solvents may include a combination of organic solvents and water, including, for example, 1,4-dioxane, THF, dimethoxyethane or dimethylformamide and water. The reaction is carried out in an appropriate solvent under nitrogen, at an elevated temperature of about 70° C. to 150° C., for about 30 seconds to 5 hours. When the reaction is substantially complete, the reaction is allowed to cool to room temperature. The reaction mixture can be partitioned between an aqueous phase and an organic phase. The aqueous phase is discarded, and the organic phase concentrated under reduced pressure, and the residue is purified by reverse phase high-performance liquid chromatography, eluting with an appropriate solvent mixture such as acetonitrile and water, to isolate compounds of Formula (B-2).

Another exemplary method of preparing compounds of Formula (C-2) is shown in Reaction Scheme No. 3.

Scheme 3

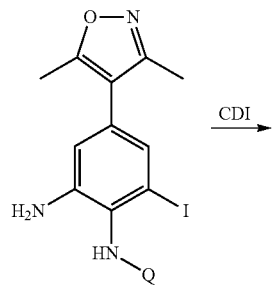

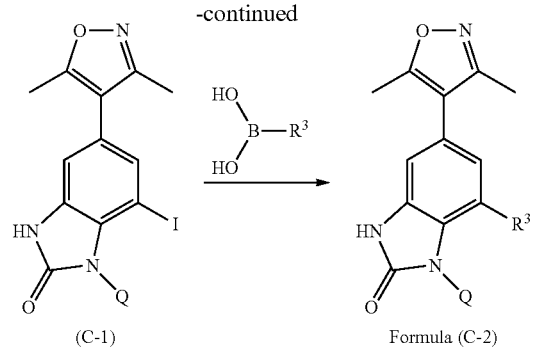

Step 1—Preparation of Formula (C-1)

An appropriate carbony-delivering reagent is reacted with the compound of Formula (C-1) (with substituent Q as either H or methyl) in an appropriate solvent, and allowed to react for a period of time such as 1-5 hours at an elevated temperature of 80-150° C. Appropriate solvents include organic solvents such as tetrahydrofuran. When the reaction is substantially complete, the compound of (C-1) is isolated by removal of solvent under vacuum and purification by conventional means, such as recrystallization or trituration in an appropriate solvent mixture, such as hexanes and ethyl acetate.

Step 2—Preparation of Formula (C-2)

The compound of Formula (C-2) can be prepared by Suzuki coupling of a compound of Formula (C-1) to boronic acid shown above in the presence of a base. As shown above, boronic acid is substituted with carbon-linked phenyl, naphthyl, or heteroaryl $R^3$ group as defined in the specification for compounds of Formula (I). It should be understood that boronate esters, or other appropriate boron complexes (i.e. —$BF_3K$ salts, etc.) may also be used in place of a boronic acid. Suitable catalysts may include palladium catalysts, such as (1,3-bis(2,6-diisopropylphenyl)imidazolidene)(3-chloropyridyl) palladium(II) dichloride (Peppsi-iPr). Suitable bases may include, for example, cesium carbonate or 1,8-diazobicycloundec-7-ene. Suitable solvents may include a combination of organic solvents and water, including, for example, 1,4-dioxane, THF, dimethoxyethane or dimethylformamide and water. The reaction is carried out in an appropriate solvent under nitrogen, at an elevated temperature of about 70° C. to 150° C., for about 30 seconds to 5 hours. When the reaction is substantially complete, the reaction is allowed to cool to room temperature.

The reaction mixture can be partitioned between an aqueous phase and an organic phase. The aqueous phase is discarded, and the organic phase concentrated under reduced pressure, and the residue is purified by reverse phase high-performance liquid chromatography, eluting with an appropriate solvent mixture such as acetonitrile and water, to isolate compounds of Formula (C-2). Alternatively, the compound of Formula (C-2) may be purified by other conventional means such as silica gel chromatography or recrystallization.

When the reactions described herein are substantially complete, the reaction may be allowed to cool to room temperature. The reaction mixture can then be concentrated and purified by any suitable method, including for example, chromatography on silica gel or preparative HPLC to obtain the compound of Formulas (I), (Ia), and (Ib), including each of the compounds in the examples provided below.

Step 3: Preparation of Formula (C1-C5)

The compound of Formula (C-4, C-5 and C-6) can be prepared as follows: Reacting (C-1) with and appropriate carbonyl source as described previously affords (C-2). (C-2) is then reacted with metalated alkyl or aryl reagents (e.g. but not limited to Li or Mg) to symmetrical carbinols (C-4), or converted to Weinreb amide (C-3) followed by reaction with metalated alkyl and aryl reagents to afford ketone (C-5). Ketone (C-5) can then we reacted again with metalated alkyl and aryl reagents to afford asymmetric carbinol (C-6).

Alternatively, compounds above can be prepared by converting (C-1) to the corresponding 2-alkoxy-benzimidazole (C-7), which is then further converted to (C-4) including (C-6) using methods above.

be considered to constitute certain preferred modes for its practice. However, those of skill in the art should, in light of the present disclosure, appreciate that many changes can be made in the specific embodiments which are disclosed, and still obtain a like or similar results without department from the spirit and the scope of the invention.

The following abbreviations are used in the Examples below:
DME 1,2-dimethoxy ethane
DMF dimethylformamide
EtOAc ethyl acetate

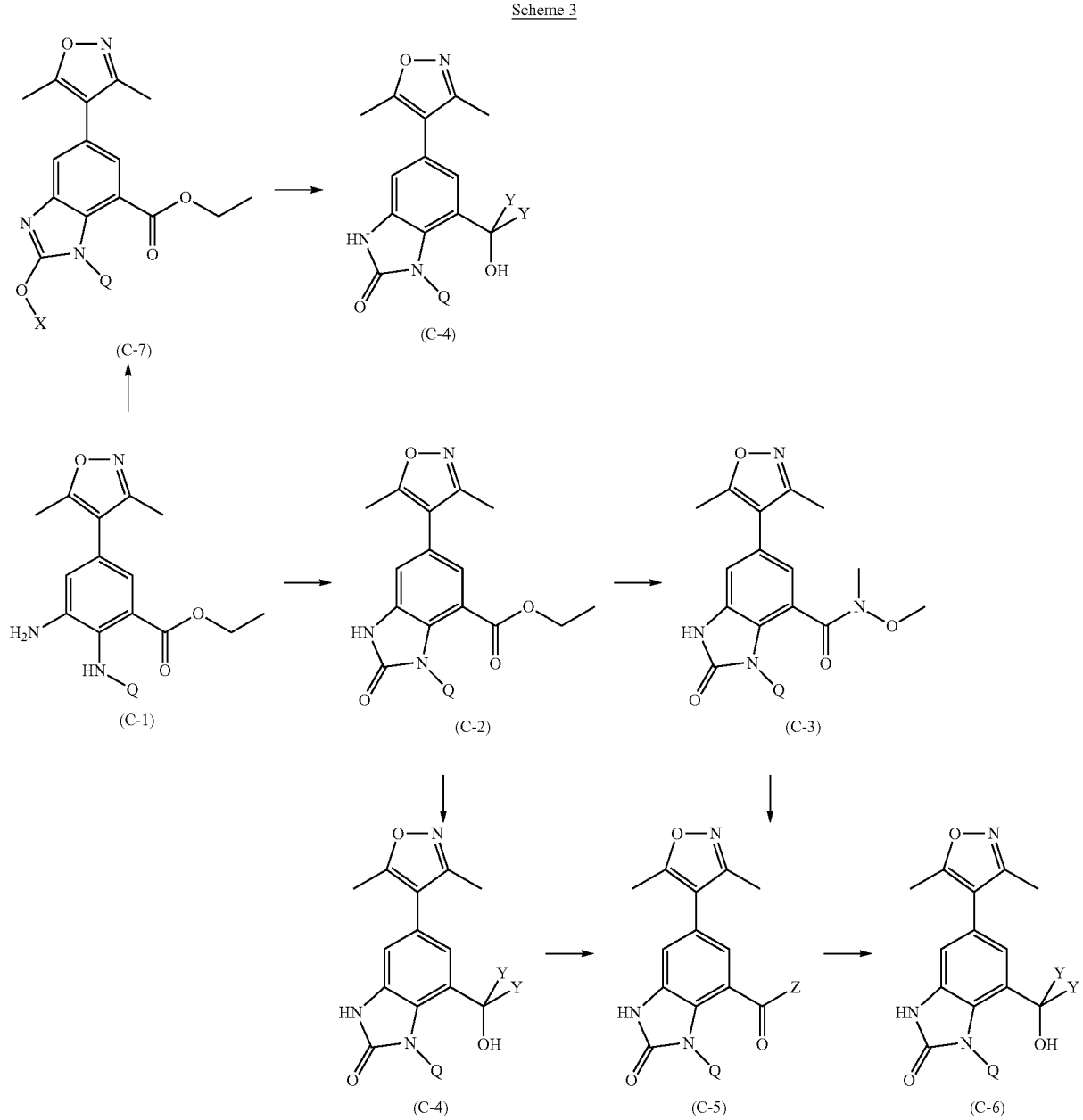

Scheme 3

The following examples are included to demonstrate certain preferred embodiments. It should be appreciated by those of skill in the art that the techniques disclosed in the examples which follow represent techniques discovered by the inventor to function well in the practice of the invention, and thus can Hepes 4-(2-hydroxyethyl)-1-piperazineethanesulfonic acid
mCPBA meta chloroperbenzoic acid
MeCN acetonitrile
NBS N-bromosuccinimide Peppsi-iPr (or PEPPSI iPr or PEPPSI™-iPr)
(1,3-bis(2,6-diisopropylphenyl)imidazolidene)(3-chloropyridyl)palladium(II) dichloride PdCl₂dppf [1,1-Bis(diphenylphosphino) ferrocene] dichloropalladium (II)

POCl₃ phosphoryl chloride rf retention factor

TEA triethylamine

TFA trifluoroacetic acid

THF tetrahydrofuran

Example 1

N-cyclopentyl-6-(3,5-dimethylisoxazol-4-yl)-2-oxo-2,3-dihydro-1H-benzo[d]imidazole-4-sulfonamide

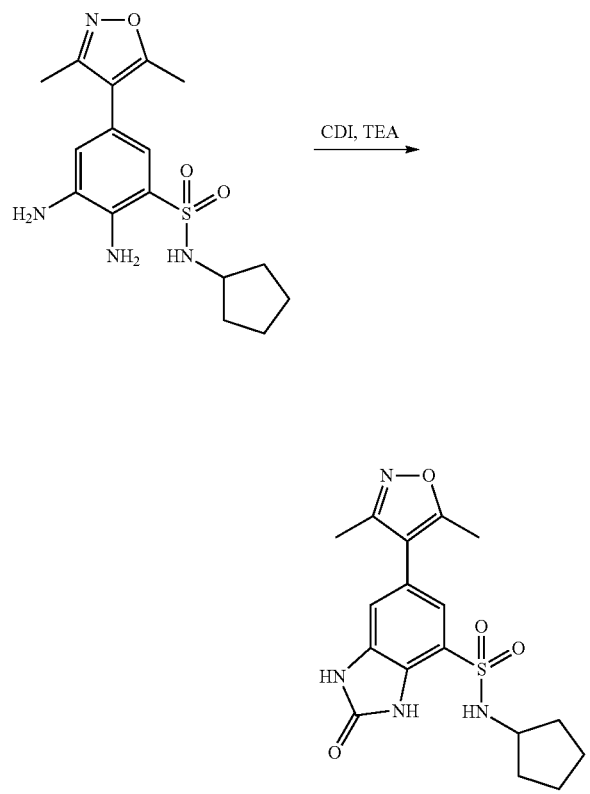

2,3-Diamino-N-cyclopentyl-5-(3,5-dimethylisoxazol-4-yl)benzenesulfonamide (58 mg, 0.17 mmol) was dissolved in DMF (2 mL). To the solution was added CDI (360 mg, 4 mmol) and TEA (1 mL). The reaction was heated at 150° C. in microwave for 10 h. The solvent was evaporated and the residue was purified by preparative HPLC (0-100% CH₃CN/H₂O) to afford N-cyclopentyl-6-(3,5-dimethylisoxazol-4-yl)-2-oxo-2,3-dihydro-1H-benzo[d]imidazole-4-sulfonamide.

$C_{17}H_{20}N_4O_4S$. 377.0 (M+1). ¹H NMR (400 MHz, CD₃OD) δ 7.34 (s, 1H), 7.18 (s, 1H), 3.63-3.58 (m, 1H), 2.41 (s, 3H), 2.25 (s, 3H), 1.70-1.60 (m, 4H), 1.49-1.31 (m, 4H).

Example 2

6-(3,5-dimethylisoxazol-4-yl)-4-(6-methylquinolin-5-yl)-1H-benzo[d]imidazol-2(3H)-one

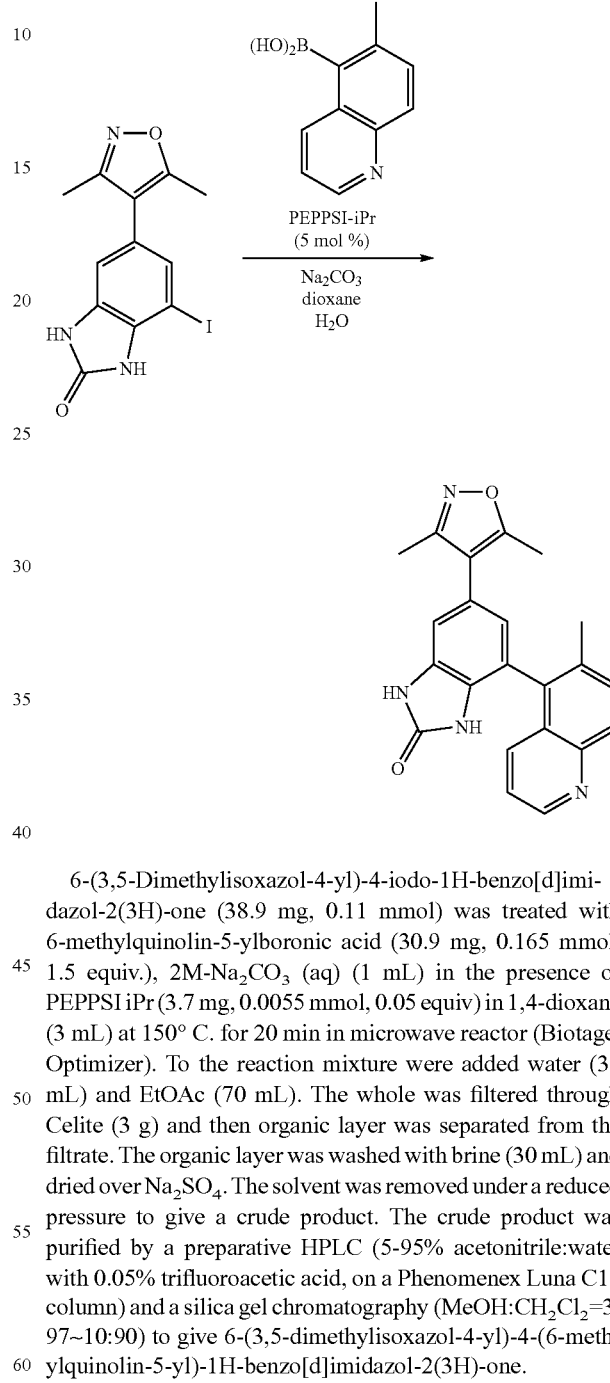

6-(3,5-Dimethylisoxazol-4-yl)-4-iodo-1H-benzo[d]imidazol-2(3H)-one (38.9 mg, 0.11 mmol) was treated with 6-methylquinolin-5-ylboronic acid (30.9 mg, 0.165 mmol, 1.5 equiv.), 2M-Na₂CO₃ (aq) (1 mL) in the presence of PEPPSI iPr (3.7 mg, 0.0055 mmol, 0.05 equiv) in 1,4-dioxane (3 mL) at 150° C. for 20 min in microwave reactor (Biotage, Optimizer). To the reaction mixture were added water (30 mL) and EtOAc (70 mL). The whole was filtered through Celite (3 g) and then organic layer was separated from the filtrate. The organic layer was washed with brine (30 mL) and dried over Na₂SO₄. The solvent was removed under a reduced pressure to give a crude product. The crude product was purified by a preparative HPLC (5-95% acetonitrile:water with 0.05% trifluoroacetic acid, on a Phenomenex Luna C18 column) and a silica gel chromatography (MeOH:CH₂Cl₂=3:97~10:90) to give 6-(3,5-dimethylisoxazol-4-yl)-4-(6-methylquinolin-5-yl)-1H-benzo[d]imidazol-2(3H)-one.

6-(3,5-dimethylisoxazol-4-yl)-4-(6-methylquinolin-5-yl)-1H-benzo[d]imidazol-2(3H)-one: $C_{22}H_{18}N_4O_2$. MS. m/z 371.1 (M+1). ¹H NMR (MeOH-d₄) δ 9.15 (d, J=5.3 Hz, 1H), 8.58 (t, J=8.7 Hz, 1H), 8.58 (d, J=9.0 Hz, 1H), 8.22 (d, J=9.0 Hz, 1H), 7.95 (dd, J=8.7, 5.3 Hz, 1H), 7.20 (d, J=1.5 Hz, 1H), 6.95 (d, J=1.5 Hz, 1H), 2.46 (s, 3H), 2.45 (s, 3H), 2.30 (s, 3H).

Example 3

4,6-bis(3,5-dimethylisoxazol-4-yl)-1H-benzo[d]imidazol-2(3H)-one

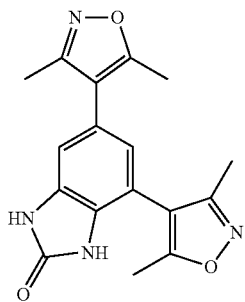 [SMILES: Cc1noc(C)c1-c1cc(-c2c(C)noc2C)c2[nH]c(=O)[nH]c2c1]

4,6-bis(3,5-dimethylisoxazol-4-yl)-1H-benzo[d]imidazol-2(3H)-one was synthesized using 3,5-dimethyl-4-(4,4,5,5-tetramethyl-1,3,2-dioxaborolan-2-yl)isoxazole and $Cs_2CO_3$ in a similar fashion as 6-(3,5-dimethylisoxazol-4-yl)-4-(6-methylquinolin-5-yl)-1H-benzo[d]imidazol-2(3H)-one (Example 2).

$C_{17}H_{16}N_4O_3$. MS. 325.1 (M+1). $^1$H NMR (MeOH-$d_4$) δ 7.04 (d, J=1.5 Hz, 1H), 6.87 (dd, J=1.5 Hz, 1H), 2.43 (s, 3H), 2.35 (s, 3H), 2.27 (s, 3H), 2.20 (s, 3H).

Example 4

6-(3,5-dimethylisoxazol-4-yl)-4-(2-phenylpyridin-3-yl)-1H-benzo[d]imidazol-2(3H)-one

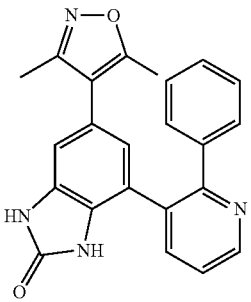

6-(3,5-dimethylisoxazol-4-yl)-4-(2-phenylpyridin-3-yl)-1H-benzo[d]imidazol-2(3H)-one was synthesized using 2-phenylpyridin-3-ylboronic acid and $Cs_2CO_3$ in a similar fashion as 6-(3,5-dimethylisoxazol-4-yl)-4-(6-methylquinolin-5-yl)-1H-benzo[d]imidazol-2(3H)-one (Example 2).

$C_{23}H_{18}N_4O_2$. MS. 383.1 (M+1). $^1$H NMR (MeOH-$d_4$) δ 8.89 (dd, J=5.7, 1.5 Hz, 1H), 8.60 (dd, J=7.9, 1.5 Hz, 1H), 8.04 (dd, J=7.9, 5.7 Hz, 1H), 7.51-7.39 (m, 5H), 6.98 (d, J=1.5 Hz, 1H), 6.75 (d, J=1.5 Hz, 1H), 2.19 (s, 3H), 2.03 (s, 3H).

Example 5

4-(3,5-dimethyl-1H-pyrazol-4-yl)-6-(3,5-dimethylisoxazol-4-yl)-1H-benzo[d]imidazol-2(3H)-one

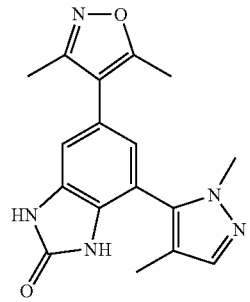 [SMILES: Cc1cnn(C)c1-c1cc(-c2c(C)noc2C)cc2[nH]c(=O)[nH]c12]

4-(1,4-dimethyl-1H-pyrazol-5-yl)-6-(3,5-dimethylisoxazol-4-yl)-1H-benzo[d]imidazol-2(3H)-one was synthesized using 3,5-dimethyl-4-(4,4,5,5-tetramethyl-1,3,2-dioxaborolan-2-yl)-1H-pyrazole and $Cs_2CO_3$ in a similar fashion as 6-(3,5-dimethylisoxazol-4-yl)-4-(6-methylquinolin-5-yl)-1H-benzo[d]imidazol-2(3H)-one (Example 2).

$C_{17}H_{17}N_5O_2$. MS. 324.1 (M+1). $^1$H NMR (MeOH-$d_4$) δ 7.51 (s, 1H), 7.11 (d, J=1.5 Hz, 1H), 6.92 (d, J=1.5 Hz, 1H), 3.74 (s, 3H), 2.43 (s, 3H), 2.28 (s, 3H), 2.00 (s, 3H).

Example 6

5-(6-(3,5-dimethylisoxazol-4-yl)-2-oxo-2,3-dihydro-1H-benzo[d]imidazol-4-yl)-1-methyl-3,4-dihydroquinolin-2(1H)-one Step 1: Preparation of 1-methyl-5-(4,4,5,5-tetramethyl-1,3,2-dioxaborolan-2-yl)-3,4-dihydroquinolin-2(1H)-one

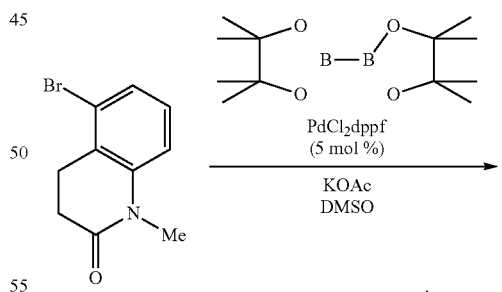

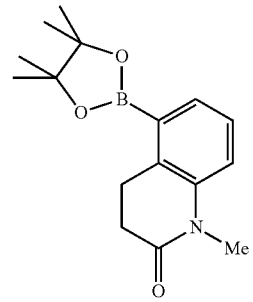

5-bromo-1-methyl-3,4-dihydroquinolin-2(1H)-one (171.4 mg, 0.714 mmol) was treated with 4,4,4',4',5,5,5',5'-octamethyl-2,2'-bi(1,3,2-dioxaborolane) (272.0 mg, 1.071 mmol, 1.5 equiv.), KOAc (210.2 mg, 2.142 mmol, 3.0 equiv) in the presence of PdCl$_2$dppf (26.1 mg, 0.0357 mmol, 0.05 equiv) in DMSO (4 mL) at 100° C. for 20 min in a microwave reactor. To the reaction mixture was added water (30 mL) and EtOAc (70 mL). The mixture was filtered through Celite (3 g) and then organic layer was separated from the filtrate. The organic layer was washed with brine (30 mL) and dried over Na$_2$SO$_4$. The solvent was removed under a reduced pressure to give a crude product. The crude product was purified by a preparative HPLC (5-95% acetonitrile:water with 0.05% trifluoroacetic acid, on a Phenomenex Luna C18 column) and a silica gel chromatography (MeOH:CH$_2$Cl$_2$=3:97~40:90) to give 1-methyl-5-(4,4,5,5-tetramethyl-1,3,2-dioxaborolan-2-yl)-3,4-dihydroquinolin-2(1H)-one (117.2 mg). $C_{16}H_{22}BNO_3$. MS. m/z 389.1 (M+1).

Step 2: Preparation of 5-(6-(3,5-dimethylisoxazol-4-yl)-2-oxo-2,3-dihydro-1H-benzo[d]imidazol-4-yl)-1-methyl-3,4-dihydroquinolin-2(1H)-one

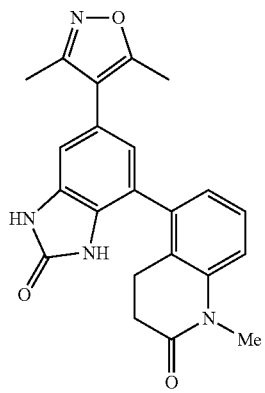 [SMILES: Cc1noc(C)c1-c1cc(-c2cccc3c2CCC(=O)N3C)c2[nH]c(=O)[nH]c2c1]

5-(6-(3,5-dimethylisoxazol-4-yl)-2-oxo-2,3-dihydro-1H-benzo[d]imidazol-4-yl)-1-methyl-3,4-dihydroquinolin-2(1H)-one was synthesized using 1-methyl-5-(4,4,5,5-tetramethyl-1,3,2-dioxaborolan-2-yl)-3,4-dihydroquinolin-2(1H)-one and Cs$_2$CO$_3$ in a similar fashion as 6-(3,5-dimethylisoxazol-4-yl)-4-(6-methylquinolin-5-yl)-1H-benzo[d]imidazol-2(3H)-one (Example 2).

5-(6-(3,5-dimethylisoxazol-4-yl)-2-oxo-2,3-dihydro-1H-benzo[d]imidazol-4-yl)-1-methyl-3,4-dihydroquinolin-2(1H)-one: $C_{22}H_{20}N_4O_3$. MS. m/z 389.1 (M+1). $^1$H NMR (MeOH-d$_4$) δ 7.41 (t, J=8.0 Hz, 1H), 7.24 (dd, J=8.0, 1.1 Hz, 1H), 7.11 (dd, J=8.0, 1.1 Hz, 1H), 7.02 (d, J=1.5 Hz, 1H), 6.84 (d, J=1.5 Hz, 1H), 3.42 (s, 3H), 2.88-2.64 (m, 2H), 2.64-2.46 (m, 2H), 2.42 (s, 3H), 2.27 (s, 3H).

Example 7

5-(3,5-dimethylisoxazol-4-yl)-1-methyl-7-(6-methylquinolin-5-yl)-1H-benzo[d]imidazol-2(3H)-one Step 1: Preparation of 4-(3,5-dimethylisoxazol-4-yl)-2-iodo-N-methyl-6-nitroaniline

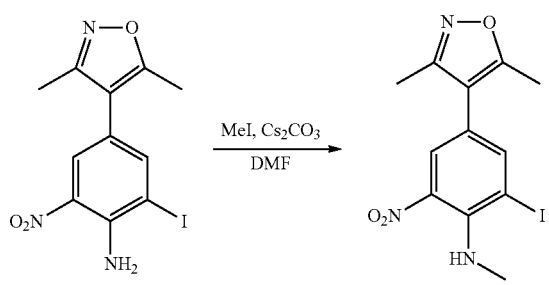

Into a flask containing 4-(3,5-dimethylisoxazol-4-yl)-2-iodo-6-nitroaniline (1000 mg, 2.78 mmol, 1 equiv) is added DMF (15 mL, 0.2 M) before adding cesium carbonate (1.4 gm, 4.17 mmol, 1.5 equiv.) and idomethane (260 μL, 4.17 mmol, 1.5 equiv). After an hour, the reaction was quenched with water and the reaction was partitioned between water and ethyl acetate. The organic layer was washed with brine and dried over sodium sulfate. Purification was carried out by flash column chromatography to furnish 4-(3,5-dimethylisoxazol-4-yl)-2-iodo-N-methyl-6-nitroaniline (615 mg, 60%).

LCMS (m/z+1) 373.85. $^1$H NMR (400 MHz, cdcl$_3$) δ 7.81 (t, J=3.0 Hz, 1H), 7.70 (d, J=2.1 Hz, 1H), 2.97 (s, 3H), 2.40 (d, J=16.8 Hz, 3H), 2.26 (d, J=14.2 Hz, 3H).

Step 2: Preparation of 4-(3,5-dimethylisoxazol-4-yl)-6-iodo-N1-methylbenzene-1,2-diamine

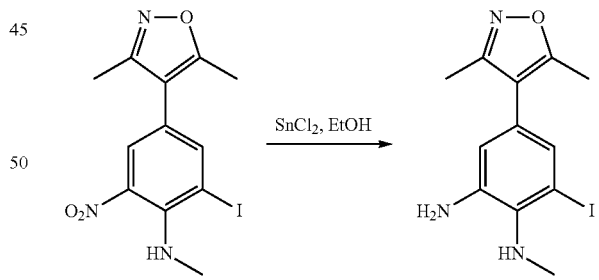

Into a microwave vial containing 4-(3,5-dimethylisoxazol-4-yl)-2-iodo-N-methyl-6-nitroaniline (610 mg, 1.64 mmol, 1 equiv) is added EtOH (12 mL, 0.25M) and tin (II) chloride (622 mg, 3.28 mmol, 2 equiv). The reaction was heated for 30 min at 110° C. The reaction was then stirred in 2N NaOH solution for 20 minutes before being partitioned between water and ethyl acetate. The organic layer was washed with brine and dried over sodium sulfate. Purification was carried out by flash column chromatography to furnish 4-(3,5-dimethylisoxazol-4-yl)-6-iodo-N1-methylbenzene-1,2-diamine.

LCMS (m/z+1) 344.02.

Step 3: Preparation of 5-(3,5-dimethylisoxazol-4-yl)-7-iodo-1-methyl-1H-benzo[d]imidazol-2(3H)-one

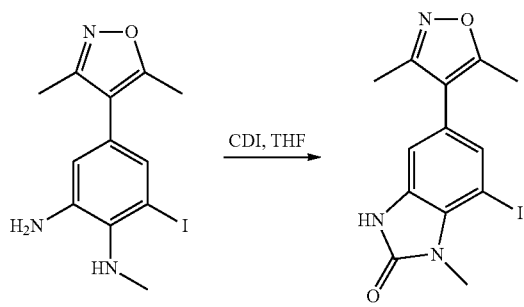 [SMILES: CNc1c(N)cc(-c2c(C)noc2C)cc1I ; Cc1noc(C)c1-c1cc(I)c2c(c1)[nH]c(=O)n2C]

Into a flask containing 4-(3,5-dimethylisoxazol-4-yl)-6-iodo-N1-methylbenzene-1,2-diamine (299 mg, 0.87 mmol, 1 equiv) is added THF (8 mL, 0.1 M) and CDI (282 mg, 1.74 mmol, 2 equiv). The reaction was heated for 2 hr at 120° C. The reaction was then concentrated in vacuo and the solid triturated with diethyl ether before being air dried to furnish 5-(3,5-dimethylisoxazol-4-yl)-7-iodo-1-methyl-1H-benzo[d]imidazol-2(3H)-one as a light yellow solid.
LCMS (m/z+1) 370.00.

Step 4: Preparation of 5-(3,5-dimethylisoxazol-4-yl)-1-methyl-7-(6-methylquinolin-5-yl)-1H-benzo[d]imidazol-2(3H)-one

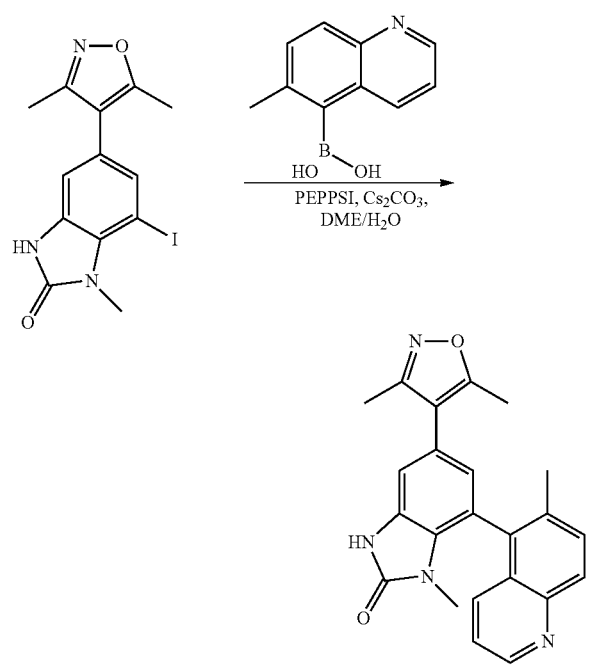

To a microwave vial containing 5-(3,5-dimethylisoxazol-4-yl)-7-iodo-1-methyl-1H-benzo[d]imidazol-2(3H)-one (40 mg, 0.11 mmol, 1 equiv.) was added 3,5-6-methylquinolin-5-ylboronic acid (51 mg, 0.27 mmol, 2.5 equiv.), $Cs_2CO_3$ (141 mg, 0.43 mmol, 4 equiv.) and PEPPSI™-IPr catalyst (8 mg, 0.02 mmol, 0.1 equiv.) and dissolved in DME-$H_2O$ (20 mL, 0.2 M, 2/1, v/v). The mixture was heated to 140 C. After 2 hr, the reaction was complete. After cooling, the reaction was extracted with EtOAc and washed with water and saturated $NH_4Cl$. After drying with $MgSO_4$, it was filtered and concentrated to dryness. Purification was carried out by reverse phase HPLC to furnish 5-(3,5-dimethylisoxazol-4-yl)-1-methyl-7-(6-methylquinolin-5-yl)-1H-benzo[d]imidazol-2(3H)-one.

LCMS (m/z+1) 385.23. $^1$H NMR (400 MHz, $cd_3od$) δ 8.82 (d, J=4.3 Hz, 1H), 8.09 (d, J=8.7 Hz, 1H), 7.82 (t, J=7.1 Hz, 2H), 7.47 (dd, J=8.5, 4.3 Hz, 1H), 7.17 (d, J=1.6 Hz, 1H), 6.82 (d, J=1.6 Hz, 1H), 2.53 (s, 3H), 2.42 (s, 3H), 2.33 (s, 3H), 2.27 (s, 3H).

Example 8

7-(1,4-dimethyl-1H-pyrazol-5-yl)-5-(3,5-dimethylisoxazol-4-yl)-1-methyl-1H-benzo[d]imidazol-2(3H)-one

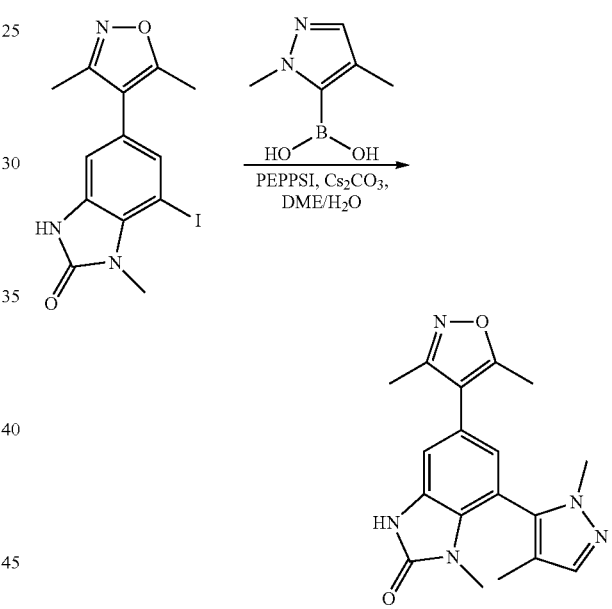

To a microwave vial containing 5-(3,5-dimethylisoxazol-4-yl)-7-iodo-1-methyl-1H-benzo[d]imidazol-2(3H)-one (40 mg, 0.11 mmol, 1 equiv.) was added 1,4-dimethyl-1H-pyrazol-5-ylboronic acid (72 mg, 0.32 mmol, 3 equiv.), $Cs_2CO_3$ (141 mg, 0.43 mmol, 4 equiv.) and PEPPSI™-IPr catalyst (8 mg, 0.02 mmol, 0.1 equiv.) and dissolved in DME-$H_2O$ (20 mL, 0.2 M, 2/1, v/v). The mixture was heated to 140° C. After 1 hr, the reaction was complete. After cooling, the reaction was extracted with EtOAc and washed with water and saturated $NH_4Cl$. After drying with $MgSO_4$, it was filtered and concentrated to dryness. Purification was carried out by reverse phase HPLC to furnish 7-(1,4-dimethyl-1H-pyrazol-5-yl)-5-(3,5-dimethylisoxazol-4-yl)-1-methyl-1H-benzo[d]imidazol-2(3H)-one.

LCMS (m/z+1) 338.19. $^1$H NMR (400 MHz, $cd_3od$) δ 7.44 (s, 1H), 7.15 (d, J=1.6 Hz, 1H), 6.88 (d, J=1.6 Hz, 1H), 3.65 (s, 3H), 90 (s, 3H), 2.42 (s, 3H), 2.27 (s, 7H), 1.95 (s, 3H).

Example 9

7-(1,4-dimethyl-1H-pyrazol-5-yl)-5-(3,5-dimethyl-isoxazol-4-yl)-1-methyl-1H-benzo[d]imidazol-2(3H)-one

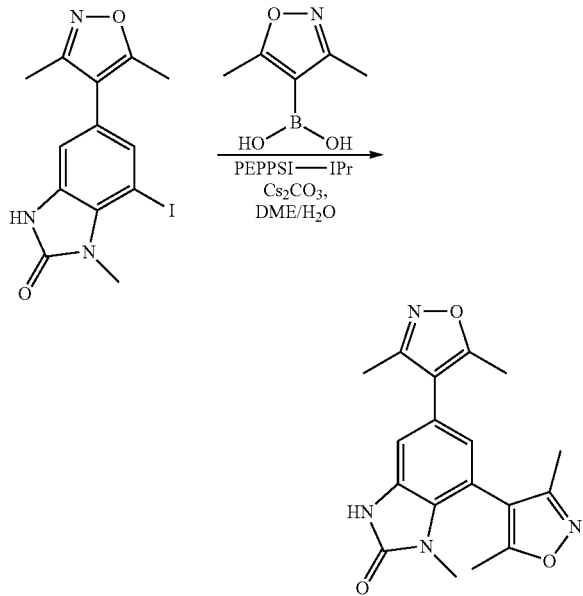

To a microwave vial containing 5-(3,5-dimethylisoxazol-4-yl)-7-iodo-1-methyl-1H-benzo[d]imidazol-2(3H)-one (40 mg, 0.11 mmol, 1 equiv.) was added 3,5-Dimethylisoxazole-4-boronic acid pinacol ester (72 mg, 0.32 mmol, 3 equiv.), Cs$_2$CO$_3$ (141 mg, 0.43 mmol, 4 equiv.) and PEPPSI™-IPr catalyst (8 mg, 0.02 mmol, 0.1 equiv.) and dissolved in DME-H$_2$O (20 mL, 0.2 M, 2/1, v/v). The mixture was heated to 140° C. After 1 hr, the reaction was complete. After cooling, the reaction was extracted with EtOAc and washed with water and saturated NH$_4$Cl. After drying with MgSO$_4$, it was filtered and concentrated to dryness. Purification was carried out by reverse phase HPLC to furnish 7-(1,4-dimethyl-1H-pyrazol-5-yl)-5-(3,5-dimethylisoxazol-4-yl)-1-methyl-1H-benzo[d]imidazol-2(3H)-one.

LCMS (m/z+1) 339.15. $^1$H NMR (400 MHz, cd$_3$od) δ 7.09 (d, J=1.6 Hz, 1H), 6.81 (d, J=1.6 Hz, 1H) 3.11 (d, J=14.5 Hz, 3H), 2.41 (s, 3H), 2.35-2.23 (m, 6H), 2.15 (s, 3H).

Example 10

5,7-bis(3,5-dimethylisoxazol-4-yl)benzo[d]oxazol-2(3H)-one

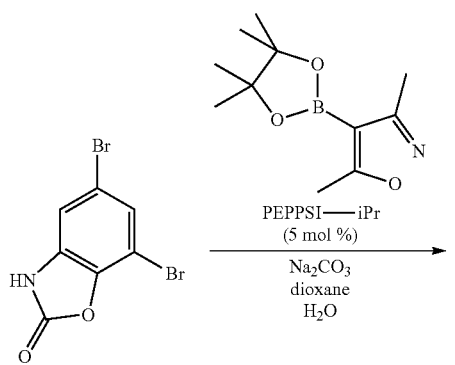

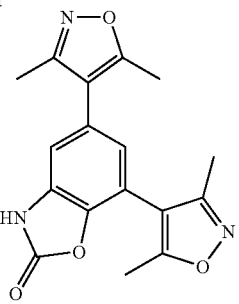

5,7-Dibromobenzo[d]oxazol-2(3H)-one (100.0 mg, 0.341 mmol) was treated with 3,5-dimethyl-4-(4,4,5,5-tetramethyl-1,3,2-dioxaborolan-2-yl)isoxazole (304.7 mg, 1.366 mmol, 4.0 equiv.), 2M-Na$_2$CO$_3$ (aq) (1 mL) in the presence of PEPPSI-IPr (11.6 mg, 0.017 mmol, 0.05 equiv) in 1,4-dioxane (3 mL) at 150° C. for 10 min in microwave reactor To the reaction mixture were added water (30 mL) and EtOAc (70 mL). The mixture was filtered through Celite (3 g) and then organic layer was separated from the filtrate. The organic layer was washed with brine (30 mL) and dried over Na$_2$SO$_4$. The solvent was removed under a reduced pressure to give a crude product. The crude product was purified by a preparative HPLC (5-95% acetonitrile:water with 0.05% trifluoroacetic acid, on a Phenomenex Luna C18 column) and a silica gel column chromatography (MeOH:CH$_2$Cl$_2$=3:97~10:90) to give 5,7-bis(3,5-dimethylisoxazol-4-yl)benzo[d]oxazol-2(3H)-one.

C$_{17}$H$_{15}$N$_3$O$_4$. MS. m/z 326.0 (M+1). $^1$H NMR (MeOH-d$_4$) δ 7.08 (s, 1H), 7.01 (s, 1H), 2.433 (s, 3H), 2.430 (s, 3H), 2.28 (s, 3H), 2.27 (s, 3H).

Example 11

5-(3,5-dimethylisoxazol-4-yl)-7-(6-methylquinolin-5-yl)benzo[d]oxazol-2(3H)-one Step 1

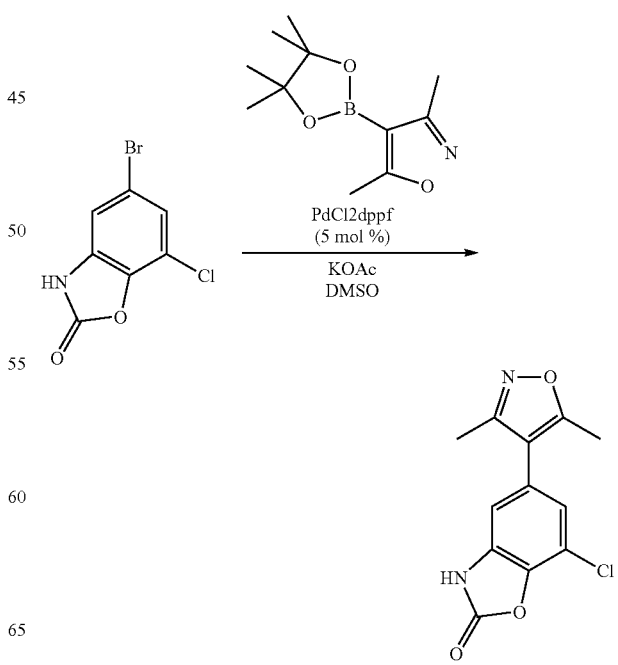

5-Bromo-7-chlorobenzo[d]oxazol-2(3H)-one (100.0 mg, 0.4025 mmol) was treated with 3,5-dimethyl-4-(4,4,5,5-tetramethyl-1,3,2-dioxaborolan-2-yl)isoxazole (89.8 mg, 0.4025 mmol, 1.0 equiv.), DBU (183.8 mg, 1.2075 mmol, 3.0 equiv.) in the presence of PdCl$_2$dppf (14.7 mg, 0.02015 mmol, 0.05 equiv) in DMSO (3 mL) and water (1 mL) at 120° C. for 1 h in an oil bath. To the reaction mixture were added water (30 mL) and EtOAc (70 mL). The mixture was filtered through Celite (3 g) and then organic layer was separated from the filtrate. The organic layer was washed with brine (30 mL) and dried over Na$_2$SO$_4$. The solvent was removed under a reduced pressure to give a crude product. The crude product was purified by a preparative HPLC (5-95% acetonitrile:water with 0.05% trifluoroacetic acid, on a Phenomenex Luna C18 column) and a silica gel column chromatography (hexane:EtOAc=1:1) to give 7-chloro-5-(3,5-dimethylisoxazol-4-yl)benzo[d]oxazol-2(3H)-one.

$C_{12}H_9ClN_2O_3$. MS. m/z 265.0 (M−1), 267.0 (M+1).

Step 2

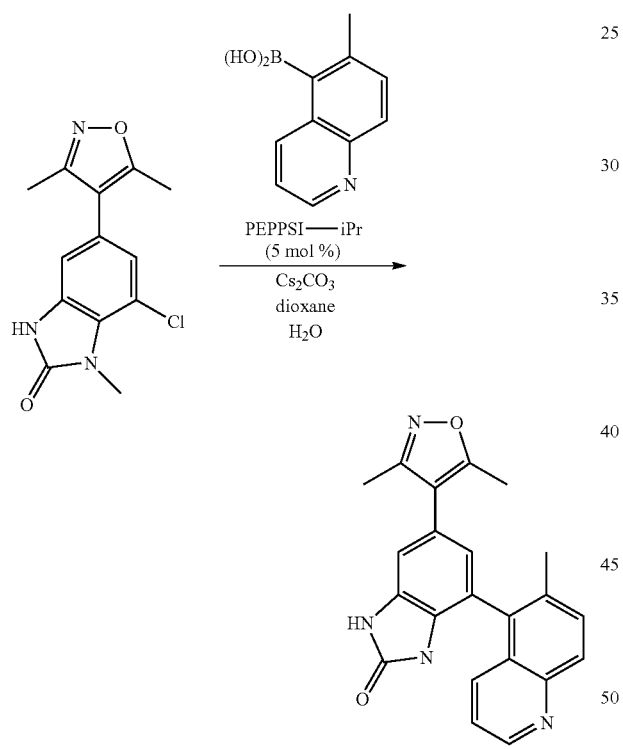

7-Chloro-5-(3,5-dimethylisoxazol-4-yl)benzo[d]oxazol-2(3H)-one (20.8 mg, 0.0786 mmol) was treated with 6-methylquinolin-5-ylboronic acid (44.1 mg, 0.2358 mmol, 3.0 equiv.), Cs$_2$CO$_3$ (153.7 mg, 0.4716 mmol, 6.0 equiv.) in the presence of PEPPSI iPr (2.9 mg, 0.00393 mmol, 0.05 equiv) in 1,4-dioxane (3 mL) and water (1 mL) at 150° C. for 1 h in a microwave reactor. To the reaction mixture were added water (30 mL) and EtOAc (70 mL). The mixture was filtered through Celite (3 g) and then organic layer was separated from the filtrate. The organic layer was washed with brine (30 mL) and dried over Na$_2$SO$_4$. The solvent was removed under a reduced pressure to give a crude product. The crude product was purified by a preparative HPLC (5-95% acetonitrile:water with 0.05% trifluoroacetic acid, on a Phenomenex Luna C18 column) to give 5-(3,5-dimethylisoxazol-4-yl)-7-(6-methylquinolin-5-yl)benzo[d]oxazol-2(3H)-one.

$C_{22}H_{17}N_3O_3$. MS. m/z 372.1 (M+1). $^1$H NMR (MeOH-d$_4$) δ 9.16 (d, J=5.3 Hz, 1H), 8.69 (d, J=8.7 Hz, 1H), 8.28 (d, J=8.9 Hz, 1H), 8.21 (d, J=8.9 Hz, 1H), 7.97 (dd, J=8.7, 5.3 Hz, 1H), 7.27 (d, J=1.6 Hz, 1H), 7.07 (d, J=1.6 Hz, 1H), 2.49 (s, 3H), 2.45 (s, 3H), 2.30 (s, 3H)

Example 12

5-(3,5-dimethylisoxazol-4-yl)-7-(2-phenylpyridin-3-yl)benzo[d]oxazol-2(3H)-one

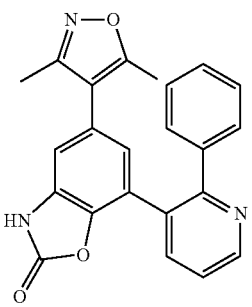 [SMILES: Cc1noc(C)c1-c1cc(-c2cccnc2-c2ccccc2)c2oc(=O)[nH]c2c1]

The title compound was synthesized using 2-phenylpyridin-3-ylboronic acid in a similar fashion with 5-(3,5-dimethylisoxazol-4-yl)-7-(6-methylquinolin-5-yl)benzo[d]oxazol-2(3H)-one (Example 11).

$C_{23}H_{17}N_3O_3$. MS. 384.1 (M+1). $^1$H NMR (MeOH-d$_4$) δ 8.02 (dd, J=5.4, 1.5 Hz, 1H), 7.68 (dd, J=8.0, 1.5 Hz, 1H), 7.10 (dd, J=8.0, 5.4 Hz, 1H), 6.67-6.55 (m, 5H), 6.21 (d, J=1.6 Hz, 1H), 5.97 (d, J=1.6 Hz, 1H), 1.35 (s, 3H), 1.19 (s, 3H).

Example 13 and

Example 14

(R)-6-(3,5-dimethylisoxazol-4-yl)-4-(6-methylquinolin-5-yl)-1H-benzo[d]imidazol-2(3H)-one and (S)-6-(3,5-dimethylisoxazol-4-yl)-4-(6-methylquinolin-5-yl)-1H-benzo[d]imidazol-2(3H)-one

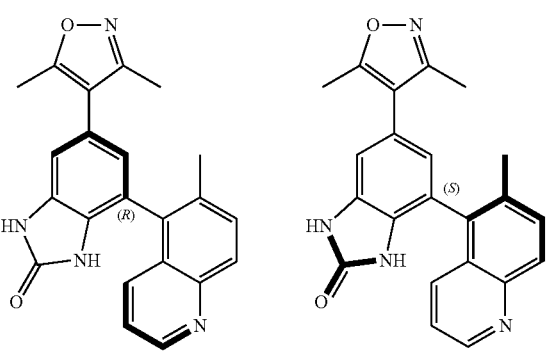

(R)-6-(3,5-Dimethylisoxazol-4-yl)-4-(6-methylquinolin-5-yl)-1H-benzo[d]imidazol-2(3H)-one and (S)-6-(3,5-dimethylisoxazol-4-yl)-4-(6-methylquinolin-5-yl)-1H-benzo[d]imidazol-2(3H)-one were obtained by resolving the racemate (Example 2) by supercritical fluid chromatography on a chiral column (25% MeOH with 0.1% v/v TFA on an SFC Chiralpak AD-H column.)

First eluting compound: (R)-6-(3,5-dimethylisoxazol-4-yl)-4-(6-methylquinolin-5-yl)-1H-benzo[d]imidazol-2(3H)-one. $C_{22}H_{18}N_4O_2$. 371.1 (M+1). SFC retention time 3.525 min (Chiralpak AD-H 250 mm×10 mm, 16 mL/min, 10 minute run time, 40° C. column oven, 10 MPa back-pressure limiter). $^1$H NMR spectra identical to racemic compound.

Second eluting compound: (S)-6-(3,5-dimethylisoxazol-4-yl)-4-(6-methylquinolin-5-yl)-1H-benzo[d]imidazol-2(3H)-one. $C_{22}H_{18}N_4O_2$. 371.1 (M+1). SFC retention time 4.992 min (Chiralpak AD-H 250 mm×10 mm, 16 mL/min, 10 minute run time, 40° C. column oven, 10 MPa back-pressure limiter). $^1$H NMR spectra identical to racemic compound.

Example 15

6-(3,5-dimethylisoxazol-4-yl)-4-(2,4-dimethylpyridin-3-yl)-1H-benzo[d]imidazol-2(3H)-one

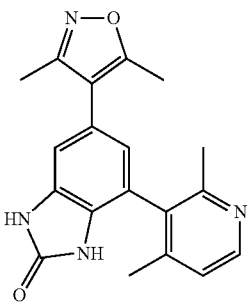 [SMILES: Cc1ccnc(C)c1-c1cc(-c2c(C)noc2C)cc2[nH]c(=O)[nH]c12]

6-(3,5-Dimethylisoxazol-4-yl)-4-(2,4-dimethylpyridin-3-yl)-1H-benzo[d]imidazol-2(3H)-one was synthesized using 2,4-dimethylpyridin-3-ylboronic acid and $Cs_2CO_3$ in a similar fashion as Example 11.

$C_{19}H_{18}N_4O_2$. MS. m/z 335.1 (M+1). $^1$H NMR (MeOH-$d_4$) δ 8.65 (d, J=6.2 Hz, 1H), 7.93 (d, J=6.2 Hz, 1H), 7.16 (d, J=1.5 Hz, 1H), 6.92 (d, J=1.5 Hz, 1H), 2.52 (s, 3H), 2.43 (s, 3H), 2.40 (s, 3H), 2.27 (s, 3H).

Example 16

4-(6-(3,5-dimethylisoxazol-4-yl)-2-oxo-2,3-dihydro-1H-benzo[d]imidazol-4-yl)cinnoline-3-carboxylic Acid

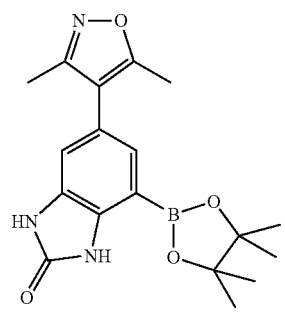

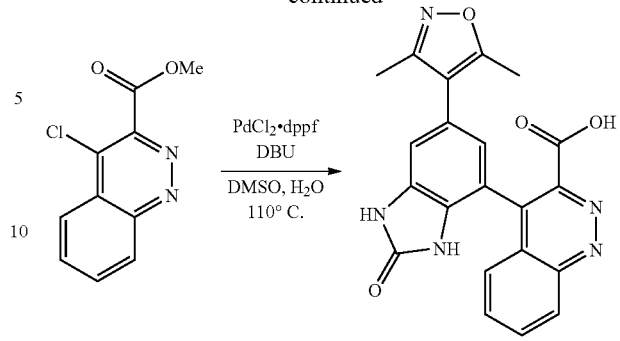

6-(3,5-dimethylisoxazol-4-yl)-4-(4,4,5,5-tetramethyl-1,3,2-dioxaborolan-2-yl)-1H-benzo[d]imidazol-2(3H)-one (100.0, 0.282 mmol) and 5-bromo-8-chloro-6-methylquinoline (94.0 mg, 0.422 mmol) was treated with $PdCl_2dppf.CH_2Cl_2$ (20.6 mg, 0.028 mmol) in the presence of 1,8-diazabicycloundec-7-ene (DBU, 300.0 mg, 1.971 mmol, 7.0 equiv) in DMSO (1 mL) and water (1 mL). The reaction mixture was heated at 110° C. for 12 min in oil bath. The reaction mixture was injected into Gilson preparative HPLC to give 4-(6-(3,5-dimethylisoxazol-4-yl)-2-oxo-2,3-dihydro-1H-benzo[d]imidazol-4-yl)cinnoline-3-carboxylic acid.

$C_{21}H_{15}N_5O_4$. MS. m/z 402.0 (M+1). $^1$H NMR (400 MHz, Methanol-$d_4$) δ 8.67 (d, J=8.8 Hz, 1H), 8.09 (t, J=8.8 Hz, 1H), 7.92 (d, J=8.8 Hz, 1H), 7.70 (d, J=8.8 Hz, 1H), 7.17 (s, 1H), 6.96 (s, 1H), 2.44 (s, 3H), 2.29 (s, 3H).

Example 17

6-(3,5-dimethylisoxazol-4-yl)-4-(3-methylisoquinolin-4-yl)-1H-benzo[d]imidazol-2(3H)-one

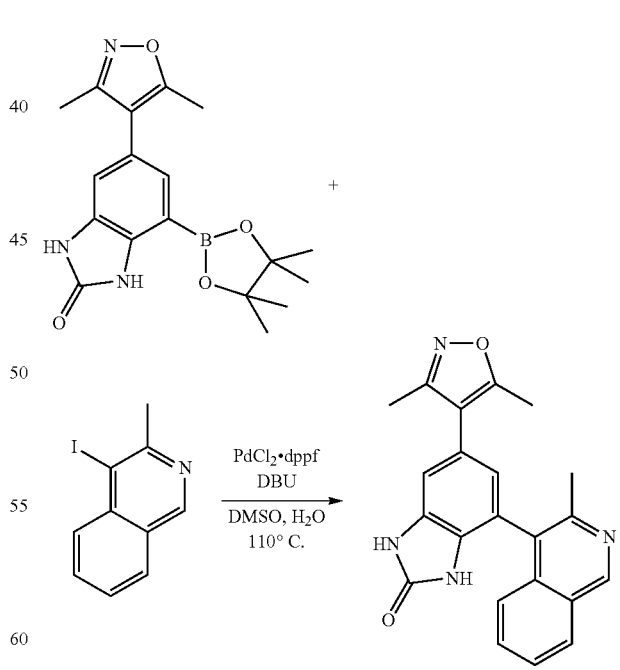

Synthesized in a similar fashion as that of Example 16.
$C_{22}H_{18}N_4O_2$. MS. m/z 371.1 (M+1). $^1$H NMR (400 MHz, Methanol-$d_4$) δ 9.26 (s, 1H), 8.16 (d, J=8.6 Hz, 1H), 7.70 (t, J=8.6 Hz, 1H), 7.64 (t, J=8.6 Hz, 1H), 7.42 (d, J=8.6 Hz, 1H), 2.50 (s, 3H), 2.45 (s, 3H), 2.29 (s, 3H).

Example 18

6-(3,5-dimethylisoxazol-4-yl)-4-(2-methylnaphthalen-1-yl)-1H-benzo[d]imidazol-2(3H)-one

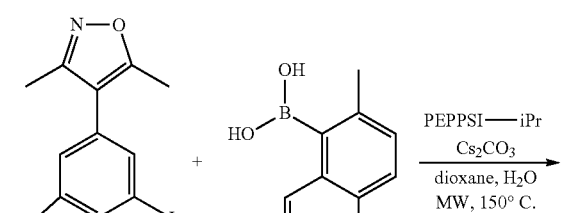

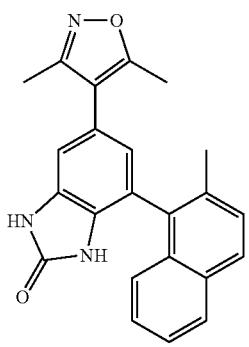

In a 2-5 mL Smith Process Vial, 6-(3,5-dimethylisoxazol-4-yl)-4-iodo-1H-benzo[d]imidazol-2(3H)-one (100.0 mg 0.282 mmol), (2-methylnaphthalen-1-yl)boronic acid (176.0 mg, 0.946 mmol, 3.36 equiv), PEPPSI-iPr (19.2 mg, 0.028 mmol, 0.1 equiv) and $Cs_2CO_3$ (337.0 mg, 1.126 mmol, 4 equiv) were placed. The mixture was suspended in 1,4-dioxane (1.5 mL) and water (0.5 mL) under $N_2$. The mixture was heated at 150° C. for 75 min using microwave reactor (Biotage Optimizer). After an aqueous work up, the crude product was purified by a silica-gel column chromatography (hexane/EtOAc 20:80) to give 6-(3,5-dimethylisoxazol-4-yl)-4-(2-methylnaphthalen-1-yl)-1H-benzo[d]imidazol-2 (3H)-one.

$C_{23}H_{19}N_3O_2$. MS. m/z 370.1 (M+1). $^1$H NMR (400 MHz, Methanol-$d_4$) δ 7.88 (d, J=8.6 Hz, 2H), 7.50 (d, J=8.6 Hz, 1H), 7.45-7.38 (m, 1H), 7.38-7.33 (m, 2H), 7.10 (s, 1H), 6.82 (s, 1H), 2.43 (s, 3H), 2.28 (s, 6H).

Example 19

4-(2-(difluoromethyl)-3-methylquinolin-4-yl)-6-(3,5-dimethylisoxazol-4-yl)-1H-benzo[d]imidazol-2(3H)-one

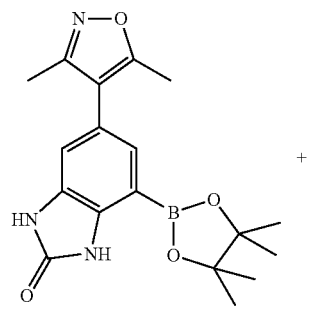

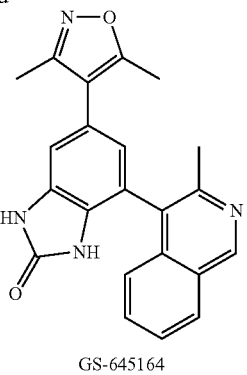

The title compound was synthesized in a similar fashion as that of Example 17.

$C_{23}H_{17}FN_4O_2$. MS. m/z 421.1 (M+1). $^1$H NMR (400 MHz, Methanol-$d_4$) δ 8.18 (d, J=9.0 Hz, 1H), 7.83-7.74 (m, 1H), 7.63-7.57 (m, 1H), 7.45 (d, J=9.4 Hz, 1H), 7.23-6.87 (m, 2H), 2.47-2.40 (m, 6H), 2.30 (s, 3H).

Example 20

Preparation of 4-chloro-5-(3,5-dimethylisoxazol-4-yl)-7-(6-methylquinolin-5-yl)-1H-benzo[d]imidazol-2(3H)-one

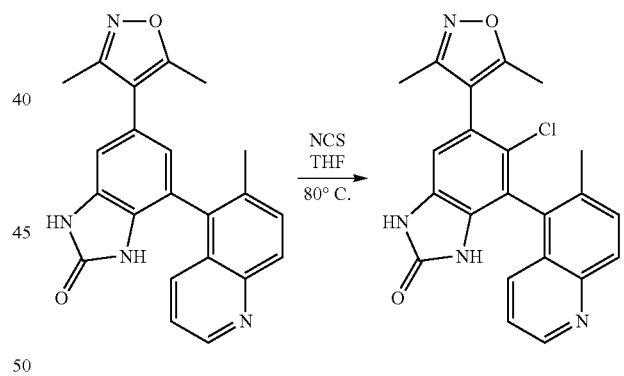

In 0.5-2 mL Smith Process Vial, the intermediate (25.0 mg, 0.067 mmol) and NCS (36.3 mg, 0.135 mmol) were dissolved into THF (2 mL). The mixture was heated at 80° C. for 2 h in an oil bath. The reaction mixture was directly injected into Gilson preparative HPLC (5-95% acetonitrile:water with 0.05% trifluoroacetic acid, on a Phenomenex Luna C18 column) to give the desired product.

C19H18N4O2. MS. m/z 405.1 (M+1), 407.1 (M+2+1). $^1$H NMR (400 MHz, Methanol-$d_4$) δ 9.25-9.05 (d, J=5.8 Hz, 1H), 8.47-8.40 (m, 1H), 8.30 (d, J=9.0 Hz, 1H), 8.20 (d, J=9.0 Hz, 1H), 7.96-7.90 (m, 1H), 7.19 (s, 1H), 2.40 (s, 3/2H), 2.39 (s, 3/2H), 2.38 (s, 3/2H), 2.34 (s, 3/2H) 2.21 (s, 3/2H), 2.19 (s, 3/2H).

Example 21

5-(6-(3,5-dimethylisoxazol-4-yl)-2-oxo-2,3-dihydro-1H-benzo[d]imidazol-4-yl)-6-methyl-1-(2,2,2-trifluoroethyl)quinolin-2(1H)-one

Step 1

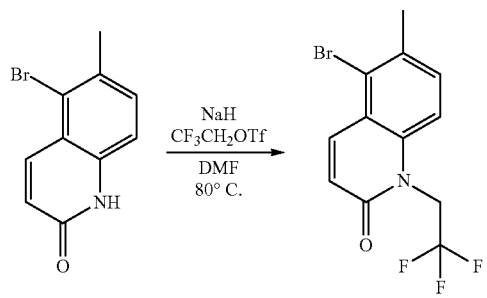 [SMILES: Cc1ccc2[nH]c(=O)ccc2c1Br ; Cc1ccc2c(ccc(=O)n2CC(F)(F)F)c1Br]

5-Bromo-6-methylquinolin-2(1H)-one (103.5 mg, 0.435 mmol) was suspended into DMF (3 mL). To the suspension, was added NaH (17.4 mg 60% in mineral oil) at room temperature. After 2 h stirring, CF$_3$CH$_2$OTf (201.8 mg, 0.869 mmol) was added into the mixture at room temperature. The reaction mixture was stirred for 2 h at the same temperature. The reaction mixture was quenched with water (30 mL). The whole was extracted with AcOEt (30 mL×3). Organic layer was washed with brine (30 mL) and dried over Na$_2$SO$_4$. The solvent was removed under a reduced pressure to give the crude product. Gilson PHPLC purification gave 5-bromo-6-methyl-1-(2,2,2-trifluoroethyl)quinolin-2(1H)-one.

$^1$H NMR (400 MHz, Methanol-d$_4$) δ 8.41 (d, J=10.0 Hz, 1H), 7.58 (s, 2H), 6.77 (d, J=10.0 Hz, 1H), 5.20 (q, J=8.7 Hz, 2H), 2.52 (d, J=1.0 Hz, 3H).

Step 2

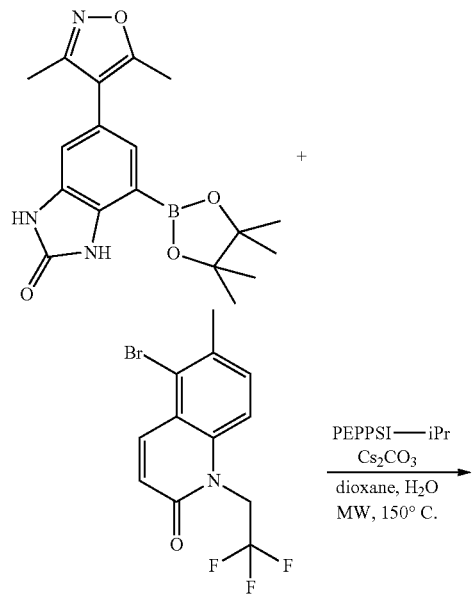

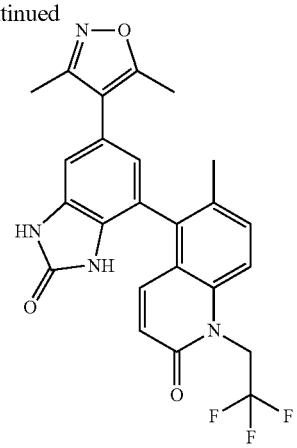

In a 2-5 mL Smith Process Vial, the boronic acid pinacol ester (29.0 mg 0.82 mmol), the bromide (26.1 mg, 0.082 mmol, 1 equiv), PEPPSI-iPr (2.8 mg, 0.004 mmol, 0.05 equiv) and Cs$_2$CO$_3$ (53.2 mg, 0.163 mmol, 2 equiv) were placed. The mixture was suspended in 1,4-dioxane and water under N$_2$. The mixture was heated at 150° C. for 20 min using microwave reactor (Biotage Optimizer). To the mixture were added EtOAc (70 mL) and water (30 mL). The whole was filtered through Celite (3 g) and the filtrate was washed with brine (30 mL), dried over Na$_2$SO$_4$ and concentrated under a reduced pressure. Obtained crude material was purified by Gilson preparative HPLC to give the desired product (23.0 mg, 60%).

C$_{24}$H$_{19}$F$_3$N$_4$O$_3$. MS. m/z 469.1 (M+1). $^1$H NMR (400 MHz, Methanol-d$_4$) δ 7.70 (d, J=9.2 Hz, 1H), 7.67 (d, J=9.2 Hz, 1H), 7.52 (d, J=10.0 Hz, 1H), 7.12 (s, 1H), 6.82 (s, 1H), 6.60 (d, J=10.0 Hz, 1H), 5.26 (q, J=13.3 Hz, 2H), 2.43 (s, 3H), 2.28 (s, 3H), 2.20 (s, 3H).

Example 22

5-(6-(3,5-dimethylisoxazol-4-yl)-2-oxo-2,3-dihydro-1H-benzo[d]imidazol-4-yl)-1,6-dimethylquinolin-2(1H)-one

Step 1

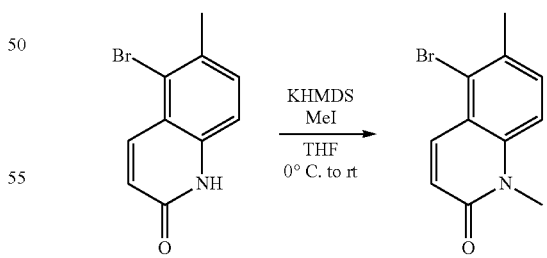

5-bromo-6-methylquinolin-2(1H)-one (500.0 mg, 2.1 mmol) in THF (10 mL) was treated with KHMDS (2.31 mL, 2.31 mmol, 1.1 equiv) at 0° C. for 15 min. To the reaction mixture was added MeI (0.26 mL 596.2 mg, 4.2 mmol, 2 equiv) was added into the mixture at 0° C. The reaction mixture was allowed to warm up to room temperature and stirred for overnight at the same temperature to form a precipitation. The precipitation was filtered off using a glass filter. The filtrate was concentrated and purified by a silica-gel column chromatography (hexane/EtOAc 50:50 to 0:100) to give 5-(6-(3,5-dimethylisoxazol-4-yl)-2-oxo-2,3-dihydro-1H-benzo[d]imidazol-4-yl)-1,6-dimethylquinolin-2(1H)-one as colorless crystals.

$C_{11}H_{10}BrNO$. MS. m/z 469.1 (M+1).

Step 2

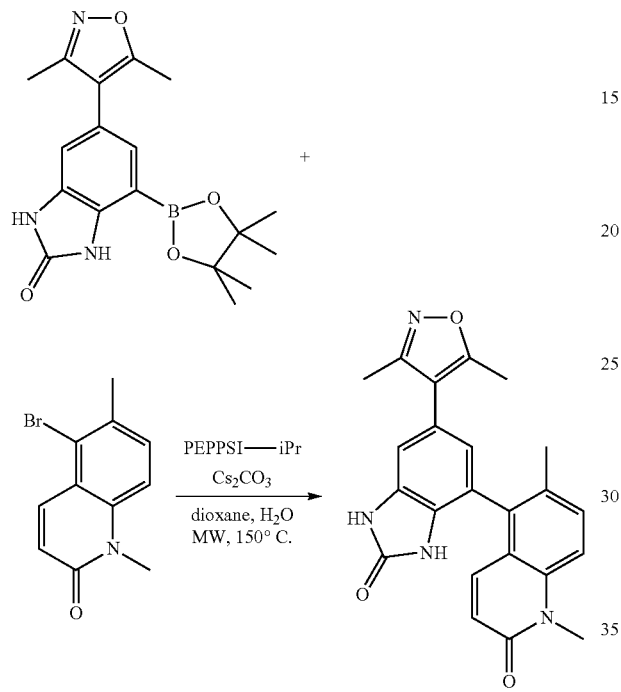

5-(6-(3,5-dimethylisoxazol-4-yl)-2-oxo-2,3-dihydro-1H-benzo[d]imidazol-4-yl)-1,6-dimethylquinolin-2(1H)-one was synthesized in a similar fashion as that of Example 21.

$C_{23}H_{20}N_4O_3$. MS. m/z 401.1 (M+1). $^1$H NMR (400 MHz, Methanol-$d_4$) δ 7.68 (d, J=9.6 Hz, 1H), 7.63 (d, J=9.6 Hz, 1H), 7.45 (d, J=9.6 Hz, 1H), 7.11 (s, 1H), 6.80 (s, 1H), 6.58 (d, J=9.6 Hz, 1H), 3.80 (s, 3H), 2.43 (s, 3H), 2.28 (s, 3H), 2.20 (s, 3H).

Example 23

4-(3,5-dicyclopropyl-1H-pyrazol-4-yl)-6-(3,5-dimethylisoxazol-4-yl)-1H-benzo[d]imidazol-2(3H)-one

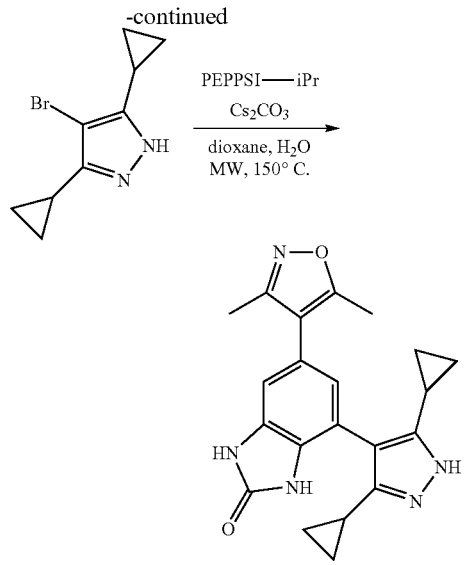

The compound of Example 23 was synthesized in a similar fashion as that of Example 22.

$C_{21}H_{21}N_5O_2$. MS. m/z 376.1 (M+1). $^1$H NMR (400 MHz, Methanol-$d_4$) δ 7.05 (s, 1H), 6.95 (s, 1H), 2.33 (s, 3H), 2.28 (s, 3H), 1.86-1.76 (m, 2H), 1.00-0.90 (m, 4H), 0.87-0.78 (m, 4H).

Example 24

4-(3,5-dicyclopropyl-1-methyl-1H-pyrazol-4-yl)-6-(3,5-dimethylisoxazol-4-yl)-1H-benzo[d]imidazol-2(3H)-one Step 1

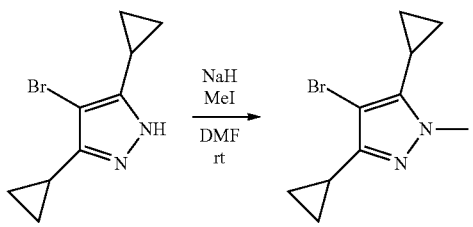

4-Bromo-3,5-dicyclopropyl-1-methyl-1H-pyrazole (50.0 mg, 0.22 mmol) was dissolved into DMF (3 mL). To the solution, was added NaH (17.6 mg 60% in mineral oil, 0.44 mmol, 2 equiv) at room temperature. After 30. min stirring, MeI (62.5 mg, 0.44 mmol, 2 equiv) was added into the mixture at room temperature. The reaction mixture was stirred for 20 min at the same temperature. The reaction mixture was quenched with water (30 mL). The whole was extracted with AcOEt (30 mL×3). Organic layer was washed with brine (30 mL) and dried over $Na_2SO_4$. The solvent was removed under a reduced pressure to give the crude product. A silica-gel column chromatography (hexane/EtOAc 87:13 to 70:30) purification gave 4-bromo-3,5-dicyclopropyl-1-methyl-1H-pyrazole (51.8 mg, 97.6%).

$C_{10}H_{13}BrN_2$. MS. m/z 241.0 (M−1+1), 243.0 (M+1+1).

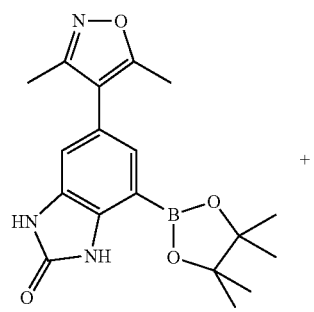

Step 2

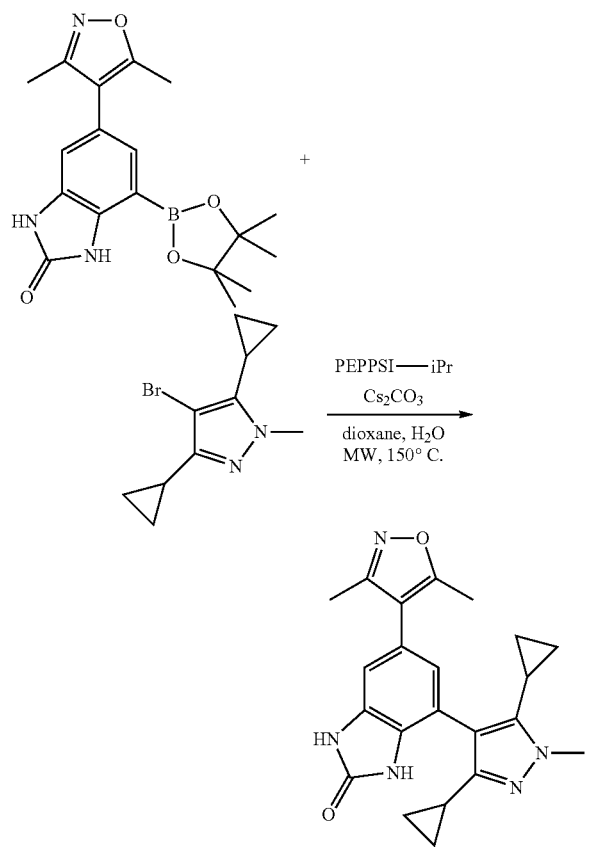

4-(3,5-dicyclopropyl-1-methyl-1H-pyrazol-4-yl)-6-(3,5-dimethylisoxazol-4-yl)-1H-benzo[d]imidazol-2(3H)-one was synthesized in a similar fashion as that of Example 21.

$C_{23}H_{20}N_4O_3$. MS. m/z 390.1 (M+1). $^1$H NMR (400 MHz, Methanol-$d_4$) δ 6.98 (s, 1H), 6.85 (s, 1H), 3.87 (s, 3H), 2.43 (s, 3H), 2.27 (s, 3H), 1.88-1.80 (m, 1H), 1.69-1.60 (m, 1H), 1.00-0.60 (m, 6H), 0.38-0.28 (m, 2H).

Example 25

6-(3,5-dimethylisoxazol-4-yl)-4-(2-(4-fluorophenyl)pyridin-3-yl)-1H-benzo[d]imidazol-2(3H)-one

Step 1

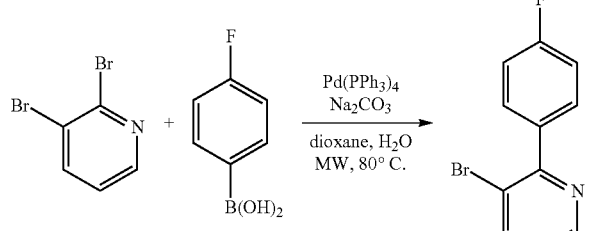

In a 2-5 mL Smith Process Vial, 2,3-dibromopyridine (300.0 mg, 1.266 mmol), 4-fluorophenyl boronic acid (177.2 mg, 1.266 mmol, 1 equiv) and Pd(PPh$_3$)$_4$ (73.2 mg, 0.063 mmol, 0.05 equiv) were placed. The mixture was suspended in 1,4-dioxane (3 mL) and 2M-Na$_2$CO$_3$ (1 mL) under a nitrogen atmosphere. The mixture was heated at 80° C. for 10 min using the microwave reactor. To the mixture were added EtOAc (70 mL) and water (30 mL). The whole was filtered through Celite (3 g) and the filtrate was washed with brine (30 mL), dried over Na$_2$SO$_4$ and concentrated under a reduced pressure. Obtained crude material was purified by Gilson preparative HPLC to give 3-bromo-2-(4-fluorophenyl)pyridine.

$C_{11}H_7BrFN$. MS. m/z 241.0 (M−1+1), 243.0 (M+1+1).

Step 2

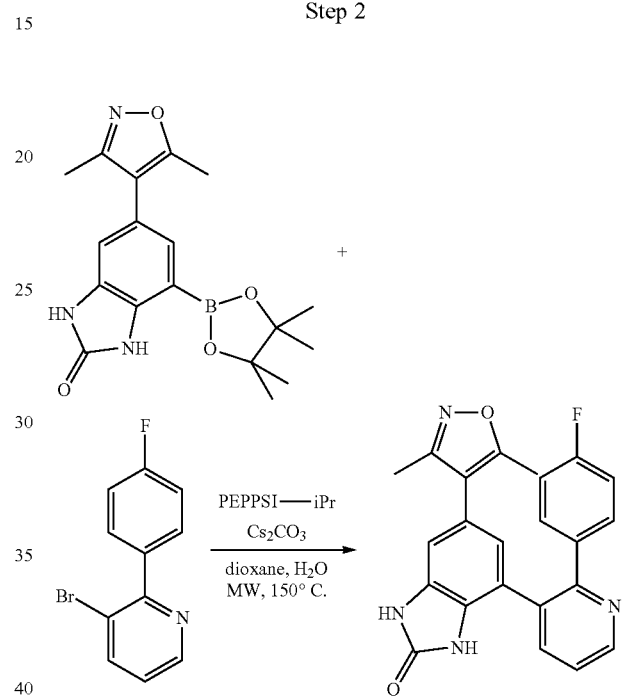

This transformation was performed in a similar fashion as that of Example 21.

$C_{23}H_{17}FN_4O_2$. MS. m/z 401.1 (M+1). $^1$H NMR (400 MHz, Methanol-$d_4$) δ 8.68 (dd, 1H, J=4.8, 1.6 Hz), 7.77 (dd, 1H, J=8.0, 1.6 Hz), 7.55 (dd, 1H, J=8.0, 4.6 Hz), 7.42-7.35 (m, 2H), 7.00 (t, 2H, J=8.0 Hz), 6.92 (d, 1H, J=1.0 Hz), 6.65 (d, 1H, J=1.0 Hz), 2.20 (s, 3H), 2.05 (s, 3H).

Example 26

6-(3,5-dimethylisoxazol-4-yl)-4-(2-(3-fluorophenyl)pyridin-3-yl)-1H-benzo[d]imidazol-2(3H)-one

Step 1

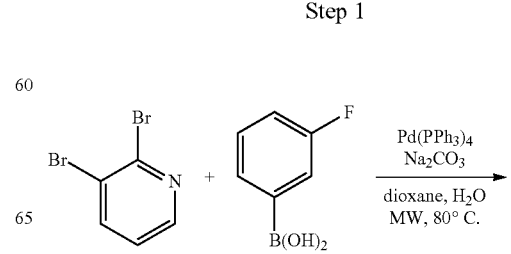

-continued

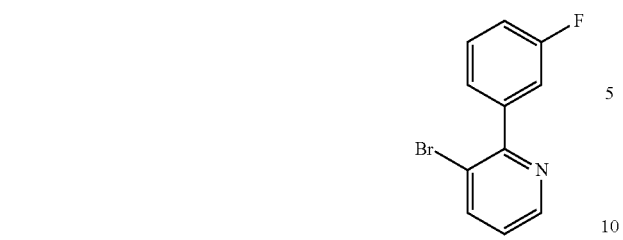

3-Bromo-2-(3-fluorophenyl)pyridine was synthesized in a similar fashion with 3-bromo-2-(4-fluorophenyl)pyridine. $C_{11}H_7BrFN$. MS. m/z 241.0 (M−1+1), 243.0 (M+1+1).

Step 2

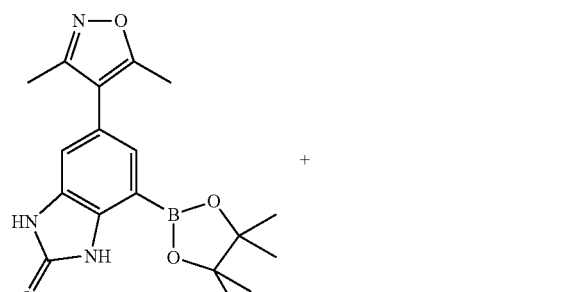

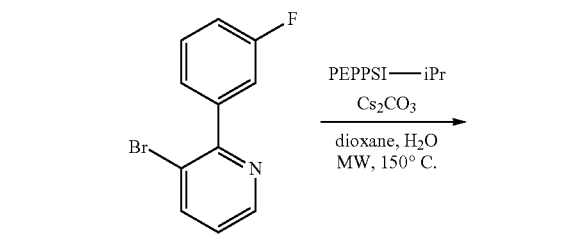

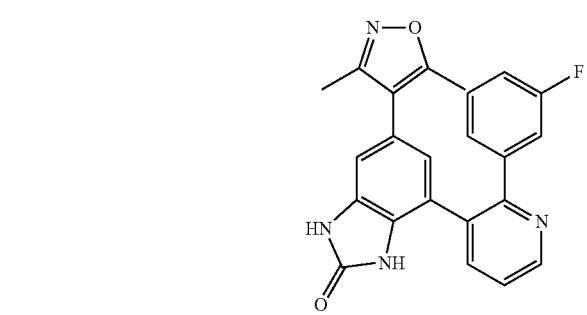

This transformation was performed in a similar fashion as that of Example 21.

$C_{23}H_{17}FN_4O_2$. MS. m/z 401.1 (M+1). $^1$H NMR (400 MHz, Methanol-$d_4$) δ 8.70 (dd, 1H, J=4.8, 1.6 Hz), 7.98 (dd, 1H, J=8.0, 1.6 Hz), 7.57 (dd, 1H, J=8.0, 4.8 Hz), 7.30-7.22 (m, 1H), 7.17-7.10 (m, 2H), 7.06-6.96 (m, 1H), 6.93 (d, 1H, J=1.0 Hz), 6.68 (d, 1H, J=1.0 Hz), 2.21 (s, 3H), 2.06 (s, 3H).

Example 27

4-(3,5-dicyclopropylisoxazol-4-yl)-6-(3,5-dimethyl-isoxazol-4-yl)-1H-benzo[d]imidazol-2(3H)-one Step 1

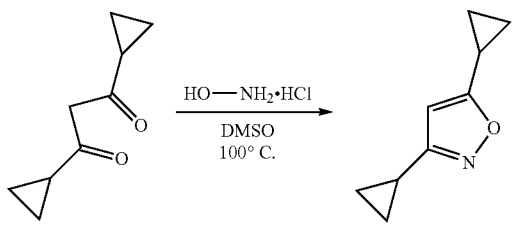

1,3-Dicyclopropylpropane-1,3-dione (300.0 mg, 1.971 mmol) and hydroxylamine hydrochloride (162.0 mg, 2.365 mmol, 2 equiv) were heated at 100° C. in DMSO (1 mL) in oil bath. After the reaction completed, the reaction mixture was directly injected into Gilead preparative HPLC to give 4-bromo-3,5-dicyclopropylisoxazole.

$C_9H_{11}ON$. MS. m/z 228.0 (M−1+1), 230.0 (M+1+1).

Step 2

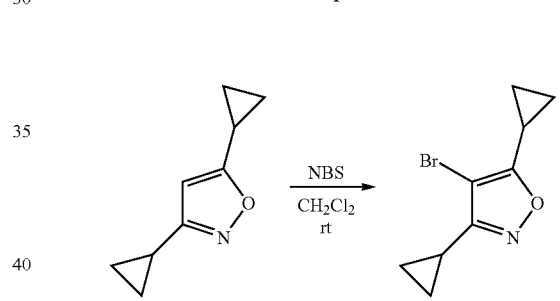

3,5-Dicyclopropylisoxazole (70.0 mg, 0.469 mmol) was treated with NBS (167.0 mg, 0.938 mmol, equiv) in $CH_2Cl_2$ at room temperature for 12 h. The solvent was removed under a reduced pressure and the residue was directly loaded onto a silica gel column chromatography (hexane EtOAc 87:13) to give 4-bromo-3,5-dicyclopropylisoxazole.

$C_9H_{10}BrON$. MS. m/z 228.0 (M−1+1), 230.0 (M+1+1).

Step 3

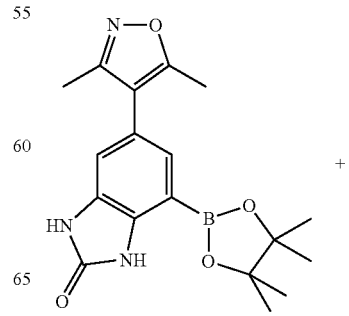

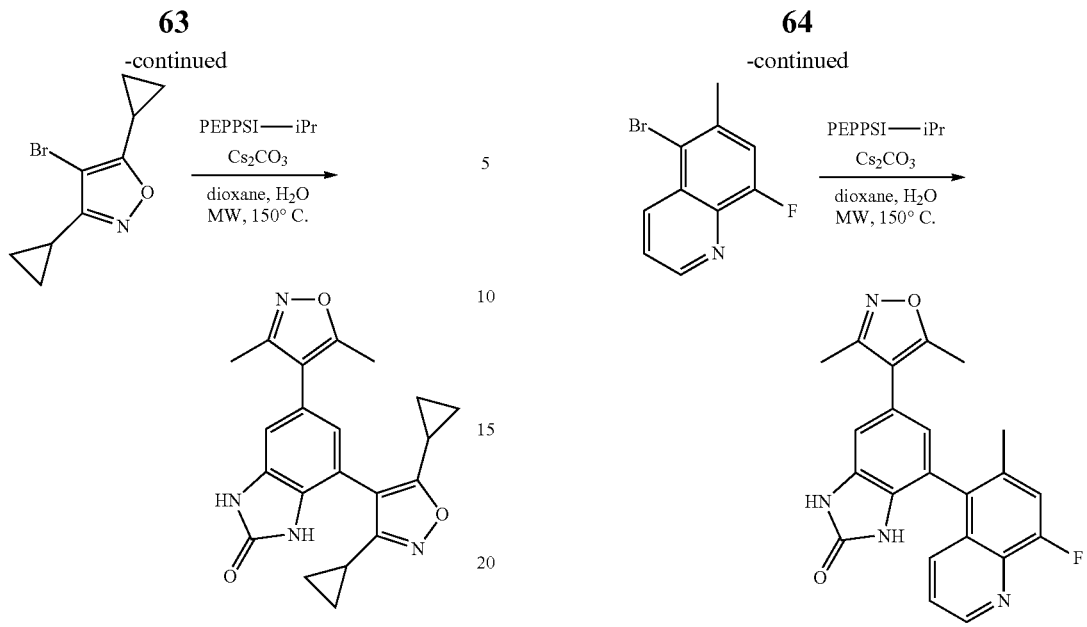

This transformation was performed in a similar fashion as that of Example 21.

$C_{21}H_{20}N_4O_3$. MS. m/z 377.1 (M+1). $^1$H NMR (400 MHz, Methanol-$d_4$) δ 7.05 (d, 1H, J=1.0 Hz), 6.95 (d, 1H, J=1.0 Hz), 2.43 (s, 3H), 2.28 (s, 3H), 1.90 (quin, 1H, J=6.4 Hz), 1.60 (quin, 1H, J=6.4 Hz), 1.01 (d, 4H, J=6.4 Hz), 0.91 (d, 4H, J=6.4 Hz).

Example 28

6-(3,5-dimethylisoxazol-4-yl)-4-(8-fluoro-6-methylquinolin-5-yl)-1H-benzo[d]imidazol-2(3H)-one Step 1

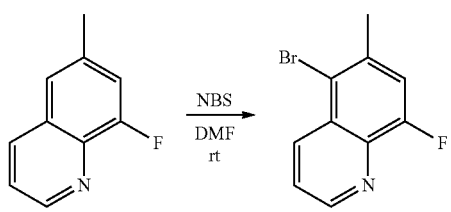

3,5-Dicyclopropylisoxazole (70.0 mg, 0.469 mmol) was treated with NBS (167.0 mg, 0.938 mmol, 2 equiv) in $CH_2Cl_2$ at room temperature for 12 h. The solvent was removed under a reduced pressure and the residue was directly loaded onto a silica gel column chromatography (hexane EtOAc 87:13) to give 5-bromo-8-fluoro-6-methylquinoline (68.7 mg, 64.2%).

$C_9H_{10}BrON$. MS. m/z 239.9 (M−1+1), 241.9 (M+1+1).

Step 2

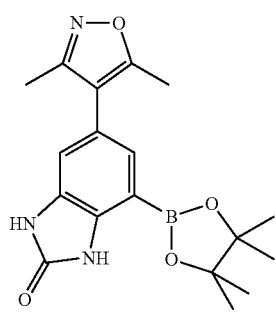

+

This transformation was performed in a similar fashion as that of Example 21.

$C_{22}H_{17}FN_4O_2$. MS. m/z 398.1 (M+1). $^1$H NMR (400 MHz, Methanol-$d_4$) δ 8.93 (d, 1H, J=4.0 Hz), 8.08 (d, 1H, J=8.0 Hz), 7.70 (d, 1H, J=11.2 Hz), 7.67 (dd, 1H, J=8.0, 4.0 Hz), 7.15 (d, 1H, J=1.0 Hz), 6.88 (d, 1H, J=1.0 Hz), 2.43 (s, 3H), 2.38 (s, 3H), 2.28 (s, 3H).

Example 29

-(3,5-dicyclopropyl-1-(2,2,2-trifluoroethyl)-1H-pyrazol-4-yl)-6-(3,5-dimethylisoxazol-4-yl)-1H-benzo[d]imidazol-2(3H)-one Step 1

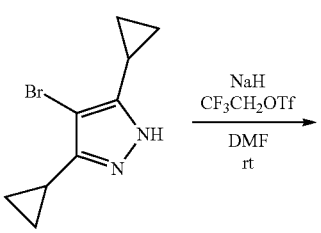

4-Bromo-3,5-dicyclopropyl-1-(2,2,2-trifluoroethyl)-1H-pyrazole was synthesized in a similar fashion with 5-bromo-6-methyl-1-(2,2,2-trifluoroethyl)quinolin-2(1H)-one.

$C_{11}H_{12}BrF_3N_2$. MS. m/z 309.0 (M−1+1), 311.0 (M+1+1).

Step 2

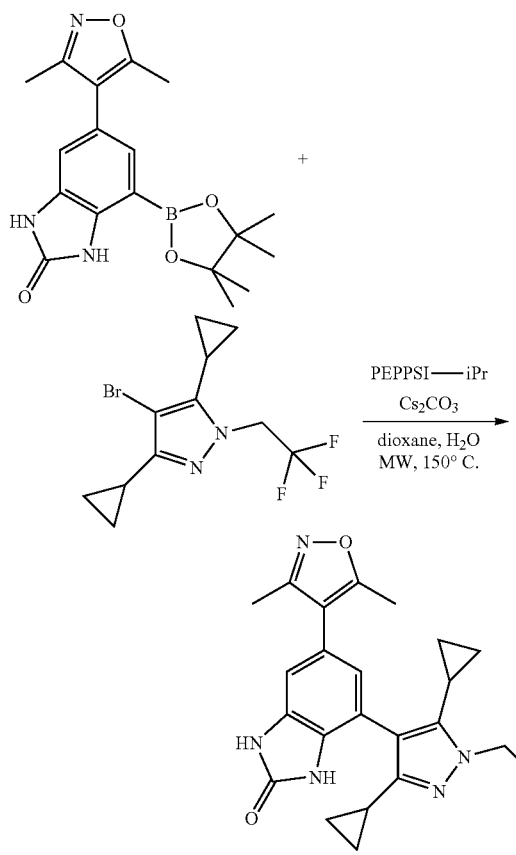

This transformation was performed in a similar fashion as that of Example 21.

$C_{23}H_{22}F_3N_5O_2$. MS. m/z 458.1 (M+1). $^1$H NMR (400 MHz, Methanol-$d_4$) δ 7.00 (d, 1H, J=1.0 Hz), 6.85 (d, 1H, J=1.0 Hz), 4.95 (q, 2H, J=9.6 Hz), 2.43 (s, 3H), 2.27 (s, 3H), 1.90-1.81 (m, 1H), 1.66-1.61 (m, 1H), 1.40-1.26 (m, 2H), 0.94-0.68 (m, 6H), 0.42-0.32 (m, 2H).

Example 30

6-(6-(3,5-dimethylisoxazol-4-yl)-2-oxo-2,3-dihydro-1H-benzo[d]imidazol-4-yl)-7-methyl-4,5-dihydro-1H-benzo[b]azepin-2(3H)-one

Step 1

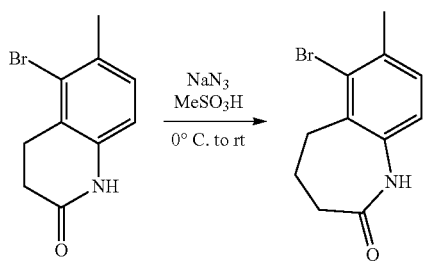

5-Bromo-6-methyl-3,4-dihydroquinolin-2(1H)-one (477.7 mg, 1.998 mmol) was treated with NaN$_3$ (194.8 mg, 0.938 mmol, 1.5 equiv) in MeSO$_3$H (3 g) at 0° C. to room temperature for 1 h. The mixture was neutralized with NaHCO$_3$ and extracted with EtOAc (30 mL×3). The organic layer was washed with brine (30 mL) and dried over Na$_2$SO$_4$. The solvent was removed under a reduced pressure and the crude product was recrystallized from EtOAc (10 mL) to give 6-bromo-7-methyl-4,5-dihydro-1H-benzo[b]azepin-2(3H)-one.

$C_{11}H_{12}BrON$. MS. m/z 254.0 (M−1+1), 256.0 (M+1+1).

Step 2

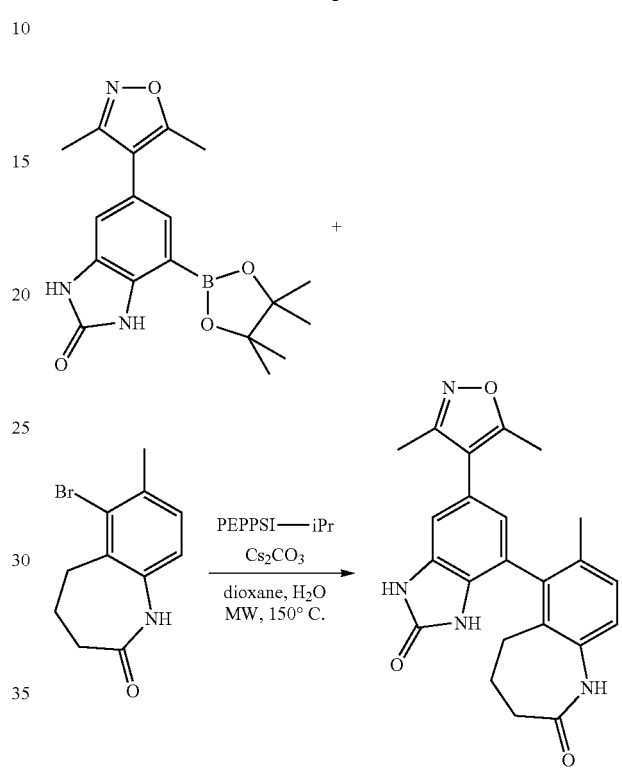

This transformation was performed in a similar fashion as that of Example 21.

$C_{23}H_{22}N_4O_3$. MS. m/z 403.1 (M+1). $^1$H NMR (400 MHz, Methanol-$d_4$) δ 8.93 (d, 1H, J=4.0 Hz), 7.24 (d, 1H, J=8.0 Hz), 7.04 (d, 1H, J=8.0 Hz), 7.03 (d, 1H, J=1.0 Hz), 6.73 (d, 1H, J=1.0 Hz), 2.60-2.22 (m, 4H), 2.41 (s, 3H), 2.26 (s, 3H), 2.05 (s, 3H), 2.04-1.94 (m, 3H).

Example 31

6-(6-(3,5-dimethylisoxazol-4-yl)-2-oxo-2,3-dihydro-1H-benzo[d]imidazol-4-yl)-7-methyl-4,5-dihydro-1H-benzo[b]azepin-2(3H)-one

Step 1

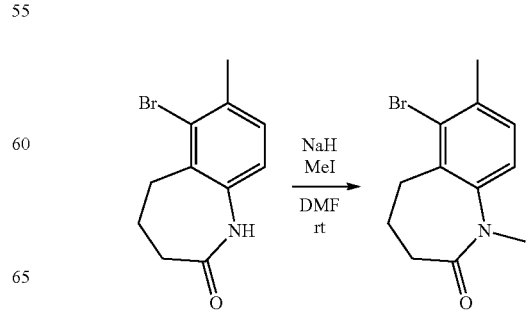

6-Bromo-7-methyl-4,5-dihydro-1H-benzo[b]azepin-2 (3H)-one (100.0 mg, 1.998 mmol) was treated with NaH (18.9 mg, 0.472 mmol, 1.2 equiv) in DMF (3 mL) at 0° C. to room temperature for 30 min. To the mixture was added MeI (111.7 mg, 0.787 mmol, 2 equiv). The mixture was stirred at to room temperature for 1 h The mixture was quenched with water and extracted with EtOAc (30 mL×3). The organic layer was washed with brine (30 mL) and dried over Na$_2$SO$_4$. The solvent was removed under a reduced pressure and the crude product was purified by a silica-gel column chromatography (hexane/EtOAc 87:13 to 50:50) to give 6-bromo-1, 7-dimethyl-4,5-dihydro-1H-benzo[b]azepin-2(3H)-one (88.5 mg, 83.9%).

$^1$H NMR (400 MHz, CDCl$_3$) δ 7.16 (d, 1H, J=8.0 Hz), 7.03 (d, 1H, J=8.0 Hz), 3.32 (s, 3H), 2.43 (s, 3H), 2.40-1.90 (broad, 6H).

Step 2

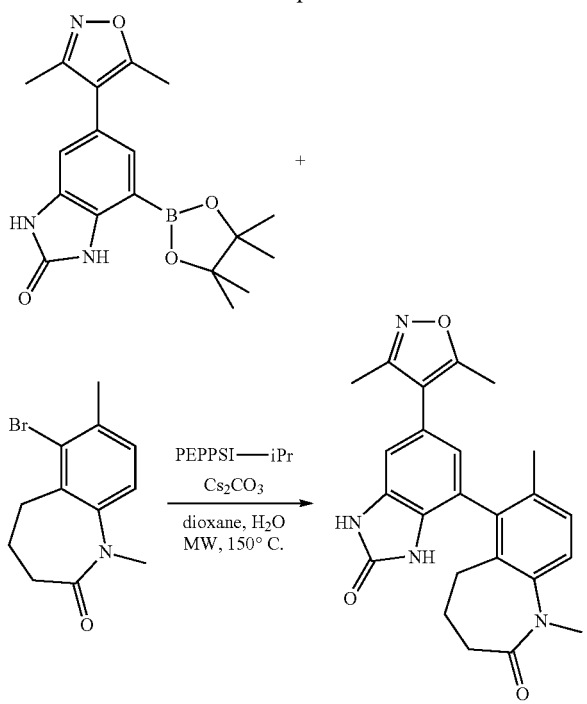

This transformation was performed in a similar fashion as that of Example 21.

C$_{24}$H$_{24}$N$_4$O$_3$. MS. m/z 417.1 (M+1). $^1$H NMR (400 MHz, Methanol-d$_4$) δ 7.34 (d, 1H, J=8.0 Hz), 7.30 (d, 1H, J=8.0 Hz), 7.04 (d, 1H, J=1.0 Hz), 6.73 (broad, 1H), 3.36 (s, 3H), 2.60-2.20 (m, 4H), 2.41 (s, 3H), 2.26 (s, 3H), 2.07 (s, 3H).

Example 32

4-(8-chloro-6-methylquinolin-5-yl)-6-(3,5-dimethyl-isoxazol-4-yl)-1H-benzo[d]imidazol-2(3H)-one Step 1

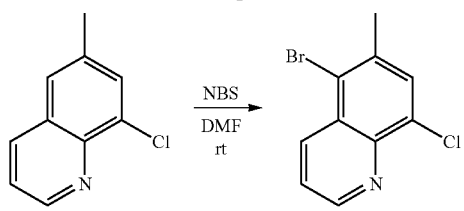

5-Bromo-8-chloro-6-methylquinoline was synthesized in a similar fashion, using 5-bromo-8-fluoro-6-methylquinoline.

C$_{10}$H$_8$ClN. MS. m/z 258.0 (M−1+1), 256.1 (M+1+1), 260.0 (M+1+2).

Step 2

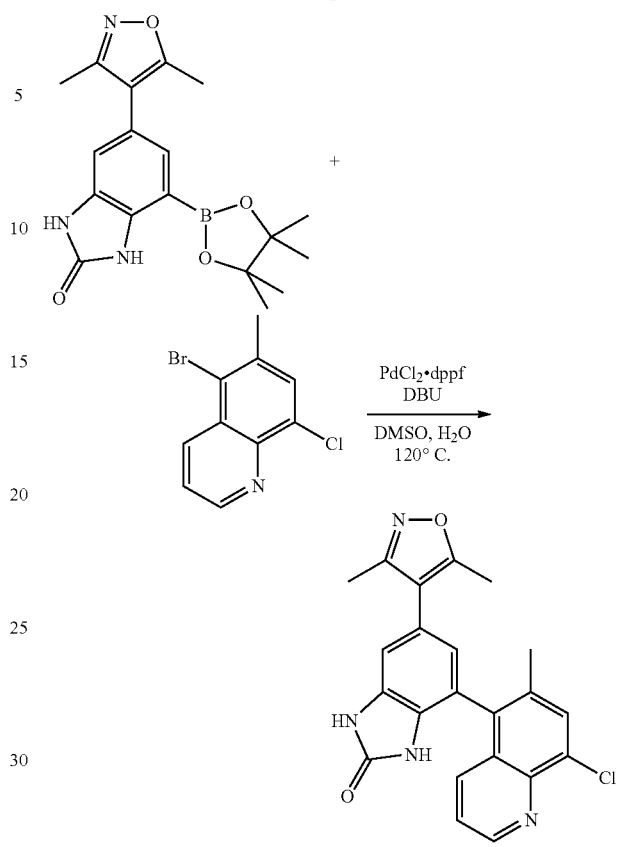

A mixture of 6-(3,5-Dimethylisoxazol-4-yl)-4-(4,4,5,5-tetramethyl-1,3,2-dioxaborolan-2-yl)-1H-benzo[d]imidazol-2(3H)-one (100.0, 0.282 mmol) and 5-bromo-8-chloro-6-methylquinoline (72.2 mg, 0.282 mmol) was treated with PdCl$_2$dppf.CH$_2$Cl$_2$ (20.9 mg, 0.028 mmol) in the presence of 1,8-Diazabicycloundec-7-ene (DBU, 204.0 mg, 1.34 mmol, 4.76 equiv) in DMSO (0.2 mL) and water (0.2 mL). The reaction mixture was heated at 120° C. in oil bath. The reaction mixture was diluted with THF (3 mL) and purified by Gilson preparative HPLC to give 4-(8-chloro-6-methylquinolin-5-yl)-6-(3,5-dimethylisoxazol-4-yl)-1H-benzo[d]imidazol-2(3H)-one Example 33

6-(3,5-dimethylisoxazol-4-yl)-4-((7-fluoroquinolin-2-yl)(hydroxy)(phenyl)methyl)-1H-benzo[d]imidazol-2(3H)-one Step 1

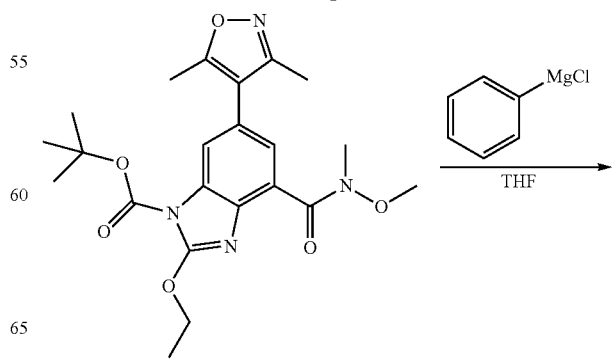

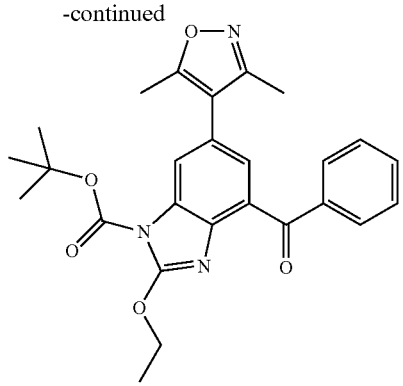

Tert-butyl 6-(3,5-dimethylisoxazol-4-yl)-2-ethoxy-4-(methoxy(methyl)carbamoyl)-1H-benzo[d]imidazole-1-carboxylate was dissolved in THF (3 mL). To the solution was added a solution of phenyl magnesium chloride (2M in THF, 0.508 mmol, 0.254 mmol) at −78° C. after the addition, the reaction was allowed to warm up to room temperature. The reaction was stirred for 17 h at the same temperature. The reaction mixture was quenched with water (30 mL). The whole was extracted with AcOEt (30 mL×3). Organic layer was washed with brine (30 mL) and dried over Na$_2$SO$_4$. The solvent was removed under a reduced pressure to give the crude product. The crude product was purified by a silica gel column chromatography (hexane:EtOAc, 7:1 to 3:1) to give tert-butyl 4-benzoyl-6-(3,5-dimethylisoxazol-4-yl)-2-ethoxy-1H-benzo[d]imidazole-1-carboxylate.

$C_{26}H_{27}N_3O_5$. MS. m/z 462.2 (M+1).

Step 2

$C_{22}H_{17}ClN_4O_2$. $^1$H NMR (400 MHz, Methanol-d$_4$) δ 8.97 (d, 1H, J=4.8, 1.6 Hz), 8.08 (d, 1H, J=8.0 Hz), 8.09 (dd, 1H, J=9.6, 1.6 Hz), 8.08 (s, 1H), 7.66 (dd, 1H, J=9.6, 4.8 Hz), 7.16 (d, 1H, J=1.0 Hz), 6.89 (d, 1H, J=1.0 Hz), 2.44 (s, 3H), 2.36 (s, 3H), 2.28 (s, 3H).

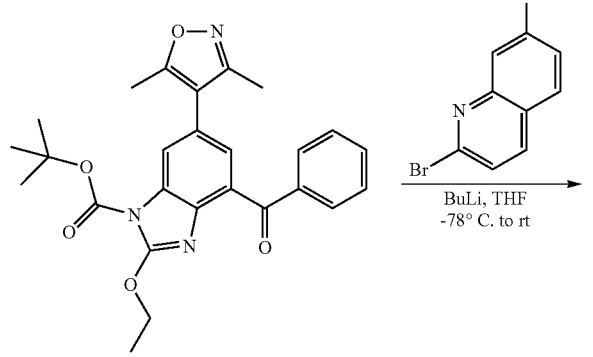

To a solution of 7-fluoro-2-bromoquinoline (54.1 mg) in THF (2 mL) was added BuLi (1.6 M, 0.25 mL) at −78° C. After 5 min, a solution of phenyl ketone (60.0 mg) in THF (1 mL) was added at −78° C. The reaction was immediately allowed to warm up to room temperature and stirred for 30 min. The reaction mixture was quenched with water (30 mL). The whole was extracted with AcOEt (30 mL×3). Organic layer was washed with brine (30 mL) and dried over Na$_2$SO$_4$. The solvent was removed under a reduced pressure to give the crude product. The crude product was treated with TFA to cleave the Boc group. The crude product was purified by a silica gel column chromatography (hexane:EtOAc, 7:1 to 3:1) to give tert-butyl 4-benzoyl-6-(3,5-dimethylisoxazol-4-yl)-2-ethoxy-1H-benzo[d]imidazole-1-carboxylate.

$C_{26}H_{27}N_3O_5$. MS. m/z 509.2 (M+1).

Step 3

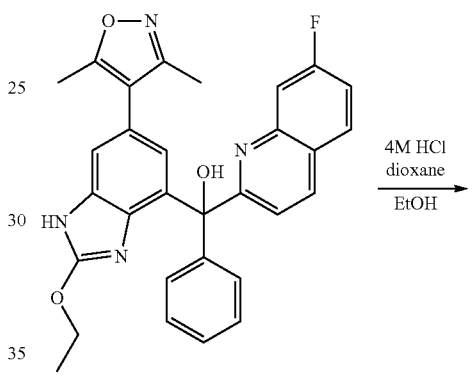

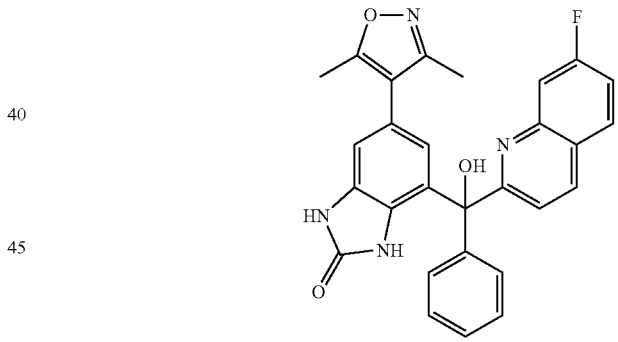

Tert-butyl 4-benzoyl-6-(3,5-dimethylisoxazol-4-yl)-2-ethoxy-1H-benzo[d]imidazole-1-carboxylate (18.0 mg) was dissolved into EtOH (2 mL) and 4M HCl/dioxane (2 mL). The solution was heated at 70° C. for 30 min. The reaction mixture was quenched with water (30 mL). The whole was extracted with EtOAc (30 mL×3). Combined organic layers were washed with brine (50 mL). The solvent was removed under a reduced pressure to give a crude product. The crude product was purified by a silica gel column chromatography (hexane: EtOAc, 7:1 to 3:1) to give tert-butyl 4-benzoyl-6-(3,5-dimethylisoxazol-4-yl)-2-ethoxy-1H-benzo[d]imidazole-1-carboxylate.

$C_{28}H_{21}FN_4O_3$. MS. m/z 481.1 (M+1). $^1$H NMR (400 MHz, Methanol-d$_4$) δ 8.31 (1, J=8.7 Hz, 1H), 8.13 (dd, J=9.2, 5.3 Hz, 1H), 7.67-7.56 (m, 3H), 7.40-7.25 (m, 5H), 6.98 (d, J=1.6 Hz, 1H), 6.61 (d, J=1.6 Hz, 1H), 2.28 (s, 3H), 2.11 (s, 3H).

Example 34

6-(3,5-dimethylisoxazol-4-yl)-4-(hydroxy(phenyl)(quinolin-2-yl)methyl)-1H-benzo[d]imidazol-2(3H)-one

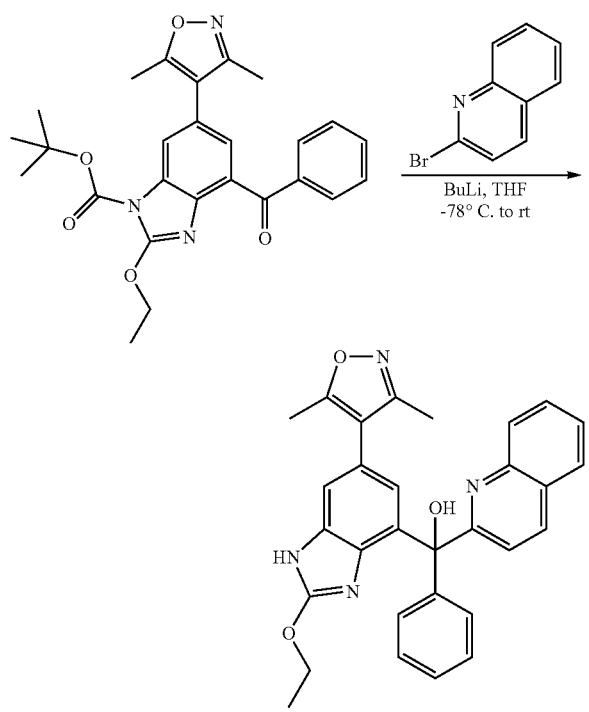

(6-(3,5-dimethylisoxazol-4-yl)-2-ethoxy-1H-benzo[d]imidazol-4-yl)(phenyl)(quinolin-2-yl)methanol was synthesized in the similar fashion with tert-butyl 4-benzoyl-6-(3,5-dimethylisoxazol-4-yl)-2-ethoxy-1H-benzo[d]imidazole-1-carboxylate. $C_{30}H_{26}N_4O_3$. MS. m/z 491.2 (M+1).

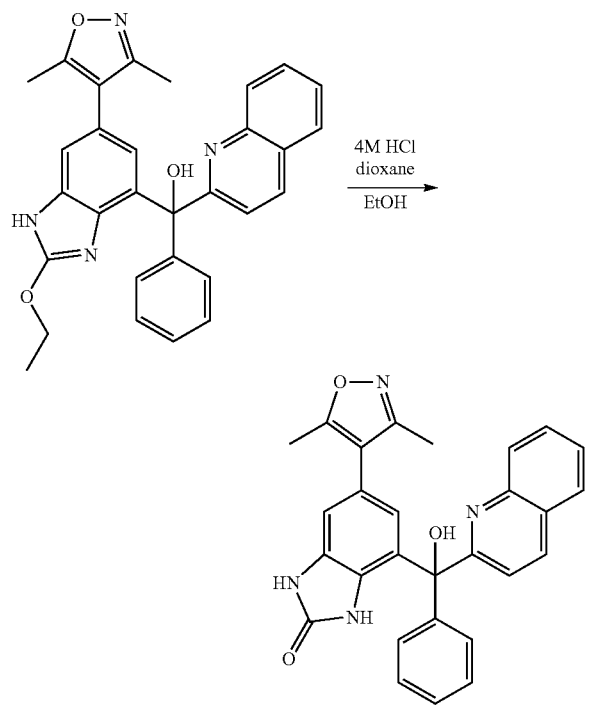

6-(3,5-dimethylisoxazol-4-yl)-4-(hydroxy(phenyl)(quinolin-2-yl)methyl)-1H-benzo[d]imidazol-2(3H)-one was synthesized in the similar fashion as that of Example 33. $C_{28}H_{22}N_4O_3$. MS. m/z 463.1 (M+1).). $^1$H NMR (400 MHz, Methanol-$d_4$) δ 8.30 (d, J=8.6 Hz, 1H), 8.09 (d, J=8.6 Hz, 1H), 7.93 (d, J=8.6 Hz, 1H), 7.77 (ddd, J=8.6, 7.0, 1.2 Hz, 1H), 7.61 (ddd, J=8.6, 7.0, 1.2 Hz, 1H), 7.54 (d, J=8.6 Hz, 1H), 7.40-7.26 (m, 5H), 6.98 (d, J=1.5 Hz, 1H), 6.61 (d, J=1.5 Hz, 1H), 2.27 (s, 3H), 2.10 (s, 3H).

Example 35

6-(3,5-dimethylisoxazol-4-yl)-4-(hydroxy(pyridin-2-yl)(quinolin-2-yl)methyl)-1H-benzo[d]imidazol-2(3H)-one

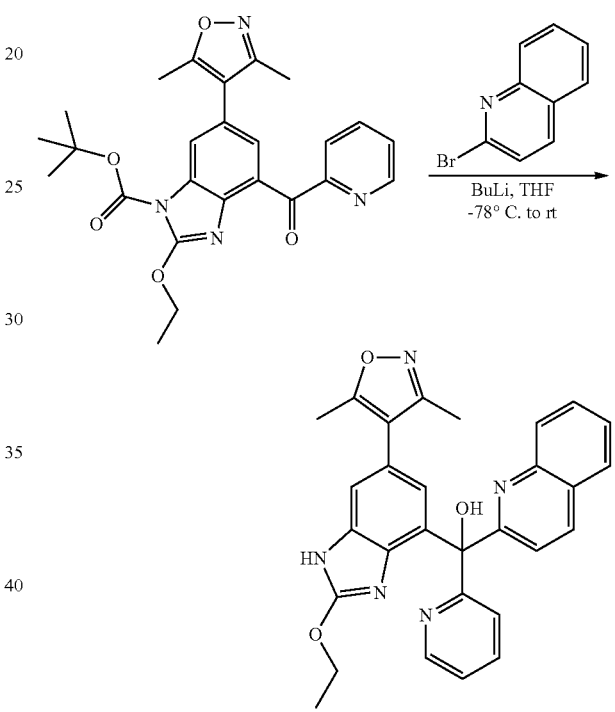

(6-(3,5-dimethylisoxazol-4-yl)-2-ethoxy-1H-benzo[d]imidazol-4-yl)(pyridin-2-yl)(quinolin-2-yl)methanol was synthesized in the similar fashion with tert-butyl 4-benzoyl-6-(3,5-dimethylisoxazol-4-yl)-2-ethoxy-1H-benzo[d]imidazole-1-carboxylate. $C_{29}H_{25}N_5O_3$. MS. m/z 492.2 (M+1).

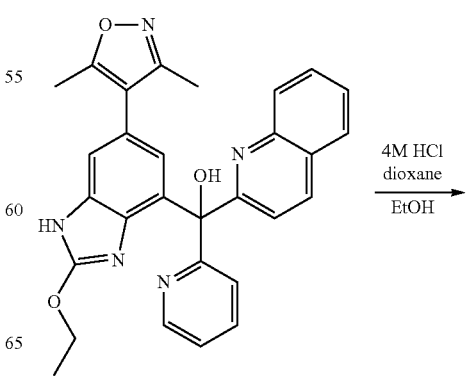

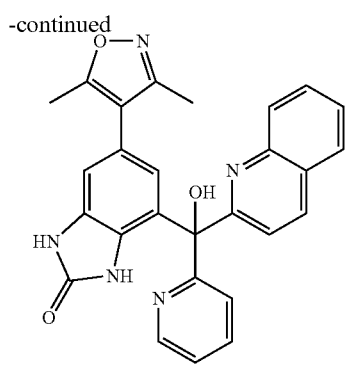

6-(3,5-dimethylisoxazol-4-yl)-4-(hydroxy(pyridin-2-yl) (quinolin-2-yl)methyl)-1H-benzo[d]imidazol-2(3H)-one was synthesized in the similar fashion as that of Example 33.

$C_{28}H_{22}N_4O_3$. MS. m/z 463.1 (M+1).). $^1$H NMR (400 MHz, Methanol-$d_4$) δ 8.78 (dd, J=6.6, 1.0 Hz, 1H), 8.66 (d, J=8.8 Hz, 1H), 8.47 (td, J=8.8, 1.0 Hz, 1H), 8.15-8.03 (m, 3H), 8.00-7.83 (m, 3H), 7.76 (t, J=8.0 Hz, 1H), 7.07 (d, J=1.0 Hz, 1H), 6.46 (d, J=1.0 Hz, 1H), 2.22 (s, 3H), 2.04 (s, 3H).

Example 36

6-(3,5-dimethylisoxazol-4-yl)-4-((7-fluoroquinolin-2-yl)(hydroxy)(pyridin-2-yl)methyl)-1H-benzo[d]imidazol-2(3H)-one Step 1

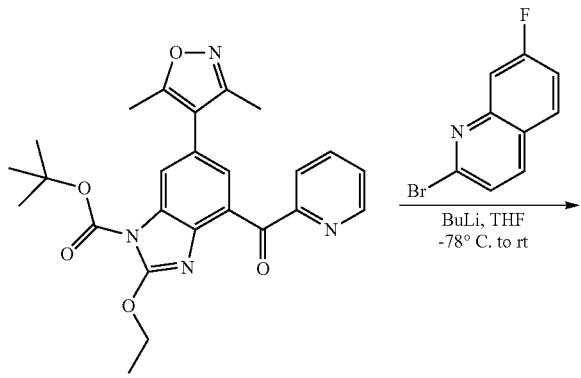

(6-(3,5-dimethylisoxazol-4-yl)-2-ethoxy-1H-benzo[d] imidazol-4-yl)(7-fluoroquinolin-2-yl)(pyridin-2-yl)methanol was synthesized in the similar fashion with tert-butyl 4-benzoyl-6-(3,5-dimethylisoxazol-4-yl)-2-ethoxy-1H-benzo[d]imidazole-1-carboxylate.

$C_{29}H_{24}FN_5O_3$. MS. m/z 510.2 (M+1).

Step 2

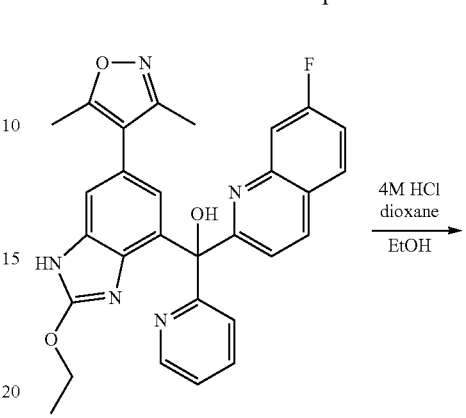

6-(3,5-dimethylisoxazol-4-yl)-4-((7-fluoroquinolin-2-yl) (hydroxy)(pyridin-2-yl)methyl)-1H-benzo[d]imidazol-2 (3H)-one was synthesized in the similar fashion as that of Example 33.

$C_{27}H_{20}FN_5O_3$. MS. m/z 482.1 (M+1). $^1$H NMR (400 MHz, Methanol-$d_4$) δ 8.52 (ddd, J=4.9, 1.8, 0.9 Hz, 1H), 8.26 (dd, J=8.9, 0.8 Hz, 1H), 8.04 (dd, J=9.2, 5.3 Hz, 1H), 7.84 (td, J=7.8, 1.8 Hz, 1H), 7.76 (d, J=7.8 Hz, 1H), 7.72 (d, J=7.8 Hz, 1H), 7.59 (dd, J=8.9, 1.8 Hz, 1H), 7.54 (d, J=8.9, 0.8 Hz, 1H), 7.33 (ddd, J=7.5, 4.9, 1.2 Hz, 1H), 6.96 (d, J=1.6 Hz, 1H), 6.72 (d, J=1.6 Hz, 1H), 2.28 (s, 3H), 2.11 (s, 3H).

Example 37

6-(3,5-dimethylisoxazol-4-yl)-4-((5-fluoropyridin-2-yl)(hydroxy)(pyridin-2-yl)methyl)-1H-benzo[d]imidazol-2(3H)-one

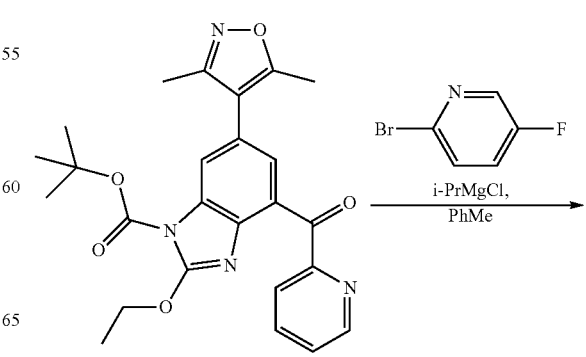

-continued

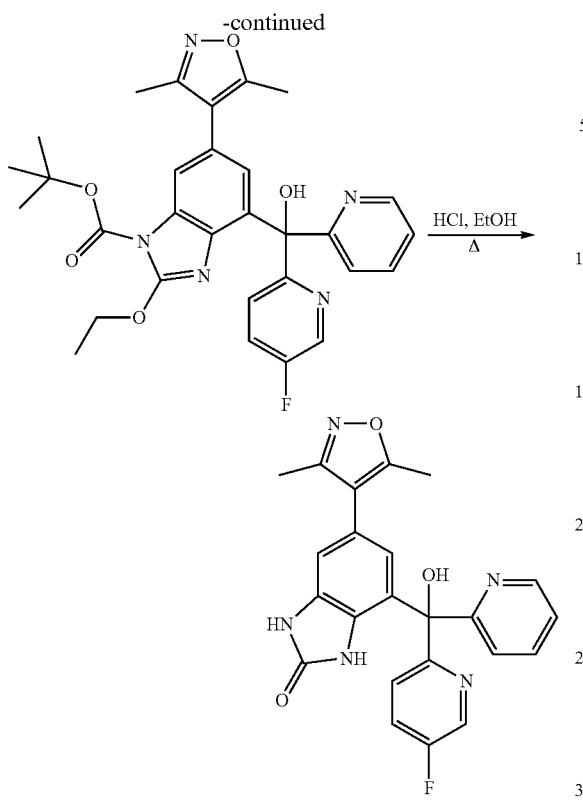

To isopropyl magnesium chloride (1.32 mL, 2.64 mmol, 2 M in THF) in toluene (4 mL) was added 2-bromo-5-fluoropyridine (388 mg, 2.05 mmol) in toluene (1 mL). After 3.5 hours the Grignard solution (1 mL, 0.65 mmol) was added to tert-butyl 6-(3,5-dimethylisoxazol-4-yl)-2 ethoxypicolinoyl-1H-benzo[d]imidazole-1-carboxylate (60 mg, 0.13 mmol) in a 1:1 mixture of toluene/2-methyl-THF (6 mL) at 0° C. and the mixture was allowed to warm to 20° C. After 16 hours, the reaction was quenched with saturated $NH_4Cl_{(aq)}$ (10 mL), extracted with ethyl acetate (3×10 mL), dried over $Na_2SO_4$, and concentrated in vacuo. The resulting residue (100 mg) was submitted to deprotection directly.

To 100 mg crude tert-butyl 6-(3,5-dimethylisoxazol-4-yl)-2-ethoxy-4-((5-fluoropyridin-2-yl)(hydroxy)(pyridin-2-yl) methyl)-1H-benzo[d]imidazole-1-carboxylate (100 mg) in ethanol (3 mL) was added hydrochloric acid (0.2 mL, 0.8 mmol, 4 M in 1,4-dioxane). The mixture was heated to 70° C. for 0.5 hours and then concentrated in vacuo. Purification by reverse-phase HPLC (25-50% acetonitrile/water with 0.01% trifluoroacetic acid, Gemini C18 5µ) afforded the TFA salt of 6-(3,5-dimethylisoxazol-4-yl)-4-((5-fluoropyridin-2-yl)(hydroxy)(pyridin-2-yl)methyl)-1H-benzo[d]imidazol-2(3H)-one as a light yellow solid.

$C_{23}H_{18}FN_5O_3$. 432.1 (M+H). $^1$H NMR (400 MHz, $d_3$-acetonitrile) δ 10.72 (s, 1H), 9.80 (s, 1H), 8.6 (m, 1H), 7.87 (m, 1H), 7.75 (m, 1H), 7.62 (m, 1H), 6.87 (s, 1H), 6.51 (s, 1H), 2.30 (s, 3H), 2.11 (s, 3H). $^{19}$F NMR (376 MHz, $d_3$-acetonitrile) δ −74.7, −130.95.

Example 38

4-((2,6-difluorophenyl)(5-fluoropyridin-2-yl)(hydroxy)methyl)-6-(3,5-dimethylisoxazol-4-yl)-1H-benzo[d]imidazol-2(3H)-one

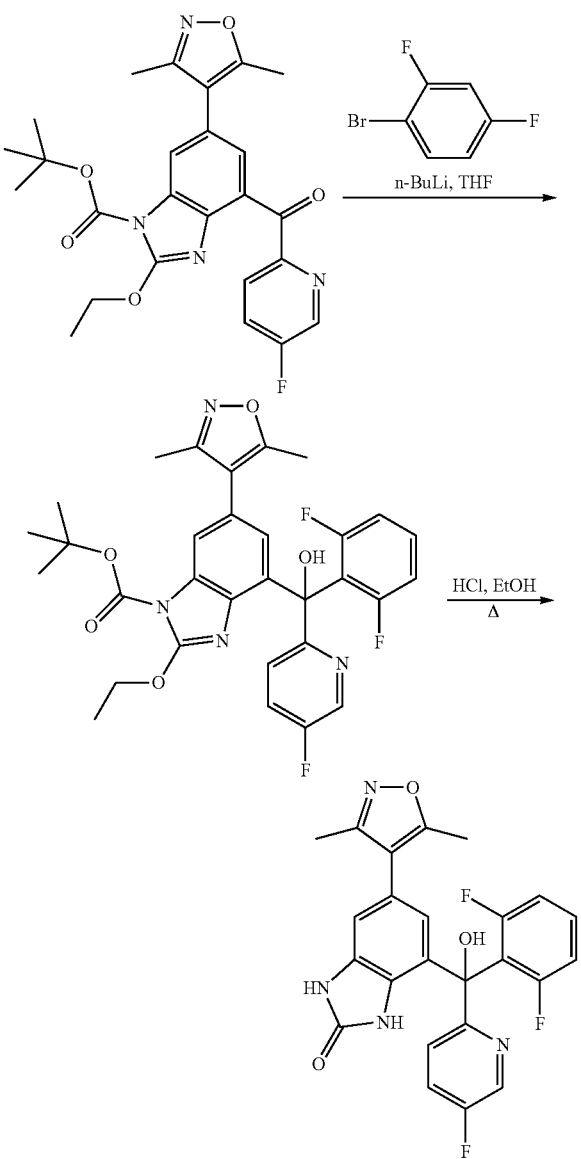

To 1-bromo-2,4-difluorobenzene (0.02 ml, 0.16 mmol) in THF (0.52 mL) at −78° C. was added n-butyllithium (0.12 mL, 0.18 mmol, 1.6 M in hexanes). After 30 minutes, tert-butyl 6-(3,5-dimethylisoxazol-4-yl)-2-ethoxy-4-(5-fluoropicolinoyl)-1H-benzo[d]imidazole-1-carboxylate (50 mg, 0.10 mmol) in THF (1 mL) was added drop-wise to the reaction. After 60 minutes, the reaction was warmed, quenched with saturated $NH_4Cl_{(aq)}$ (10 mL), extracted with ethyl acetate (3×10 mL), dried over $Na_2SO_4$, and concentrated in vacuo. To the crude residue in ethanol (3.5 mL) was added hydrochloric acid (0.35 mL, 1.4 mmol, 4 M in 1,4-dioxane) and the mixture was heated to 70° C. in a microwave reactor for 45 minutes. Purification by reverse-phase HPLC (40-50% acetonitrile/ water with 0.01% trifluoroacetic acid, Gemini C18 5µ) gave the trifluoroacetate salt of 4-((2,6-difluorophenyl)(5-fluoropyridin-2-yl)(hydroxy)methyl)-6-(3,5-dimethylisoxazol-4-yl)-1H-benzo[d]imidazol-2(3H)-one as a white solid.

$C_{24}H_{17}F_3N_4O_3$. 467.03 (M+H). $^1$H NMR (400 MHz, d$_3$-acetonitrile) δ 8.74 (s, 1H), 8.65 (s, 1H), 8.49 (s, 1H), 7.55 (m, 1H), 6.95 (m, 3H), 6.70 (s, 1H), 2.35 (s, 3H), 2.22 (s, 3H). $^{19}$F NMR (377 MHz, d$_3$-acetonitrile) δ −77, −107, −131.

Example 39

4-((2,4-difluorophenyl)(5-fluoropyridin-2-yl)(hydroxy)methyl)-6-(3,5-dimethylisoxazol-4-yl)-1H-benzo[d]imidazol-2(3H)-one

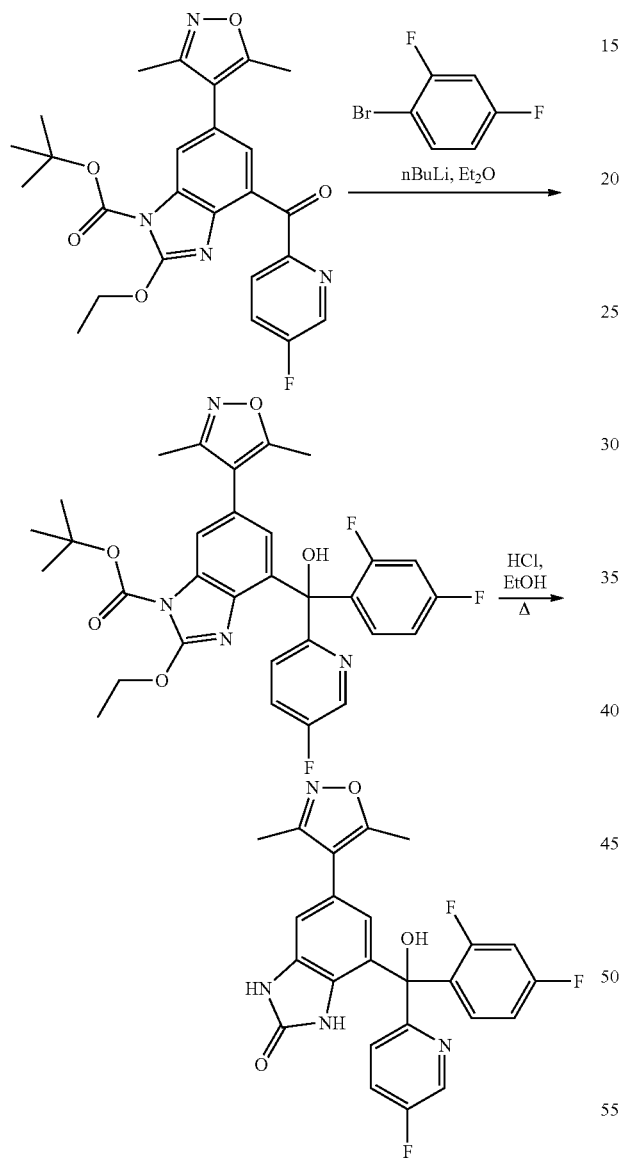

In a synthetic process following that described for Example 40, reaction of tert-butyl 6-(3,5-dimethylisoxazol-4-yl)-2-ethoxy-4-(5-fluoropicolinoyl)-1H-indole-1-carboxylate (50 mg, 0.13 mmol) with the organolithium species resulting from metal-halogen exchange with 1-bromo-2,4-difluorobenzene in diethyl ether gave, after silica gel chromatography, 4-((2,4-difluorophenyl)(5-fluoropyridin-2-yl)(hydroxy)methyl)-6-(3,5-dimethylisoxazol-4-yl)-1H-benzo[d]imidazol-2(3H)-one as a white solid.

$C_{24}H_{17}F_3N_4O_3$. 467.1 (M+H). $^1$H NMR (400 MHz, d$_3$-acetonitrile) δ 8.68 (s, 1H), 8.49 (s, 1H), 7.56 (m, 1H), 7.45 (m, 1H), 7.12 (m, 1H), 6.99-6.89 (m, 3H), 6.50 (s, 1H), 5.56 (s, 1H), 2.29 (s, 3H), 2.12 (s, 3H). $^{19}$F NMR (377 MHz, d$_3$-acetonitrile) δ −105, −111, −132.

Example 40

4-((3,5-difluorophenyl)(5-fluoropyridin-2-yl)(hydroxy)methyl)-6-(3,5-dimethylisoxazol-4-yl)-1H-benzo[d]imidazol-2(3H)-one

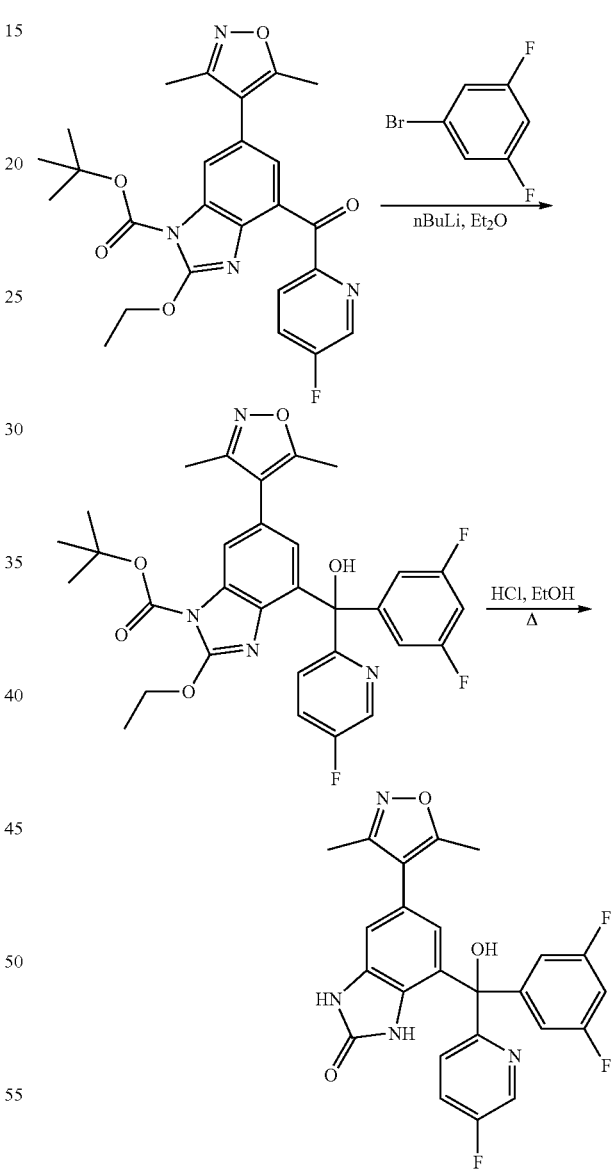

In a synthetic process following that described for Example 40, reaction of tert-butyl 6-(3,5-dimethylisoxazol-4-yl)-2-ethoxy-4-(5-fluoropicolinoyl)-1H-indole-1-carboxylate (50 mg, 0.13 mmol) with the organolithium species resulting from metal halogen exchange of 1-bromo-3,5-difluorobenzene in diethyl ether gave, after purification of final material by reverse-phase HPLC (40-50% acetonitrile/water with 0.01% trifluoroacetic acid, Gemini C18 5μ) the trifluoroacetate salt of 4-((3,5-difluorophenyl)(5-fluoropyridin-2-yl)(hydroxy)methyl)-6-(3,5-dimethylisoxazol-4-yl)-1H-benzo[d]imidazol-2(3H)-one as a white solid.

C24H17F3N4O3. 467.1 (M+H). 1H NMR (400 MHz, d$_6$-DMSO) δ 10.73 (s, 1H), 9.76 (s, 1H), 8.52 (m, 1H), 7.77 (m, 1H), 7.09 (m, 1H), 6.92 (s, 1H), 6.33 (s, 1H), 2.25 (s, 3H), 2.07 (s, 3H). $^{19}$F NMR (377 MHz, d$_6$-DMSO) δ −75, −111, −130.

Example 41

4-((2,5-difluorophenyl)(5-fluoropyridin-2-yl)(hydroxy)methyl)-6-(3,5-dimethylisoxazol-4-yl)-1H-benzo[d]imidazol-2(3H)-one

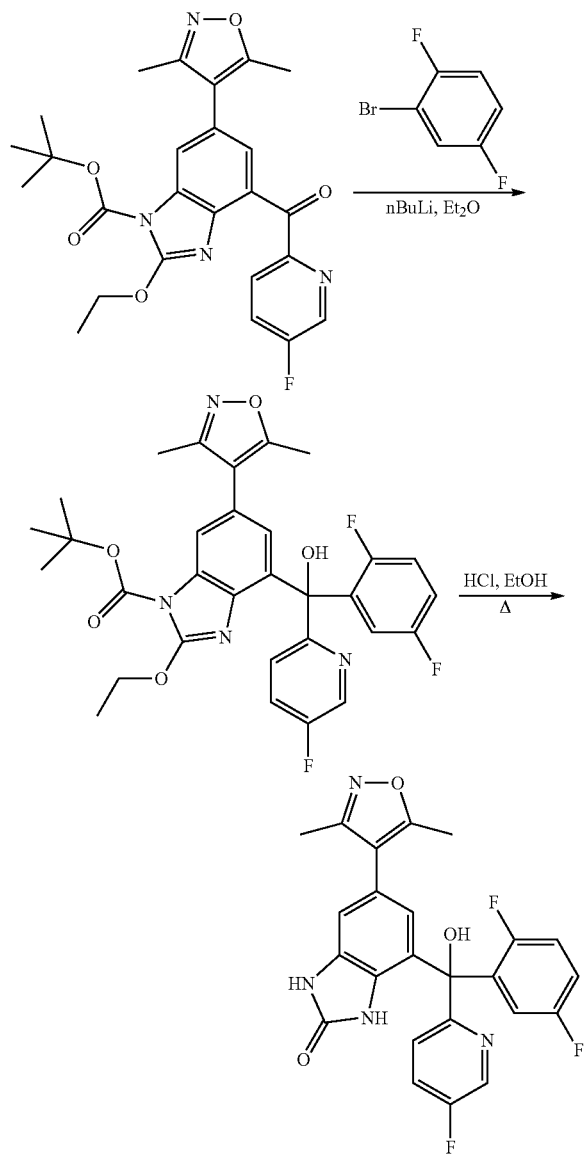

In a synthetic process following that described for Example 40, reaction of tert-butyl 6-(3,5-dimethylisoxazol-4-yl)-2-ethoxy-4-(5-fluoropicolinoyl)-1H-indole-1-carboxylate (50 mg, 0.13 mmol) with the organolithium species resulting from metal halogen exchange of 1-bromo-2,5-difluorobenzene in diethyl ether gave after purification of final material by reverse-phase HPLC (40-50% acetonitrile/water with 0.01% trifluoroacetic acid, Gemini C18 5μ) the trifluoroacetate salt of 4-((2,5-difluorophenyl)(5-fluoropyridin-2-yl)(hydroxy)methyl)-6-(3,5-dimethylisoxazol-4-yl)-1H-benzo[d]imidazol-2(3H)-one as a white solid.

C$_{24}$H$_{17}$F$_3$N$_4$O$_3$. 466.9 (M+H). $^1$H NMR (400 MHz, d$_6$-DMSO) δ 10.74 (s, 1H), 9.87 (s, 1H), 8.48 (m, 1H), 7.75 (m, 1H), 7.64 (m, 1H), 7.30 (s, 1H), 7.21-7.07 (m, 3H), 6.86 (s, 1H), 6.38 (s, 1H), 2.26 (s, 3H), 2.07 (s, 3H). $^{19}$F NMR (377 MHz, d$_6$-DMSO) δ −76, −114, −120, −130.

Example 42

6-(3,5-dimethylisoxazol-4-yl)-4-((5-fluoropyridin-2-yl)(hydroxy)(2,4,5-trifluorophenyl)methyl)-1H-benzo[d]imidazol-2(3H)-one

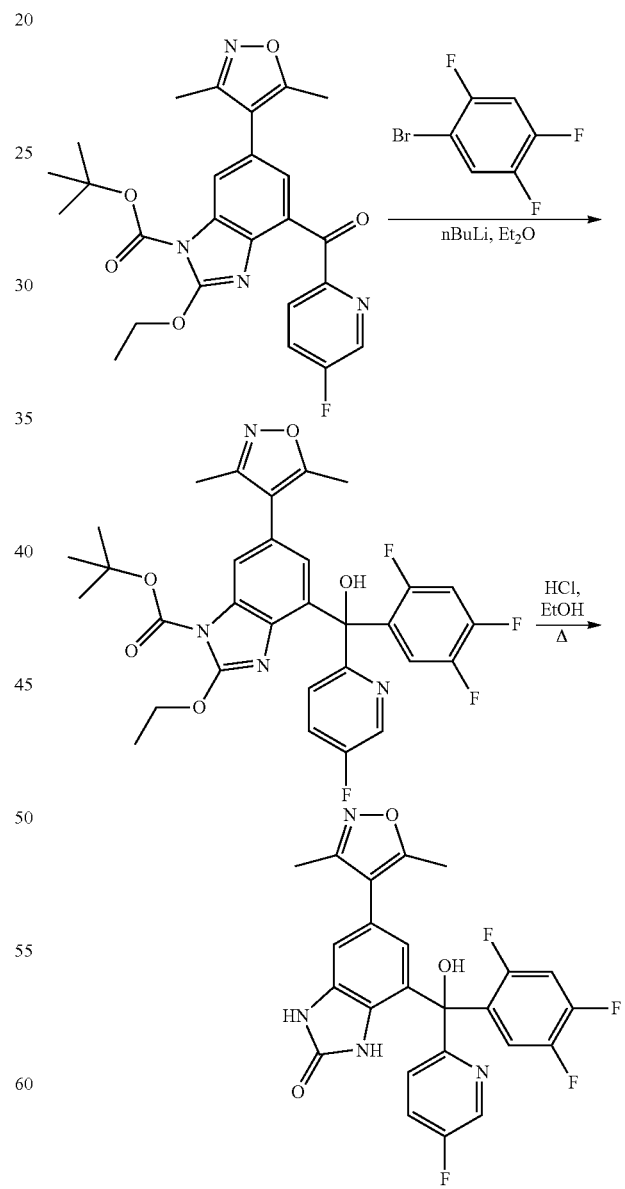

In a synthetic process following that described for Example 40, reaction of tert-butyl 6-(3,5-dimethylisoxazol-4-yl)-2- ethoxy-4-(5-fluoropicolinoyl)-1H-indole-1-carboxylate (50 mg, 0.13 mmol) with the organolithium species resulting from metal halogen exchange of 1-bromo-2,4,5-trifluorobenzene in diethyl ether gave, after purification of final material by reverse-phase HPLC (40-50% acetonitrile/water with 0.01% trifluoroacetic acid, Gemini C18 5μ), the trifluoroacetate salt of 6-(3,5-dimethylisoxazol-4-yl)-4-((5-fluoropyridin-2-yl)(hydroxy)(2,4,5-trifluorophenyl)methyl)-1H-benzo[d]imidazol-2(3H)-one as a white solid.

$C_{24}H_{16}F_4N_4O_3$. 485.12 (M+H). $^1$H NMR (400 MHz, $d_3$-acetonitrile), 8.69 (s, 1H), 8.49 (s, 1H), 7.59 (m, 1H), 7.13 (m, 1H), 6.98 (s, 1H), 6.52 (m, 1H), 2.29 (s, 3H), 2.13 (s, 3H). $^{19}$F NMR (377 MHz, $d_3$-acetonitrile) δ −77, −110, −137, −135, −145.

Example 43

6-(3,5-dimethylisoxazol-4-yl)-4-((5-fluoropyridin-2-yl)(hydroxy)(pyrazin-2-yl)methyl)-1H-benzo[d]imidazol-2(3H)-one

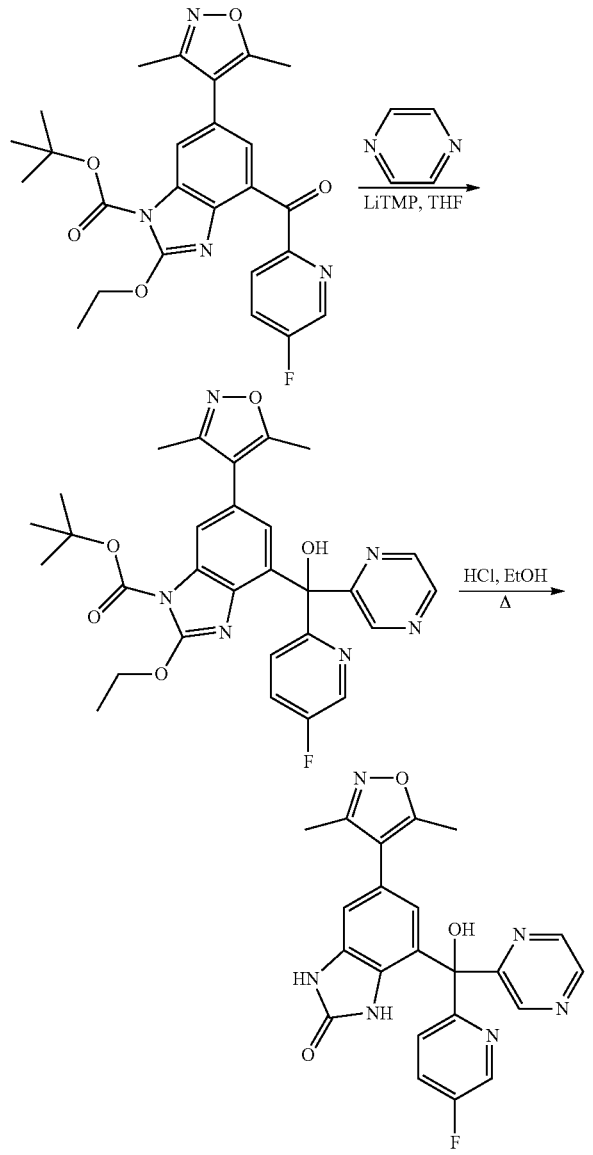

In a synthetic process following that described for Example 40, reaction of tert-butyl 6-(3,5-dimethylisoxazol-4-yl)-2-ethoxy-4-(5-fluoropicolinoyl)-1H-indole-1-carboxylate (50 mg, 0.13 mmol) with the organolithium species resulting from deprotonoation of pyrazine by LiTMP in THF (using the literature method described in *J. Org. Chem.* 1995, 60, 3781-3786.) Following final deprotection, the combined organics were washed with water (30 mL) and brine (30 mL), and dried over Na2SO4. Purification by flash chromatography (0-100% hexanes/ethyl acetate) gave 6-(3,5-dimethylisoxazol-4-yl)-4-((5-fluoropyridin-2-yl)(hydroxy)(pyrazin-2-yl)methyl)-1H-benzo[d]imidazol-2(3H)-one as a white solid.

C22H17FN6O3. 433.1 (M+H). 1H NMR (400 MHz, d3-acetonitrile), 8.88 (s, 1H), 8.56-8.44 (m, 3H), 7.72 (m, 1H), 7.61 (m, 1H), 6.97 (s, 1H), 6.57 (m, 1H), 2.29 (s, 3H), 2.13 (s, 3H). $^{19}$F NMR (377 MHz, $d_3$-acetonitrile) δ −130.

Example 44

6-(3,5-dimethylisoxazol-4-yl)-4-((5-fluoropyridin-2-yl)(hydroxy)(6-(trifluoromethyl)pyridin-2-yl)methyl)-1H-benzo[d]imidazol-2(3H)-one Step 1

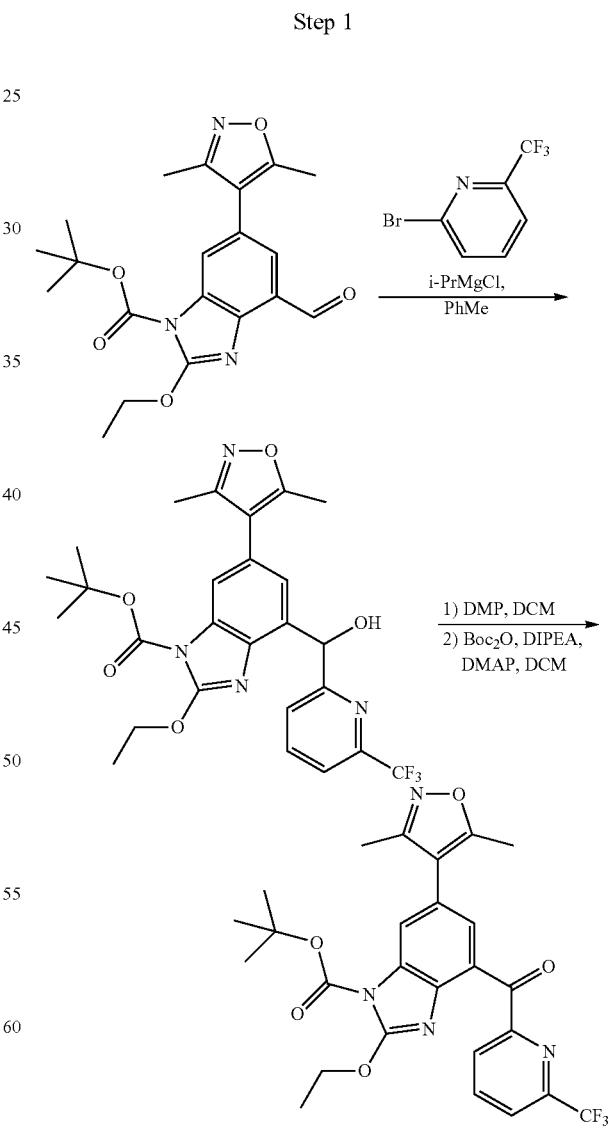

To isopropylmagnesium chloride (0.63 mL, 1.26 mmol, 2 M in THF) in toluene (1.4 mL) was added 2-bromo-5-trifluoromethylpyridine (300 mg, 1.6 mmol) in toluene (4 mL). After 3.5 hours, the Grignard solution (1.9 mL, 0.8 mmol) was added to tert-butyl 6-(3,5-dimethylisoxazol-4-yl)-2-ethoxy-4-formyl-1H-indole-1-carboxylate (100 mg, 0.26 mmol) in toluene (9 mL) at 0° C. and the mixture was allowed to warm to 20° C. After 16 hours, the reaction was quenched with saturated NH$_4$Cl$_{(aq)}$ (10 mL), extracted with ethyl acetate (3×10 mL), dried over Na$_2$SO$_4$, and concentrated in vacuo. The resulting unpurified product, 100 mg, was treated to oxidation in 10 mL DCM with Dess-Martin periodinane reagent (154.1 mg, 0.34 mmol). After 15 minutes, the reaction was quenched with saturated Na$_2$S$_2$O$_{3(aq)}$ (10 mL) and extracted with dichloromethane (3×10 mL). The combined organics were washed with water (30 mL) and brine (30 mL), and dried over Na$_2$SO$_4$. Purification by flash chromatography (0-50% ethyl acetate/hexane) afforded tert-butyl 6-(3,5-dimethylisoxazol-4-yl)-2-ethoxy-4-(6-(trifluoromethyl)picolinoyl)-1H-benzo[d]imidazole-1-carboxylate (30 mg, 23%) as an amber residue contaminated with unreacted aldehyde.

$C_{26}H_{25}F_3N_4O_5$: 531.0 (M+H).

Step 2

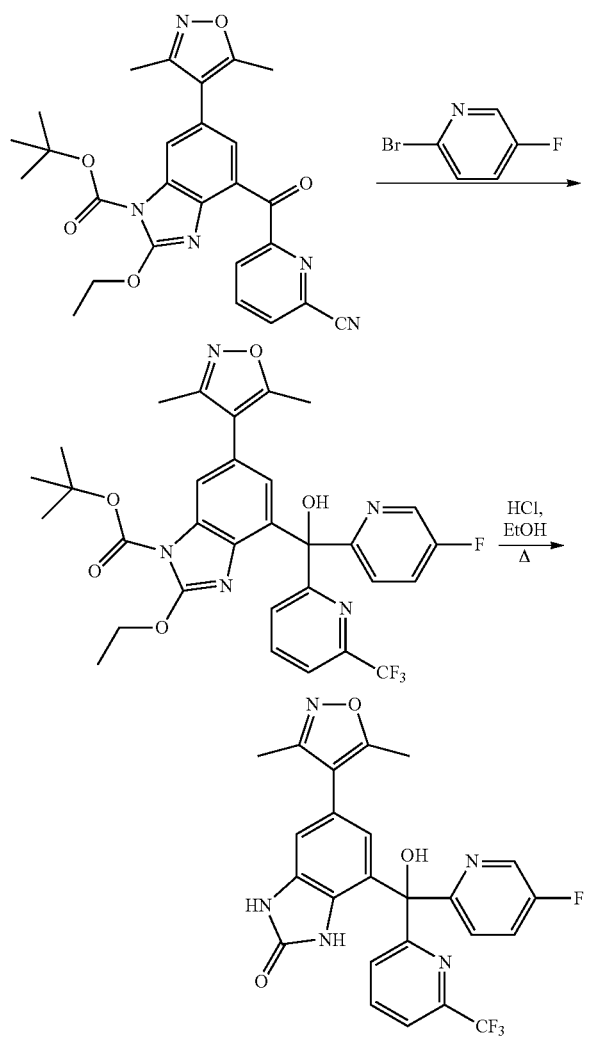

To isopropylmagnesium chloride (1.32 mL, 2.64 mmol, 2 M in THF) in toluene (4 mL) was added 2-bromo-5-fluoropyridine (388 mg, 2.05 mmol) in toluene (1 mL). After 3.5 hours the Grignard solution (1 mL, 0.65 mmol) was added to tert-butyl 6-(3,5-dimethylisoxazol-4-yl)-2 ethoxypicolinoyl-1H-benzo[d]imidazole-1-carboxylate (30 mg, 0.13 mmol) in toluene (6 mL) at 0° C. and the mixture was allowed to warm to 20° C. After 16 hours, the reaction was quenched with saturated NH$_4$Cl$_{(aq)}$ (10 mL), extracted with ethyl acetate (3×10 mL), dried over Na$_2$SO$_4$, and concentrated in vacuo. The resulting residue (100 mg) was dissolved in ethanol (3 mL) to which was added hydrochloric acid (0.2 mL, 0.8 mmol, 4 M in 1,4-dioxane). The mixture was heated to 70° C. for 0.75 hours and then concentrated in vacuo. Purification by reverse-phase HPLC (25-50% acetonitrile/water with 0.01% trifluoroacetic acid, Gemini C18 5μ) afforded the TFA salt of 6-(3,5-dimethylisoxazol-4-yl)-4-((5-fluoropyridin-2-yl)(hydroxy)(6-(trifluoromethyl)pyridin-2-yl)methyl)-1H-benzo[d]imidazol-2(3H)-one as a light yellow solid.

$C_{24}H_{17}F_4N_5O_3$. 500.12 (M+H). 1H NMR (400 MHz, d$_3$-acetonitrile) δ 8.82 (s, 1H), 8.76 (s, 1H), 8.45 (d, J=2.7 Hz, 1H), 8.05 (m, 1H), 7.86 (m, 1H), 7.75 (m, 2H), 7.62 (m, 1H), 6.93 (s, 1H), 6.58 (s, 1H), 6.93 (s, 1H), 6.25 (s, 1H), 2.31 (s, 3H), 2.16 (s, 3H). $^{19}$F NMR (377 MHz, d$_3$-acetonitrile) δ –68, –76, –131.

Example 45 tert-Butyl 6-(3,5-dimethylisoxazol-4-yl)-2-ethoxy-4-(hydroxy(5-(trifluoromethyl)pyridin-2-yl)methyl)-1H-benzo[d]imidazole-1-carboxylate

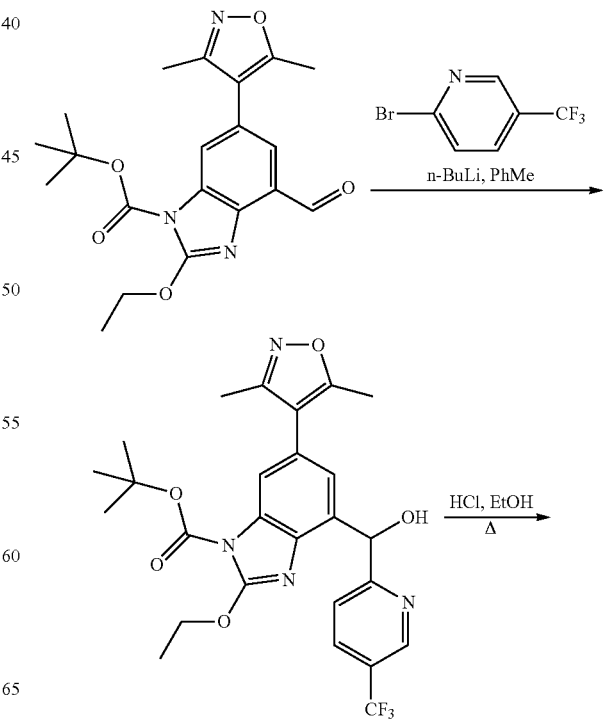

-continued

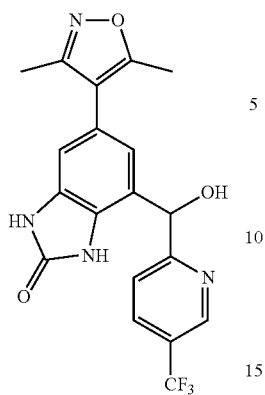

To 2-bromo-5-trifluoromethylpyridine (200 mg, 0.89 mmol) in THF (4 mL) at −78° C. was added n-butyllithium (0.36 mL, 0.9 mmol, 2.5M in hexanes). After 15 minutes, tert-butyl 6-(3,5-dimethylisoxazol-4-yl)-2-ethoxy-4-formyl-1H-indole-1-carboxylate (60 mg, 0.16 mmol) in THF (1 mL) was added drop-wise to the reaction. After 60 minutes, the reaction was warmed, quenched with water (10 mL), extracted with ethyl acetate (3×10 mL), dried over $Na_2SO_4$, and concentrated in vacuo. Purification of the resulting residue by flash column (0-50% ethyl acetate/hexanes) afforded 30 mg tert-butyl 6-(3,5-dimethylisoxazol-4-yl)-2-ethoxy-4-(hydroxy(5-(trifluoromethyl)pyridin-2-yl)methyl)-1H-benzo[d]imidazole-1-carboxylate that was submitted to directly to final deprotection.

30 mg (0.056 mmol) tert-butyl 6-(3,5-dimethylisoxazol-4-yl)-2-ethoxy-4-(hydroxy(5-(trifluoromethyl)pyridin-2-yl) methyl)-1H-benzo[d]imidazole-1-carboxylate was dissolved in 3 mL ethanol, and hydrochloric acid (0.1 mL, 0.4 mmol, 4 M in 1,4-dioxane) was added. The mixture was heated to 70° C. for 0.5 hours and then concentrated in vacuo. Purification by reverse-phase HPLC (25-50% acetonitrile/water with 0.01% trifluoroacetic acid, Gemini C18 5µ) afforded the TFA salt of 6-(3,5-dimethylisoxazol-4-yl)-4-(hydroxy(5-(trifluoromethyl)pyridin-2-yl)methyl)-1H-benzo[d]imidazol-2 (3H)-one as a light yellow solid.

$C_{19}H_{15}F_3N_4O_3$. 405.1 (M+H). 1H NMR (400 MHz, d3-acetonitrile) δ 8.91 (s, 1H), 8.76 (s, 1H), 8.3 (s, 1H), 7.98 (d, J=8.1, 1H), 7.70 (d, J=8.1, 1H), 6.71 (m, 2H), 5.98 (s, 1H), 2.24 (s, 3H), 2.08 (s, 3H). $^{19}F$ NMR (376 MHz, $d_3$-acetonitrile) δ −63.45, −74.7.

Example 46

6-(3,5-dimethylisoxazol-4-yl)-4-(hydroxy(pyrrolidin-2-yl)methyl)-1H-benzo[d]imidazol-2(3H)-one

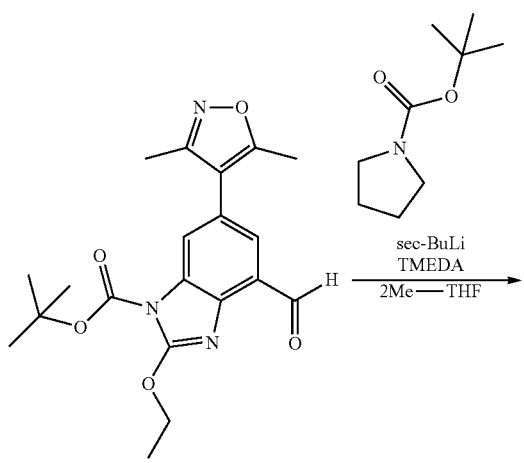

-continued

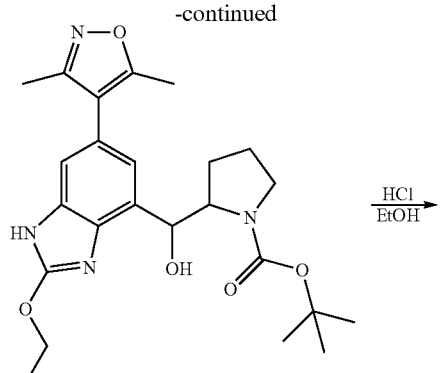

N-Boc-pyrrolidine (150 mg, 0.39 mmol) and TMEDA (0.2 mL, 158 mg, 1.36 mmol) was dissolved in dry MeTHF (2.6 mL) under Ar and cooled to −78° C. Sec-BuLi (1.4M, 0.97 mL, 1.36 mmol) was added dropwise and the reaction was allowed to stir at −78° C. for 40 mins. tert-butyl 6-(3,5-dimethylisoxazol-4-yl)-2-ethoxy-4-formyl-1H-benzo[d] imidazole-1-carboxylate (150 mg, 0.39 mmol) was dissolved in MeTHF (0.5 mL) and added dropwise via syringe to the reaction and allowed to stir at −78° C. for 10 minutes. The reaction was quenched with water and extracted three times with EtOAc, combined organic layers were washed once with brine, concentrated, and purified by reverse-phase HPLC to give tert-butyl 2-((6-(3,5-dimethylisoxazol-4-yl)-2-ethoxy-1H-benzo[d]imidazol-4-yl)(hydroxy)methyl)pyrrolidine-1-carboxylate (53 mg, 30%) as a white powder. The solid (50 mg, 0.11 mmol) was dissolved in EtOH (5 mL) and HCl (1 mL) and heated for 12 hours at 65° C. The reaction was cooled and concentrated to afford the desired product as a white powder.

$C_{17}H_{20}N_4O_3$ 329.3 (M+1). $^1H$ NMR (400 MHz, DMSO-d6) δ 10.93 (s, 2H), 10.83 (d, J=11.8 Hz, 2H), 9.07 (s, 2H), 8.47 (s, 1H), 7.03 (d, J=1.5 Hz, 1H), 6.99 (s, 1H), 6.86 (s, 1H), 6.84 (d, J=1.6 Hz, 1H), 6.38 (d, J=4.0 Hz, 1H), 6.10 (d, J=4.2 Hz, 1H), 5.28 (s, 1H), 4.98 (s, 1H), 3.70 (d, J=7.6 Hz, 1H), 3.25-3.07 (m, 4H), 2.39 (s, 3H), 2.38 (s, 2H), 2.21 (s, 3H), 2.20 (s, 2H), 1.96 (q, J=7.4 Hz, 3H), 1.86 (s, 2H), 1.77 (s, 2H), 1.67 (s, 1H). (1:1.4 mixture of diastereomers)

Example 47
4-(3-cyclopropyl-1-hydroxy-1-(pyridin-2-yl)propyl)-6-(3,5-dimethylisoxazol-4-yl)-1H-benzo[d]imidazol-2(3H)-one

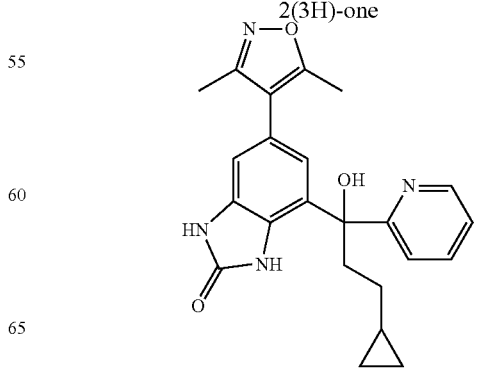

Magnesium metal (39.0 mg, 2.0 mmol) and iodine (one crystal) was taken up in dry diethyl ether (1.2 mL) and (2-bromoethyl)cyclopropane (200 mg, 1.3 mmol) was added dropwise until iodine color faded. The remainder was then added dropwise over 15 minutes to maintain a gentle reflux and then cooled to 0° C. (2-cyclopropylethyl)magnesium bromide (1.1 M, 0.38 mL, 0.41 mmol) was added to a cooled (0° C.) solution of (6-(3,5-dimethylisoxazol-4-yl)-2-ethoxy-1H-benzo[d]imidazol-4-yl)(pyridin-2-yl)methanone (50 mg, 0.14 mmol) in dry THF (1.0 mL) under argon and allowed to stir for 10 minutes. The reaction was quenched with water, extracted three times with EtOAc, and combined organic layers were concentrated and purified by reverse-phase HPLC to give 3-cyclopropyl-1-(6-(3,5-dimethylisoxazol-4-yl)-2-ethoxy-1H-benzo[d]imidazol-4-yl)-1-(pyridin-2-yl)propan-1-ol intermediate. The intermediate was taken up in EtOH (1.5 mL) and 0.2 mL concentrated HCl and heated to 65° C. for 2 hours and concentrated to afford the desired product as a white powder.

$C_{23}H_{24}N_4O_3$ 405.2 (M+1). $^1$H NMR (400 MHz, Methanol-d4) δ 8.73 (ddd, J=5.8, 1.6, 0.7 Hz, 1H), 8.43 (td, J=8.0, 1.6 Hz, 1H), 8.09 (dt, J=8.2, 1.0 Hz, 1H), 7.87 (ddd, J=7.4, 5.7, 1.2 Hz, 1H), 7.13 (d, J=1.5 Hz, 1H), 6.96 (d, J=1.4 Hz, 1H), 2.68 (ddd, J=10.6, 8.6, 5.1 Hz, 2H), 2.40 (s, 3H), 2.23 (s, 3H), 1.37 (ddd, J=11.8, 7.2, 4.7 Hz, 1H), 1.26-1.13 (m, 1H), 0.76-0.66 (m, 1H), 0.43 (ddt, J=8.7, 5.4, 2.4 Hz, 2H), 0.06--0.05 (m, 2H).

Example 48

6-(3,5-dimethylisoxazol-4-yl)-4-(2-ethyl-1-hydroxy-1-(pyridin-2-yl)butyl)-1H-benzo[d]imidazol-2(3H)-one

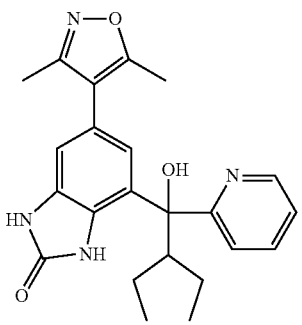 [SMILES: CCC(CC)C(O)(c1ccccn1)c1cc(-c2c(C)noc2C)cc2[nH]c(=O)[nH]c12]

(6-(3,5-dimethylisoxazol-4-yl)-2-ethoxy-1H-benzo[d]imidazol-4-yl)(pyridin-2-yl)methanone (50 mg, 0.14 mmol) was dissolved in dry THF (1.4 mL) and cooled to 0° C. Pentan-3-ylmagnesium bromide (2.0 M, 0.21 mL, 0.41 mmol) was added dropwise and the reaction was allowed to stir for 10 mins and then quenched with water. Reaction was extracted three times with EtOAc and combined organic layers were washed once with water, concentrated, and purified by reverse-phase HPLC to give 1-(6-(3,5-dimethylisoxazol-4-yl)-2-ethoxy-1H-benzo[d]imidazol-4-yl)-2-ethyl-1-(pyridin-2-yl)butan-1-ol intermediate. The intermediate was taken up in EtOH (1.5 mL) and 0.2 mL concentrated HCl and heated to 65° C. for 2 hours and concentrated to afford the desired product as a white powder.

$C_{23}H_{26}N_4O_3$ 407.3 (M+1). $^1$H NMR (400 MHz, Methanol-d4) δ 8.78 (d, J=5.6 Hz, 1H), 8.54 (t, J=7.6 Hz, 1H), 8.23 (d, J=7.8 Hz, 1H), 7.98 (t, J=6.4 Hz, 1H), 7.21 (d, J=1.2 Hz, 1H), 6.97 (d, J=1.1 Hz, 1H), 2.71 (s, 1H), 2.41 (s, 3H), 2.25 (s, 3H), 1.88-1.76 (m, 1H), 1.59-1.29 (m, 3H), 1.09 (t, J=7.4 Hz, 3H), 0.85 (t, J=7.5 Hz, 3H).

Example 49

4-((2,6-difluorophenyl)(hydroxy)(pyrazin-2-yl)methyl)-6-(3,5-dimethylisoxazol-4-yl)-1H-benzo[d]imidazol-2(3H)-one

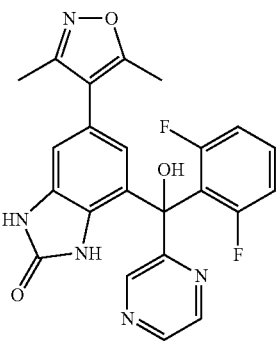

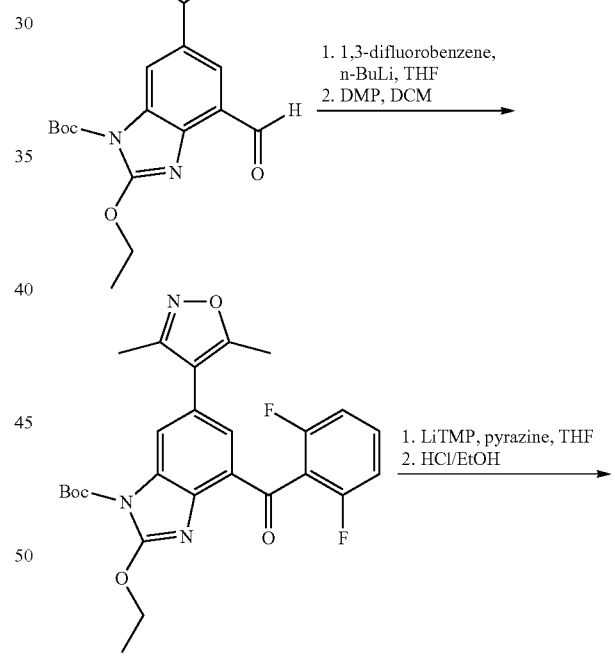

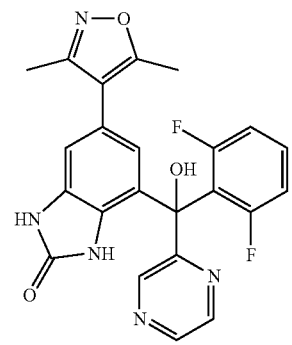 [SMILES: Cc1noc(C)c1-c1cc(C(O)(c2cccnn2)c2c(F)cccc2F)c2[nH]c(=O)[nH]c2c1]

n-BuLi (0.58 mL, 0.93 mmol) was added dropwise to a solution of 1,3-difluorobenzene (0.102 mL, 0.1 mmol) in THF (5 mL) cooled to −78° C. and allowed to stir for 1 hour. tert-butyl 6-(3,5-dimethylisoxazol-4-yl)-2-ethoxy-4-formyl-1H-benzo[d]imidazole-1-carboxylate (200 mg, 0.52 mmol) in THF was added and the reaction was allowed to stir for 5 mins at −78° C., quenched with ammonium chloride, extracted with EtOAc and concentrated. The crude was then taken up in DCM (2 mL), Des-Martin periodinane (290 mg, 0.78 mmol) was added and the reaction was allowed to stir for 15 mins. The reaction was quenched with sat. Na2S2O3, extracted with EtOAc, concentrated and purified by silica gel chromatography to give tert-butyl 4-(2,6-difluorobenzoyl)-6-(3,5-dimethylisoxazol-4-yl)-2-ethoxy-1H-benzo[d]imidazole-1-carboxylate.

n-BuLi (0.21 mL, 0.33 mmol) was added dropwise to a solution of 2,2,6,6-tetramethylpiperidine (0.06 mL, 0.33 mmol) in THF (0.7 mL) at 0° C. and was allowed to stir for 5 minutes. Pyrazine (24 mg, 0.3 mmol) in THF (0.4 mL) was added and the reaction was stirred for an additional 5 minutes and then cooled to −78° C. tert-butyl 4-(2,6-difluorobenzoyl)-6-(3,5-dimethylisoxazol-4-yl)-2-ethoxy-1H-benzo[d]imidazole-1-carboxylate (50 mg, 0.10 mmol) in THF (0.4 mL) was added, the solution was allowed to stir for 5 minutes and then quenched with water. Solution was extracted three times with EtOAc, washed once with brine and concentrated. Crude was purified by reverse-phase HPLC and then taken up in EtOH (3 mL) and HCl (0.1 mL) and heated to 65° C. for 2 hours. Reaction was cooled and concentrated to afford desired product as a pale brown powder.

$C_{25}H_{21}F_2N_5O_3$ 478.5 (M+1). $^1$H NMR (400 MHz, Methanol-d4) δ 9.02 (s, 1H), 8.57 (d, J=26.1 Hz, 2H), 7.44 (tt, J=8.3, 5.9 Hz, 1H), 7.02-6.89 (m, 4H), 2.33 (s, 3H), 2.16 (s, 3H).

Example 50

4-((2,6-difluorophenyl)(hydroxy)(pyridazin-3-yl)methyl)-6-(3,5-dimethylisoxazol-4-yl)-1H-benzo[d]imidazol-2(3H)-one The following compound was made in a similar fashion as that of Example 49, but using pyridazine instead of pyrazine.

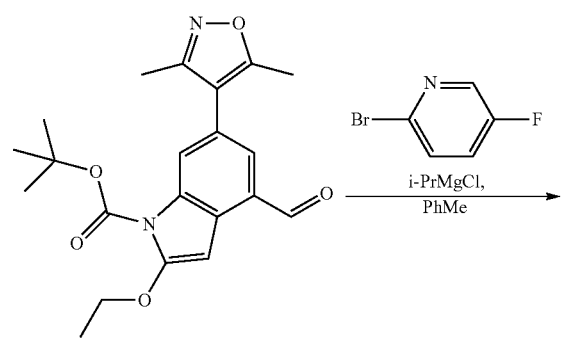

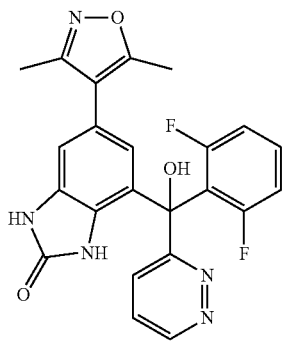

$C_{25}H_{21}F_2N_5O_3$ 478.5 (M+1). $^1$H NMR (400 MHz, Methanol-d4) δ 9.48 (s, 1H), 8.88-8.81 (m, 1H), 8.42 (dd, J=8.7, 5.0 Hz, 1H), 7.54 (tt, J=8.4, 6.1 Hz, 1H), 7.05 (dd, J=10.6, 8.6 Hz, 2H), 6.98 (d, J=1.5 Hz, 1H), 6.91-6.87 (m, 1H), 2.32 (s, 3H), 2.15 (s, 3H).

Example 51

Example 52, and

Example 53

6-(3,5-dimethylisoxazol-4-yl)-4-((5-fluoropyridin-2-yl)(hydroxy)methyl)-1H-benzo[d]imidazol-2(3H)-one 6-(3,5-dimethylisoxazol-4-yl)-4-((5-fluoropyridin-2-yl)(hydroxy)(2,4,6-trifluorophenyl)methyl)-1H-benzo[d]imidazol-2(3H)-one and 6-(3,5-dimethylisoxazol-4-yl)-4-(fluorobis(5-fluoropyridin-2-yl)methyl)-1H-benzo[d]imidazol-2(3H)-one

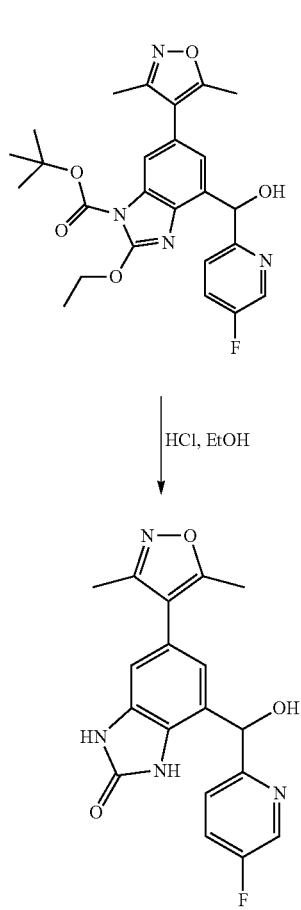
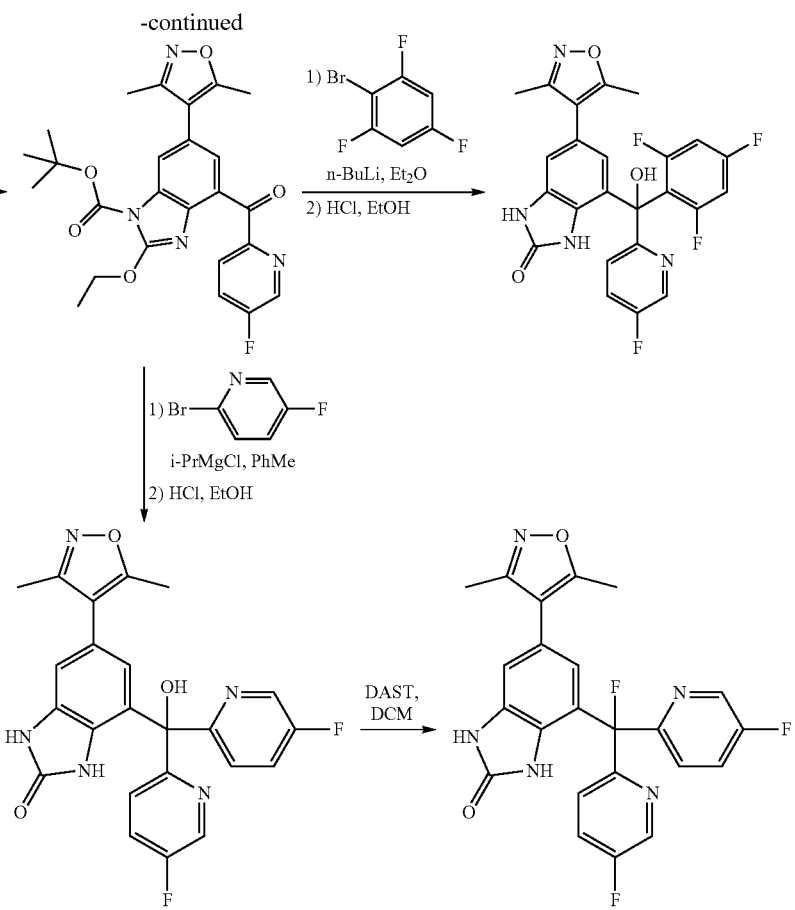

To isopropylmagnesium chloride (0.63 mL, 1.26 mmol, 2 M in tetrahydrofuran) in toluene (1.4 mL) was added 2-bromo-5-fluoropyridine (184.6 mg, 1.05 mmol) in toluene (0.48 mL). After 3.5 hours, the Grignard solution (1.9 mL, 0.65 mmol) was added to tert-butyl 6-(3,5-dimethylisoxazol-4-yl)-2-ethoxy-4-formyl-1H-indole-1-carboxylate (62.2 mg, 0.16 mmol) in tetrahydrofuran (9 mL) at 0° C. and the mixture was allowed to warm to 20° C. After 16 hours, the reaction was quenched with saturated NH4Cl(aq) (10 mL), extracted with ethyl acetate (3×10 mL), dried over Na2SO4, and concentrated in vacuo. Purification by flash chromatography (0-50% ethyl acetate/hexane) afforded tert-butyl 6-(3,5-dimethylisoxazol-4-yl)-2-ethoxy-4-((5-fluoropyridin-2-yl)(hydroxy)methyl)-1H-benzo[d]imidazole-1-carboxylate as a yellow residue.

To tert-butyl 6-(3,5-dimethylisoxazol-4-yl)-2-ethoxy-4-((5-fluoropyridin-2-yl)(hydroxy)methyl)-1H-benzo[d]imidazole-1-carboxylate (41.2 mg, 0.09 mmol) in ethanol (5 mL) was added hydrochloric acid (0.66 mL, 2.64 mmol, 4 M in 1,4-dioxane). The mixture was heated to 60° C. for 6 hours and then concentrated in vacuo. Purification by reverse-phase HPLC (25-50% acetonitrile/water with 0.01% trifluoroacetic acid, Gemini C18 5µ) afforded 6-(3,5-dimethylisoxazol-4-yl)-4-((5-fluoropyridin-2-yl)(hydroxy)methyl)-1H-benzo[d]imidazol-2(3H)-one as a white solid.

$C_{18}H_{15}FN_4O_3$. 335.03 (M+1). $^1H$ NMR (400 MHz, DMSO-$d_6$) δ 10.73 (s, 1H), 10.70 (s, 1H), 8.45 (d, J=2.9 Hz, 1H), 7.80 (dd, J=8.7, 4.7 Hz, 1H), 7.73 (td, J=8.8, 2.9 Hz, 1H), 6.81 (d, J=1.6 Hz, 1H), 6.74 (d, J=1.5 Hz, 1H), 6.03 (s, 1H), 2.31 (s, 3H), 2.12 (s, 3H). 19F NMR (376 MHz, DMSO-d6) δ −76.42, −131.97.

To tert-butyl 6-(3,5-dimethylisoxazol-4-yl)-2-ethoxy-4-((5-fluoropyridin-2-yl)(hydroxy)methyl)-1H-benzo[d]imidazole-1-carboxylate (57 mg, 0.12 mmol) in dichloromethane (6 mL) was added Dess-Martin periodinane (154.1 mg, 0.34 mmol). After 15 minutes, the reaction was quenched with saturated Na2S2O3(aq) (10 mL) and extracted with dichloromethane (3×10 mL). The combined organics were washed with water (30 mL) and brine (30 mL), and dried over Na2SO4. To the crude solution was added N,N-diisopropylethylamine (0.05 mL, 0.26 mmol), 4-(dimethylamino)pyridine (6.8 mg, 0.05 mmol), and di-tert-butyl dicarbonate (120.9 mg). After 90 minutes, the reaction mixture was washed with water (2×30 mL), dried over $Na_2SO_4$, and concentrated in vacuo. Purification by flash chromatography (0-50% ethyl acetate/hexane) afforded tert-butyl 6-(3,5-dimethylisoxazol-4-yl)-2-ethoxy-4-(5-fluoropicolinoyl)-1H-benzo[d]imidazole-1-carboxylate as an amber residue.

To 1-bromo-2,4,6-trifluorobenzene (0.02 ml, 0.16 mmol) in diethyl ether (0.52 mL) at −78° C. was added n-butyllithium (0.12 mL, 0.18 mmol, 1.6 M in hexanes). After 30 minutes, tert-butyl 6-(3,5-dimethylisoxazol-4-yl)-2-ethoxy-4-(5-fluoropicolinoyl)-1H-benzo[d]imidazole-1-carboxylate (50 mg, 0.10 mmol) in diethyl ether (1 mL) was added dropwise to the reaction. After 60 minutes, the reaction was warmed, quenched with saturated $NH_4Cl_{(aq)}$ (10 mL), extracted with ethyl acetate (3×10 mL), dried over $Na_2SO_4$, and concentrated in vacuo. To the crude residue in ethanol (3.5 mL) was added hydrochloric acid (0.35 mL, 1.4 mmol, 4 M in 1,4-dioxane) and the mixture was heated to 70° C. in a microwave reactor for 45 minutes. Purification by reverse-phase HPLC (40-50% acetonitrile/water with 0.01% trifluoroacetic acid, Gemini C18 5μ) afforded 6-(3,5-dimethylisoxazol-4-yl)-4-((5-fluoropyridin-2-yl)(hydroxy)(2,4,6-trifluorophenyl)methyl)-1H-benzo[d]imidazol-2(3H)-one as a white solid.

$C_{24}H_{16}F_4N_4O_3$. 485.12 (M+1). $^1$H NMR (400 MHz, chloroform-d) δ 9.40 (s, 1H), 9.18 (s, 1H), 8.48 (d, J=2.7 Hz, 1H), 7.40 (td, J=8.3, 2.8 Hz, 1H), 7.15 (dd, J=8.8, 4.2 Hz, 1H), 6.99 (s, 1H), 6.68-6.56 (m, 3H), 2.31 (s, 3H), 2.16 (s, 3H). 19F NMR (377 MHz, chloroform-d) δ −76.51, −102.54--103.06 (m), −106.62 (p, J=7.9 Hz), −127.18 (dd, J=7.3, 3.8 Hz).

To isopropylmagnesium chloride (0.34 ml, 0.57 mmol, 2 M in tetrahydrofuran) in toluene (0.26 mL) was added 2-bromo-5-fluoropyridine (100 mg, 0.57 mmol) in toluene (0.78 mL). After 4 hours, the Grignard solution (1.2 mL, 0.47 mmol) was added to tert-butyl dimethylisoxazol-4-yl)-2-ethoxy-4-((5-fluoropyridin-2-yl)(hydroxy)methyl)-1H-benzo[d]imidazole-1-carboxylate (57 mg, 0.12 mmol) in tetrahydrofuran (6 mL) at 0° C. After 60 minutes, the reaction was quenched with saturated $NH_4Cl_{(aq)}$ (10 mL), extracted with ethyl acetate (3×10 mL), dried over $Na_2SO_4$, and concentrated in vacuo. To the crude dissolved in ethanol (2.5 mL) was added hydrochloric acid (0.29 mL, 1.17 mmol, 4 M in 1,4-dioxane) and the mixture was heated to 70° C. in a microwave reactor for 45 minutes. Purification by reverse-phase HPLC (30-45% acetonitrile/water with 0.01% trifluoroacetic acid, Gemini C18 5μ) afforded 4-(bis(5-fluoropyridin-2-yl)(hydroxy)methyl)-6-(3,5-dimethylisoxazol-4-yl)-1H-benzo[d]imidazol-2(3H)-one as a white solid.

$C_{23}H_{17}F_2N_5O_3$. 450.11 (M+1). $^1$H NMR (400 MHz, DMSO-$d_6$) δ 10.72 (s, 1H), 9.75 (s, 1H), 8.52-8.48 (m, 2H), 7.74 (td, J=8.8, 2.9 Hz, 2H), 7.63 (dd, J=8.9, 4.7 Hz, 2H), 6.84 (d, J=1.2 Hz, 1H), 6.45 (d, J=1.3 Hz, 1H), 2.27 (s, 3H), 2.08 (s, 3H). $^{19}$F NMR (376 MHz, DMSO-$d_6$) δ −75.01, −130.07 (dd, J=8.8, 4.4 Hz).

To 4-(bis(5-fluoropyridin-2-yl)(hydroxy)methyl)-6-(3,5-dimethylisoxazol-4-yl)-1H-benzo[d]imidazol-2(3H)-one (10.4 mg, 0.02 mmol) in dichloromethane (2.3 mL) added (diethylamino)sulfur trifluoride (9.15 μl, 0.07 mmol) and stirred for 60 minutes before adding more (diethylamino)sulfur trifluoride (0.01 ml, 0.07 mmol). After 60 minutes from the second addition, the reaction was poured into saturated $NaHCO_{3(aq)}$ (5 mL), the layers were separated, and the aqueous was extracted with dichloromethane (2×5 mL). The combined organics were dried over $Na_2SO_4$ and concentrated in vacuo. Purification by reverse-phase HPLC (25-75% acetonitrile/water with 0.01% trifluoroacetic acid, Gemini C18 5μ) afforded 6-(3,5-dimethylisoxazol-4-yl)-4-(fluorobis(5-fluoropyridin-2-yl)methyl)-1H-benzo[d]imidazol-2(3H)-one as an off-white solid.

$C_{23}H_{16}F_3N_5O_2$. 452.05 (M+1). $^1$H NMR (400 MHz, DMSO-$d_6$) δ 10.85 (s, 1H), 10.35 (s, 1H), 8.55 (d, J=2.9 Hz, 2H), 7.82 (td, J=8.6, 2.9 Hz, 2H), 7.64 (dd, J=8.8, 4.4 Hz, 2H), 6.92 (s, 1H), 6.40 (s, 1H), 2.27 (s, 3H), 2.07 (s, 3H). $^{19}$F NMR (376 MHz, DMSO-$d_6$) δ −74.14, −127.97 (dt, J=8.3, 4.0 Hz), −136.81.

Example 54

4-((5-chloropyridin-2-yl)(hydroxy)(pyridin-2-yl)methyl)-6-(3,5-dimethylisoxazol-4-yl)-1H-benzo[d]imidazol-2(3H)-one

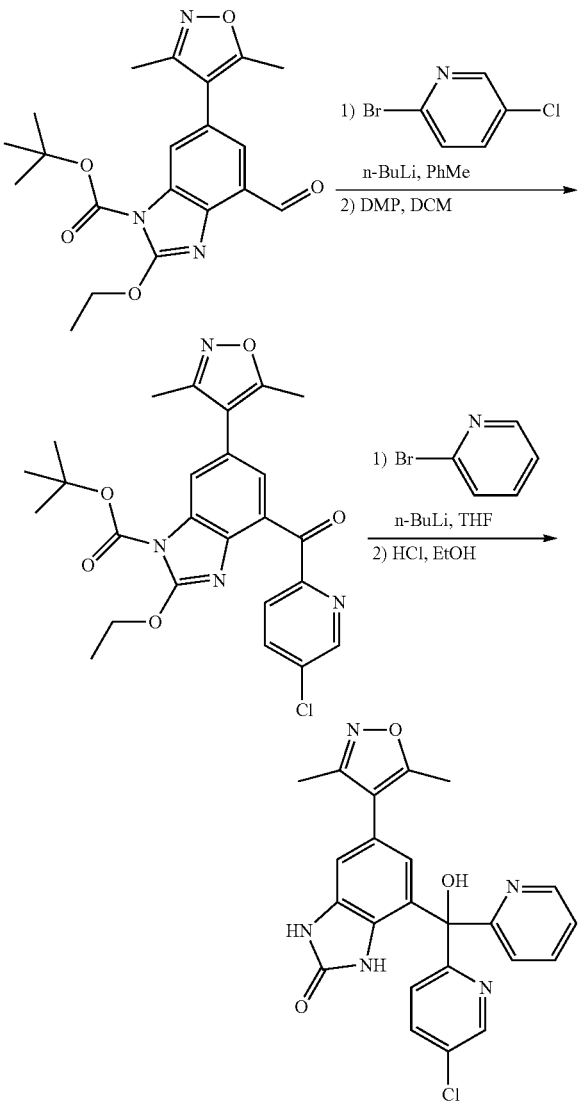

To 2-bromo-5-chloropyridine (55.42 mg, 0.29 mmol) in toluene (1 mL) at −78° C. was added n-butyllithium (0.41 mL, 0.65 mmol, 1.6 M in tetrahydrofuran). After 60 minutes, tert-butyl 6-(3,5-dimethylisoxazol-4-yl)-2-ethoxy-4-formyl-1H-indole-1-carboxylate (100 mg, 0.26 mmol) in toluene (0.3 mL) was added drop-wise to the reaction. After 60 minutes, the reaction was warmed, quenched with saturated $NH_4Cl_{(aq)}$ (10 mL), extracted with ethyl acetate (3×10 mL), dried over $Na_2SO_4$, and concentrated in vacuo. The crude material was dissolved in dichloromethane (6 mL) and Dess-Martin periodinane (143.06 mg, 0.34 mmol) was added. After 10 minutes, the reaction was quenched with saturated $Na_2S_2O_{3(aq)}$ (10 mL) and extracted with dichloromethane (3×10 mL). The combined organics were washed with water (30 mL) and brine (30 mL), dried over $Na_2SO_4$, and concentrated in vacuo. Purification by flash chromatography (0-50% ethyl acetate/hexanes) afforded tert-butyl 4-(5-chloropicolinoyl)-6-(3,5-dimethylisoxazol-4-yl)-2-ethoxy-1H-benzo[d]imidazole-1-carboxylate as an yellow residue.

To 2-bromopyridine (0.02 ml, 0.2 mmol) in tetrahydrofuran (4 mL) at −78° C. was added n-butyllithium (0.15 mL, 0.24 mmol, 1.6 M in hexanes). After 30 minutes, tert-butyl 4-(5-chloropicolinoyl)-6-(3,5-dimethylisoxazol-4-yl)-2-ethoxy-1H-benzo[d]imidazole-1-carboxylate (33 mg, 0.07 mmol) in tetrahydrofuran (1 mL) was added drop-wise to the reaction. After 30 minutes, the reaction was warmed, quenched with saturated $NH_4Cl_{(aq)}$ (10 mL), extracted with ethyl acetate (3×10 mL), dried over $Na_2SO_4$, and concentrated in vacuo. To the crude residue in ethanol (3 mL) was added hydrochloric acid (0.17 mL, 0.66 mmol, 4 M in 1,4-dioxane) and the mixture was heated to 70° C. in a microwave reactor for 45 minutes. Purification by reverse-phase HPLC (23-40% acetonitrile/water with 0.01% trifluoroacetic acid, Gemini C18 5μ) afforded 4-((5-chloropyridin-2-yl)(hydroxy)(pyridin-2-yl)methyl)-6-(3,5-dimethylisoxazol-4-yl)-1H-benzo[d]imidazol-2(3H)-one as an off-white solid.

$C_{23}H_{18}ClN_5O_3$. 448.22 (M+1). $^1$H NMR (400 MHz, DMSO-$d_6$) δ 10.78 (s, 1H), 9.90 (s, 1H), 8.62-8.53 (m, 2H), 8.04-7.96 (m, 2H), 7.66 (dd, J=8.2, 5.2 Hz, 2H), 7.53-7.45 (m, 1H), 6.87 (d, J=1.1 Hz, 1H), 6.44 (d, J=1.6 Hz, 1H), 2.27 (s, 3H), 2.07 (s, 3H).

Example 55

4-(bis(5-chloropyridin-2-yl)(hydroxy)methyl)-6-(3,5-dimethylisoxazol-4-yl)-1H-benzo[d]imidazol-2(3H)-one The following analog was prepared in the same fashion as 4-((5-chloropyridin-2-yl)(hydroxy)(pyridin-2-yl)methyl)-6-(3,5-dimethylisoxazol-4-yl)-1H-benzo[d]imidazol-2(3H)-one by substituting 2-bromo-5-chloropyridine for 2-bromopyridine.

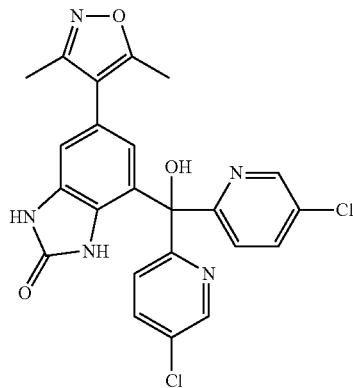 [SMILES: Cc1noc(C)c1-c1cc(C(O)(c2ccc(Cl)cn2)c2ccc(Cl)cn2)c2[nH]c(=O)[nH]c2c1]

4-(bis(5-chloropyridin-2-yl)(hydroxy)methyl)-6-(3,5-dimethylisoxazol-4-yl)-1H-benzo[d]imidazol-2(3H)-one as an off-white solid.

$C_{23}H_{17}Cl_2N_5O_3$. 482.29 (M+1). $^1$H NMR (400 MHz, DMSO-$d_6$) δ 10.81 (s, 1H), 9.85 (s, 1H), 8.59-8.52 (m, 2H), 8.48 (d, J=3.3 Hz, 1H), 8.01 (dd, J=8.3, 2.5 Hz, 1H), 7.77 (d, J=8.6 Hz, 1H), 7.18 (d, J=5.0 Hz, 1H), 7.06 (s, 1H), 6.88 (d, J=1.1 Hz, 1H), 6.34 (d, J=1.5 Hz, 1H), 2.25 (s, 3H), 2.05 (s, 3H).

Example 56

6-(3,5-dimethylisoxazol-4-yl)-4-(hydroxy(pyrazin-2-yl)(2,4,6-trifluorophenyl)methyl)-1H-benzo[d]imidazol-2(3H)-one

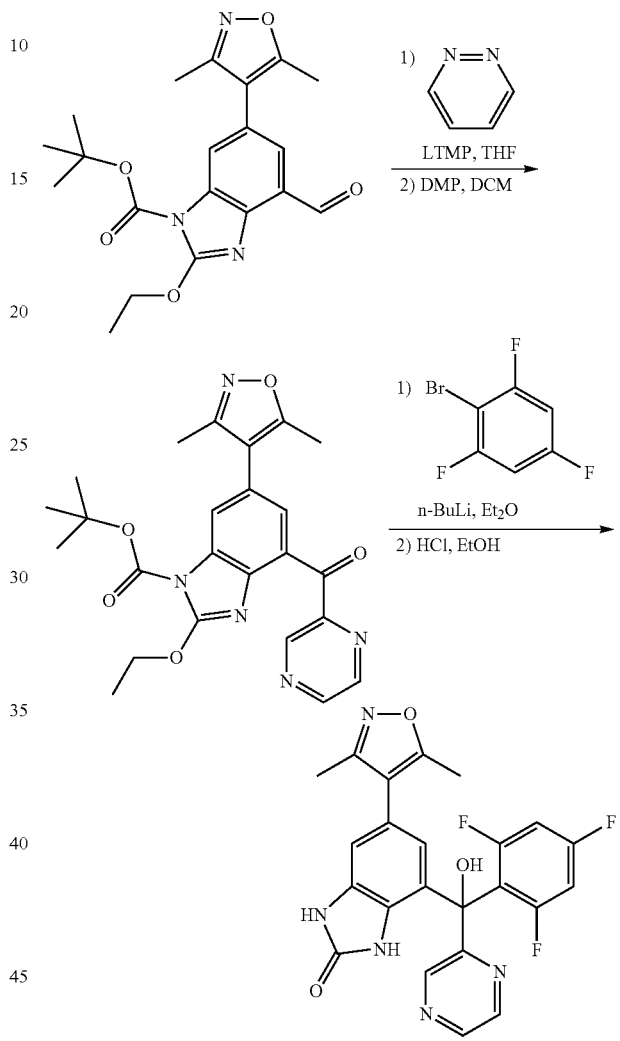

To 2,2,6,6-tetramethylpiperidine (0.27 mL, 1.56 mmol) in tetrahydrofuran (16 mL) at −78° C. was added n-butyllithium (0.97 mL, 1.56 mmol, 1.6 M in hexanes). After 5 minutes, the reaction was warmed to 0° C. After stirring for 30 minutes, the reaction was cooled to −78° C., and pyrazine (137 mg, 1.69 mmol) in tetrahydrofuran (3.3 mL) and tert-butyl dimethylisoxazol-4-yl)-2-ethoxy-4-formyl-1H-indole-1-carboxylate (498 mg, 1.3 mmol) in tetrahydrofuran (2.6 mL) were added simultaneously in a drop-wise manner. After stirring for 60 minutes, the reaction was quenched with saturated $NH_4Cl_{(aq)}$ (10 mL), extracted with ethyl acetate (3×10 mL), dried over $Na_2SO_4$, and concentrated in vacuo. Purification by flash chromatography (0-100% ethyl acetate/hexane) afforded tert-butyl 6-(3,5-dimethylisoxazol-4-yl)-2-ethoxy-4-(hydroxy(pyrazin-2-yl)methyl)-1H-benzo[d]imidazole-1-carboxylate. To tert-butyl 6-(3,5-dimethylisoxazol-4-yl)-2-ethoxy-4-(hydroxy(pyrazin-2-yl)methyl)-1H-benzo[d]imidazole-1-carboxylate (50 mg, 0.11 mmol) in dichloromethane (2.5 mL) was added Dess-Martin periodinane (72.4 mg, 0.16 mmol). After 15 minutes, the reaction was quenched with saturated $Na_2S_2O_{3(aq)}$ (10 mL) and extracted with dichloromethane (3×10 mL), dried over $Na_2SO_4$, and concentrated in vacuo. Purification by flash chromatography (0-100% ethyl acetate/hexanes) afforded tert-butyl 6-(3,5-dimethylisoxazol-4-yl)-2-ethoxy-4-(pyrazine-2-carbonyl)-1H-benzo[d]imidazole-1-carboxylate as a yellow oil.

To 1-bromo-2,4,6-trifluorobenzene (0.01 ml, 0.12 mmol) in diethyl ether (0.5 mL) at −78° C. was added n-$_{butyllithium}$ (0.13 mL, 0.14 mmol, 1.6 M in hexanes). After 30 tert-butyl 6-(3,5-dimethylisoxazol-4-yl)-2-ethoxy-4-(pyrazine-2-carbonyl)-1H-benzo[d]imidazole-1-carboxylate (36.6 mg, 0.08 mmol) in diethyl ether (1 mL) was added drop-wise to the reaction. After 90 minutes, the reaction was warmed, quenched with saturated $NH_4Cl_{(aq)}$ (10 mL), extracted with ethyl acetate (3×10 mL), dried over $Na_2SO_4$, and concentrated in vacuo. To the crude residue in ethanol (1.5 mL) was added hydrochloric acid (0.20 mL, 0.79 mmol, 4 M in 1,4-dioxane) and the mixture was heated to 70° C. in a microwave reactor for 45 minutes. Purification by reverse-phase HPLC (35-50% acetonitrile/water with 0.01% trifluoroacetic acid, Gemini C18 5μ) afforded 6-(3,5-dimethylisoxazol-4-yl)-4-(hydroxy(pyrazin-2-yl)(2,4,6-trifluorophenyl)methyl)-1H-benzo[d]imidazol-2(3H)-one as a pale yellow solid.

$C_{23}H_{16}F_3N_5O_3$. 468.09 (M+1). $^1$H NMR (400 MHz, DMSO-$d_6$) δ 10.74 (s, 1H), 9.89 (s, 1H), 9.12 (d, J=1.2 Hz, 1H), 8.60-8.49 (m, 2H), 7.39 (s, 1H), 7.10 (t, J=9.7 Hz, 2H), 6.83-6.77 (m, 1H), 6.63 (d, J=1.3 Hz, 1H), 2.28 (s, 3H), 2.09 (s, 3H). $^{19}$F NMR (377 MHz, DMSO-$d_6$) δ −74.73, −100.62 (t, J=9.1 Hz), −108.90 (p, J=8.8 Hz).

Example 57

6-(3,5-dimethylisoxazol-4-yl)-4-(1-methyl-4-phenyl-1H-pyrazol-5-yl)-1H-benzo[d]imidazol-2(3H)-one Step 1: 1-Methyl-4-phenyl-5-(4,4,5,5-tetramethyl-1,3,2-dioxaborolan-2-yl)-1H-pyrazole

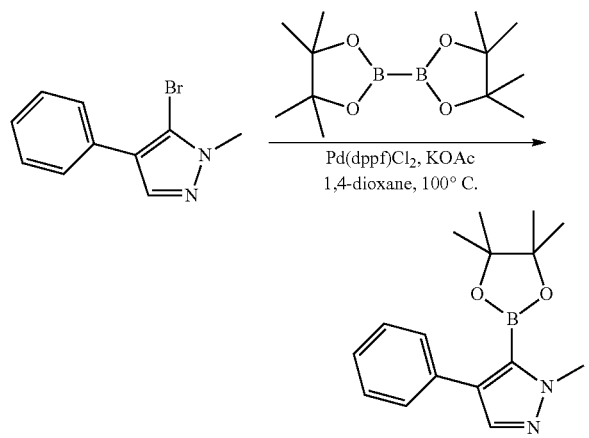

5-bromo-1-methyl-4-phenyl-1H-pyrazole (87 mg, 0.37 mmol) and 3,5-Dimethylisoxazole-4-boronic acid pinacol ester (373 mg, 1.47 mmol) was added to a 1,4-dioxane (2 ml).

To the above mixture were added $Pd(dppf)Cl_2$ (27 mg, 0.037 mmol) and potassium acetate (181 mg, 1.85 mmol). The reaction mixture was heated at 100° C. for 2 h. The reaction mixture was then diluted with EtOAc (100 ml), washed with bring (50 ml×2). The organic solvent was evaporated and the residue was dissolved in DCM and purified with combi-flash column chromatography (product came out at 45% EtOAc/Hexane) to afford 141 mg product 1-methyl-4-phenyl-5-(4,4,5,5-tetramethyl-1,3,2-dioxaborolan-2-yl)-1H-pyrazole.

$C16H21BN2O2$. 285.3 (M+1).

Step 2: Preparation of 4-(2-ethoxy-4-(1-methyl-4-phenyl-1H-pyrazol-5-yl)-1H-benzo[d]imidazol-6-yl)-3,5-dimethylisoxazole

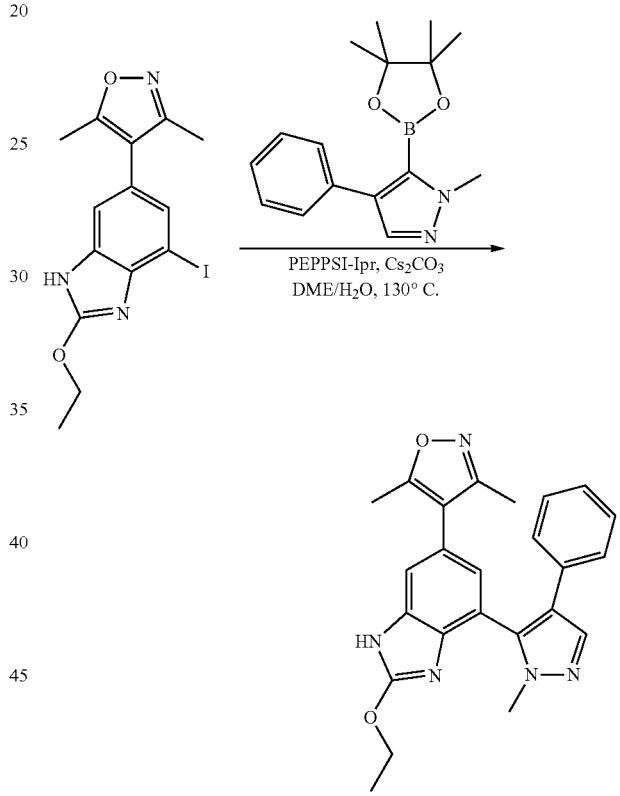

4-(2-ethoxy-4-iodo-1H-benzo[d]imidazol-6-yl)-3,5-dimethylisoxazole (100 mg, 0.26 mmol) and 1-methyl-4-phenyl-5-(4,4,5,5-tetramethyl-1,3,2-dioxaborolan-2-yl)-1H-pyrazole (37 mg, 0.13 mmol) was added to a solvent mixture of 1,2-dimethoxyethane (2 ml) and water (1 ml). To the above mixture were added PEPPSI-Ipr (18 mg, 0.026 mmol) and $CsCO_3$ (127 mg, 0.39 mmol). The reaction mixture was heated at 130° C. in microwave reactor for 30 mins. The reaction mixture was then filtered and organic solvent was evaporated and the residue was purified with Prep HPLC (0-100% $CH_3CN/H_2O$) to afford 8 mg product 4-(2-ethoxy-4-(1-methyl-4-phenyl-1H-pyrazol-5-yl)-1H-benzo[d]imidazol-6-yl)-3,5-dimethylisoxazole.

$C_{24}H_{23}N_5O_2$. 414.5 (M+1).

Step 3

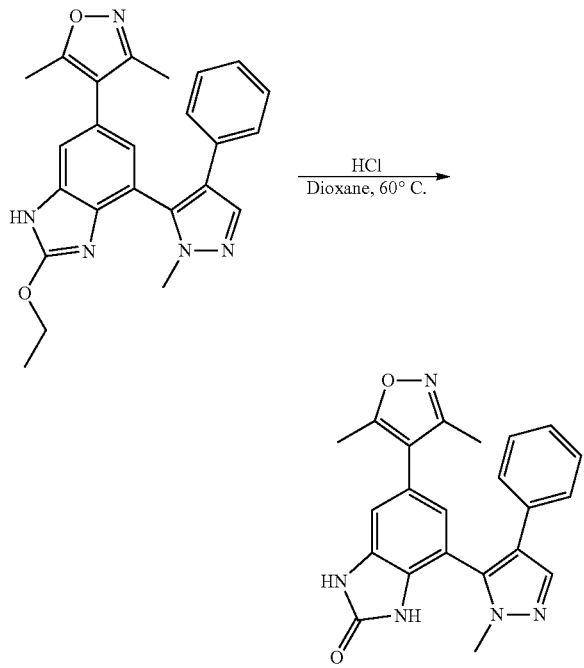

4-(2-ethoxy-4-(1-methyl-4-phenyl-1H-pyrazol-5-yl)-1H-benzo[d]imidazol-6-yl)-3,5-dimethylisoxazole (8 mg, 0.019 mmol) was dissolved in dioxane (0.5 ml), to the solution was added concentrated HCl (0.1 ml), heated at 60° C. for 2 h. Solvent was evaporated and the residue was purified with Prep HPLC (0-100% CH3CN/H2O) to afford 2 mg product 6-(3,5-dimethylisoxazol-4-yl)-4-(1-methyl-4-phenyl-1H-pyrazol-5-yl)-1H-benzo[d]imidazol-2(3H)-one.

C22H19N5O2. 386.2 (M+1). 1H NMR (400 MHz, CD3OD) δ 8.20 (s, 1H), 7.91 (s, 1H), 7.64 (d, J=7.6 Hz, 2H), 7.55 (d, J=7.6 Hz, 2H), 6.94 (s, 1H), 6.86 (s, 1H), 3.87 (s, 3H), 2.39 (s, 3H), 2.22 (s, 3H).

Example 58

6-(3,5-dimethylisoxazol-4-yl)-4-(4-methyl-1-phenyl-1H-pyrazol-5-yl)-1H-benzo[d]imidazol-2(3H)-one

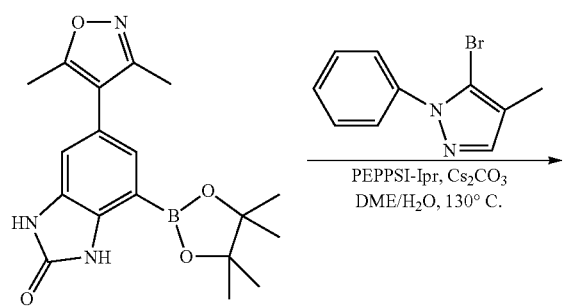

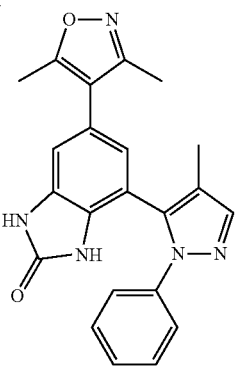

6-(3,5-dimethylisoxazol-4-yl)-4-(4,4,5,5-tetramethyl-1,3,2-dioxaborolan-2-yl)-1H-benzo[d]imidazol-2(3H)-one (30 mg, 0.084 mmol) and 5-bromo-4-methyl-1-phenyl-1H-pyrazole (30 mg, 0.13 mmol) was added to a solvent mixture of 1,2-dimethoxyethane (2 ml) and water (1 ml). To the above mixture were added PEPPSI-Ipr (5.4 mg, 0.008 mmol) and Cs2CO3 (83 mg, 0.25 mmol). The reaction mixture was heated at 130° C. in microwave reactor for 30 mins. The reaction mixture was then filtered and organic solvent was evaporated and the residue was purified with Prep HPLC (0-100% CH3CN/H2O) to afford 3.9 mg product 6-(3,5-dimethylisoxazol-4-yl)-4-(4-methyl-1-phenyl-1H-pyrazol-5-yl)-1H-benzo[d]imidazol-2(3H)-one (yield=12%).

C22H19N5O2. 386.3 (M+1). 1H NMR (400 MHz, CD3OD) δ 8.10 (s, 1H), 7.77 (d, J=8.0 Hz, 2H), 7.42 (t, J=8.0 Hz, 2H), 7.23-7.22 (m, 2H), 6.94 (s, 1H), 2.37 (s, 3H), 2.29 (s, 3H), 2.21 (s, 3H).

The following compounds were made in similar fashion as that of Example 58.

Example 59

6-(3,5-dimethylisoxazol-4-yl)-4-(4-methyl-1-phenyl-1H-pyrazol-3-yl)-1H-benzo[d]imidazol-2(3H)-one $C_{22}H_{19}N_5O_2$. 386.1 (M+1). $^1$H NMR (400 MHz, CD$_3$OD) δ 7.98 (s, 1H), 7.73 (d, J=8.4 Hz, 2H), 7.58 (d, J=8.4 Hz, 2H), 7.48 (s, 1H), 6.94 (s, 1H), 6.90 (s, 1H), 2.34 (s, 3H), 2.19 (s, 3H), 2.10 (s, 3H).

Example 60

4-(1,4-dicyclopropyl-1H-pyrazol-3-yl)-6-(3,5-dimethylisoxazol-4-yl)-1H-benzo[d]imidazol-2(3H)-one

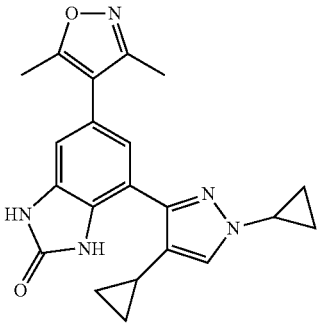 [SMILES: Cc1noc(C)c1-c1cc(-c2nn(C3CC3)cc2C2CC2)c2[nH]c(=O)[nH]c2c1]

$C_{21}H_{21}N_5O_2$. 376.2 (M+1). $^1$H NMR (400 MHz, $CD_3OD$) δ 7.62 (s, 1H), 7.48 (s, 1H), 6.97 (s, 1H), 3.71-3.31 (m, 1H), 2.27 (s, 3H), 2.27 (s, 3H), 1.78-1.75 (m, 2H), 1.16-1.06 (m, 2H), 1.05-1.02 (m, 2H), 0.61-0.59 (m, 2H).

Example 61

4-(4-cyclopropyl-1-methyl-1H-pyrazol-5-yl)-6-(3,5-dimethylisoxazol-4-yl)-1H-benzo[d]imidazol-2(3H)-one

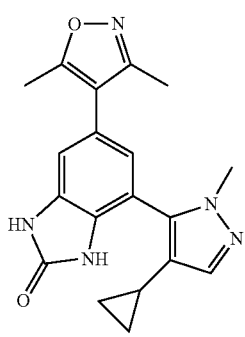 [SMILES: Cc1noc(C)c1-c1cc(-c2c(C3CC3)cnn2C)c2[nH]c(=O)[nH]c2c1]

$C_{19}H_{19}N_5O_2$. 350.2 (M+1). $^1$H NMR (400 MHz, $CD_3OD$) δ 7.19 (s, 1H), 7.00 (s, 1H), 6.86 (s, 1H), 3.59 (s, 3H), 2.34 (s, 3H), 2.18 (s, 3H), 1.45-1.41 (m, 1H), 0.65-0.63 (m, 2H), 0.45-0.38 (m, 2H).

Example 62

4-(4-cyclopropyl-1-methyl-1H-pyrazol-3-yl)-6-(3,5-dimethylisoxazol-4-yl)-1H-benzo[d]imidazol-2(3H)-one

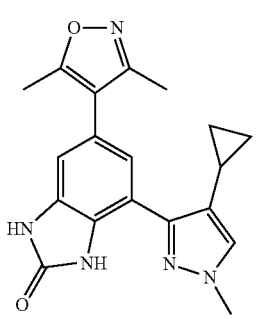 [SMILES: Cc1noc(C)c1-c1cc(-c2nn(C)cc2C2CC2)c2[nH]c(=O)[nH]c2c1]

$C_{19}H_{19}N_5O_2$. 350.2 (M+1). $^1$H NMR (400 MHz, $CD_3OD$) δ 7.53 (s, 1H), 7.30 (s, 1H), 6.87 (s, 1H), 3.82 (s, 3H), 2.18 (s, 3H), 1.72 (s, 3H), 1.72-1.68 (m, 1H), 0.83-0.75 (m, 2H), 0.50-0.42 (m, 2H).

Example 63

4-(1,3-dicyclopropyl-1H-pyrrol-2-yl)-6-(3,5-dimethylisoxazol-4-yl)-1H-benzo[d]imidazol-2(3H)-one

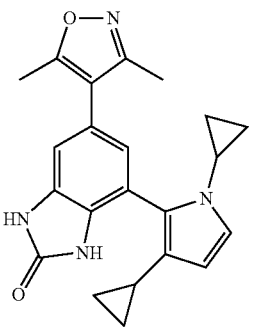 [SMILES: Cc1noc(C)c1-c1cc(-c2c(C3CC3)ccn2C2CC2)c2[nH]c(=O)[nH]c2c1]

$C_{21}H_{21}N_5O_2$. 376.2 (M+1). $^1$H NMR (400 MHz, $CD_3OD$) δ 7.23 (s, 1H), 7.09 (s, 1H), 6.99 (s, 1H), 3.48-3.42 (m, 3H), 2.27 (s, 3H), 2.00 (s, 3H), 1.51-1.23 (m, 1H), 0.91-0.85 (m, 2H), 0.80-0.71 (m, 4H), 0.56-0.46 (m, 2H).

Example 64

4-(2-cyclopropylphenyl)-6-(3,5-dimethylisoxazol-4-yl)-1H-benzo[d]imidazol-2(3H)-one

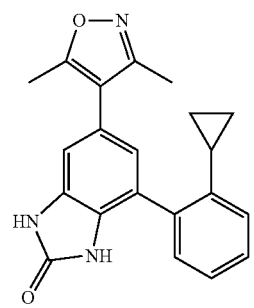 [SMILES: Cc1noc(C)c1-c1cc(-c2ccccc2C2CC2)c2[nH]c(=O)[nH]c2c1]

$C_{21}H_{19}N_3O_2$. 346.1 (M+1). $^1$H NMR (400 MHz, $CD_3OD$) δ 7.35-7.31 (m, 1H), 7.25-7.24 (m, 1H), 7.24-7.03 (m, 1H), 6.99 (s, 1H), 6.87 (s, 1H), 2.42 (s, 3H), 2.26 (s, 3H), 1.77-1.73 (m, 1H), 0.79-0.77 (m, 2H), 0.67 (bs, 2H).

Example 65

5-(3,5-dimethylisoxazol-4-yl)-1-methyl-7-(3-methylcinnolin-4-yl)-1H-benzo[d]imidazol-2(3H)-one

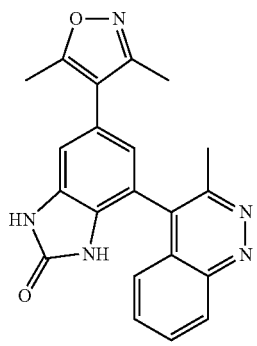 [SMILES: Cc1noc(C)c1-c1cc(-c2c(C)nnc3ccccc23)c2[nH]c(=O)[nH]c2c1]

$C_{22}H_{19}N_5O_2$. 386.2 (M+1). $^1$H NMR (400 MHz, $CD_3OD$) δ 8.42 (d, J=8.8 Hz, 1H), 7.84 (t, J=7.6 Hz, 1H), 7.73 (t, J=7.6 Hz, 1H), 7.44 (d, J=8.8 Hz, 1H), 7.14 (s, 1H), 6.83 (s, 1H), 2.68 (s, 3H), 2.55 (s, 3H), 2.33 (s, 3H), 2.17 (s, 3H).

Example 66

6-(3,5-dimethylisoxazol-4-yl)-4-(4-methyl-1-(tetrahydro-2H-pyran-2-yl)-1H-pyrazol-5-yl)-1H-benzo[d]imidazol-2(3H)-one

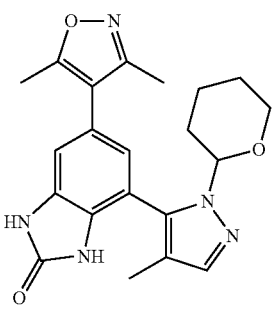 [SMILES: Cc1cnn(C2CCCCO2)c1-c1cc(-c2c(C)noc2C)cc2[nH]c(=O)[nH]c12]

$C_{21}H_{23}N_5O_3$. 386.2 (M+1). $^1$H NMR (400 MHz, $CD_3OD$) δ 7.23 (s, 1H), 7.00 (s, 1H), 6.86 (s, 1H), 3.83-3.57 (m, 1H), 3.38-3.33 (m, 2H), 2.34 (s, 3H), 2.55 (s, 3H), 2.18 (s, 3H), 1.99 (s, 3H), 1.58-1.40 (m, 6H).

Example 67

4-(2-cyclobutylpyridin-3-yl)-6-(3,5-dimethylisoxazol-4-yl)-1H-benzo[d]imidazol-2(3H)-one

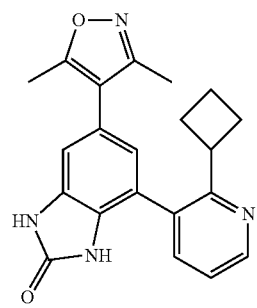 [SMILES: Cc1noc(C)c1-c1cc(-c2cccnc2C2CCC2)c2[nH]c(=O)[nH]c2c1]

$C_{21}H_{20}N_4O_2$. 361.3 (M+1). $^1$H NMR (400 MHz, $CD_3OD$) δ 8.69 (d, J=4.8 Hz, 1H), 8.31 (d, J=8.4 Hz, 1H), 7.87-7.83 (m, 1H), 7.04 (s, 1H), 6.85 (s, 1H), 3.90-3.86 (m, 1H), 2.33 (s, 3H), 2.30 (bs, 1H), 2.14 (s, 3H), 2.11 (bs, 1H), 1.92 (bs, 2H), 1.78-1.71 (m, 2H).

Example 68

4-(4-amino-2-cyclopropylpyridin-3-yl)-6-(3,5-dimethylisoxazol-4-yl)-1H-benzo[d]imidazol-2(3H)-one

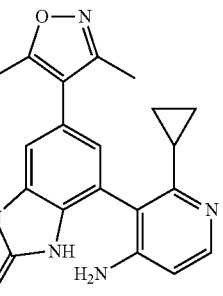

$C_{20}H_{19}N_5O_2$. 362.3 (M+1). $^1$H NMR (400 MHz, $CD_3OD$) δ 10.63 (s, 1H), 10.42 (s, 1H), 7.82 (s, 1H), 6.81 (s, 1H), 6.61 (s, 1H), 6.40 (s, 1H), 5.21 (s, 2H), 2.28 (s, 3H), 2.17 (s, 3H), 1.45-1.43 (m, 1H), 0.98-0.85 (m, 2H), 0.69-0.63 (m, 2H), 0.47-0.44 (m, 2H).

Example 69

4-(4-cyclopropylthiazol-5-yl)-6-(3,5-dimethylisoxazol-4-yl)-1H-benzo[d]imidazol-2(3H)-one

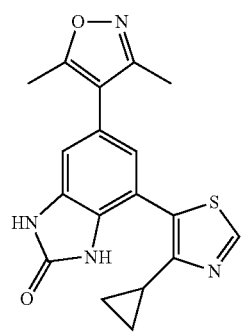 [SMILES: Cc1noc(C)c1-c1cc(-c2scnc2C2CC2)c2[nH]c(=O)[nH]c2c1]

$C_{18}H_{16}N_4O_2S$. 353.3 (M+1). $^1$H NMR (400 MHz, $CD_3OD$) δ 8.81 (s, 1H), 6.98 (s, 1H), 6.88 (s, 1H), 2.26 (s, 3H), 2.19 (s, 3H), 1.78 (bs, 1H), 0.86 (bs, 2H), 0.82 (bs, 2H).

Example 70

4-([2,3'-bipyridin]-3-yl)-6-(3,5-dimethylisoxazol-4-yl)-1H-benzo[d]imidazol-2(3H)-one

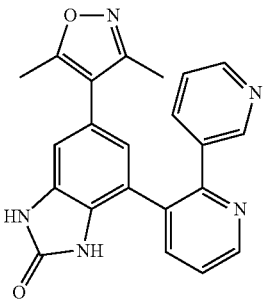 [SMILES: Cc1noc(C)c1-c1cc(-c2cccnc2-c2cccnc2)c2[nH]c(=O)[nH]c2c1]

$C_{22}H_{17}N_5O_2$. 384.3 (M+1). $^1$H NMR (400 MHz, $CD_3OD$) δ 8.83 (dd, J=1.2, 4.8 Hz, 1H), 8.75 (s, 1H), 8.63 (d, J=5.2 Hz, 1H), 8.23 (d, J=7.2 Hz, 1H), 8.08 (dd, J=1.2, 8.0 Hz, 1H), 7.72-7.67 (m, 2H), 6.99 (d, J=1.2 Hz, 1H), 6.86 (s, 1H), 2.29 (s, 3H), 2.12 (s, 3H).

Example 71

4-(4-cyclopropylpyridin-3-yl)-6-(3,5-dimethylisoxazol-4-yl)-1H-benzo[d]imidazol-2(3H)-one

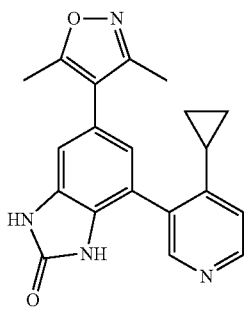 [SMILES: Cc1noc(C)c1-c1cc(-c2cnccc2C2CC2)c2[nH]c(=O)[nH]c2c1]

$C_{20}H_{18}N_4O_2$. 347.3 (M+1). $^1$H NMR (400 MHz, $CD_3OD$) δ 8.34 (d, J=6.4 Hz, 1H), 8.28 (s, 1H), 6.98-6.97 (m, 1H), 6.93 (d, J=6.4 Hz, 1H), 6.84 (d, J=1.2 Hz, 1H), 2.34 (s, 3H), 2.17 (s, 3H), 1.85-1.75 (m, 1H), 0.95 (bs, 2H), 0.78 (bs, 2H).

Example 72

4-(3-cyclopropylpyridin-4-yl)-6-(3,5-dimethylisoxazol-4-yl)-1H-benzo[d]imidazol-2(3H)-one

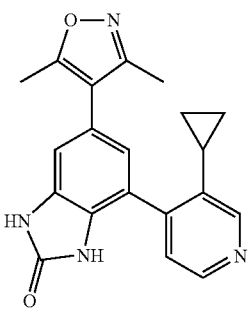 [SMILES: Cc1noc(C)c1-c1cc(-c2ccncc2C2CC2)c2[nH]c(=O)[nH]c2c1]

$C_{20}H_{18}N_4O_2$. 347.3 (M+1). $^1$H NMR (400 MHz, $CD_3OD$) δ 8.58 (d, J=5.2 Hz, 1H), 8.43 (s, 1H), 7.82 (d, J=6.4 Hz, 1H), 7.05 (d, J=1.2 Hz, 1H), 6.94 (d, J=1.6 Hz, 1H), 2.34 (s, 3H), 2.18 (s, 3H), 1.88-1.84 (m, 1H), 1.00-0.95 (m, 2H), 0.85-0.81 (m, 2H).

Example 73

4-(2-cyclopropylpyridin-3-yl)-6-(3,5-dimethylisoxazol-4-yl)-1H-benzo[d]imidazol-2(3H)-one

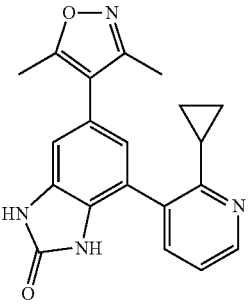 [SMILES: Cc1noc(C)c1-c1cc(-c2cccnc2C2CC2)c2[nH]c(=O)[nH]c2c1]

$C_{20}H_{18}N_4O_2$. 347.2 (M+1). $^1$H NMR (400 MHz, $CD_3OD$) δ 8.57 (d, J=8.4 Hz, 1H), 8.19 (d, J=8.4 Hz, 1H), 7.70-7.67 (m, 1H), 7.10 (s, 1H), 6.99 (s, 1H), 2.43 (s, 3H), 2.27 (s, 3H), 2.14-2.08 (m, 1H), 1.15 (bs, 4H).

Example 74

2-cyclopropyl-3-(6-(3,5-dimethylisoxazol-4-yl)-2-oxo-2,3-dihydro-1H-benzo[d]imidazol-4-yl)pyridine 1-oxide

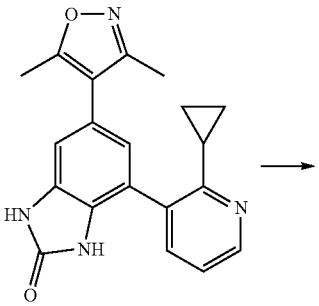

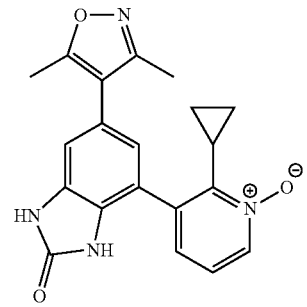

4-(2-cyclopropylpyridin-3-yl)-6-(3,5-dimethylisoxazol-4-yl)-1H-benzo[d]imidazol-2(3H)-one (35 mg, 0.1 mmol) was dissolved in MeOH/DCM (1/1 mL). To the solution was added 3-Chloroperoxybenzoic acid (69.75 mg, 0.4 mol) and the mixture stirred at RT overnight. The organic solvent was evaporated and the residue was purified with Prep HPLC (0-100% $CH_3CN/H_2O$) to afford 2-cyclopropyl-3-(6-(3,5-dimethylisoxazol-4-yl)-2-oxo-2,3-dihydro-1H-benzo[d]imidazol-4-yl)pyridine 1-oxide.

$C_{20}H_{18}N_4O_3$. 363.2 (M+1). $^1$H NMR (400 MHz, $CD_3OD$) δ 8.47 (dd, J=1.2, 6.4 Hz, 1H), 7.64 (dd, J=1.2, 6.4 Hz, 1H), 7.54 (t, J=6.4 Hz, 1H), 7.08 (d, J=1.2 Hz, 1H), 6.94 (d, J=1.2 Hz, 1H), 2.42 (s, 3H), 2.25 (s, 3H), 2.04-1.99 (m, 1H), 0.96 (bs, 1H), 0.75 (bs, 1H), 0.61 (bs, 1H), 0.54 (bs, 1H).

Example 75

4-(5-amino-2-cyclopropylpyridin-3-yl)-6-(3,5-dimethylisoxazol-4-yl)-1H-benzo[d]imidazol-2(3H)-one

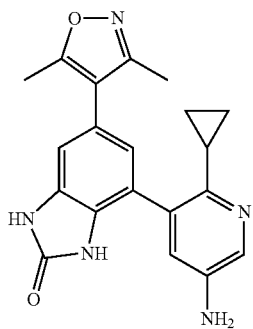 [SMILES: Cc1noc(C)c1-c1cc(-c2cc(N)cnc2C2CC2)c2[nH]c(=O)[nH]c2c1]

6-(3,5-dimethylisoxazol-4-yl)-4-(4,4,5,5-tetramethyl-1,3,2-dioxaborolan-2-yl)-1H-benzo[d]imidazol-2(3H)-one (150 mg, 0.42 mmol) and 5-bromo-6-cyclopropylpyridin-3-amine (180 mg, 0.84 mmol) were added to a solvent mixture of 1,2-dimethoxyethane (2 mL) and water (1 mL). To the mixture were added PEPPSI-Ipr (29 mg, 0.03 mmol) and $Cs_2CO_3$ (413 mg, 1 mmol). The reaction mixture was heated at 130° C. in microwave reactor for 30 mins. The reaction mixture was then filtered and organic solvent was evaporated and the residue was purified with Prep HPLC (0-100% $CH_3CN/H_2O$) to afford 129 mg of 4-(5-amino-2-cyclopropylpyridin-3-yl)-6-(3,5-dimethylisoxazol-4-yl)-1H-benzo[d]imidazol-2(3H)-one.

C20H19N5O2. 362.1 (M+1). 1H NMR (400 MHz, CD3OD) δ 10.98 (s, 1H), 10.81 (s, 1H), 7.79 (s, 1H), 7.05 (s, 1H), 6.99 (s, 2H), 2.26 (s, 3H), 2.18 (s, 3H), 1.62 (bs, 1H), 0.82 (bs, 2H), 0.62 (bs, 2H).

Example 76

6-cyclopropyl-5-(6-(3,5-dimethylisoxazol-4-yl)-2-oxo-2,3-dihydro-1H-benzo[d]imidazol-4-yl)nicotinonitrile

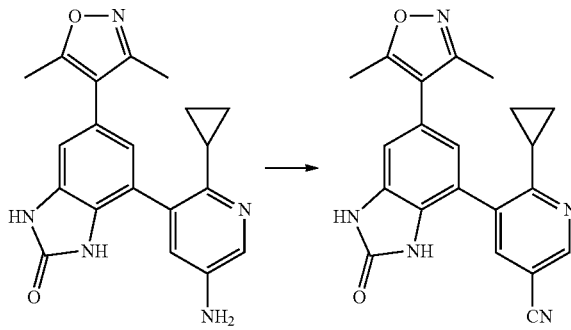

4-(5-amino-2-cyclopropylpyridin-3-yl)-6-(3,5-dimethylisoxazol-4-yl)-1H-benzo[d]imidazol-2(3H)-one (21 mg, 0.058 mmol) was suspended in a mixture of water (1 mL) and con. HCl (1 mL), cooled suspension to 0° C., a solution of sodium nitrite (4 mg, 0.058 mmol) in water was added slowly. After 5 mins, the reaction mixture was neutralised by the addition of $NaHCO_3$ solution. Then the resultant suspension was added in aliquots to a solution of copper (I) cyanide (5 mg, 0.058 mmol) and sodium cyanide (6 mg, 0.11 mmol) in water at room temperature. Heated to 70° C. for 30 mins. Extracted with EtOAc, evaporated organic solvent, the residue was purified with Prep HPLC. (0-100% $CH_3CN/H_2O$) to afford 1.2 mg of 6-cyclopropyl-5-(6-(3,5-dimethylisoxazol-4-yl)-2-oxo-2,3-dihydro-1H-benzo[d]imidazol-4-yl)nicotinonitrile.

C21H17N5O2. 372.4 (M+1). 1H NMR (400 MHz, CD3OD) δ 8.63 (s, 1H), 7.79 (s, 1H), 7.06 (s, 1H), 6.99 (s, 1H), 2.25 (s, 3H), 2.18 (s, 3H), 1.88-1.80 (m, 1H), 0.88-0.83 (m, 2H), 0.78-0.75 (m, 2H).

Example 77

4-(5-bromo-2-cyclopropylpyridin-3-yl)-6-(3,5-dimethylisoxazol-4-yl)-1H-benzo[d]imidazol-2(3H)-one

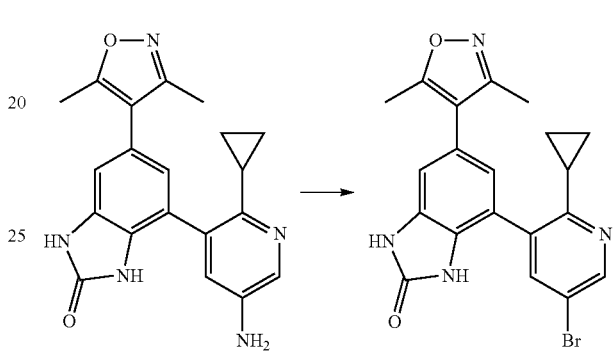

4-(5-amino-2-cyclopropylpyridin-3-yl)-6-(3,5-dimethylisoxazol-4-yl)-1H-benzo[d]imidazol-2(3H)-one (75 mg, 0.21 mmol) was dissolved in acetonitrile (2 ml), at room temperature added tert-butyl nitrite (32 mg, 0.31 mmol) and $CuBr_2$ (56 mg, 0.25 mmol), stirred at room temperature for 1 h. The reaction mixture was diluted with EtOAc, washed with brine, evaporated organic solvent, purified with Prep HPLC. (0-100% $CH_3CN/H_2O$) to afford 6 mg of 4-(5-bromo-2-cyclopropylpyridin-3-yl)-6-(3,5-dimethylisoxazol-4-yl)-1H-benzo[d]imidazol-2(3H)-one.

C20H17BrN4O2. 425.3 (M+1). 1H NMR (400 MHz, CD3OD) δ 8.42 (s, 1H), 7.61 (s, 1H), 6.99 (s, 1H), 6.96 (s, 1H), 2.33 (s, 3H), 2.18 (s, 3H), 1.78-1.70 (m, 1H), 0.88-0.81 (m, 2H), 0.71-0.64 (m, 2H).

Example 78

N-(6-cyclopropyl-5-(6-(3,5-dimethylisoxazol-4-yl)-2-oxo-2,3-dihydro-1H-benzo[d]imidazol-4-yl)pyridin-3-yl)acetamide

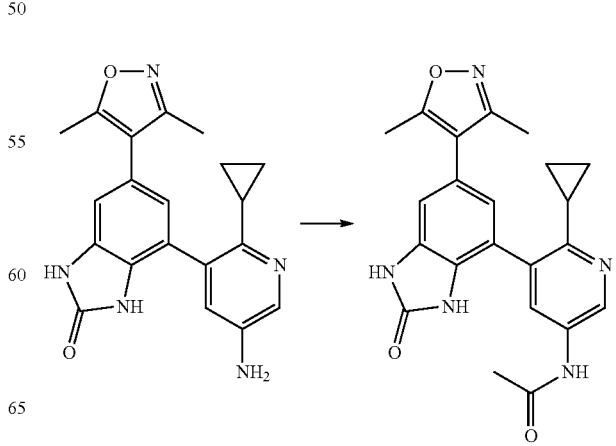

4-(5-Amino-2-cyclopropylpyridin-3-yl)-6-(3,5-dimethylisoxazol-4-yl)-1H-benzo[d]imidazol-2(3H)-one (75 mg, 0.21 mmol) was dissolved in acetonitrile (2 mL), at room temperature added tert-butyl nitrite (32 mg, 0.31 mmol) and CuBr$_2$ (56 mg, 0.25 mmol), stirred at room temperature for 1 h. The reaction mixture was diluted with EtOAc, washed with brine, evaporated organic solvent, purified with Prep HPLC. (0-100% CH$_3$CN/H$_2$O) to afford 16 mg of N-(6-cyclopropyl-5-(6-(3,5-dimethylisoxazol-4-yl)-2-oxo-2,3-dihydro-1H-benzo[d]imidazol-4-yl)pyridin-3-yl)acetamide.

C$_{22}$H$_{21}$N$_5$O$_3$. 404.4 (M+1). $^1$H NMR (400 MHz, CD$_3$OD) δ 8.89 (s, 1H), 7.78 (s, 1H), 7.06 (s, 1H), 7.03 (s, 1H), 2.33 (s, 3H), 2.17 (s, 3H), 2.12 (s, 3H), 1.82-1.78 (m, 1H), 099-0.94 (m, 2H), 0.77-0.74 (m, 2H).

Example 79

4-(4-bromo-2-cyclopropylpyridin-3-yl)-6-(3,5-dimethylisoxazol-4-yl)-1H-benzo[d]imidazol-2(3H)-one

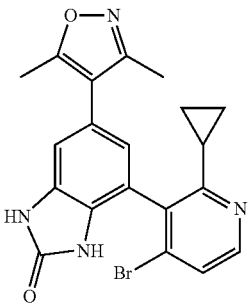 [SMILES: Cc1noc(C)c1-c1cc(-c2c(Br)ccnc2C2CC2)c2[nH]c(=O)[nH]c2c1]

4-(4-bromo-2-cyclopropylpyridin-3-yl)-6-(3,5-dimethylisoxazol-4-yl)-1H-benzo[d]imidazol-2(3H)-one was made in similar fashion to 4-(5-bromo-2-cyclopropylpyridin-3-yl)-6-(3,5-dimethylisoxazol-4-yl)-1H-benzo[d]imidazol-2(3H)-one C$_{20}$H$_{17}$BrN$_4$O$_2$. 425.3 (M+1). $^1$H NMR (400 MHz, CD$_3$OD) δ 8.18 (d, J=2.8 Hz, 1H), 7.55 (d, J=2.8 Hz, 1H), 6.98 (s, 1H), 6.78 (s, 1H), 2.35 (s, 3H), 2.20 (s, 3H), 1.75-1.65 (m, 1H), 1.03-0.88 (m, 2H), 0.82-0.68 (m, 2H).

Example 80

4-(2,4-dicyclopropylpyridin-3-yl)-6-(3,5-dimethylisoxazol-4-yl)-1H-benzo[d]imidazol-2(3H)-one

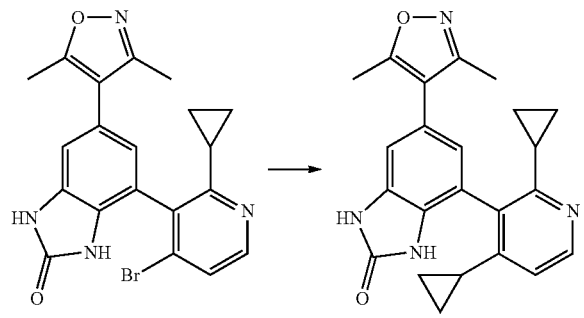 [SMILES: Cc1noc(C)c1-c1cc(-c2c(Br)ccnc2C2CC2)c2[nH]c(=O)[nH]c2c1 ; Cc1noc(C)c1-c1cc(-c2c(C3CC3)ccnc2C2CC2)c2[nH]c(=O)[nH]c2c1]

4-(4-bromo-2-cyclopropylpyridin-3-yl)-6-(3,5-dimethylisoxazol-4-yl)-1H-benzo[d]imidazol-2(3H)-one (17 mg, 0.04 mmol) and cyclopropyl boronic acid (100 mg, 1.2 mmol) were dissolved in dioxane (2 mL). To the reaction mixture were added K$_3$PO$_4$ (50 mg, 0.24 mol) and dichloro 1,1'-bis (diphenylphosphino)ferrocene palladium (II) dichloromethane (10 mg, 0.012 mmol). The reaction mixture was heated at 100° C. for 3 h. Solvent was evaporated, the residue was dissolved in EtOAc, washed with brine, evaporated organic solvent and the residue was purified with Prep HPLC (0-100% CH$_3$CN/H$_2$O) to afford 5.4 mg of 4-(2,4-dicyclopropylpyridin-3-yl)-6-(3,5-dimethylisoxazol-4-yl)-1H-benzo[d]imidazol-2(3H)-one.

C23H22N4O2. 387.3 (M+1). 1H NMR (400 MHz, CD3OD) δ 8.30 (d, J=6.4 Hz, 1H), 7.19 (d, J=6.4 Hz, 1H), 7.05 (s, 1H), 6.91 (s, 1H), 2.38 (s, 3H), 2.21 (s, 3H), 1.95-1.88 (m, 1H), 1.72-1.67 (m, 1H), 1.17-1.14 (m, 2H), 1.07-0.95 (m, 6H).

Example 81

6-(3,5-dimethylisoxazol-4-yl)-4-(6-(trifluoromethoxy)quinolin-5-yl)-1H-benzo[d]imidazol-2(3H)-one Step 1

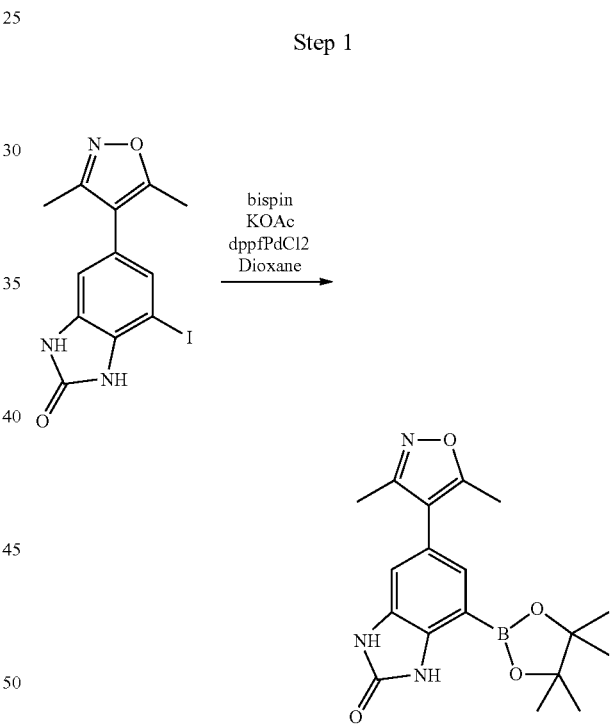

Degassed dioxane (120 mL) was added to a round-bottom flask containing 6-(3,5-dimethylisoxazol-4-yl)-4-iodo-1H-benzo[d]imidazol-2(3H)-one (6 g, 16.9 mmol), dppfPdCl$_2$ (630 mg, 5%), KOAc, (3.3 g, 2 equiv) and bispinacolato diboron (8.6 g, 2 equiv). The reaction mixture was sonicated to eliminate lumps, and was then heated to 120° C. overnight. The reaction was complete via TLC and HPLC analysis. The reaction mixture was dry-loaded onto silica gel and purified by flash chromatography (rf 0.4 in ethyl acetate, eluting with ethyl acetate/methanol. 6-(3,5-dimethylisoxazol-4-yl)-4-(4,4,5,5-tetramethyl-1,3,2-dioxaborolan-2-yl)-1H-benzo[d]imidazol-2(3H)-one was isolated and subjected to high-vacuum drying overnight, and contained an equivalent of pinacol side-products by NMR.

Step 2

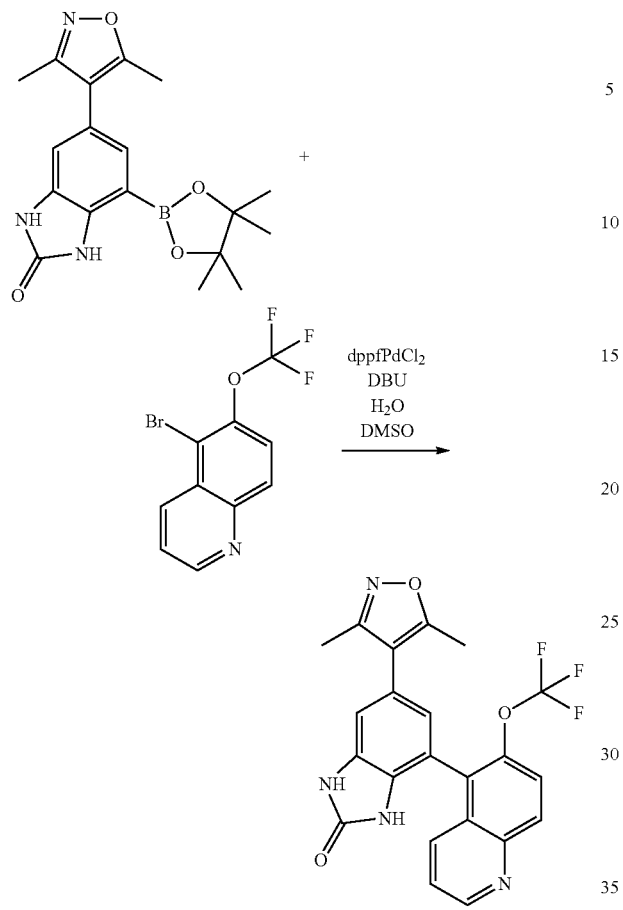

A solution of 5-bromo-6-(trifluoromethoxy)quinoline (obtained by bromination of 6-trifluoromethoxyquinoline) (50 mg, 0.17 mmol), 6-(3,5-dimethylisoxazol-4-yl)-4-(4,4,5,5-tetramethyl-1,3,2-dioxaborolan-2-yl)-1H-benzo[d]imidazol-2(3H)-one (91 mg, 0.26 mmol), dichloro 1,1-bis(diphenylphosphino)ferrocene palladium(II) dichloromethane (12.7 mg, 0.02 mmol), 1,8-diazabicyclo[5.4.0]undec-7-ene (0.2 mL, 1.37 mmol), DMSO (0.2 mL) and water (0.2 mL) under nitrogen was heated at 120° C. for 1 h. The reaction mixture was filtered and purified by reverse-phase HPLC to give 6-(3,5-dimethylisoxazol-4-yl)-4-(6-(trifluoromethoxy)quinolin-5-yl)-1H-benzo[d]imidazol-2(3H)-one.

$C_{22}H_{15}F_3N_4O_3$. 441.1 (M+1). $^1$H NMR (400 MHz, DMSO-$d_6$) δ 10.88 (s, 1H), 10.53 (d, J=2.0 Hz, 1H), 9.00 (dd, J=4.2, 1.7 Hz, 1H), 8.25 (d, J=9.3 Hz, 1H), 7.94-7.82 (m, 2H), 7.58 (dd, J=8.6, 4.2 Hz, 1H), 7.08-6.97 (m, 1H), 6.88 (d, J=1.5 Hz, 1H), 2.39 (s, 3H), 2.21 (s, 3H).

Example 82

4-(5,7-difluoroquinolin-4-yl)-6-(3,5-dimethylisoxazol-4-yl)-1H-benzo[d]imidazol-2(3H)-one

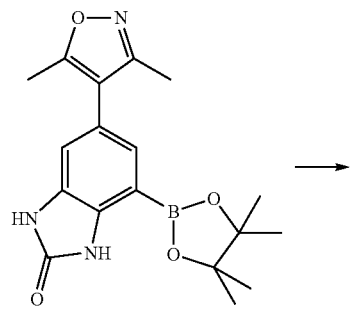

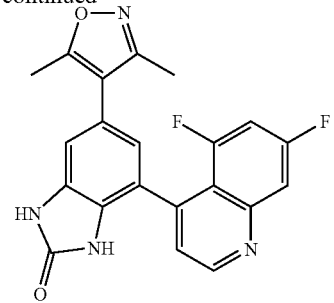

A mixture of 6-(3,5-dimethylisoxazol-4-yl)-4-(4,4,5,5-tetramethyl-1,3,2-dioxaborolan-2-yl)-1H-benzo[d]imidazol-2(3H)-one_(0.05 g), commercially available 4-bromo-5,7-difluoroquinoline (0.137 g), Peppsi catalyst (0.009 g), and $Cs_2CO_3$ (0.183 g) were stirred under $N_2$ in water/dioxane (1 mL each) at 140° C. for 30 min. After cooling to room temperature, brine (1 mL) was added, the organic layer separated and volatiles removed under vacuum. The residue was purified by preparative HPLC (5-95% MeCN in $H_2O$) to afford the title compound.

$C_{21}H_{14}F_2N_4O_2$; 393.20 (M+1). $^1$H NMR (400 MHz, DMSO-d6) δ 10.85 (s, $^1$H), 10.59 (d, J=1.7 Hz, 1H), 9.01 (d, J=4.5 Hz, 1H), 7.78 (dt, J=9.6, 1.7 Hz, 1H), 7.66-7.37 (m, 2H), 6.95 (dt, J=18.3, 1.2 Hz, 2H), 2.38 (s, 3H), 2.32 (s, 3H).

Example 83

4-(5,8-difluoroquinolin-4-yl)-6-(3,5-dimethylisoxazol-4-yl)-1H-benzo[d]imidazol-2(3H)-one

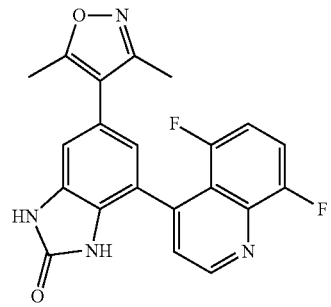 [SMILES: Cc1noc(C)c1-c1cc(-c2ccnc3c(F)ccc(F)c23)c2[nH]c(=O)[nH]c2c1]

4-(5,8-difluoroquinolin-4-yl)-6-(3,5-dimethylisoxazol-4-yl)-1H-benzo[d]imidazol-2(3H)-one was made in a similar fashion as that of Example 82.

C21H14F2N4O2; 393.18 (M+1). 1H NMR (400 MHz, DMSO-d6) δ 10.85 (d, J=1.5 Hz, 1H), 10.57 (d, J=1.8 Hz, 1H), 9.03 (d, J=4.4 Hz, 1H), 7.76-7.60 (m, 1H), 7.35 (ddd, J=12.3, 8.7, 3.9 Hz, 1H), 6.94 (dd, J=13.6, 1.6 Hz, 2H), 2.39 (s, 3H), 2.21 (s, 3H).

Example 84

4-(5-chloroquinolin-4-yl)-6-(3,5-dimethylisoxazol-4-yl)-1H-benzo[d]imidazol-2(3H)-one

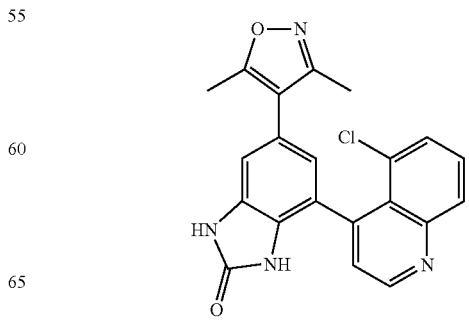

The boronic acid (0.05 g), bromide (0.137 g), Peppsi catalyst (0.009 g), Cs2CO3 (0.183 g) was stirred under N2 in water/dioxane (1 ml each) at 140 C for 30 min. After cooling to RT, brine (1 mL) was added, the organic layer separated and volatiles removed under vacuum. The residue was purified by preparative HPLC (5-95% MeCN in H2O) to afford the title compound.

C21H15ClN4O2; 391.15 (M+1). 1H NMR (400 MHz, DMSO-d6) δ 10.78 (d, J=1.9 Hz, 1H), 10.52 (d, J=1.9 Hz, 1H), 8.63 (d, J=5.6 Hz, 1H), 8.11 (dd, J=6.8, 2.6 Hz, 1H), 8.04 (d, J=5.7 Hz, 0H), 7.83-7.72 (m, 1H), 2.36 (s, 3H), 2.18 (s, 3H).

The following compounds were prepared in a similar fashion to that of Example 82, using the appropriate bromo or chloro derivative:

Example 85

6-(3,5-dimethylisoxazol-4-yl)-4-(6-(2,2,2-trifluoroethoxy)quinolin-5-yl)-1H-benzo[d]imidazol-2(3H)-one

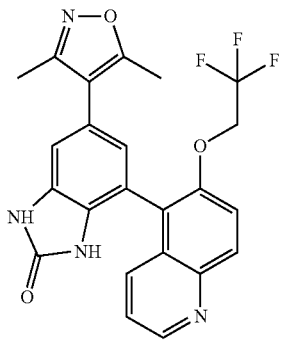 [SMILES: Cc1noc(C)c1-c1cc(-c2c(OCC(F)(F)F)ccc3ncccc23)c2[nH]c(=O)[nH]c2c1]

$C_{23}H_{17}F_3N_4O_3$. 455.1 (M+1). $^1$H NMR (400 MHz, DMSO-$d_6$) δ 10.77 (d, J=2.0 Hz, 1H), 10.38 (d, J=2.0 Hz, 1H), 8.87 (dd, J=4.5, 1.6 Hz, 1H), 8.17 (d, J=9.3 Hz, 1H), 7.89 (dd, J=9.0, 5.4 Hz, 2H), 7.52 (dd, J=8.6, 4.2 Hz, 1H), 6.97 (d, J=1.5 Hz, 1H), 6.81 (d, J=1.6 Hz, 1H), 4.86 (ddq, J=56.9, 12.0, 8.9 Hz, 2H), 2.39 (s, 3H), 2.21 (s, 3H).

Example 86

6-(3,5-dimethylisoxazol-4-yl)-4-(6-methyl-2-(trifluoromethyl)quinolin-5-yl)-1H-benzo[d]imidazol-2(3H)-one

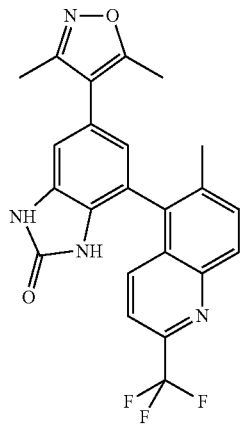 [SMILES: Cc1ccc2nc(C(F)(F)F)ccc2c1-c1cc(-c2c(C)noc2C)cc2[nH]c(=O)[nH]c12]

$C_{23}H_{17}F_3N_4O_2$. 439.2 (M+1). $^1$H NMR (400 MHz, DMSO-$d_6$) δ 10.89 (s, 1H), 10.39 (d, J=2.1 Hz, 1H), 8.16 (d, J=8.7 Hz, 1H), 7.98 (d, J=8.8 Hz, 1H), 7.93 (d, J=8.8 Hz, 1H), 7.86 (d, J=8.8 Hz, 1H), 7.02 (d, J=1.4 Hz, 1H), 6.84 (d, J=1.5 Hz, 1H), 2.41 (s, 3H), 2.32 (s, 3H), 2.24 (s, 3H).

Example 87

6-(3,5-dimethylisoxazol-4-yl)-4-(3-(trifluoromethyl)quinolin-4-yl)-1H-benzo[d]imidazol-2(3H)-one

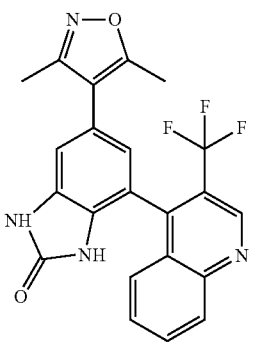 [SMILES: Cc1noc(C)c1-c1cc(-c2c(C(F)(F)F)cnc3ccccc23)c2[nH]c(=O)[nH]c2c1]

$C_{22}H_{15}F_3N_4O_2$. 425.2 (M+1). $^1$H NMR (400 MHz, DMSO-$d_6$) δ 10.95 (s, 1H), 10.54 (d, J=1.9 Hz, 1H), 9.29 (s, 1H), 8.24 (d, J=8.4 Hz, 1H), 7.96 (t, J=7.7 Hz, 1H), 7.67 (t, J=7.6 Hz, 1H), 7.47-7.37 (m, 1H), 7.06 (d, J=1.5 Hz, 1H), 6.92 (d, J=1.6 Hz, 1H), 2.40 (s, 3H), 2.22 (s, 3H).

Example 88

4-(6-cyclopropylquinolin-5-yl)-6-(3,5-dimethylisoxazol-4-yl)-1H-benzo[d]imidazol-2(3H)-one

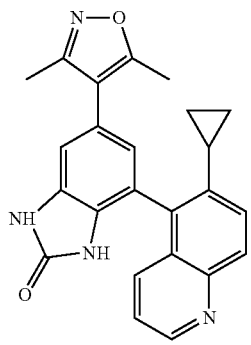 [SMILES: Cc1noc(C)c1-c1cc(-c2c(C3CC3)ccc3ncccc23)c2[nH]c(=O)[nH]c2c1]

$C_{24}H_{20}N_4O_2$. 397.1 (M+1). $^1$H NMR (400 MHz, DMSO-$d_6$) δ 10.83 (d, J=1.9 Hz, 1H), 10.39 (d, J=2.1 Hz, 1H), 8.83-8.78 (m, 1H), 7.99 (d, J=8.9 Hz, 1H), 7.64 (d, J=8.5 Hz, 1H), 7.41 (dd, J=8.6, 4.2 Hz, 1H), 7.34 (d, J=9.0 Hz, 1H), 6.99 (d, J=1.5 Hz, 1H), 6.82 (d, J=1.5 Hz, 1H), 2.41 (s, 3H), 2.23 (s, 3H), 1.80-1.73 (m, 1H), 0.86 (t, J=6.8 Hz, 4H).

Example 89

6-(3,5-dimethylisoxazol-4-yl)-4-(3-methylquinolin-4-yl)-1H-benzo[d]imidazol-2(3H)-one

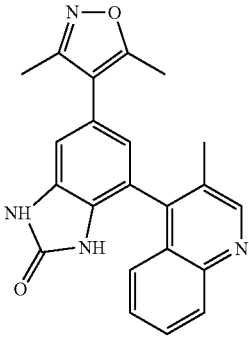 [SMILES: Cc1cnc2ccccc2c1-c1cc(-c2c(C)noc2C)cc2[nH]c(=O)[nH]c12]

C$_{22}$H$_{18}$N$_4$O$_2$. 371.1 (M+1). $^1$H NMR (400 MHz, DMSO-d$_6$) δ 10.95 (d, J=1.9 Hz, 1H), 10.49 (d, J=2.0 Hz, 1H), 9.09 (s, 1H), 8.15 (d, J=8.4 Hz, 1H), 7.84 (t, J=7.8 Hz, 1H), 7.62 (t, J=7.5 Hz, 1H), 7.49 (d, J=8.4 Hz, 1H), 7.05 (d, J=1.5 Hz, 1H), 6.87 (d, J=1.5 Hz, 1H), 2.41 (s, 3H), 2.29 (s, 3H), 2.24 (s, 3H).

Example 90

6-(3,5-dimethylisoxazol-4-yl)-4-(3-methylcinnolin-4-yl)-1H-benzo[d]imidazol-2(3H)-one

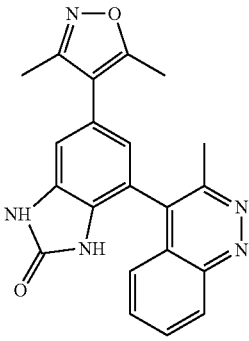 [SMILES: Cc1noc(C)c1-c1cc(-c2c(C)nnc3ccccc23)c2[nH]c(=O)[nH]c2c1]

C$_{21}$H$_{17}$N$_5$O$_2$. 372.1 (M+1). $^1$H NMR (400 MHz, DMSO-d$_6$) δ 10.97 (s, 1H), 10.55 (d, J=2.0 Hz, 1H), 8.62-8.41 (m, 1H), 7.97-7.85 (m, 1H), 7.78 (ddd, J=8.4, 6.9, 1.4 Hz, 1H), 7.47 (d, J=8.5 Hz, 1H), 7.15-7.02 (m, 1H), 6.95 (d, J=1.5 Hz, 1H), 2.69 (s, 3H), 2.42 (s, 3H), 2.25 (s, 3H).

Example 91

6-(3,5-dimethylisoxazol-4-yl)-4-(3-fluoro-6-methoxyquinolin-5-yl)-1H-benzo[d]imidazol-2(3H)-one

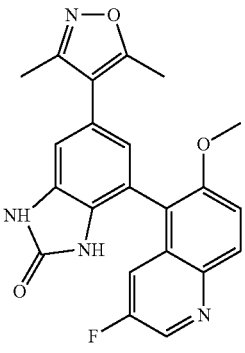 [SMILES: COc1ccc2ncc(F)cc2c1-c1cc(-c2c(C)noc2C)cc2[nH]c(=O)[nH]c12]

C$_{22}$H$_{17}$FN$_4$O$_3$. 405.1 (M+1). $^1$H NMR (400 MHz, DMSO-d$_6$) δ 10.80 (d, J=2.0 Hz, 1H), 10.41 (s, 1H), 8.79 (d, J=2.7 Hz, 1H), 8.17 (d, J=9.4 Hz, 1H), 7.77 (d, J=9.4 Hz, 1H), 7.50-7.41 (m, 1H), 7.00-6.90 (m, 1H), 6.88-6.76 (m, 1H), 3.89 (s, 3H), 2.41 (s, 3H), 2.24 (s, 3H). $^{19}$F NMR (376 MHz, DMSO-d$_6$) δ −128.19 (d, J=10.8 Hz).

Example 92

6-(3,5-dimethylisoxazol-4-yl)-4-(2,6-dimethylquinolin-5-yl)-1H-benzo[d]imidazol-2(3H)-one

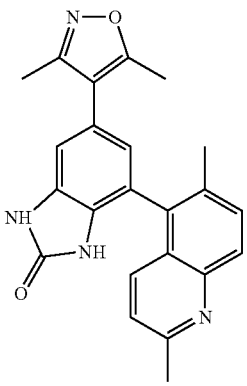 [SMILES: Cc1ccc2c(-c3cc(-c4c(C)noc4C)cc4[nH]c(=O)[nH]c34)c(C)ccc2n1]

C$_{23}$H$_{20}$N$_4$O$_2$. 385.1 (M+1). $^1$H NMR (400 MHz, DMSO-d$_6$) δ 10.94 (s, 1H), 10.40 (d, J=1.9 Hz, 1H), 8.11 (d, J=8.5 Hz, 2H), 7.99 (d, J=8.8 Hz, 1H), 7.68 (d, J=8.7 Hz, 1H), 7.03 (d, J=1.6 Hz, 1H), 6.82 (d, J=1.5 Hz, 1H), 2.85 (s, 3H), 2.41 (s, 3H), 2.31 (s, 3H), 2.24 (s, 3H).

Example 93

4-(3-chloroquinolin-4-yl)-6-(3,5-dimethylisoxazol-4-yl)-1H-benzo[d]imidazol-2(3H)-one

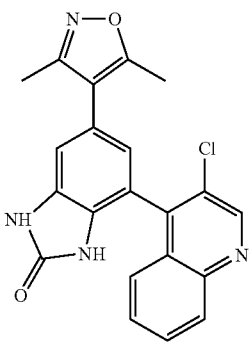 [SMILES: Cc1noc(C)c1-c1cc(-c2c(Cl)cnc3ccccc23)c2[nH]c(=O)[nH]c2c1]

C$_{21}$H$_{15}$ClN$_4$O$_2$. 391.1 (M+1). $^1$H NMR (400 MHz, DMSO-d$_6$) δ 10.95 (d, J=1.9 Hz, 1H), 10.61 (s, 1H), 9.03 (s, 1H), 8.22-8.02 (m, 1H), 7.91-7.77 (m, 1H), 7.69-7.58 (m, 1H), 7.47 (d, J=8.4 Hz, 1H), 7.06 (d, J=1.5 Hz, 1H), 6.92 (d, J=1.6 Hz, 1H), 2.42 (s, 3H), 2.24 (s, 3H).

Example 94

4-(6-(difluoromethoxy)quinolin-5-yl)-6-(3,5-dimethylisoxazol-4-yl)-1H-benzo[d]imidazol-2(3H)-one

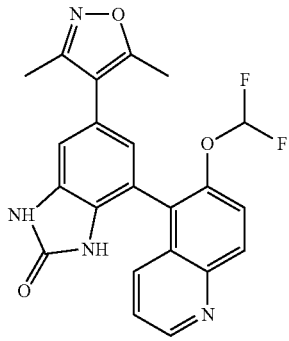 [SMILES: Cc1noc(C)c1-c1cc(-c2c(OC(F)F)ccc3ncccc23)c2[nH]c(=O)[nH]c2c1]

$C_{22}H_{16}F_2N_4O_3$. 423.1 (M+1). $^1$H NMR (400 MHz, DMSO-$d_6$) δ 10.86 (s, 1H), 10.50 (s, 1H), 8.98-8.92 (m, 1H), 8.22 (d, J=9.3 Hz, 1H), 7.86 (d, J=8.6 Hz, 1H), 7.80 (d, J=9.2 Hz, 1H), 7.58-7.51 (m, 1H), 7.23 (dd, J=74.5, 72.9 Hz, 1H), 7.04-6.98 (m, 1H), 6.87 (d, J=1.6 Hz, 1H), 2.41 (s, 3H), 2.24 (s, 3H).

Example 95

4-(3-chloro-8-fluoroquinolin-4-yl)-6-(3,5-dimethylisoxazol-4-yl)-1H-benzo[d]imidazol-2(3H)-one

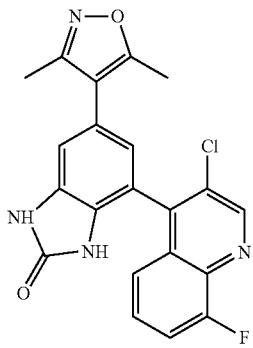 [SMILES: Cc1noc(C)c1-c1cc(-c2c(Cl)cnc3c(F)cccc23)c2[nH]c(=O)[nH]c2c1]

$C_{21}H_{14}ClFN_4O_2$. 409.1 (M+1). $^1$H NMR (400 MHz, DMSO-$d_6$) δ 10.95 (d, J=2.0 Hz, 1H), 10.58 (d, J=2.0 Hz, 1H), 9.08 (s, 1H), 7.73-7.47 (m, 2H), 7.34-7.21 (m, 1H), 7.15-7.00 (m, 1H), 6.94 (t, J=1.3 Hz, 1H), 2.42 (s, 3H), 2.24 (s, 3H).

Example 96

6-(3,5-dimethylisoxazol-4-yl)-4-(2-methylbenzo[d]thiazol-7-yl)-1H-benzo[d]imidazol-2(3H)-one

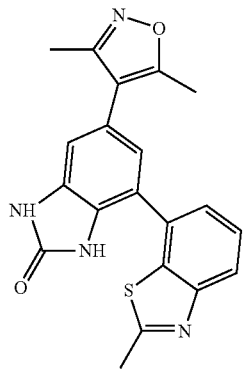 [SMILES: Cc1nc2cccc(-c3cc(-c4c(C)noc4C)cc4[nH]c(=O)[nH]c34)c2s1]

$C_{20}H_{16}N_4O_2S$. 377.1 (M+1). $^1$H NMR (400 MHz, DMSO-$d_6$) δ 10.91 (d, J=2.2 Hz, 1H), 10.68 (d, J=2.0 Hz, 1H), 7.95 (dd, J=8.0, 1.1 Hz, 1H), 7.59 (t, J=7.8 Hz, 1H), 7.50 (dd, J=7.4, 1.1 Hz, 1H), 7.09-7.01 (m, 1H), 7.00-6.92 (m, 1H), 2.80 (s, 3H), 2.43 (s, 3H), 2.26 (s, 3H).

Example 97

6-(3,5-dimethylisoxazol-4-yl)-4-(2-methyl-1H-pyrrolo[2,3-b]pyridin-3-yl)-1H-benzo[d]imidazol-2(3H)-one

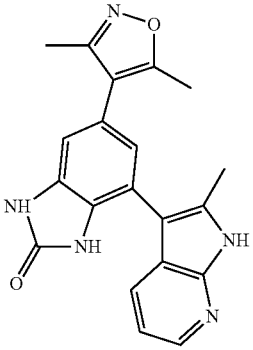 [SMILES: Cc1noc(C)c1-c1cc(-c2c(C)[nH]c3ncccc23)c2[nH]c(=O)[nH]c2c1]

$C_{20}H_{17}N_5O_2$. 360.2 (M+1). $^1$H NMR (400 MHz, DMSO-$d_6$) δ 11.73 (s, 1H), 10.75 (d, J=1.8 Hz, 1H), 10.40 (d, J=1.8 Hz, 1H), 8.14 (dd, J=4.7, 1.6 Hz, 1H), 7.64 (d, J=7.8 Hz, 1H), 7.02 (dd, J=7.8, 4.7 Hz, 1H), 6.86 (m, 2H), 2.42 (s, 3H), 2.37 (s, 3H), 2.25 (s, 3H).

Example 98

6-(3,5-dimethylisoxazol-4-yl)-4-(6-methyl-1,7-naphthyridin-5-yl)-1H-benzo[d]imidazol-2(3H)-one

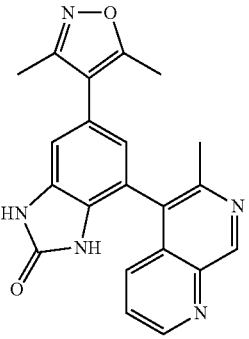 [SMILES: Cc1noc(C)c1-c1cc(-c2c(C)ncc3ncccc23)c2[nH]c(=O)[nH]c2c1]

$C_{21}H_{17}N_5O_2$. 372.1 (M+1). $^1$H NMR (400 MHz, DMSO-$d_6$) δ 10.93 (d, J=1.9 Hz, 1H), 10.48 (d, J=1.9 Hz, 1H), 9.52 (s, 1H), 9.06 (dd, J=4.0, 1.7 Hz, 1H), 7.86-7.67 (m, 2H), 7.03 (d, J=1.6 Hz, 1H), 6.89 (d, J=1.6 Hz, 1H), 2.48 (s, 3H), 2.41 (s, 3H), 2.24 (s, 3H).

Example 99

6-(3,5-dimethylisoxazol-4-yl)-4-(8-methoxy-3-methylquinolin-4-yl)-1H-benzo[d]imidazol-2(3H)-one

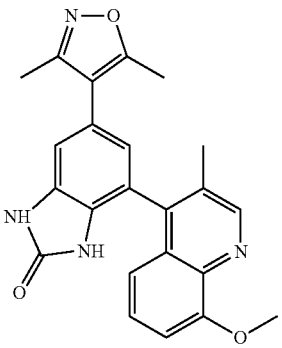 [SMILES: COc1cccc2c(-c3cc(-c4c(C)noc4C)cc4[nH]c(=O)[nH]c34)c(C)cnc12]

$C_{23}H_{20}N_4O_3$. 401.1 (M+1). $^1$H NMR (400 MHz, DMSO-$d_6$) δ 10.87 (s, 1H), 10.69-10.18 (m, 1H), 8.81 (s, 1H), 7.38 (s, 1H), 7.13 (s, 1H), 7.01 (d, J=5.0 Hz, 1H), 6.90 (d, J=7.4 Hz, 1H), 6.79 (d, J=4.9 Hz, 1H), 3.97 (s, 3H), 2.41 (s, 3H), 2.23 (d, J=4.8 Hz, 6H).

Example 100

4-(3-chloro-2-methylquinolin-4-yl)-6-(3,5-dimethyl-isoxazol-4-yl)-1H-benzo[d]imidazol-2(3H)-one

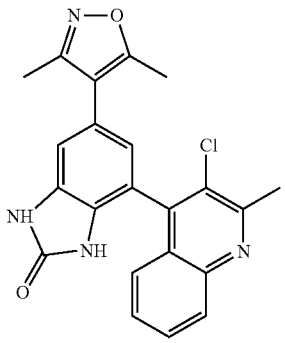 [SMILES: Cc1nc2ccccc2c(-c2cc(-c3c(C)noc3C)cc3[nH]c(=O)[nH]c23)c1Cl]

$C_{22}H_{17}ClN_4O_2$. 405.1 (M+1). $^1$H NMR (400 MHz, DMSO-$d_6$) δ 10.90 (s, 1H), 10.55 (s, 1H), 8.04 (s, 1H), 7.76 (s, 1H), 7.52 (s, 1H), 7.37 (s, 1H), 7.05 (s, 1H), 6.89 (s, 1H), 2.81 (s, 3H), 2.42 (s, 3H), 2.25 (d, J=4.1 Hz, 3H).

Example 101

6-(3,5-dimethylisoxazol-4-yl)-4-(3-ethyl-2-methylquinolin-4-yl)-1H-benzo[d]imidazol-2(3H)-one

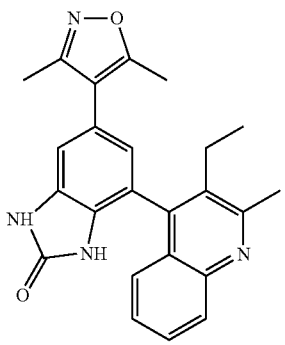 [SMILES: CCc1c(C)nc2ccccc2c1-c1cc(-c2c(C)noc2C)cc2[nH]c(=O)[nH]c12]

$C_{24}H_{22}N_4O_2$. 399.2 (M+1). $^1$H NMR (400 MHz, DMSO-$d_6$) δ 10.86 (s, 1H), 10.43 (s, 1H), 7.95 (s, 1H), 7.63 (s, 1H), 7.40 (d, J=8.8 Hz, 1H), 7.17 (d, J=8.2 Hz, 1H), 7.01 (s, 1H), 6.81 (s, 1H), 2.76 (s, 5H), 2.41 (s, 3H), 2.23 (s, 3H), 1.00 (d, J=7.8 Hz, 3H).

Example 102

4-(6-(3,5-dimethylisoxazol-4-yl)-2-oxo-2,3-dihydro-1H-benzo[d]imidazol-4-yl)-3-methylquinoline-8-carbonitrile

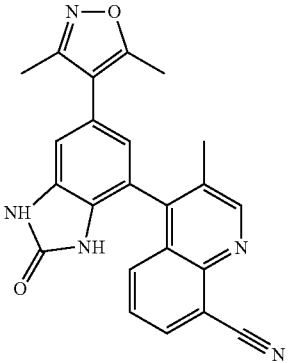 [SMILES: Cc1cnc2c(C#N)cccc2c1-c1cc(-c2c(C)noc2C)cc2[nH]c(=O)[nH]c12]

$C_{23}H_{17}N_5O_2$. 396.1 (M+1). $^1$H NMR (400 MHz, DMSO-$d_6$) δ 10.93 (d, J=1.8 Hz, 1H), 10.45 (d, J=1.9 Hz, 1H), 9.10 (s, 1H), 8.31 (dd, J=6.9, 1.6 Hz, 1H), 7.88-7.51 (m, 2H), 7.16-6.92 (m, 1H), 6.88 (d, J=1.6 Hz, 1H), 2.41 (s, 3H), 2.30 (s, 3H), 2.24 (s, 3H).

Example 103

4-(3-(difluoromethyl)quinolin-4-yl)-6-(3,5-dimethyl-isoxazol-4-yl)-1H-benzo[d]imidazol-2(3H)-one

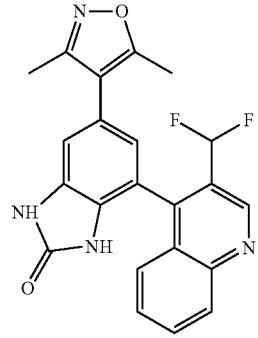 [SMILES: Cc1noc(C)c1-c1cc(-c2c(C(F)F)cnc3ccccc23)c2[nH]c(=O)[nH]c2c1]

$C_{22}H_{16}F_2N_4O_2$. 407.1 (M+1). $^1$H NMR (400 MHz, DMSO-$d_6$) δ 10.96 (d, J=1.8 Hz, 1H), 10.54 (d, J=1.9 Hz, 1H), 9.22 (s, 1H), 8.19 (dd, J=8.5, 1.2 Hz, 1H), 8.06-7.78 (m, 1H), 7.64 (ddd, J=8.3, 6.8, 1.3 Hz, 1H), 7.54-7.35 (m, 1H), 7.08 (d, J=1.6 Hz, 1H), 7.05-6.67 (m, 2H).

Example 104

4-(6-(3,5-dimethylisoxazol-4-yl)-2-oxo-2,3-dihydro-1H-benzo[d]imidazol-4-yl)cinnoline-3-carboxylic Acid

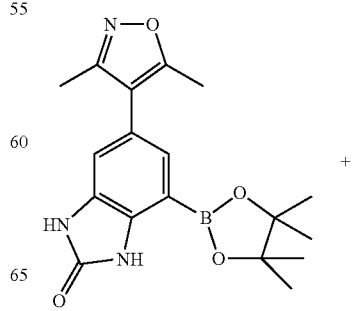

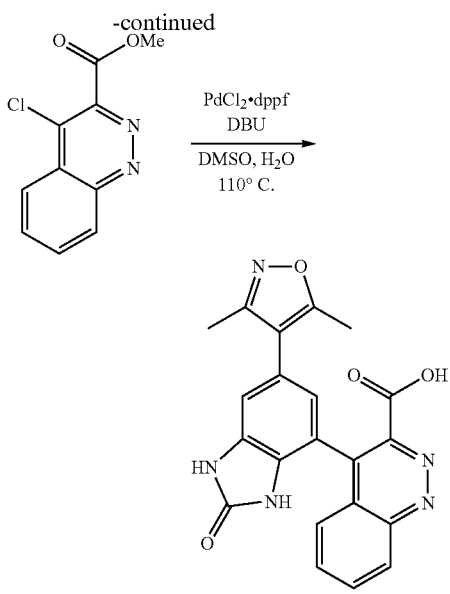

A mixture of 6-(3,5-dimethylisoxazol-4-yl)-4-(4,4,5,5-tetramethyl-1,3,2-dioxaborolan-2-yl)-1H-benzo[d]imidazol-2(3H)-one (100.0 mg, 0.282 mmol) and methyl 4-chlorocinnoline-3-carboxylate (94.0 mg, 0.422 mmol) was treated with PdCl$_2$dppf.CH$_2$Cl$_2$ (20.6 mg, 0.028 mmol) in the presence of 1,8-Diazabicycloundec-7-ene (DBU, 300.0 mg, 1.971 mmol, 7.0 equiv) in DMSO (1 mL) and water (1 mL). The reaction mixture was heated at 110° C. for 12 min in oil bath. The reaction mixture was purified by HPLC to give 4-(6-(3,5-dimethylisoxazol-4-yl)-2-oxo-2,3-dihydro-1H-benzo[d]imidazol-4-yl)cinnoline-3-carboxylic acid.

C$_{21}$H$_{15}$N$_5$O$_4$. MS. m/z 402.0 (M+1). $^1$H NMR (400 MHz, Methanol-d$_4$) δ 8.67 (d, J=8.8 Hz, 1H), 8.09 (t, J=8.8 Hz, 1H), 7.92 (d, J=8.8 Hz, 1H), 7.70 (d, J=8.8 Hz, 1H), 7.17 (s, 1H), 6.96 (s, 1H), 2.44 (s, 3H), 2.29 (s, 3H).

Example 105

6-(3,5-dimethylisoxazol-4-yl)-4-(3-methylisoquinolin-4-yl)-1H-benzo[d]imidazol-2(3H)-one

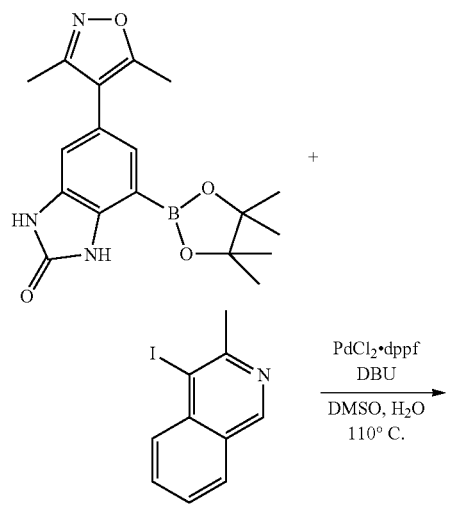

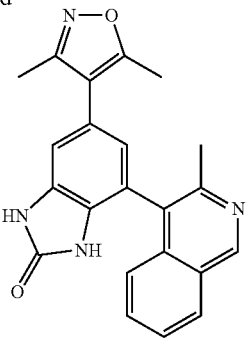

6-(3,5-Dimethylisoxazol-4-yl)-4-(3-methylisoquinolin-4-yl)-1H-benzo[d]imidazol-2(3H)-one was prepared from 4-iodo-3-methylisoquinoline in a similar fashion as Example 104.

C$_{22}$H$_{18}$N$_4$O$_2$. MS. m/z 371.1 (M+1). $^1$H NMR (400 MHz, Methanol-d$_4$) 9.26 (s, 1H), 8.16 (d, J=7.7 Hz, 1H), 7.67 (m, 2H), 7.42 (d, J=8.2 Hz, 1H), 7.15 (s, 1H), 6.91 (s, 1H), 2.50 (s, 3H), 2.45 (s, 3H), 2.29 (s, 3H).

Example 106

6-(3,5-dimethylisoxazol-4-yl)-4-(2-methylnaphthalen-1-yl)-1H-benzo[d]imidazol-2(3H)-one

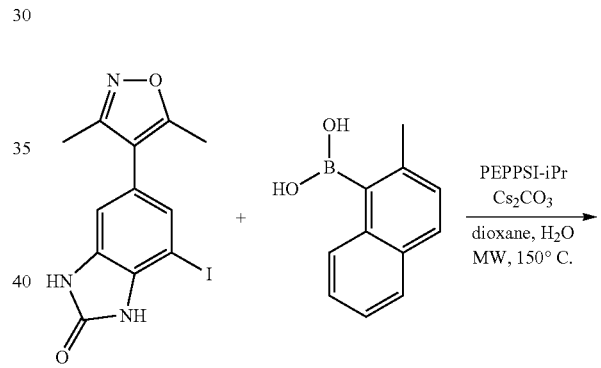

In a 2-5 mL Smith Process Vial, 6-(3,5-dimethylisoxazol-4-yl)-4-iodo-1H-benzo[d]imidazol-2(3H)-one (100.0 mg 0.282 mmol), (2-methylnaphthalen-1-yl)boronic acid (176.0 mg, 0.946 mmol, 3.36 equiv), PEPPSI-iPr (19.2 mg, 0.028 mmol, 0.1 equiv) and Cs$_2$CO$_3$ (337.0 mg, 1.126 mmol, 4 equiv) were placed. The mixture was suspended in 1,4-dioxane (1.5 mL) and water (0.5 mL) under N2. The mixture was heated at 150° C. for 75 min using microwave reactor (Biotage Optimizer). After an aqueous work up, the crude product was purified by a silica-gel column chromatography (hexane/EtOAc 20:80) to give 6-(3,5-dimethylisoxazol-4-yl)-4-(2-methylnaphthalen-1-yl)-1H-benzo[d]imidazol-2(3H)-one.

C23H19N3O2. MS. m/z 370.1 (M+1). 1H NMR (400 MHz, Methanol-d4) δ 7.88 (d, J=8.6 Hz, 2H), 7.50 (d, J=8.6 Hz, 1H), 7.45-7.38 (m, 1H), 7.38-7.33 (m, 2H), 7.10 (s, 1H), 6.82 (s, 1H), 2.43 (s, 3H), 2.28 (s, 6H).

Example 107

4-(2-(difluoromethyl)-3-methylquinolin-4-yl)-6-(3,5-dimethylisoxazol-4-yl)-1H-benzo[d]imidazol-2(3H)-one

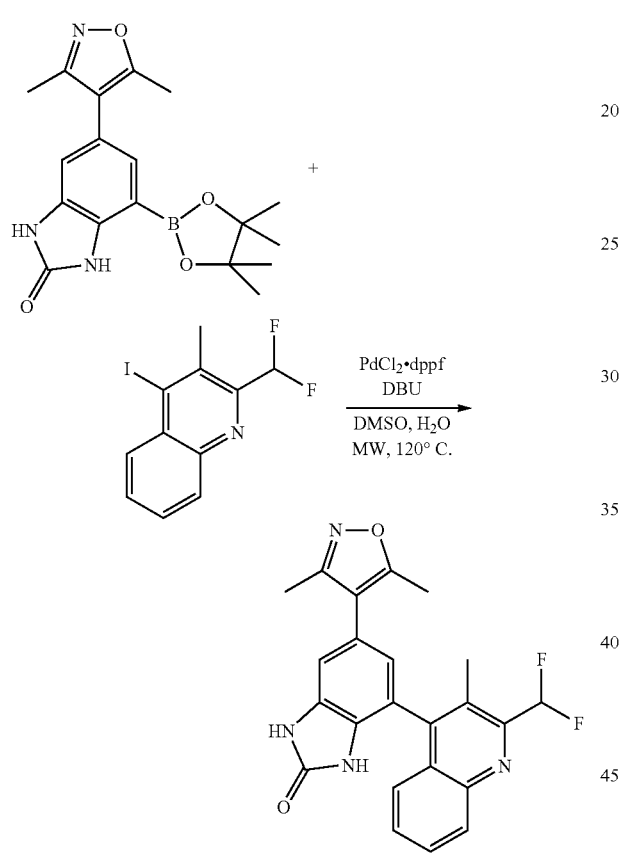

4-(2-(Difluoromethyl)-3-methylquinolin-4-yl)-6-(3,5-dimethylisoxazol-4-yl)-1H-benzo[d]imidazol-2(3H)-one was prepared from 2-(difluoromethyl)-4-iodo-3-methylquinoline in a similar fashion as Example 104.

$C_{23}H_{18}F_2N_4O_2$. MS. m/z 421.1 (M+1). $^1$H NMR (400 MHz, Methanol-$d_4$) δ 8.18 (d, J=9.0 Hz, 1H), 7.83-7.74 (m, 1H), 7.63-7.57 (m, 1H), 7.45 (d, J=9.4 Hz, 1H), 7.23-6.87 (m, 2H), 2.44 (s, 6H), 2.30 (s, 3H).

Example 108

4-chloro-5-(3,5-dimethylisoxazol-4-yl)-7-(6-methylquinolin-5-yl)-1H-benzo[d]imidazol-2(3H)-one In 0.5-2 mL Smith Process Vial, the substrate (25.0 mg, 0.067 mmol) and NCS (36.3 mg, 0.135 mmol) were dissolved into THF (2 mL) The mixture was heated at 80° C. for 2 h in an oil bath. The reaction mixture was purified by HPLC (5-95% acetonitrile:water with 0.05% trifluoroacetic acid, on a Phenomenex Luna C18 column) to give the desired product.

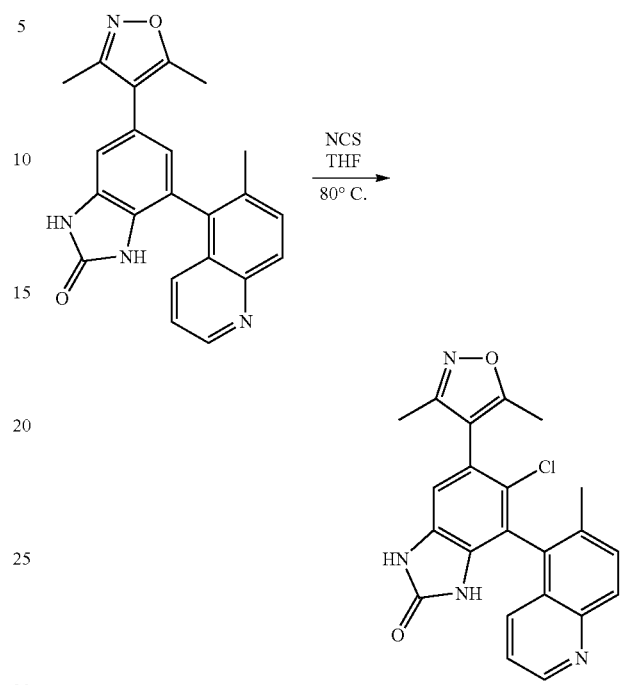

$C_{22}H_{17}ClN_4O_2$. MS. m/z 405.1 (M+1), 407.1 (M+2+1). $^1$H NMR (400 MHz, Methanol-$d_4$) δ 9.25-9.05 (d, J=5.8 Hz, 1H), 8.47-8.40 (m, 1H), 8.30 (d, J=9.0 Hz, 1H), 8.20 (d, J=9.0 Hz, 1H), 7.96-7.90 (m, 1H), 7.19 (s, 1H), 2.40 (s, 3/2H), 2.39 (s, 3/2H), 2.38 (s, 3/2H), 2.34 (s, 3/2H) 2.21 (s, 3/2H), 2.19 (s, 3/2H).

Example 109

6-(3,5-dimethylisoxazol-4-yl)-4-(8-fluoro-6-methylquinolin-5-yl)-1H-benzo[d]imidazol-2(3H)-one

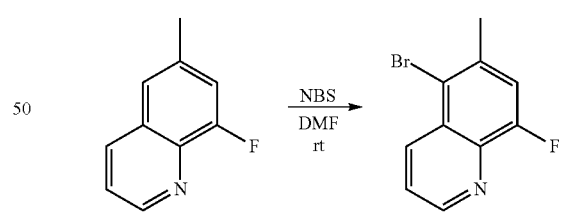

Step 1

3,5-Dicyclopropylisoxazole (70.0 mg, 0.469 mmol) was treated with NBS (167.0 mg, 0.938 mmol, 2 equiv) in CH2Cl2 at room temperature for 12 h. The solvent was removed under a reduced pressure and the residue was directly loaded onto a silica gel column chromatography (hexane EtOAc 87:13) to give 5-bromo-8-fluoro-6-methylquinoline.

C9H10BrON. MS. m/z 239.9 (M−1+1), 241.9 (M+1+1).

Step 2

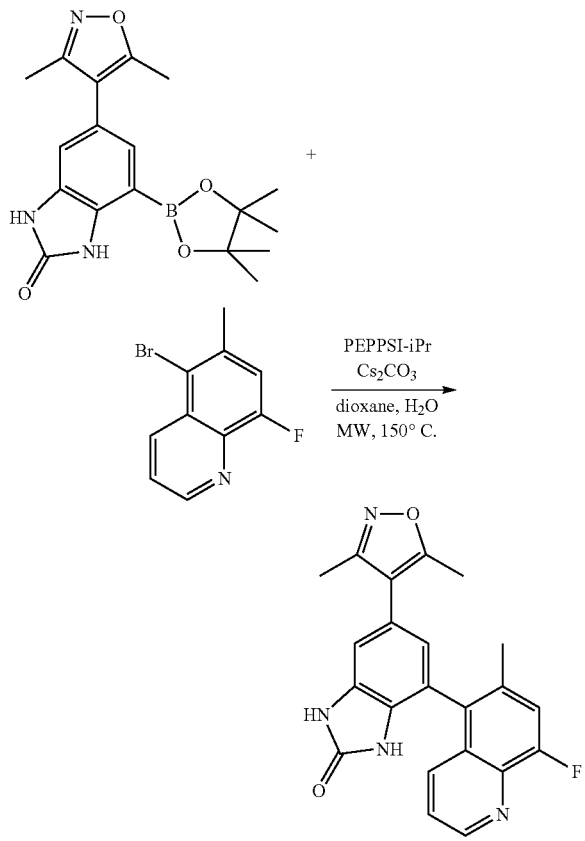

$C_{22}H_{17}FN_4O_2$. MS. m/z 398.1 (M+1). $^1$H NMR (400 MHz, Methanol-$d_4$) δ 8.93 (d, 1H, J=4.0 Hz), 8.08 (d, 1H, J=8.0 Hz), 7.70 (d, 1H, J=11.2 Hz), 7.67 (dd, 1H, J=8.0, 4.0 Hz), 7.15 (d, 1H, J=1.0 Hz), 6.88 (d, 1H, J=1.0 Hz), 2.43 (s, 3H), 2.38 (s, 3H), 2.28 (s, 3H).

Example 110

Example 111, and

Example 112

7-(3,5-dimethyl-1H-pyrazol-4-yl)-5-(3,5-dimethyl-isoxazol-4-yl)-1-methyl-1H-benzo[d]imidazol-2(3H)-one

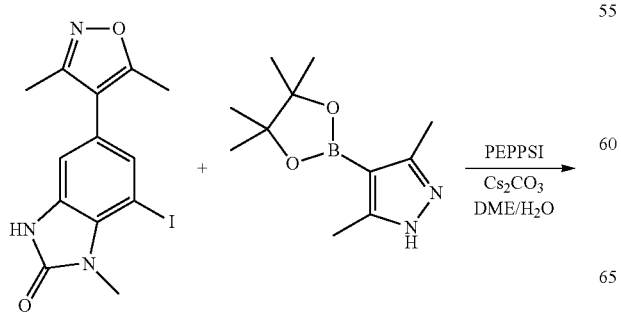

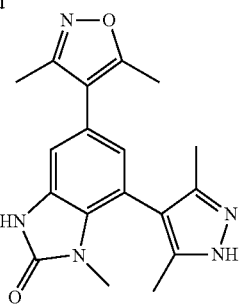

5-(3,5-dimethylisoxazol-4-yl)-7-iodo-1-methyl-1H-benzo[d]imidazol-2(3H)-one (60 mg, 0.16 mmol) was placed in a microwave vial followed by the addition of PEPPSI (11 mg, 0.016 mmol) and cesium carbonate (158.9 mg, 4.9 mmol). The material was then dissolved in 1.5 mL of DME and 1.5 mL of water. The vial was then placed in the microwave where it was heated to 165° C. for one hour. The crude solution was then diluted with water and extracted 3 times with ethyl acetate. Combined organic layers were washed with brine, dried over sodium sulphate, filtered, concentrated in vacuo, and purified via HPLC to afford 7-(3,5-dimethyl-1H-pyrazol-4-yl)-5-(3,5-dimethylisoxazol-4-yl)-1-methyl-1H-benzo[d]imidazol-2(3H)-one.

$C_{18}H_{19}N_5O_2$; 338.2 (m/z+1). $^1$H NMR (400 MHz, cd$_3$od) δ 7.03 (d, J=1.6 Hz, 1H), 6.75 (d, J=1.6 Hz, 1H), 3.01 (s, 3H), 2.41 (s, 3H), 2.26 (s, 3H), 2.12 (s, 6H).

Example 113

6-(3,5-dimethylisoxazol-4-yl)-4-(1-(4-fluorophenyl)vinyl)-1H-benzo[d]imidazol-2(3H)-one

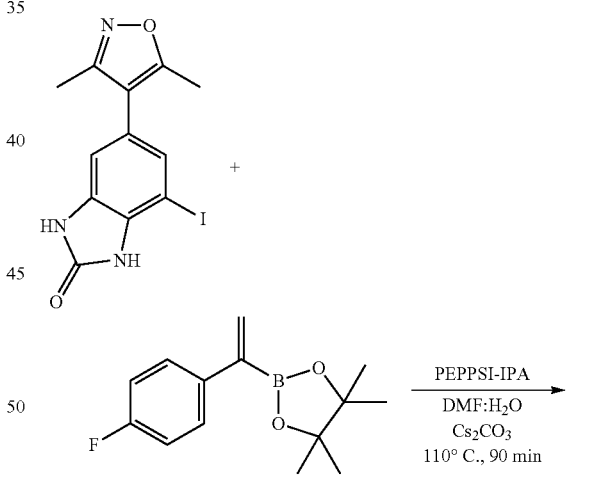

6-(3,5-Dimethylisoxazol-4-yl)-4-iodo-1H-benzo[d]imidazol-2(3H)-one (100 mg, 0.28 mmol), 1-(4-Fluorophenyl)vinylboronic acid, pinacol ester (209.59 mg, 0.84 mmol), PEPPSI"-IPr catalyst (19.19 mg, 0.03 mmol), 1,8-Diazabicyclo[5.4.0]undec-7-ene solution (0.25 ml, 1.69 mmol) were mixed in 1-Methyl-2-pyrrolidinone (6 ml) and Water (3 ml) in sealed in a microwave vial and heated to 110° C. for 30 minutes in a microwave reactor. The reaction mixture was then cooled and partitioned between water and ethyl acetate. The organic layer was washed with water then brine and dried over sodium sulfate. Purification on silica gel (Hexane/EtOAc) followed by preparative HPLC afforded 6-(3,5-dimethylisoxazol-4-yl)-4-(1-(4-fluorophenyl)vinyl)-1H-benzo[d]imidazol-2(3H)-one.

C20H16FN3O2; 350.2 (M+1). 1H NMR (400 MHz, DMSO-d6) δ 7.35 (dd, J=8.7, 5.6 Hz, 2H), 7.16 (t, J=8.8 Hz, 2H), 6.86 (d, J=1.6 Hz, 1H), 6.59 (d, J=1.6 Hz, 1H), 5.81 (s, 1H), 5.44 (s, 1H), 2.32 (s, 3H), 2.14 (s, 3H). 19F NMR (376 MHz, DMSO-d6) δ −114.96 (ddd, J=14.4, 9.1, 5.5 Hz).

The following compound(s) were made in a similar fashion using appropriately substituted boronic acids or esters.

Example 114

6-(3,5-dimethylisoxazol-4-yl)-4-(2-(morpholinomethyl)phenyl)-1H-benzo[d]imidazol-2(3H)-one

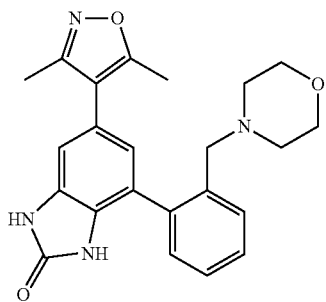 [SMILES: Cc1noc(C)c1-c1cc(-c2ccccc2CN2CCOCC2)c2[nH]c(=O)[nH]c2c1]

$C_{23}H_{24}N_4O_3$; 405.2 (M+1). 1H NMR (400 MHz, DMSO-d6) δ 7.52 (dd, J=7.4, 1.7 Hz, 1H), 7.40 (dtd, J=14.7, 7.3, 1.7 Hz, 2H), 7.30 (dd, J=7.2, 1.8 Hz, 1H), 6.90 (d, J=1.6 Hz, 1H), 6.78 (d, J=1.6 Hz, 1H), 3.47 (t, J=4.4 Hz, 3H), 2.41 (s, 3H), 2.24 (s, 5H), 1.66 (d, J=5.6 Hz, 1H), 1.54 (dq, J=13.7, 6.9, 6.3 Hz, 2H).

Example 115

6-(3,5-dimethylisoxazol-4-yl)-4-(1-(4-fluorophenyl)ethyl)-1H-benzo[d]imidazol-2(3H)-one

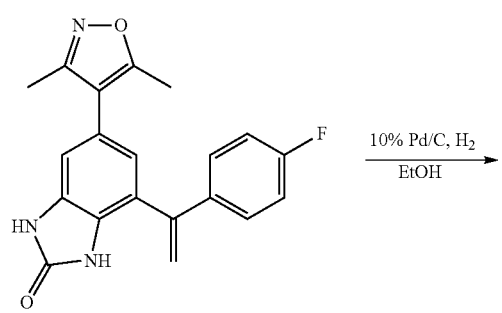

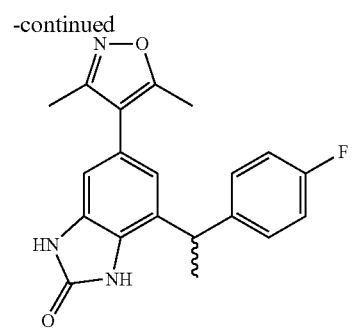

GS-646621

A suspension of 6-(3,5-dimethylisoxazol-4-yl)-4-(1-(4-fluorophenyl)vinyl)-1H-benzo[d]imidazol-2(3H)-one (60 mg, 0.172 mmol) and 10% palladium on carbon (20 mg) in 5 mL ethanol was purged with hydrogen gas and allowed to stir for 2 hours. The reaction mixture was then filtered and the solvents evaporated. Residue was purified by preparative HPLC which afforded 6-(3,5-dimethylisoxazol-4-yl)-4-(1-(4-fluorophenyl)ethyl)-1H-benzo[d]imidazol-2(3H)-one.

$C_{20}H_{18}FN_3O_2$; 352.2 (M+1). $^1$H NMR (400 MHz, DMSO-d6) δ 10.92 (s, 1H), 10.71 (s, 1H), 7.45 (dd, J=8.6, 5.7 Hz, 2H), 7.12 (t, J=8.9 Hz, 2H), 6.84 (d, J=1.5 Hz, 1H), 6.73 (d, J=1.5 Hz, 1H), 4.43 (q, J=7.2 Hz, 1H), 2.35 (s, 3H), 2.17 (s, 3H), 1.61 (d, J=7.2 Hz, 3H). $^{19}$F NMR (376 MHz, DMSO-d6) δ −117.55 (tt, J=9.1, 5.6 Hz).

Example 116

5-(3,5-dimethylisoxazol-4-yl)-1-ethyl-7-(6-methylquinolin-5-yl)-1H-benzo[d]imidazol-2(3H)-one

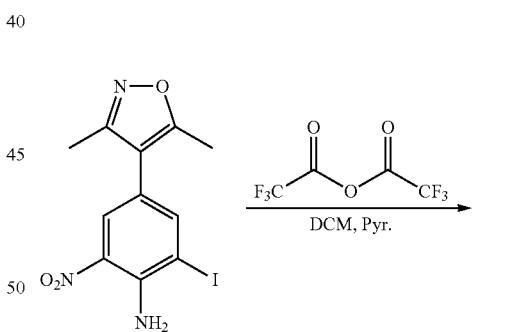

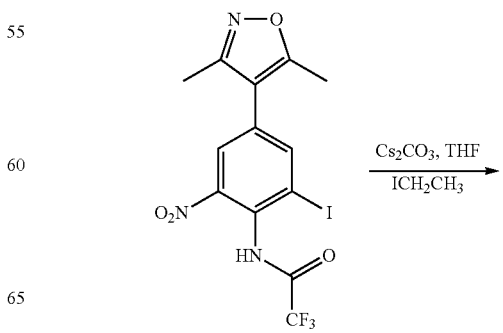

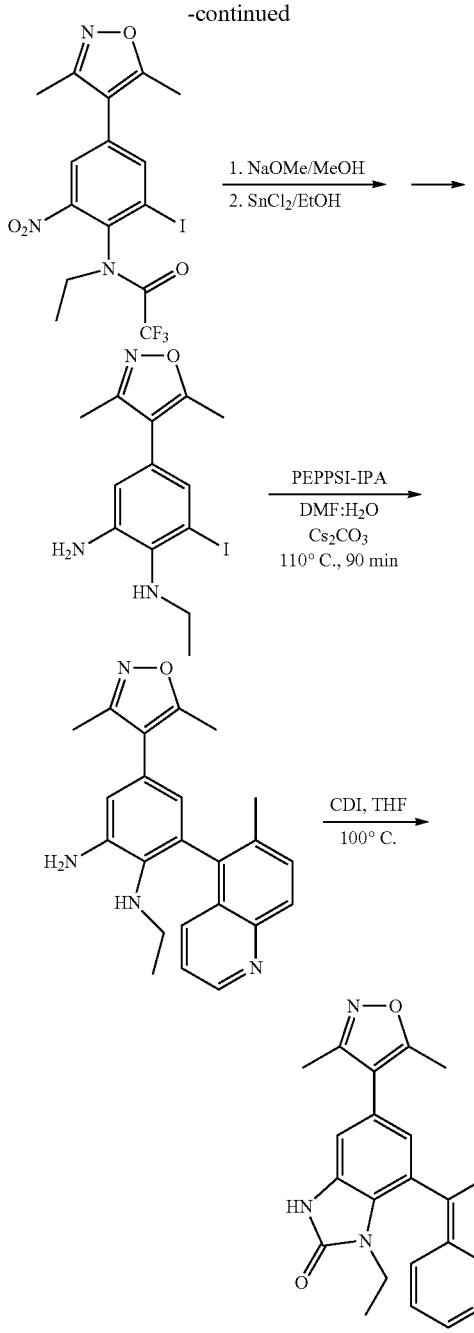

Step 1

4-(3,5-Dimethylisoxazol-4-yl)-2-iodo-6-nitroaniline (4 g, 11.1 mmol) was dissolved in 100 mL DCM and to the solution was added pyridine (2.7 mL, 33.3 mmol) before cooling to 0° C. under argon. To the solution was then added dropwise triflic anhydride (3 g, 14.5 mmol) before allowing the reaction to slowly warm to room temperature overnight. The reaction mixture was suspended slowly into stirring DCM/water before extracting 3 times with DCM. Organics were then washed with water, brine then dried over sodium sulfate. Solvent was removed under reduced pressure to yield crude N-(4-(3,5-dimethylisoxazol-4-yl)-2-iodo-6-nitrophenyl)-2,2,2-trifluoroacetamide as a brown oil.

Step 2

A mixture of N-(4-(3,5-dimethylisoxazol-4-yl)-2-iodo-6-nitrophenyl)-2,2,2-trifluoroacetamide (2.2 g, 4.83 mmol), cesium carbonate (3.94 g, 12.08 mmol) and N,N-Dimethylformamide (100 ml) was stirred at room temperature under argon. To the mixture was added iodoethane (3.77 g, 24.17 mmol) and reaction was heated to 45° C. overnight. Crude mixture was diluted in EtOAc and water and extracted 3 times with EtOAc. Organics were washed with water, aq LiCl, then brine, dried over sodium sulfate and evaporated to dryness under reduced pressure to afford crude N-(4-(3,5-dimethylisoxazol-4-yl)-2-iodo-6-nitrophenyl)-N-ethyl-2,2,2-trifluoroacetamide as a dark oil.

Step 3

Crude N-(4-(3,5-dimethylisoxazol-4-yl)-2-iodo-6-nitrophenyl)-N-ethyl-2,2,2-trifluoroacetamide (1.5 g, 3.1 mmol) was dissolved in 100 mL of methanol. To the mixture was added 1M sodium methoxide in methanol (15.5 mL, 15.5 mmol) and reaction stirred at room temperature until complete. Reaction was then quenched with 15 mL of 1M HCl or until pH is approximately neutral then diluted with aqueous ammonium chloride. Methanol was removed under reduced pressure and then remaining suspension was extracted with EtOAc. The solution was washed with water, brine then dried over sodium sulfate. Solvents were removed under reduced pressure the residue was then dissolved in 20 mL of ethanol and placed in a sealed pressure tube with stannous chloride (2.2 g, 11.62 mmol). The mixture was heated at 120° C. for 1 hour. Reaction mixture was cooled to room temperature. To the mixture was added 1M NaOH (10 mL) and the mixture was stirred at room temperature for 30 minutes. At this point the reaction mixture was diluted with water and extracted with EtOAc (3 times). The solution was washed with water, brine and dried over sodium sulfate. Solvents were removed under reduced pressure and crude product was purified by silica gel chromatography (Hexanes/EtOAc as the eluent) to provide 4-(3,5-dimethylisoxazol-4-yl)-N1-ethyl-6-iodobenzene-1,2-diamine (310 mg, 22%).

Step 4

4-(3,5-Dimethylisoxazol-4-yl)-N1-ethyl-6-iodobenzene-1,2-diamine (105 mg, 0.29 mmol), 6-methylquinolin-5-ylboronic acid (274.86 mg, 1.47 mmol), 1,8-Diazabicyclo[5.4.0]undec-7-ene (0.26 mL, 1.76 mmol), 1-Methyl-2-pyrrolidinone (5 mL), and water (2 mL) were placed in microwave vial, pre-stirred for 2 minutes, then heated to 110° C. for 15 minutes. Reaction mixture was diluted with EtOAc and aqueous ammonium chloride and extracted with EtOAc (3 times). Organics were washed with ammonium chloride, water and brine and dried over sodium sulfate. Solvent was evaporated to dryness. Crude material was purified by silica gel chromatography (DCM/MeOH as eluent) to afford 4-(3,5-dimethylisoxazol-4-yl)-N1-ethyl-6-(6-methylquinolin-5-yl)benzene-1,2-diamine.

Step 5

4-(3,5-Dimethylisoxazol-4-yl)-N1-ethyl-6-(6-methylquinolin-5-yl)benzene-1,2-diamine (90 mg, 0.24 mmol) and 1,1'-carbonyldiimidazole (86.2 mg, 0.53 mmol) were added to tetrahydrofuran (10 ml) in a sealed vessel and heated to 105° C. overnight. The reaction mixture was the diluted in EtOAc and aqueous ammonium chloride and extracted with EtOAc (3 times). Organics were washed with ammonium chloride, water and brine and dried over sodium sulfate. Solvent was evaporated to dryness Crude material was purified by silica gel chromatography (DCM/MeOH as eluent) then by preparative HPLC to afford 5-(3,5-dimethylisoxazol-4-yl)-1-ethyl-7-(6-methylquinolin-5-yl)-1H-benzo[d]imidazol-2(3H)-one.

$C_{24}H_{22}N_4O_2$. 399.2 (M+1). 1H NMR (400 MHz, Methanol-d4) δ 8.86 (d, J=4.2 Hz, 1H), 8.12 (d, J=8.7 Hz, 1H), 7.97-7.89 (m, 1H), 7.85 (d, J=8.7 Hz, 1H), 7.51 (dd, J=8.6, 4.3 Hz, 1H), 7.19 (d, J=1.6 Hz, 1H), 6.82 (d, J=1.6 Hz, 1H), 3.19-3.00 (m, J=7.1 Hz, 2H), 2.43 (s, 3H), 2.36 (s, 3H), 2.27 (s, 3H), 0.52 (t, J=7.1 Hz, 3H).

Example 117

5-(3,5-dimethylisoxazol-4-yl)-7-(6-methylquinolin-5-yl)-1-(2,2,2-trifluoroethyl)-1H-benzo[d]imidazol-2(3H)-one

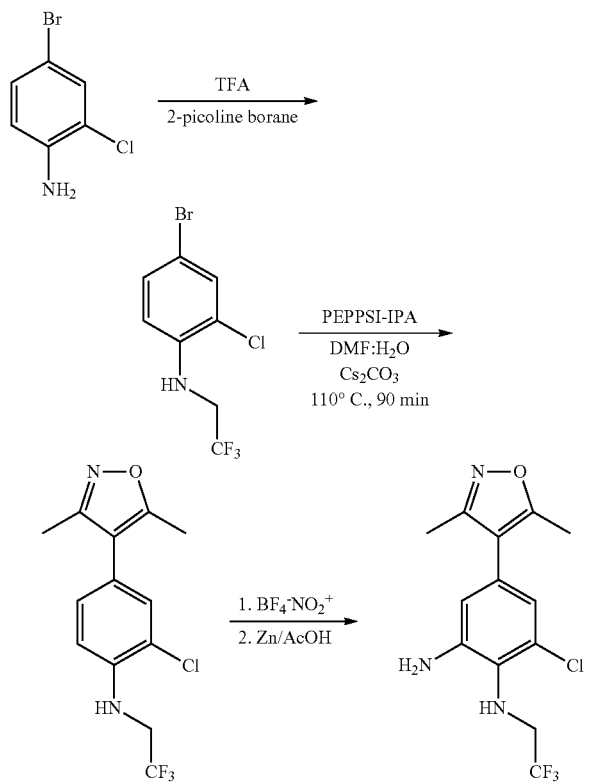

Step 1

4-Bromo-2-chloroaniline (5000 mg, 24.22 mmol) was dissolved in trifluoroacetic acid (40 ml) and 1,2-dimethoxyethane (50 ml) then cooled under argon to 0° C. To the mixture was added 2-picoline borane complex (12951.34 mg, 121.08 mmol) and then the reaction mixture was heated 110° C. for 90 minutes. Solvents were removed under reduced pressure and crude material was taken up in 1N HCl and stirred at 110° C. 30 minutes. Crude mixture was then diluted with EtOAc and water and extracted EtOAc (3 times). Organics were washed with water then brine, dried over sodium sulfate and evaporated to dryness under reduced pressure. Crude material was purified by silica gel chromatography using EtOAc/Hexanes as the eluent to afford 4-bromo-2-chloro-N-(2,2,2-trifluoroethyl)aniline.

Step 2

A mixture of 4-Bromo-2-chloro-N-(2,2,2-trifluoroethyl) aniline (5280 mg, 18.3 mmol), 3,5-dimethylisoxazole-4-boronic acid, pinacol ester (4082.76 mg, 18.3 mmol), PEPPSI"-IPr catalyst (1247.24 mg, 1.83 mmol), Cesium carbonate (17889.52 mg, 54.91 mmol) in 120 mL DME:H$_2$O (2:1) was heated to 90° C. under argon. The reaction mixture was then cooled and partitioned between water and ethyl acetate. The organic layer was washed with water then brine and dried over sodium sulfate. Purification on silica gel (Hexanes/EtOAc) afforded 2-chloro-4-(3,5-dimethylisoxazol-4-yl)-N-(2,2,2-trifluoroethyl)aniline.

Step 3

2-Chloro-4-(3,5-dimethylisoxazol-4-yl)-N-(2,2,2-trifluoroethyl)aniline (200 mg, 0.66 mmol) was dissolved in dichloromethane (10 mL) and acetonitrile (10 mL) and cooled to 0° C. under argon. To reaction mixture was added 0.5M nitronium tetrafluoroborate (1.84 ml) slowly over 20 minutes. Reaction mixture was stirred at 0° C., for 1 hour and allowed to warm to room temperature. After 3 hours, the reaction mixture was cooled to 0° C. again and 0.5M nitronium tetrafluoroborate in sulfolane (1.84 ml) was added and the reaction solution was stirred at room temperature overnight. Reaction solvents were removed under reduced pressure and the residue taken up in EtOAc and the solution was washed with aq. NaHCO$_3$, then water, brine and dried over sodium sulfate. Solvents were removed under reduced pressure to yield a dark red oil/liquid. This material was dissolved in 2 mL of ethanol and 2 mL of acetic acid. To the solution was added Zinc dust and suspension was stirred. After 30 minutes of stirring the zinc dust was filtered off and the solvents were removed under reduced pressure. The residue was dissolved in EtOAc and the solution was washed with aq. NaHCO$_3$, then water, brine and dried over sodium sulfate. Solvent was removed and the crude residue was purified by silica gel chromatography (Hexanes/EtOAc as the eluent) to afford 6-chloro-4-(3,5-dimethylisoxazol-4-yl)-N1-(2,2,2-trifluoroethyl)benzene-1,2-diamine as a light colored oil.

Example 118

The following compound was synthesized in a similar fashion as that of Example 117.

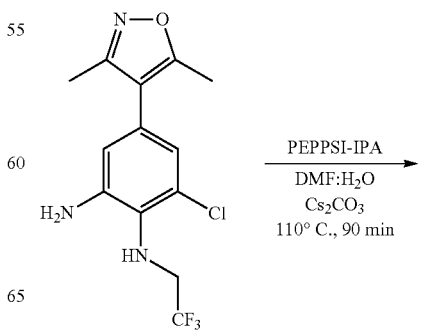

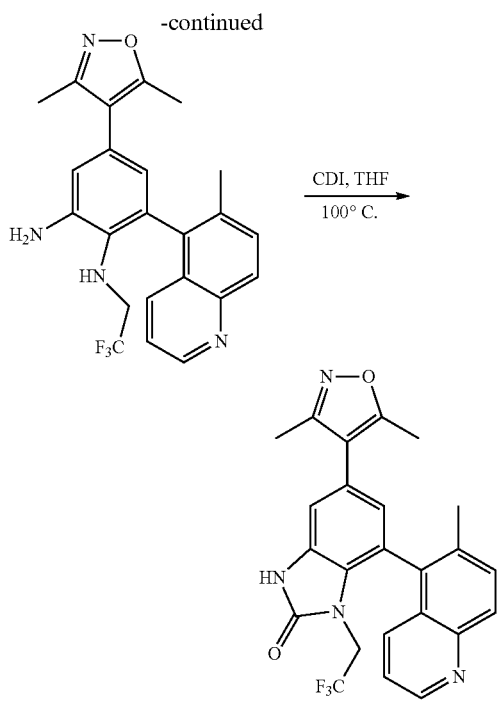

$C_{24}H_{19}F_3N_4O_2$; 453.3 (M+1). 1H NMR (400 MHz, DMSO-d6) δ 11.51 (s, 1H), 8.86 (dd, J=4.2, 1.6 Hz, 1H), 8.16-7.97 (m, 1H), 7.78 (d, J=8.7 Hz, 1H), 7.73-7.61 (m, 1H), 7.44 (dd, J=8.6, 4.2 Hz, 1H), 7.14 (d, J=1.7 Hz, 1H), 6.81 (d, J=1.7 Hz, 1H), 3.89-3.58 (m, 2H), 2.39 (s, 3H), 2.22 (d, J=4.6 Hz, 6H). 19F NMR (376 MHz, DMSO-d6) δ −69.65 (t, J=8.9 Hz).

Example 119

5-(3,5-dimethylisoxazol-4-yl)-1-methyl-7-(6-methylquinolin-5-yl)-1H-benzo[d]imidazol-2(3H)-one Step 1: 4-(3,5-dimethylisoxazol-4-yl)-2-iodo-N-methyl-6-nitroaniline

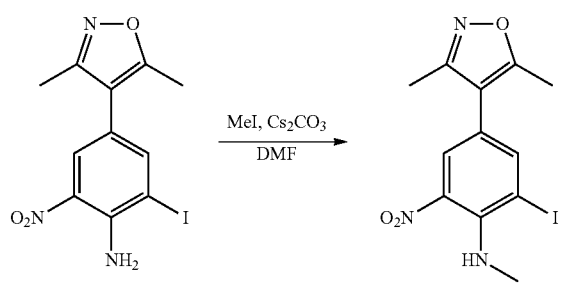

To a flask containing 4-(3,5-dimethylisoxazol-4-yl)-2-iodo-6-nitroaniline (1000 mg, 2.78 mmol, 1 equiv) was added DMF (15 mL, 0.2 M), cesium carbonate (1.4 gm, 4.17 mmol, 1.5 equiv.) and idomethane (260 μL, 4.17 mmol, 1.5 equiv). After an hour, the reaction was quenched with water and partitioned between water and ethyl acetate. The organic layer was washed with brine and dried over sodium sulfate. Purification was carried out by flash column chromatography to furnish 4-(3,5-dimethylisoxazol-4-yl)-2-iodo-N-methyl-6-nitroaniline (615 mg, 60%). ¹H NMR (400 MHz, cdcl₃) δ 7.81 (t, J=3.0 Hz, 1H), 7.70 (d, J=2.1 Hz, 1H), 2.97 (s, 3H), 2.40 (d, J=16.8 Hz, 3H), 2.26 (d, J=14.2 Hz, 3H).

LCMS (m/z+1) 373.

Step 2: 5-(3,5-dimethylisoxazol-4-yl)-1-methyl-7-(6-methylquinolin-5-yl)-1H-benzo[d]imidazol-2(3H)-one

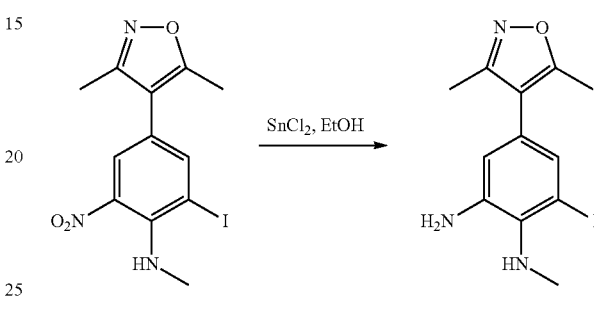

To a microwave vial containing 4-(3,5-dimethylisoxazol-4-yl)-2-iodo-N-methyl-6-nitroaniline (610 mg, 1.64 mmol, 1 equiv) was added EtOH (12 mL, 0.25M) and tin (II) chloride (622 mg, 3.28 mmol, 2 equiv). The reaction mixture was heated for 30 min at 110° C. The reaction was then stirred in 2N NaOH solution for 20 minutes and partitioned between water and ethyl acetate. The organic layer was washed with brine and dried over sodium sulfate. Purification was carried out by flash column chromatography to furnish 4-(3,5-dimethylisoxazol-4-yl)-6-iodo-N1-methylbenzene-1,2-diamine.

LCMS (m/z+1) 344.02

Step 3: 5-(3,5-dimethylisoxazol-4-yl)-7-iodo-1-methyl-1H-benzo[d]imidazol-2(3H)-one

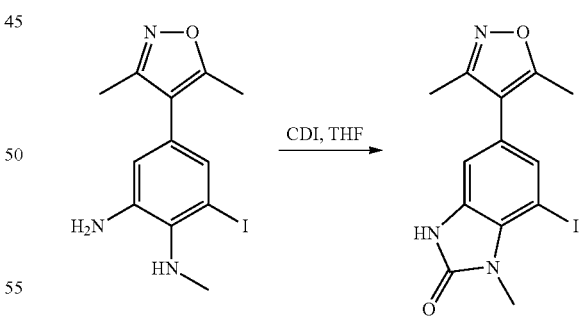

To a flask containing 4-(3,5-dimethylisoxazol-4-yl)-6-iodo-N1-methylbenzene-1,2-diamine (299 mg, 0.87 mmol, 1 equiv) was added THF (8 mL) and CDI (282 mg, 1.74 mmol, 2 equiv). The reaction mixture was heated for 2 hr at 120° C. The reaction mixture was then concentrated in vacuo and the solid triturated with diethyl ether to furnish 5-(3,5-dimethylisoxazol-4-yl)-7-iodo-1-methyl-1H-benzo[d]imidazol-2(3H)-one as a light yellow solid.

LCMS (m/z+1) 370.00.

Step 4

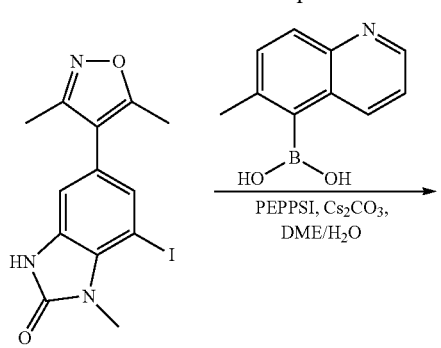

PEPPSI, Cs₂CO₃,
DME/H₂O

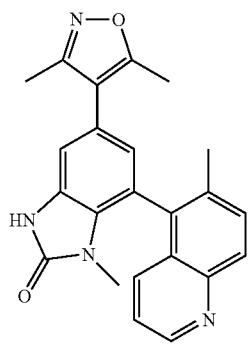

To a microwave vial containing 5-(3,5-dimethylisoxazol-4-yl)-7-iodo-1-methyl-1H-benzo[d]imidazol-2(3H)-one (40 mg, 0.11 mmol, 1 equiv.) were added 3,5-6-methylquinolin-5-ylboronic acid (51 mg, 0.27 mmol, 2.5 equiv.), Cs₂CO₃ (141 mg, 0.43 mmol, 4 equiv.) and PEPPSI™-IPr catalyst (8 mg, 0.02 mmol, 0.1 equiv.) in DME-H₂O (20 mL, 0.2 M, 2/1, v/v). The mixture was heated to 140° C. After 2 hr, the reaction was complete. Following cooling, the reaction mixture was extracted with EtOAc and washed with water, saturated NH₄Cl. After drying with MgSO₄, it was filtered and concentrated to dryness under reduced pressure. Purification was carried out by reverse phase HPLC to furnish the title compound.

¹H NMR (400 MHz, cd₃od) δ 8.82 (d, J=4.3 Hz, 1H), 8.09 (d, J=8.7 Hz, 1H), 7.82 (t, J=7.1 Hz, 2H), 7.47 (dd, J=8.5, 4.3 Hz, 1H), 7.17 (d, J=1.6 Hz, 1H), 6.82 (d, J=1.6 Hz, 1H), 2.53 (s, 3H), 2.42 (s, 3H), 2.33 (s, 3H), 2.27 (s, 3H). LCMS (m/z+1) 385.23.

Example 120

7-(1,4-dimethyl-1H-pyrazol-5-yl)-5-(3,5-dimethyl-isoxazol-4-yl)-1-methyl-1H-benzo[d]imidazol-2(3H)-one

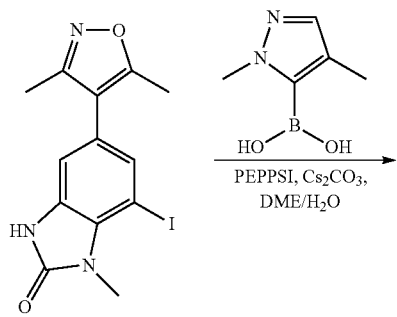

PEPPSI, Cs₂CO₃,
DME/H₂O

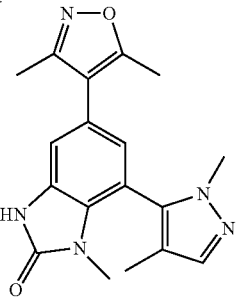

To a microwave vial containing 5-(3,5-dimethylisoxazol-4-yl)-7-iodo-1-methyl-1H-benzo[d]imidazol-2(3H)-one (40 mg, 0.11 mmol, 1 equiv.) were added 1,4-dimethyl-1H-pyrazol-5-ylboronic acid (72 mg, 0.32 mmol, 3 equiv.), Cs₂CO₃ (141 mg, 0.43 mmol, 4 equiv.) and PEPPSI™-IPr catalyst (8 mg, 0.02 mmol, 0.1 equiv.) and DME-H₂O (20 mL, 0.2 M, 2/1, v/v). The mixture was heated to 140° C. After 1 hr, the reaction was complete. Following cooling, the reaction was extracted with EtOAc and the organic solution was washed with water, saturated NH₄Cl. After drying with MgSO₄, it was filtered and concentrated to dryness under reduced pressure. Purification of the residue was carried out by reverse phase HPLC to furnish the desired product.

1H NMR (400 MHz, cd3od) δ 7.44 (s, 1H), 7.15 (d, J=1.6 Hz, 1H), 6.88 (d, J=1.6 Hz, 1H), 3.65 (s, 3H), 90 (s, 3H), 2.42 (s, 3H), 2.27 (s, 7H), 1.95 (s, 3H). LCMS (m/z+1) 338.19.

Example 121

5,7-bis(3,5-dimethylisoxazol-4-yl)-1-methyl-1H-benzo[d]imidazol-2(3H)-one

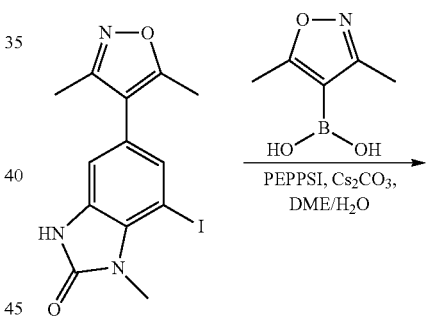

PEPPSI, Cs₂CO₃,
DME/H₂O

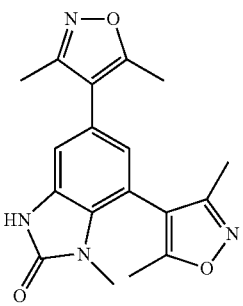

To a microwave vial containing 5-(3,5-dimethylisoxazol-4-yl)-7-iodo-1-methyl-1H-benzo[d]imidazol-2(3H)-one (40 mg, 0.11 mmol, 1 equiv.) were added 3,5-dimethylisoxazole-4-boronic acid pinacol ester (72 mg, 0.32 mmol, 3 equiv.), Cs₂CO₃ (141 mg, 0.43 mmol, 4 equiv.), PEPPSI™-IPr catalyst (8 mg, 0.02 mmol, 0.1 equiv.) and DME-H₂O (20 mL, 0.2 M, 2/1, v/v). The mixture was heated to 140° C. After 1 hr, the reaction was complete. Following cooling, the reaction mixture was extracted with EtOAc and the organic solution was washed with water, saturated NH₄Cl. After drying with MgSO₄, it was filtered and concentrated to dryness. The resulting solid was washed with EtOAc. Purification of the residue was carried out by reverse phase HPLC to furnish the title compound.

1H NMR (400 MHz, cd3od) δ 7.09 (d, J=1.6 Hz, 1H), 6.81 (d, J=1.6 Hz, 1H) 3.11 (d, J=14.5 Hz, 3H), 2.41 (s, 3H), 2.35-2.23 (m, 6H), 2.15 (s, 3H). LCMS (m/z+1) 339.15.

Example 122

6-(3,5-dimethylisoxazol-4-yl)-4-(1-ethyl-4-methyl-1H-pyrazol-5-yl)-1H-benzo[d]imidazol-2(3H)-one

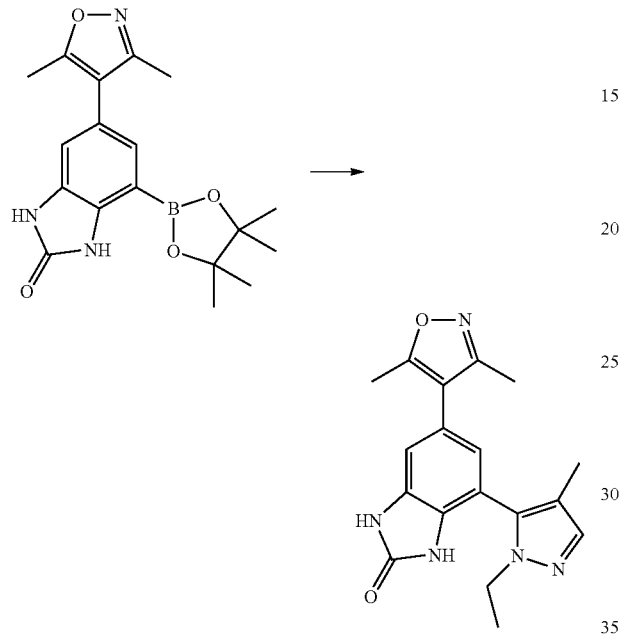

To a microwave vial containing 6-(3,5-dimethylisoxazol-4-yl)-4-(4,4,5,5-tetramethyl-1,3,2-dioxaborolan-2-yl)-1H-benzo[d]imidazol-2(3H)-one (40 mg, 0.11 mmol, 1 equiv.) were added 5-bromo-1-ethyl-4-methyl-1H-pyrazole 11 (64 mg, 0.34 mmol, 3 equiv.), Pd(dppf)Cl2.CH2Cl2 (9 mg, 0.011 mmol, 0.1 equiv.), DBU (101 µL, 6 equiv.) and DMSO-H2O (4 mL, 0.2 M, 2/1, v/v). The mixture was heated to 120° C. for 30 min in microwave. The reaction was concentrated under reduced pressure and purification was carried out by reverse phase HPLC.

1H NMR (400 MHz, Methanol-d4) δ 7.45 (d, J=0.8 Hz, 1H), 7.09 (d, J=1.6 Hz, 1H), 6.88 (d, J=1.6 Hz, 1H), 4.02 (dd, J=28.3, 7.2 Hz, 1H), 2.43 (s, 4H), 2.27 (s, 4H), 1.96 (d, J=0.7 Hz, 3H), 1.25 (t, J=7.2 Hz, 4H). LCMS (m/z+1) 338.22.

Example 123

5-(6-(3,5-dimethylisoxazol-4-yl)-2-oxo-2,3-dihydro-1H-benzo[d]imidazol-4-yl)-1-methyl-1H-pyrazole-4-carboxamide

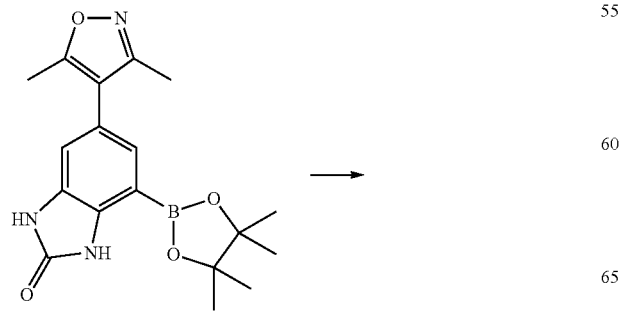

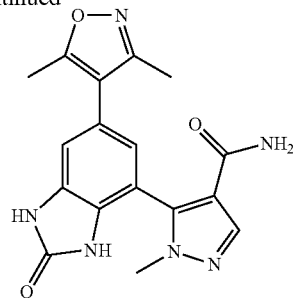

To a microwave vial containing 6-(3,5-dimethylisoxazol-4-yl)-4-(4,4,5,5-tetramethyl-1,3,2-dioxaborolan-2-yl)-1H-benzo[d]imidazol-2(3H)-one (100 mg, 0.28 mmol, 1 equiv.) was added 5-bromo-1-methyl-1H-pyrazole-4-carbonitrile (130 mg, 0.30 mmol, 2.5 equiv.), Pd(dppf)Cl2.CH2Cl2 (23 mg, 0.03 mmol, 0.1 equiv.) and DBU (253 µL, 1.69 mmol, 6 equiv.) and dissolved in DMSO-H2O (4 mL, 0.2 M, 2/1, v/v). The mixture was heated to 120° C. for 30 min in microwave. The reaction was concentrated in vacuo and purification was then carried out by reverse phase HPLC.

LCMS (m/z+1) 352.99. 1H NMR (400 MHz, Methanol-d4) δ 8.04 (s, 1H), 7.10 (d, J=1.6 Hz, 1H), 6.95 (d, J=1.6 Hz, 1H), 3.72 (s, 4H), 2.40 (d, J=15.8 Hz, 4H), 2.25 (d, J=16.4 Hz, 4H).

Example 124

1-cyclopropyl-5-(3,5-dimethylisoxazol-4-yl)-7-(6-methylquinolin-5-yl)-1H-benzo[d]imidazol-2(3H)-one Step 1: 5-(3,5-dimethylisoxazol-4-yl)-7-iodo-1-methyl-1H-benzo[d]imidazol-2(3H)-one

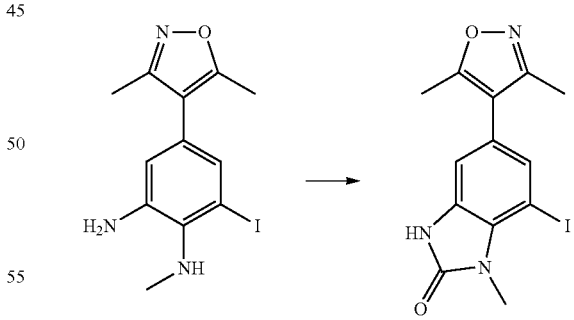

To a mixture of N1-cyclopropyl-4-(3,5-dimethylisoxazol-4-yl)-6-iodobenzene-1,2-diamine (170 mg, 0.46 mmol, 1 equiv.) in a pressure tube was added THF (5 mL) and CDI (223 mg, 1.38 mmol, 3 equiv.). The mixture was heated to 120° C. for 30 minutes in a microwave reactor. The reaction was concentrated in vacuo and purified by HPLC to provide 1-cyclopropyl-5-(3,5-dimethylisoxazol-4-yl)-7-iodo-1H-benzo[d]imidazol-2(3H)-one LCMS (m/z+1) 396.3.

Step 4

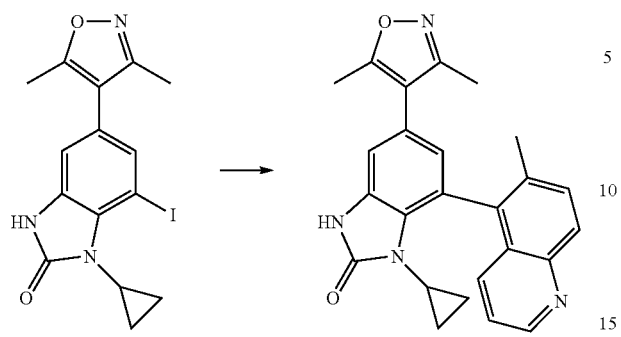

To a microwave vial containing 1-cyclopropyl-5-(3,5-dimethylisoxazol-4-yl)-7-iodo-1H-benzo[d]imidazol-2(3H)-one (25 mg, 0.063 mmol, 1 equiv.) was added 3,5-6-methylquinolin-5-ylboronic acid (71 mg, 0.38 mmol, 6 equiv.), Pd(dppf)Cl$_2$.CH$_2$Cl$_2$ (11 mg, 0.013 mmol, 0.1 equiv.) and DBU (76 mL, 0.51 mmol, 8 equiv.) and dissolved in DMSO-H2O (4 mL, 0.2 M, 2/1, v/v). The mixture was heated to 140° C. for 30 minutes in the microwave reactor. Purification was carried out by reverse phase HPLC.

1H NMR (400 MHz, Methanol-d4) δ 8.80 (dd, J=4.4, 1.6 Hz, 1H), 8.10-7.98 (m, 1H), 7.93 (dd, J=8.6, 1.3 Hz, 1H), 7.79 (d, J=8.7 Hz, 1H), 7.47 (dd, J=8.6, 4.3 Hz, 1H), 7.13 (d, J=1.7 Hz, 1H), 6.85 (d, J=1.7 Hz, 1H), 4.57 (s, 0H), 2.42 (s, 3H), 2.39 (s, 3H), 2.27 (s, 3H), 1.93 (dt, J=7.0, 3.4 Hz, 1H). LCMS (m/z+1) 411.24.

Example 125, and

Example 126

To a mixture of 4-(3,5-dimethylisoxazol-4-yl)-6-iodo-N1-methylbenzene-1,2-diamine (1.89 g, 5.5 mmol, 1 equiv.) in a pressure tube was added THF (5 mL) and CDI (2.67 g, 18.5 mmol, 3 equiv.). The mixture was heated to 120° C. for 30 minutes in a microwave reactor. The reaction was concentrated in vacuo and purified by HPLC to provide 5-(3,5-dimethylisoxazol-4-yl)-7-iodo-1-methyl-1H-benzo[d]imidazol-2(3H)-one.

LCMS (m/z+1) 370.16.

Step 2: N-cyclopropyl-4-(3,5-dimethylisoxazol-4-yl)-2-iodo-6-nitroaniline

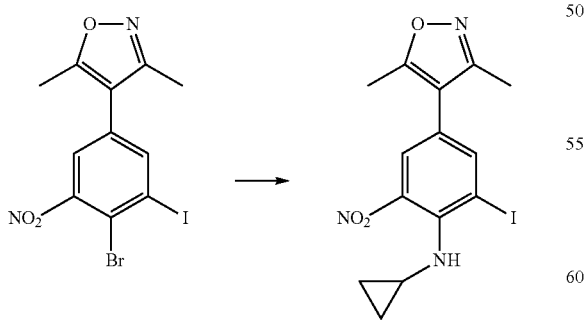

To a mixture of 4-(4-bromo-3-iodo-5-nitrophenyl)-3,5-dimethylisoxazole (1 g, 2.36 mmol, 1 equiv.) in a pressure tube was added NMP (10 mL) and cyclopropylamine (982 μL, 14.2 mmol, 6 equiv.). The mixture was heated to 130° C. for 60 minutes in a microwave reactor. The reaction was concentrated under reduced pressure and purified by flash column chromatography to provide N-cyclopropyl-4-(3,5-dimethylisoxazol-4-yl)-2-iodo-6-nitroaniline.

LCMS (m/z+1) 400.02

Step 3: 1-cyclopropyl-5-(3,5-dimethylisoxazol-4-yl)-7-iodo-1H-benzo[d]imidazol-2(3H)-one

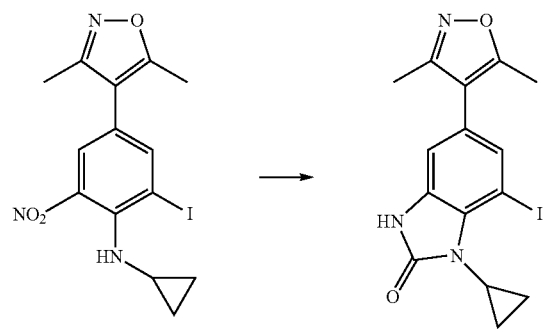 [SMILES: Cc1noc(C)c1-c1cc(I)c(NC2CC2)c([N+](=O)[O-])c1 ; Cc1noc(C)c1-c1cc(I)c2c(c1)[nH]c(=O)n2C1CC1]

6-(3,5-dimethylisoxazol-4-yl)-4-(6-(trifluoromethyl)quinolin-5-yl)-1H-benzo[d]imidazol-2(3H)-one and 6-(3,5-dimethylisoxazol-4-yl)-4-(6-(trifluoromethyl)quinolin-7-yl)-1H-benzo[d]imidazol-2(3H)-one

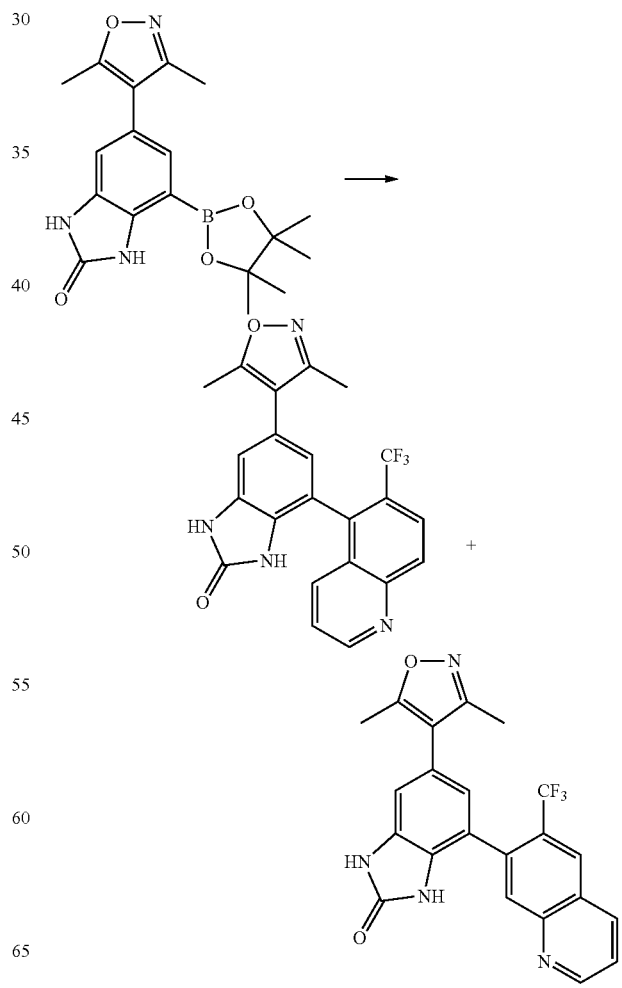

To a microwave vial containing 6-(3,5-dimethylisoxazol-4-yl)-4-(4,4,5,5-tetramethyl-1,3,2-dioxaborolan-2-yl)-1H-benzo[d]imidazol-2(3H)-one (100 mg, 0.28 mmol, 1 equiv.) was added 5-chloro-6-(trifluoromethyl)quinolone (140 mg, 0.56 mmol, 2 equiv.), Cs2CO3 (450 mg, 1.41 mmol, 5 equiv.) and PEPPSI™-IPr catalyst (45 mg, 0.056 mmol, 0.2 equiv.) and dissolved in DME-H2O (4 mL, 0.2 M, 2/1, v/v). The mixture was heated to 120° C. for 30 min in microwave. The reaction was concentrated in vacuo and purification was carried out by reverse phase HPLC.

1H NMR (400 MHz, Methanol-d4) δ 9.00 (dd, J=4.2, 1.6 Hz, 1H), 8.32 (d, J=9.1 Hz, 1H), 8.19 (d, J=9.0 Hz, 1H), 7.97-7.76 (m, 1H), 7.56 (dd, J=8.6, 4.3 Hz, 1H), 7.16 (d, J=1.5 Hz, 1H), 6.91 (d, J=1.4 Hz, 1H), 2.42 (s, 3H), 2.27 (s, 3H). LCMS (m/z+1) 425.38.

1H NMR (400 MHz, Methanol-d4) δ 9.03 (ddd, J=20.6, 4.3, 1.6 Hz, 1H), 8.69-8.48 (m, 1H), 8.32 (d, J=9.0 Hz, 0H), 8.19 (d, J=9.0 Hz, 0H), 8.09 (s, 1H), 7.86 (d, J=8.7 Hz, 0H), 7.72 (dd, J=8.4, 4.4 Hz, 1H), 7.56 (dd, J=8.6, 4.3 Hz, 0H), 7.12 (dd, J=32.1, 1.5 Hz, 1H), 6.93 (d, J=10.3 Hz, 1H), 2.42 (s, 3H), 2.27 (s, 3H). LCMS (m/z+1) 425.38.

Example 127 and

Example 128

(S)-6-(3,5-dimethylisoxazol-4-yl)-4-(6-(trifluoromethyl)quinolin-5-yl)-1H-benzo[d]imidazol-2(3H)-one and (R)-6-(3,5-dimethylisoxazol-4-yl)-4-(6-(trifluoromethyl)quinolin-5-yl)-1H-benzo[d]imidazol-2(3H)-one

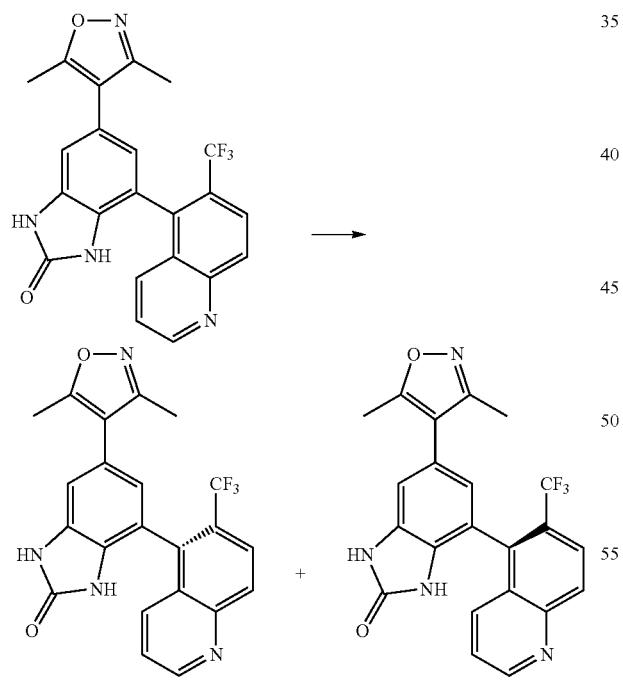

The crude was separated to provide the two atropisomers using HPLC chiral separation.

1H NMR (400 MHz, Methanol-d4) δ 9.00 (dd, J=4.2, 1.6 Hz, 1H), 8.32 (d, J=9.1 Hz, 1H), 8.19 (d, J=9.0 Hz, 1H), 7.97-7.76 (m, 1H), 7.56 (dd, J=8.6, 4.3 Hz, 1H), 7.16 (d, J=1.5 Hz, 1H), 6.91 (d, J=1.4 Hz, 1H), 2.42 (s, 3H), 2.27 (s, 3H). LCMS (m/z+1) 425.38.

Example 129

5-(3,5-dimethylisoxazol-4-yl)-1-methyl-7-(6-(trifluoromethyl)quinolin-5-yl)-1H-benzo[d]imidazol-2(3H)-one

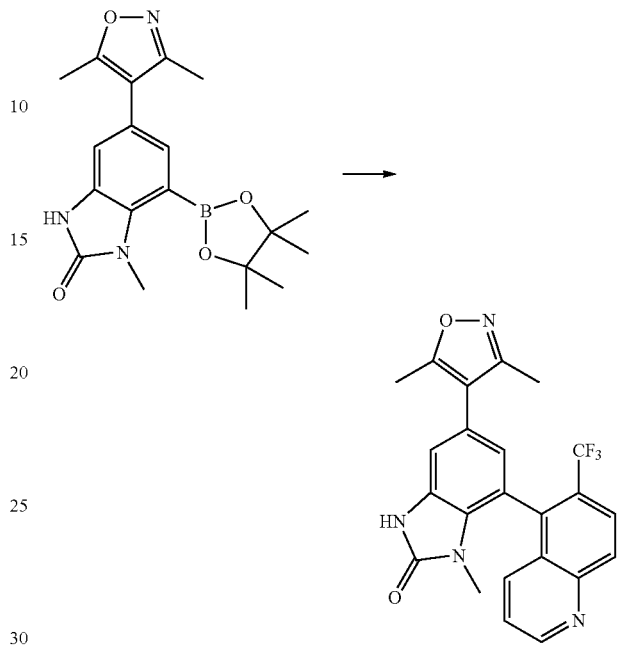

GS-645618

To a microwave vial containing 5-(3,5-dimethylisoxazol-4-yl)-1-methyl-7-(4,4,5,5-tetramethyl-1,3,2-dioxaborolan-2-yl)-1H-benzo[d]imidazol-2(3H)-one (30 mg, 0.08 mmol, 1 equiv.) was added 5-bromo-6-(trifluoromethyl)quinoline (68 mg, 0.24 mmol, 3 equiv.), Cs$_2$CO$_3$ (105 mg, 0.33 mmol, 4 equiv.) and PEPPSI™-IPr catalyst (11 mg, 0.016 mmol, 0.2 equiv.) and dissolved in DME-H$_2$O (4 mL, 0.2 M, 2/1, v/v). The mixture was heated to 120° C. for 30 min in microwave. The reaction was concentrated in vacuo and purification was then carried out by reverse phase HPLC.

1H NMR (400 MHz, Methanol-d4) δ 9.28 (s, 1H), 8.30-8.19 (m, 1H), 7.98 (ddd, J=8.5, 6.9, 1.4 Hz, 1H), 7.70 (ddd, J=8.3, 6.9, 1.2 Hz, 1H), 7.59-7.44 (m, 1H), 7.23 (d, J=1.6 Hz, 1H), 6.92 (d, J=1.5 Hz, 1H), 2.54 (s, 4H), 2.41 (s, 3H), 2.25 (s, 4H). LCMS (m/z+1) 385.22

Example 130

5-(3,5-dimethylisoxazol-4-yl)-1-methyl-7-(6-(trifluoromethoxy)quinolin-5-yl)-1H-benzo[d]imidazol-2(3H)-one

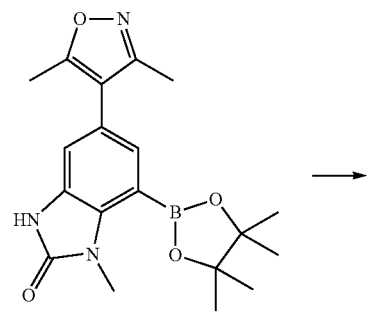

143

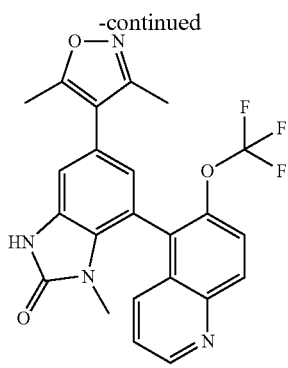

To a microwave vial containing 5-(3,5-dimethylisoxazol-4-yl)-1-methyl-7-(4,4,5,5-tetramethyl-1,3,2-dioxaborolan-2-yl)-1H-benzo[d]imidazol-2(3H)-one (52 mg, 0.14 mmol, 1 equiv.) was added 5-bromo-6-(trifluoromethoxy)quinoline (124 mg, 0.42 mmol, 3 equiv.), Cs2CO3 (230 mg, 0.70 mmol, 5 equiv.) and PEPPSI™-IPr catalyst (9.5 mg, 0.014 mmol, 0.1 equiv.) and dissolved in DME-H2O (4 mL, 0.2 M, 2/1, v/v). The mixture was heated to 120° C. for 30 min in microwave. The reaction was concentrated in vacuo and purification was then carried out by reverse phase HPLC.

1H NMR (400 MHz, Methanol-d4) δ 8.97 (dd, J=4.3, 1.6 Hz, 1H), 8.31 (d, J=9.4 Hz, 1H), 8.11-7.83 (m, 2H), 7.59 (dd, J=8.6, 4.3 Hz, 1H), 7.20 (d, J=1.6 Hz, 1H), 6.89 (s, 1H), 2.61 (s, 3H), 2.41 (s, 3H), 2.26 (s, 3H). $^{19}$F NMR (376 MHz, Methanol-$d_4$) δ-58.53. LCMS (m/z+1) 455.29

Example 131

4-(6-(3,5-dimethylisoxazol-4-yl)-2-oxo-2,3-dihydro-1H-benzo[d]imidazol-4-yl)-3-methylquinoline 1-oxide

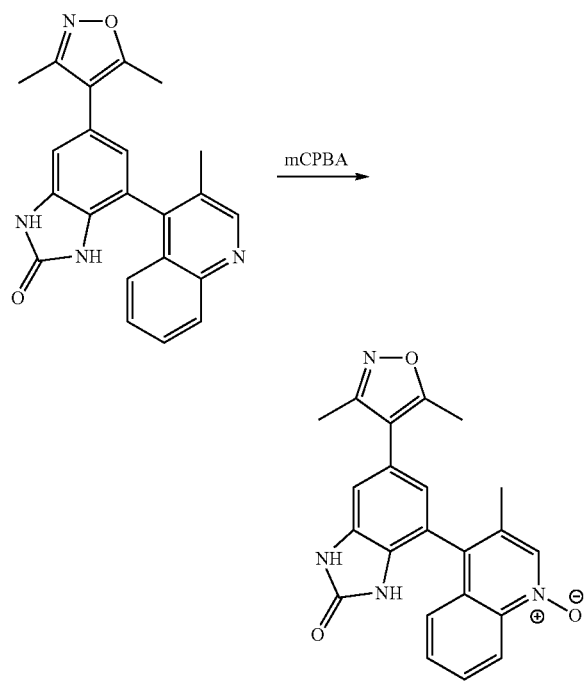

144

6-(3,5-dimethylisoxazol-4-yl)-4-(hydroxydi(pyridin-2-yl)methyl)-1H-benzo[d]imidazol-2(3H)-one

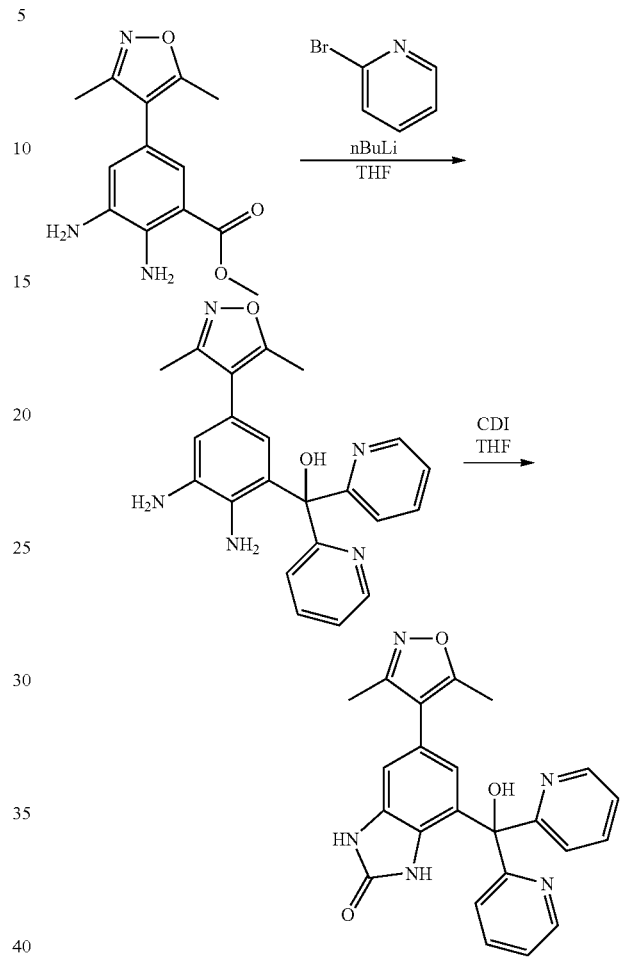

Butyllithium (1.6M solution in hexanes, 24 mL, 38 mmol) was added dropwise over 20 minutes to a solution of 2-bromopyridine (3.7 mL, 38 mmol in methyl-THF (100 mL) at −78° C. The reaction mixture was stirred for 1 hour and a solution of methyl 2,3-diamino-5-(3,5-dimethylisoxazol-4-yl)benzoate (2.0 g, 7.7 mmol) in 20 mL of methyl-THF was added. The reaction mixture was warmed to room temperature, stirred for 30 minutes and quenched with water. The reaction mixture was extracted with ethyl acetate and purified by silica gel chromatography (90:9:1 ethyl acetate/methanol/ammonium hydroxide) to give (2,3-diamino-5-(3,5-dimethylisoxazol-4-yl)phenyl)di(pyridin-2-yl)methanol as an orange powder.

CDI (1.1 g, 6 mmol) was added to a solution of (2,3-diamino-5-(3,5-dimethylisoxazol-4-yl)phenyl)di(pyridin-2-yl)methanol (1.43 g, 3.7 mmol) in THF (10 mL) and the reaction mixture was stirred for 3 days. The reaction mixture was diluted with 100 mL water and 100 mL ethyl acetate and sonicated and filtered to yield the desired product.

C23H19N5O3. 414.1 (M+1). 1H NMR (400 MHz, DMSO-d6) δ 10.69 (d, J=1.6 Hz, 1H), 9.79 (s, 1H), 8.49 (ddd, J=4.9, 1.8, 0.9 Hz, 2H), 7.80 (td, J=7.7, 1.8 Hz, 2H), 7.58 (dt, J=8.0, 1.1 Hz, 2H), 7.30 (ddd, J=7.5, 4.8, 1.1 Hz, 2H), 6.86 (s, 1H), 6.81 (d, J=1.5 Hz, 1H), 6.56 (d, J=1.6 Hz, 1H), 2.26 (s, 3H), 2.06 (s, 3H).

The following compound was made similarly to 6-(3,5-dimethylisoxazol-4-yl)-4-(hydroxydi(pyridin-2-yl)methyl)-1H-benzo[d]imidazol-2(3H)-one using 2-pyridyl-6-magnesiumbromide:

Example 134

A solution of 6-(3,5-dimethylisoxazol-4-yl)-4-(3-methylquinolin-4-yl)-1H-benzo[d]imidazol-2(3H)-one (30 mg, 0.08 mmol) and mCPBA (100 mg, 0.58 mmol) in dichloromethane (0.5 mL) and methanol (0.5 mL) was stirred for 1 hour at room temperature. The reaction was quenched with sodium sulfite solution, extracted with ethyl acetate and purified by reverse-phase HPLC.

C22H18N4O3. 387.1 (M+1). $^1$H NMR (400 MHz, DMSO-$d_6$) δ 10.90 (d, J=1.9 Hz, 1H), 10.48 (d, J=2.0 Hz, 1H), 8.73 (s, 1H), 8.62-8.56 (m, 1H), 7.81-7.75 (m, 1H), 7.63 (ddd, J=8.3, 6.9, 1.3 Hz, 1H), 7.41 (dd, J=8.6, 1.3 Hz, 1H), 7.10-7.02 (m, 1H), 6.88 (d, J=1.6 Hz, 1H), 2.43 (s, 3H), 2.25 (s, 3H), 2.17 (s, 3H).

Example 132

(R)-5-(6-(3,5-dimethylisoxazol-4-yl)-2-oxo-2,3-dihydro-1H-benzo[d]imidazol-4-yl)-6-methylquinoline 1-oxide

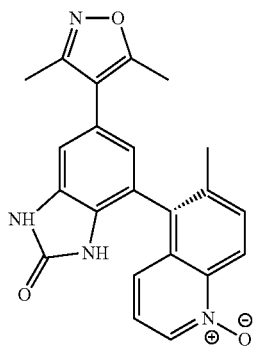

$C_{22}H_{18}N_4O_3$. 387.1 (M+1). $^1$H NMR (400 MHz, DMSO-$d_6$) δ 10.86 (d, J=2.2 Hz, 1H), 10.40 (s, 1H), 8.63-8.48 (m, 2H), 7.80 (d, J=9.0 Hz, 1H), 7.34 (dd, J=8.8, 6.0 Hz, 1H), 7.26-7.15 (m, 1H), 7.05-6.96 (m, 1H), 6.81 (t, J=1.2 Hz, 1H), 2.40 (s, 3H), 2.24 (d, J=7.9 Hz, 6H).

Example 133

6-(3,5-dimethylisoxazol-4-yl)-4-(hydroxybis(6-methylpyridin-2-yl)methyl)-1H-benzo[d]imidazol-2(3H)-one

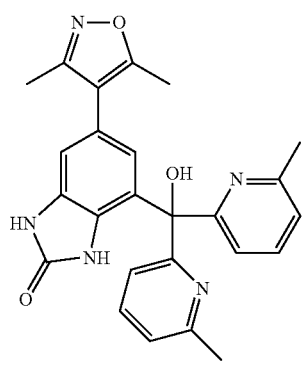 [SMILES: Cc1cccc(C(O)(c2cccc(C)n2)c2cc(-c3c(C)noc3C)cc3[nH]c(=O)[nH]c23)n1]

GS-694472 $C_{25}H_{23}N_5O_3$. 442.1 (M+1). $^1$H NMR (400 MHz, DMSO-$d_6$) δ 10.77 (s, 1H), 10.07 (s, 1H), 7.89 (d, J=17.5 Hz, 2H), 7.51 (t, J=8.0 Hz, 2H), 7.39 (d, J=37.6 Hz, 2H), 6.86 (d, J=1.3 Hz, 1H), 2.50 (s, 6H), 2.27 (s, 3H), 2.08 (s, 3H).

Example 135

6-(3,5-dimethylisoxazol-4-yl)-4-(1-hydroxy-2-methyl-1-(pyridin-2-yl)butyl)-1H-benzo[d]imidazol-2(3H)-one Step 1

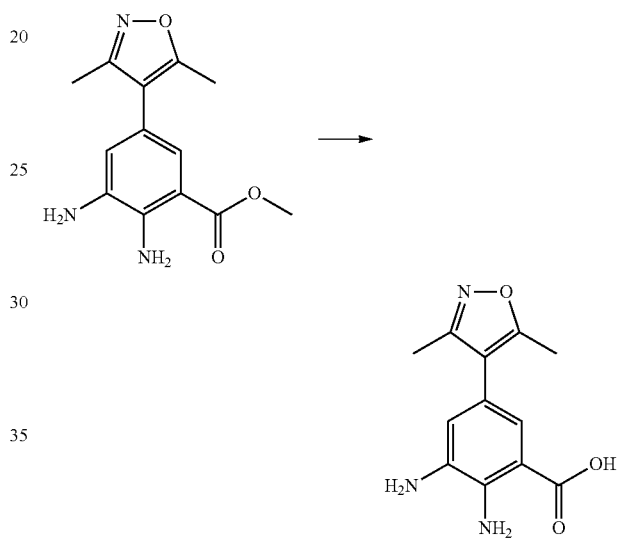

Methyl ester (25 g, 0.096 mol) was dissolved in a mixture of MeOH (400 mL) and 1 M NaOH (200 mL), an air condenser was attached and the reaction was heated to 60° C. for 1.5 hours. Reaction was allowed to cool to room temperature and concentrated in vacuo. The residue was then diluted in a minimal amount of water and neutralized with 1 M HCl until pH 6-7. The precipitate was collected by vacuum filtration, taken up in MeOH, and concentrated in vacuo to give 2,3-diamino-5-(3,5-dimethylisoxazol-4-yl)benzoic acid as a brown powder. Material was used without further purification.

C12H13N3O3 248.1 (M+1)

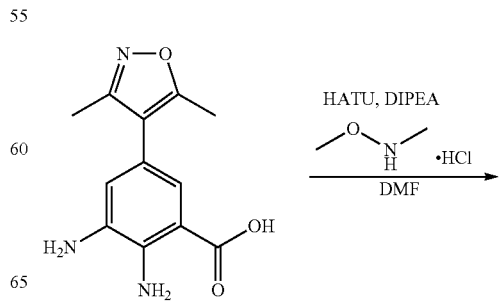

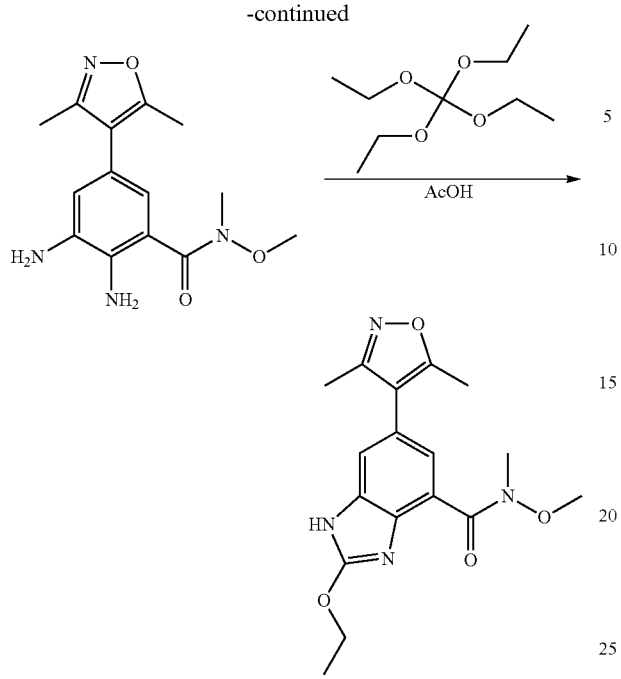
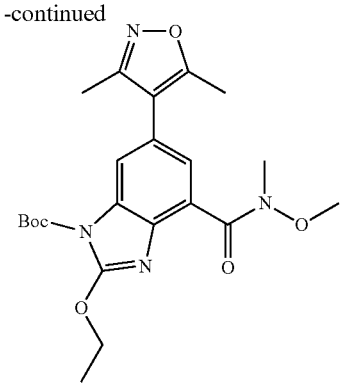

2,3-diamino-5-(3,5-dimethylisoxazol-4-yl)benzoic acid (22 g, 0.089 mol) was dissolved in DMF (C=3.0 M) and HATU (1.3 eq), DIPEA (7 eq), and N,O-dimethylhydroxylamine hydrochloride (2.5 eq) were added in one portion and the reaction was allowed to stir under air at room temperature for 1 hr. The reaction was concentrated in vacuo and the residue was dissolved in ethyl acetate. The solution was washed once with NaHCO₃ and three times with brine. The crude was concentrated in vacuo and purified via silica gel chromatography to give 2,3-diamino-5-(3,5-dimethylisoxazol-4-yl)-N-methoxy-N-methylbenzamide as a light brown powder.

2,3-diamino-5-(3,5-dimethylisoxazol-4-yl)-N-methoxy-N-methylbenzamide (25 g, 0.086 mol) was dissolved in a 1:1 mixture (32 mL total) of tetraethylorthocarbonate and AcOH and allowed to stir under air at room temperature for 1.5 hr. The reaction mixture was concentrated in vacuo at room temperature and the crude residue was dissolved in EtOAc. The solution was washed three times with bicarb, once with water, and organic layer was concentrated in vacuo to give 6-(3,5-dimethylisoxazol-4-yl)-2-ethoxy-N-methoxy-N-methyl-1H-benzo[d]imidazole-4-carboxamide as a dark oil. Crude material was used without further purification.

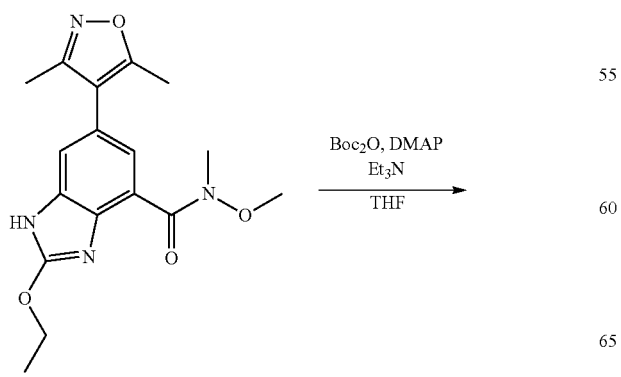

6-(3,5-dimethylisoxazol-4-yl)-2-ethoxy-N-methoxy-N-methyl-1H-benzo[d]imidazole-4-carboxamide (23 g, 0.067 mol) was dissolved in THF (80 mL, 1.0 M) and Boc₂O (2 eq), DMAP (0.4 eq), and triethylamine (3.5 eq) were added to the reaction mixture and allowed to stir under air at room temperature for 1 hr. Reaction mixture was then concentrated in vacuo and purified by silica gel chromatography (80-100% EtOAc/hex) to give tert-butyl dimethylisoxazol-4-yl)-2-ethoxy-4-(methoxy(methyl)carbamoyl)-1H-benzo[d]imidazole-1-carboxylate %) as a white powder.

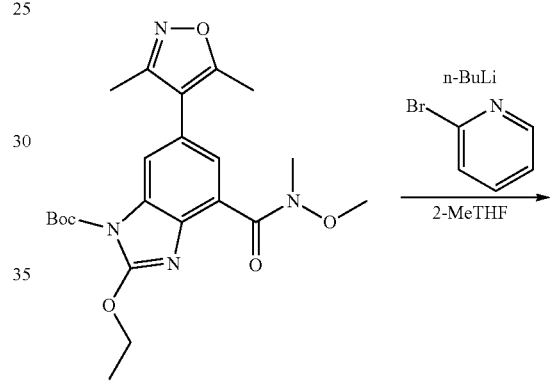
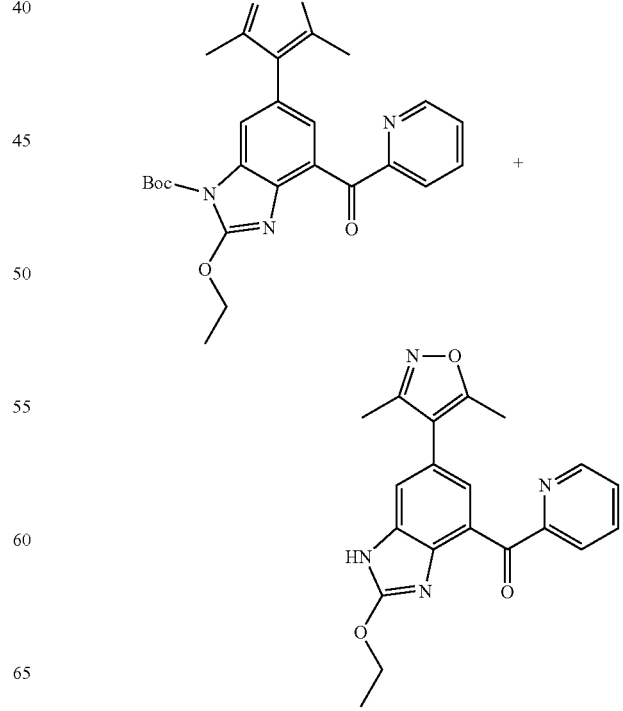

2-bromopyridine (4.5 mmol, 2 eq) was dissolved in 2-MeTHF (C=0.15 M) and cooled to −78° C. under Ar. n-BuLi (1.6 M, 2 eq) was added dropwise to the solution over 15 minutes and the reaction was allowed to stir at −78° C. for 1 hour. tert-butyl 6-(3,5-dimethylisoxazol-4-yl)-2-ethoxy-4-(methoxy(methyl)carbamoyl)-1H-benzo[d]imidazole-1-carboxylate (1 g, 2.25 mmol) was dissolved in a minimal amount of 2-MeTHF and added to the reaction via syringe in one portion and the reaction was then allowed to slowly warm to room temperature. The reaction was quenched with water, diluted with EtOAc, washed twice with brine, and concentrated in vacuo. The crude material was purified by silica gel chromatography to give tert-butyl 6-(3,5-dimethylisoxazol-4-yl)-2-ethoxy-4-picolinoyl-1H-benzo[d]imidazole-1-carboxylate (300 mg, 29%) as a yellow powder and (6-(3,5-dimethylisoxazol-4-yl)-2-ethoxy-1H-benzo[d]imidazol-4-yl)(pyridin-2-yl)methanone (460 mg, 56%) as a pale yellow powder.

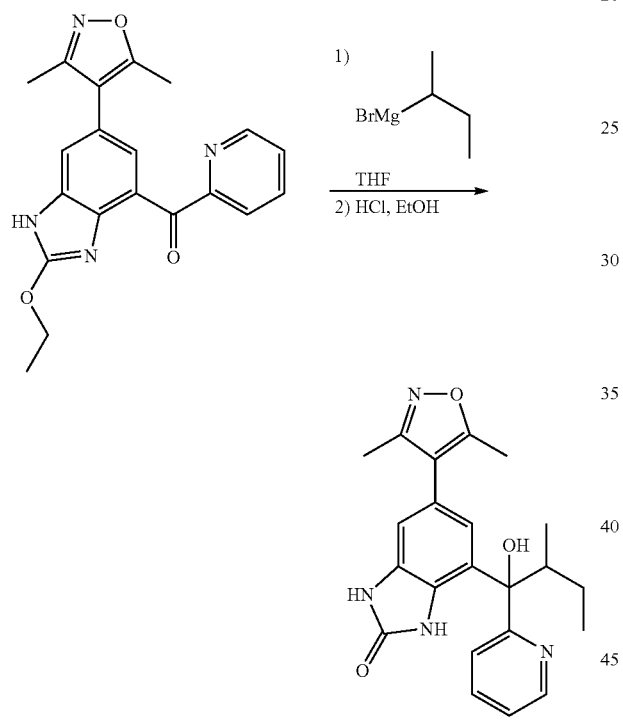

(6-(3,5-dimethylisoxazol-4-yl)-2-ethoxy-1H-benzo[d]imidazol-4-yl)(pyridin-2-yl)methanone (20 mg, 0.055 mmol) was dissolved in dry THF (0.55 mL) under argon. Sec-butylmagnesium bromide (1.0 M in THF, 0.27 mL, 0.28 mmol) was added dropwise and the reaction was allowed to stir for 10 minutes. The reaction was quenched with water, concentrated and purified by reverse-phase HPLC to give 1-(6-(3,5-dimethylisoxazol-4-yl)-2-ethoxy-1H-benzo[d]imidazol-4-yl)-2-methyl-1-(pyridin-2-yl)butan-1-ol intermediate. Intermediate was taken up in 0.5 mL EtOH and 0.3 mL 4.0M HCl/dioxane and heated to 65° C. for 1 hr. Reaction was concentrated and purified by reverse phase HPLC to afford the desired product $C_{22}H_{24}N_4O_3$ 393.5 (M+1). $^1$H NMR (400 MHz, DMSO-$d_6$) δ 10.64 (s, 1H), 9.99 (s, 1H), 8.54 (s, 1H), 7.84 (s, 2H), 7.27 (s, 1H), 7.11 (t, J=1.8 Hz, 1H), 6.71 (d, J=3.1 Hz, 1H), 2.36 (d, J=5.7 Hz, 3H), 2.18 (d, J=5.8 Hz, 3H), 0.87 (t, J=7.3 Hz, 5H), 0.80 (d, J=7.2 Hz, 3H), 0.62 (d, J=6.5 Hz, 2H).

Example 136

4-(cyclopropyl(hydroxy)(pyridin-2-yl)methyl)-6-(3,5-dimethylisoxazol-4-yl)-1H-benzo[d]imidazol-2(3H)-one

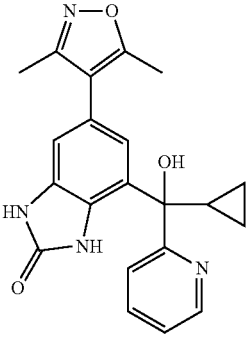 [SMILES: Cc1noc(C)c1-c1cc(C(O)(c2ccccn2)C2CC2)c2[nH]c(=O)[nH]c2c1]

(6-(3,5-dimethylisoxazol-4-yl)-2-ethoxy-1H-benzo[d]imidazol-4-yl)(pyridin-2-yl)methanone (40 mg, 0.11 mmol) was dissolved in dry THF (1.1 mL) and cyclopropylmagnesium bromide (0.5 M in diethylether, 1.1 mL, 0.55 mmol) was added dropwise at rt and the reaction was allowed to stir for 10 minutes. The reaction was quenched with water, concentrated, and purified by reverse-phase HPLC to give cyclopropyl(6-(3,5-dimethylisoxazol-4-yl)-2-ethoxy-1H-benzo[d]imidazol-4-yl)(pyridin-2-yl)methanol intermediate which was taken up in 1.0 mL EtOH and 0.7 mL 4.0M HCl/dioxane and heated for 2 hours at 65° C. Reaction was then concentrated down and purified by reverse-phase HPLC to afford the desired product as a white powder.

C21H20N4O3 377.3 (M+1)
1H NMR (400 MHz, DMSO-d6) δ 10.66 (s, 1H), 9.73 (s, 1H), 8.54 (s, 1H), 7.92 (s, 1H), 7.71 (d, J=8.0 Hz, 1H), 7.40 (s, 1H), 7.27 (s, 1H), 6.81 (s, 1H), 2.39 (s, 3H), 2.21 (s, 3H), 2.01 (s, 1H), 0.54 (d, J=5.6 Hz, 3H), 0.29 (d, J=10.3 Hz, 1H).

Example 137

6-(3,5-dimethylisoxazol-4-yl)-4-(1-hydroxy-1-(pyridin-2-yl)propyl)-1H-benzo[d]imidazol-2(3H)-one

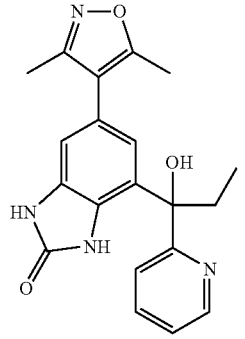 [SMILES: CCC(O)(c1ccccn1)c1cc(-c2c(C)noc2C)cc2[nH]c(=O)[nH]c12]

(6-(3,5-dimethylisoxazol-4-yl)-2-ethoxy-1H-benzo[d]imidazol-4-yl)(pyridin-2-yl)methanone (20 mg, 0.055 mmol) was dissolved in dry THF (0.5 mL) and ethylmagnesium bromide (1.0 M, 0.27 mL, 0.27 mmol) was added dropwise. The reaction was allowed to stir at r.t. for 10 minutes and then a mixture of EtOH (1 mL) and 4.0M HCl/dioxane (0.5 mL) was added and the reaction was heated to 65° C. for 3 hours. The reaction was concentrated and purified by reverse-phase HPLC to afford the desired product as a white powder.

C20H20N4O3 365.1 (M+1). 1H NMR (400 MHz, DMSO-d6) δ 10.67 (s, 1H), 9.89 (s, 1H), 8.57 (s, 1H), 7.88 (s, 2H), 7.35 (s, 1H), 6.97 (s, 1H), 6.75 (s, 1H), 2.42 (d, J=9.1 Hz, 2H), 2.35 (s, 3H), 2.17 (s, 3H), 0.79 (t, J=7.2 Hz, 3H).

Example 138

4-(cyclopentyl(hydroxy)(pyridin-2-yl)methyl)-6-(3,5-dimethylisoxazol-4-yl)-1H-benzo[d]imidazol-2(3H)-one

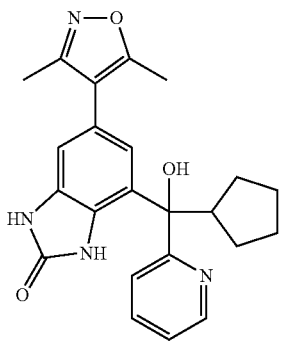 [SMILES: Cc1noc(C)c1-c1cc(C(O)(c2ccccn2)C2CCCC2)c2[nH]c(=O)[nH]c2c1]

(6-(3,5-dimethylisoxazol-4-yl)-2-ethoxy-1H-benzo[d]imidazol-4-yl)(pyridin-2-yl)methanone (50 mg, 0.14 mmol) was dissolved in dry THF (1.4 mL) under argon and cooled to 0° C. Cyclopentylmagnesium chloride (2.0 M, 0.14 mL, 0.28 mmol) was added dropwise and reaction was allowed to stir for 10 minutes then quenched with water. Reaction mixture was extracted three times with EtOAc and combined organic layers were washed once with water and concentrated. Residue was taken up in EtOH (1.5 mL) and 4.0M HCl/dioxane (0.75 mL) and heated to 65° C. for 2 hours. Reaction was concentrated and purified by reverse-phase HPLC to afford the desired product as a white powder.

$C_{23}H_{24}N_4O_3$. 405.2 (M+1). 1H NMR (400 MHz, DMSO-d6) δ 10.77 (d, J=5.3 Hz, 1H), 10.03 (s, 1H), 8.67 (s, 1H), 8.14 (s, 1H), 7.94 (s, 1H), 7.61 (s, 1H), 7.19 (s, 1H), 6.80 (s, 1H), 3.55-3.45 (m, 1H), 2.39 (s, 3H), 2.22 (s, 3H), 1.69-1.60 (m, 2H), 1.55 (dd, J=5.4 Hz, 3H), 1.46 (d, J=7.7 Hz, 1H), 1.31 (d, J=11.1 Hz, 1H), 1.12 (s, 1H).

Example 139

6-(3,5-dimethylisoxazol-4-yl)-4-(1-hydroxy-1-(pyridin-2-yl)pent-4-en-1-yl)-1H-benzo[d]imidazol-2(3H)-one

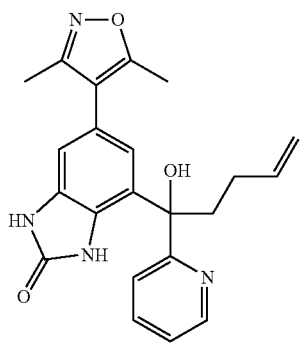 [SMILES: C=CCCC(O)(c1ccccn1)c1cc(-c2c(C)noc2C)cc2[nH]c(=O)[nH]c12]

Magnesium metal (20 mg, 0.82 mmol) was taken up in THF (1.5 mL) and (bromomethyl)cyclopropane (100 mg, 0.71 mmol) was added dropwise and the reaction was heated to 65° C. for 1 hr. (Cyclopropylmethyl)magnesium bromide (0.5 M, 0.83 mL, 0.41 mmol) was then added dropwise to a solution of (6-(3,5-dimethylisoxazol-4-yl)-2-ethoxy-1H-benzo[d]imidazol-4-yl)(pyridin-2-yl)methanone (50 mg, 0.14 mmol) in dry THF (1.4 mL) which was cooled to 0° C. Reaction mixture was allowed to stir for 10 mins, quenched with water and extracted three times with EtOAc. Combined organic layers were washed once with water and concentrated. Residue was dissolved in a mixture of EtOH (1.5 mL) and 4.0M HCl/dioxane (0.75 mL) and heated for 2 hours at 65° C. Reaction was then concentrated and purified by reverse-phase HPLC to afford the desired product as a white powder.

$C_{22}H_{22}N_4O_3$. 391.5 (M+1). 1H NMR (400 MHz, DMSO-d6) δ 10.68 (s, 1H), 9.93 (s, 1H), 8.55 (s, 1H), 7.88 (s, 2H), 7.32 (s, 1H), 6.95 (s, 1H), 6.75 (s, 1H), 5.82 (dd, J=9.8, 7.0 Hz, 1H), 5.00-4.85 (m, 3H), 2.35 (s, 3H), 2.16 (s, 3H), 2.10-1.90 (m, 4H).

Example 140

6-(3,5-dimethylisoxazol-4-yl)-4-(4,4,4-trifluoro-1-hydroxy-1-(pyridin-2-yl)butyl)-1H-benzo[d]imidazol-2(3H)-one

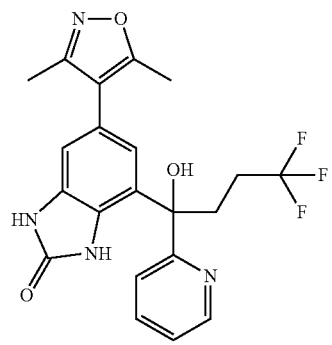 [SMILES: Cc1noc(C)c1-c1cc(C(O)(CCC(F)(F)F)c2ccccn2)c2[nH]c(=O)[nH]c2c1]

(6-(3,5-dimethylisoxazol-4-yl)-2-ethoxy-1H-benzo[d]imidazol-4-yl)(pyridin-2-yl)methanone (50 mg, 0.14 mmol) was dissolved in dry THF (1.4 mL) and cooled to 0° C. (3,3,3-trifluoropropyl)magnesium bromide (0.5 M, 0.55 mL, 0.28 mmol) was added dropwise and the reaction was allowed to stir for 10 mins and then quenched with water. Reaction was extracted three times with EtOAc and combined organic layers were washed once with water and concentrated. Residue was taken up in EtOH (1.5 mL) and 4.0M HCl/dioxane (0.75 mL), heated to 65° C. for two hours, concentrated, then purified by reverse-phase HPLC to afford the desired product as a white powder.

$C_{21}H_{19}F_3N_4O_3$ 433.4 (M+1). ¹H NMR (400 MHz, DMSO-d6) δ 10.72 (s, 1H), 10.05 (s, 1H), 8.56 (d, J=4.6 Hz, 1H), 7.88 (s, 2H), 7.31 (s, 1H), 6.82 (s, 1H), 6.76 (s, 1H), 2.67 (s, 1H), 2.60 (d, J=4.0 Hz, 1H), 2.32 (s, 4H), 2.16 (s, 2H), 2.13 (s, 3H).

Example 141

6-(3,5-dimethylisoxazol-4-yl)-4-(1-hydroxy-2-methyl-1-(pyridin-2-yl)propyl)-1H-benzo[d]imidazol-2(3H)-one

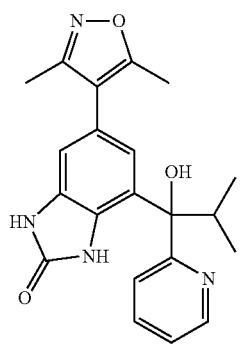 [SMILES: Cc1noc(C)c1-c1cc(C(O)(c2ccccn2)C(C)C)c2[nH]c(=O)[nH]c2c1]

(6-(3,5-dimethylisoxazol-4-yl)-2-ethoxy-1H-benzo[d]imidazol-4-yl)(pyridin-2-yl)methanone (50 mg, 0.14 mmol) was dissolved in dry THF (1.4 mL) and cooled to 0° C. Isopropylmagnesium bromide (2.0 M, 0.14 mL, 0.28 mmol) was added dropwise and the reaction was allowed to stir for 10 mins and then quenched with water. Reaction was extracted three times with EtOAc and combined organic layers were washed once with water and concentrated. Residue was taken up in EtOH (1.5 mL) and 4.0M HCl/dioxane (0.75 mL), heated to 65° C. for two hours, concentrated, then purified by reverse-phase HPLC to afford the desired product as a white powder.

C21H22N4O3 379.3 (M+1). 1H NMR (400 MHz, DMSO-d6) δ 10.70 (s, 1H), 10.01 (d, J=2.1 Hz, 1H), 8.60 (s, 1H), 7.91 (s, 2H), 7.41 (s, 1H), 7.15 (s, 1H), 6.74 (s, 1H), 3.17 (s, 1H), 2.37 (s, 3H), 2.33 (d, J=1.7 Hz, 0H), 2.20 (s, 3H), 2.15 (s, 0H), 1.23 (d, J=6.7 Hz, 1H), 0.93 (d, J=6.0 Hz, 3H), 0.65 (d, J=6.9 Hz, 3H).

Example 142

4-(cyclobutyl(hydroxy)(pyridin-2-yl)methyl)-6-(3,5-dimethylisoxazol-4-yl)-1H-benzo[d]imidazol-2(3H)-one

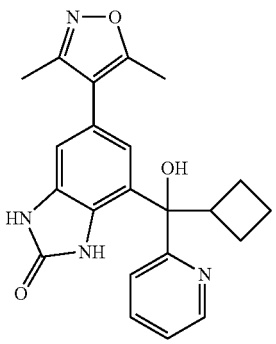 [SMILES: Cc1noc(C)c1-c1cc(C(O)(c2ccccn2)C2CCC2)c2[nH]c(=O)[nH]c2c1]

(6-(3,5-dimethylisoxazol-4-yl)-2-ethoxy-1H-benzo[d]imidazol-4-yl)(pyridin-2-yl)methanone (50 mg, 0.14 mmol) was dissolved in dry THF (1.4 mL) and cooled to 0° C. Cylobutylmagnesium chloride (0.5 M, 1.1 mL, 0.55 mmol) was added dropwise and the reaction was allowed to stir for 10 mins and then quenched with water. Reaction was extracted three times with EtOAc and combined organic layers were washed once with water, concentrated, and purified by reverse-phase HPLC to give cyclobutyl(6-(3,5-dimethylisoxazol-4-yl)-2-ethoxy-1H-benzo[d]imidazol-4-yl)(pyridin-2-yl)methanol intermediate. The intermediate was taken up in EtOH (1.5 mL) and 4.0 M HCl/dioxane and heated to 65° C. for 2 hours, concentrated and purified by reverse-phase HPLC to afford the desired product as a white powder.

C22H22N4O3 391.5 (M+1). 1H NMR (400 MHz, DMSO-d6) δ 10.70 (s, 1H), 9.93 (d, J=2.6 Hz, 1H), 8.58 (s, 1H), 7.96 (s, 1H), 7.72 (d, J=8.0 Hz, 1H), 7.43 (s, 1H), 7.00 (s, 1H), 6.79 (d, J=2.1 Hz, 1H), 3.82-3.71 (m, 1H), 2.39 (s, 3H), 2.21 (s, 3H), 2.19-2.10 (m, 1H), 2.02-1.94 (m, 1H), 1.91 (s, 1H), 1.80 (q, J=9.1 Hz, 1H), 1.67 (t, J=9.7 Hz, 1H), 1.44 (q, J=6.2, 3.9 Hz, 1H).

Example 143

6-(3,5-dimethylisoxazol-4-yl)-4-(1-hydroxy-3,3-dimethyl-1-(pyridin-2-yl)butyl)-1H-benzo[d]imidazol-2(3H)-one

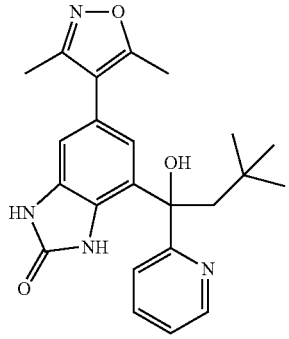 [SMILES: Cc1noc(C)c1-c1cc(C(O)(CC(C)(C)C)c2ccccn2)c2[nH]c(=O)[nH]c2c1]

(6-(3,5-dimethylisoxazol-4-yl)-2-ethoxy-1H-benzo[d]imidazol-4-yl)(pyridin-2-yl)methanone (50 mg, 0.14 mmol) was dissolved in dry THF (1.4 mL) and cooled to 0° C. Neopentylmagnesium chloride (1.0 M, 0.55 mL, 0.55 mmol) was added dropwise and the reaction was allowed to stir for 10 mins and then quenched with water. Reaction was extracted three times with EtOAc and combined organic layers were washed once with water, concentrated, and purified by reverse-phase HPLC to give 1-(6-(3,5-dimethylisoxazol-4-yl)-2-ethoxy-1H-benzo[d]imidazol-4-yl)-3,3-dimethyl-1-(pyridin-2-yl)butan-1-ol intermediate. The intermediate was taken up in EtOH (1.5 mL) and 4.0 M HCl/dioxane and heated to 65° C. for 2 hours, concentrated and purified by reverse-phase HPLC to afford the desired product as a white powder.

C23H26N4O3 407.3 (M+1). 1H NMR (400 MHz, DMSO-d6) δ 10.70 (d, J=4.6 Hz, 1H), 9.94 (d, J=2.5 Hz, 1H), 8.58 (s, 1H), 7.98 (s, 2H), 7.38 (s, 1H), 7.09 (d, J=2.5 Hz, 1H), 6.73 (d, J=2.9 Hz, 1H), 2.51 (s, 2H), 2.35 (s, 3H), 2.17 (d, J=1.0 Hz, 3H), 0.79 (s, 9H).

Example 144

4-(cyclohexyl(hydroxy)(pyridin-2-yl)methyl)-6-(3,5-dimethylisoxazol-4-yl)-1H-benzo[d]imidazol-2(3H)-one

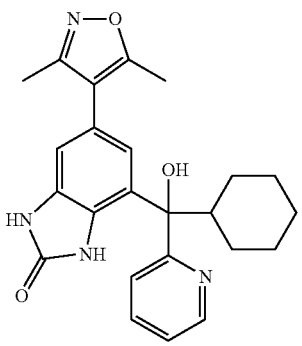

(6-(3,5-dimethylisoxazol-4-yl)-2-ethoxy-1H-benzo[d]imidazol-4-yl)(pyridin-2-yl)methanone (50 mg, 0.14 mmol) was dissolved in dry THF (1.4 mL) and cooled to 0° C. Cyclohexylmagnesium chloride (2.0 M, 0.21 mL, 0.41 mmol) was added dropwise and the reaction was allowed to stir for 10 mins and then quenched with water. Reaction was extracted three times with EtOAc and combined organic layers were washed once with water, concentrated, and purified by reverse-phase HPLC to give cyclohexyl(6-(3,5-dimethylisoxazol-4-yl)-2-ethoxy-1H-benzo[d]imidazol-4-yl)(pyridin-2-yl)methanol intermediate. The intermediate was taken up in EtOH (1.5 mL) and 0.2 mL concentrated HCl and heated to 65° C. for 2 hours and concentrated afford the desired product as a white powder.

C24H26N4O3 419.8 (M+1). 1H NMR (400 MHz, Methanol-d4) δ 8.77 (d, J=5.7 Hz, 1H), 8.54 (t, J=7.5 Hz, 1H), 8.15 (d, J=7.9 Hz, 1H), 7.97 (dd, J=7.3, 5.7 Hz, 1H), 7.24 (d, J=1.4 Hz, 1H), 6.99 (d, J=1.2 Hz, 1H), 2.84 (d, J=10.6 Hz, 1H), 2.42 (s, 3H), 2.27 (s, 3H), 2.00-1.72 (m, 5H), 1.55-1.33 (m, 5H).

Example 145

4-((6-chloropyridin-2-yl)(hydroxy)(pyridin-2-yl)methyl)-6-(3,5-dimethylisoxazol-4-yl)-1H-benzo[d]imidazol-2(3H)-one

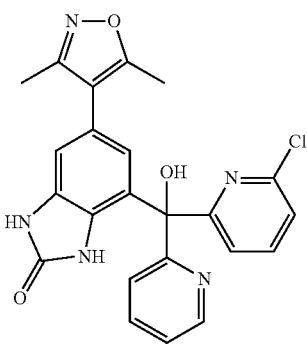 [SMILES: Cc1noc(C)c1-c1cc(C(O)(c2ccccn2)c2cccc(Cl)n2)c2[nH]c(=O)[nH]c2c1]

To a solution of 2-bromo-6-chloropyridine (83 mg, 0.43 mmol) in 2-MeTHF (1.5 mL) cooled to −78° C. was added n-BuLi (1.6 M, 0.27 mL, 0.43 mmol) dropwise and the reaction was allowed to stir for 40 mins. A solution of (6-(3,5-dimethylisoxazol-4-yl)-2-ethoxy-1H-benzo[d]imidazol-4-yl)(pyridin-2-yl)methanone (100 mg, 0.22 mmol) in 2-MeTHF (0.5 mL) was added to the reaction and the reaction was allowed to stir for an additional 10 mins at −78° C. and then quenched with water. The reaction mixture was extracted three times with EtOAc and combined organic layers were washed once with water, concentrated, and purified by silica gel chromatography to yield (6-chloropyridin-2-yl)(6-(3,5-dimethylisoxazol-4-yl)-2-ethoxy-1H-benzo[d]imidazol-4-yl)(pyridin-2-yl)methanol (51 mg, 41%) as a white solid. The solid (26.5 mg, 0.055 mmol) was taken up in EtOH (1 mL) and 4M HCl/dioxane (0.5 mL) and heated for two hours at 65° C. and then concentrated to afford the desired product as a pale yellow powder.

C23H18ClN5O3 448.9 (M+1). 1H NMR (400 MHz, DMSO-d6) δ 10.80-10.72 (m, 1H), 9.87 (s, 1H), 8.54 (d, J=4.8 Hz, 1H), 7.89 (t, J=7.9 Hz, 2H), 7.63 (d, J=8.1 Hz, 1H), 7.56 (d, J=7.7 Hz, 1H), 7.45 (d, J=7.9 Hz, 1H), 7.39 (s, 1H), 6.86 (s, 1H), 6.51 (s, 1H), 2.30 (s, 3H), 2.10 (s, 3H).

Example 146

6-(3,5-dimethylisoxazol-4-yl)-4-(hydroxy(6-(2-methoxyethoxy)pyridin-2-yl)(pyridin-2-yl)methyl)-1H-benzo[d]imidazol-2(3H)-one

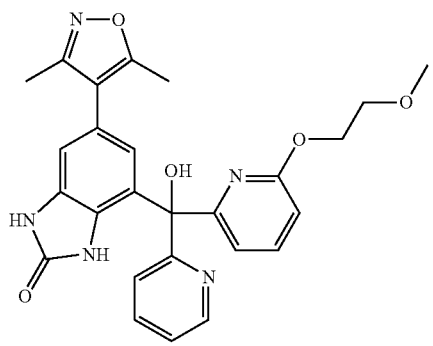 [SMILES: COCCOc1cccc(C(O)(c2ccccn2)c2cc(-c3c(C)noc3C)cc3[nH]c(=O)[nH]c23)n1]

2-methoxyethanol (25 mg, 0.33 mmol) was dissolved in THF (0.5 mL) and cooled to 0° C. Sodium hydride (8 mg, 0.33 mmol) was added in one portion and the reaction was allowed to come to rt and stir for 10 minutes. The reaction was then cooled back to 0° C. and tert-butyl 4-((6-chloropyridin-2-yl)(hydroxy)(pyridin-2-yl)methyl)-6-(3,5-dimethylisoxazol-4-yl)-2-ethoxy-1H-benzo[d]imidazole-1-carboxylate (24 mg, 0.04 mmol) was added and the reaction was sealed and heated to 80° C. overnight. Reaction was concentrated and the residue was taken up in EtOH (1.5 mL) and 4M HCl/dioxane (0.5 mL) and heated for 2 hours at 60° C. The reaction was cooled to rt and filtered to remove the sodium salt. Filtrate was concentrated to afford the desired product as a brown film.

C26H25N5O5 488.5 (M+1). 1H NMR (400 MHz, DMSO-d6) δ 10.81 (s, 1H), 9.97 (s, 1H), 8.63 (s, 1H), 7.77 (d, J=7.9 Hz, 1H), 7.69 (s, 1H), 7.28 (s, 1H), 6.89 (s, 1H), 6.81-6.72 (m, 1H), 6.41 (s, 1H), 4.10 (d, J=4.5 Hz, 2H), 3.75-3.61 (m, 2H), 3.15 (s, 3H), 2.26 (s, 3H), 2.06 (s, 3H).

Example 147

6-(3,5-dimethylisoxazol-4-yl)-4-(hydroxy(6-methylpyridin-2-yl)(pyridin-2-yl)methyl)-1H-benzo[d]imidazol-2(3H)-one

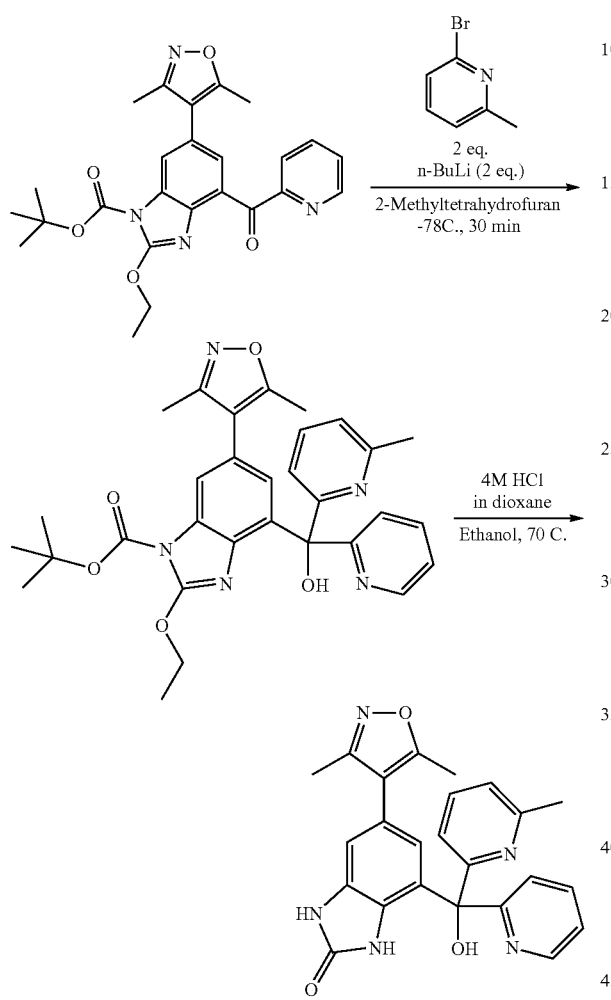

In a 2-neck, 50-mL round-bottom flask, a solution of 6-bromo-2-picoline (28.6 mg, 0.177 mmol) in 2 mL of 2-methyltetrahydrofuran was cooled to −78° C. in a dry ice/acetone bath while stirring under nitrogen. To this stirring solution, a 1.42 M n-butyllithium solution in hexanes (0.12 mL, 0.17 mmol) was added dropwise and the reaction mixture was stirred at −78° C. for 30 minutes. Tert-butyl 6-(3,5-dimethylisoxazol-4-yl)-2-ethoxy-4-picolinoyl-1H-benzo[d]imidazole-1-carboxylate (34.8 mg, 0.0752 mmol) was added dropwise in a solution of 1 mL of 2-methyltetrahydrofuran. The reaction mixture was warmed to room temperature for 30 minutes before the reaction was quenched with brine and diluted with ethyl acetate. The organic layer was separated and saved and the aqueous layer was extracted three times with ethyl acetate. The organic layers were dried over sodium sulfate, decanted and concentrated. C31H33N5O5. 556.1 (M+1).

The crude intermediate was taken up in 2 mL of ethanol and transferred to a microwave vial. 4M hydrochloric acid in dioxane (0.10 mL, 0.40 mmol) was added to the reaction mixture and the vial was sealed and heated at 70° C. for 1 hour or until reaction completion. The reaction mixture was concentrated and the product was isolated by preparatory HPLC as a yellow oil.

C24H21N5O3. 428.0 (M+1). 1H NMR (400 MHz, Methanol-d4) δ 8.68 (ddd, J=5.3, 1.8, 0.9 Hz, 1H), 8.25-8.16 (m, 2H), 7.92 (dt, J=8.1, 1.0 Hz, 1H), 7.73-7.61 (m, 3H), 7.09 (d, J=1.5 Hz, 1H), 6.42 (d, J=1.5 Hz, 1H), 2.75 (s, 3H), 2.31 (s, 3H), 2.14 (s, 3H).

Example 148

6-(3,5-dimethylisoxazol-4-yl)-4-((6-ethylpyridin-2-yl)(hydroxy)(pyridin-2-yl)methyl)-1H-benzo[d]imidazol-2(3H)-one A procedure similar to that used for Example 162 was used to produce the intermediate ($C_{32}H_{35}N_5O_5$. 570.1 (M+1)), which was taken directly to the deprotection step to yield a yellow oil.

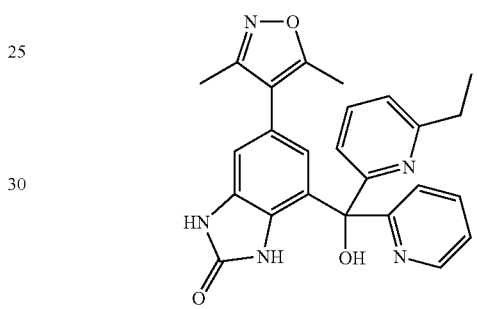

$C_{25}H_{23}N_5O_3$. 442.0 (M+1). $^1$H NMR (400 MHz, Methanol-$d_4$) δ 8.75-8.68 (m, 1H), 8.29 (td, J=7.9, 1.7 Hz, 1H), 8.18 (t, J=7.9 Hz, 1H), 7.94 (dt, J=8.1, 1.0 Hz, 1H), 7.76 (ddd, J=7.7, 5.4, 1.1 Hz, 1H), 7.70-7.62 (m, 2H), 7.09 (d, J=1.5 Hz, 1H), 6.43 (d, J=1.5 Hz, 1H), 3.00 (q, J=7.6 Hz, 2H), 2.31 (s, 3H), 2.13 (s, 3H), 1.32 (t, J=7.6 Hz, 3H).

Example 149

6-(3,5-dimethylisoxazol-4-yl)-4-(hydroxy(phenyl)(pyridin-2-yl)methyl)-1H-benzo[d]imidazol-2(3H)-one

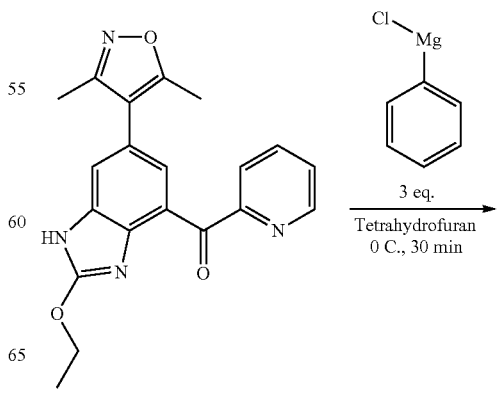

159

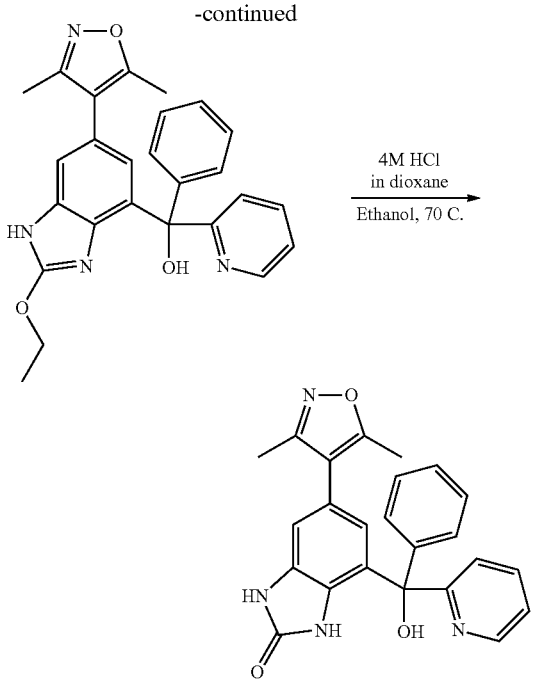

In a 2-neck, 50-mL round bottom flask, a solution of (6-(3,5-dimethylisoxazol-4-yl)-2-ethoxy-1H-benzo[d]imidazole-4-yl)(pyridin-2-yl)methanone (31.5 mg, 0.0870 mmol) in 2 mL of tetrahydrofuran was cooled to 0° C. while stirring under nitrogen. A 2M solution of phenylmagnesium chloride in tetrahydrofuran (0.13 mL, 0.26 mmol) was added dropwise to the reaction mixture and allowed to warm to room temperature for 30 minutes. The reaction mixture was quenched with 2 M aqueous hydrochloric acid and neutralized with aqueous sodium bicarbonate. The aqueous layer was extracted with ethyl acetate three times, and the combined organic layers were concentrated and taken directly to the deprotection step. $C_{26}H_{24}N_4O_3$, 441.1 (M+1).

The crude intermediate was dissolved in 3 mL of ethanol and transferred to a microwave vial. Hydrochloric acid in dioxane (0.10 mL, 0.40 mmol) was added and the reaction vial was sealed and heated at 70° C. for 1 hour. The reaction mixture was concentrated down and the product was isolated by preparatory HPLC as a white solid.

C26H24N4O3. 413.1 (M+1). 1H NMR (400 MHz, Methanol-d4) δ 8.80 (ddd, J=5.6, 1.7, 0.8 Hz, 1H), 8.38 (td, J=7.9, 1.7 Hz, 1H), 7.89 (ddd, J=7.8, 5.6, 1.2 Hz, 1H), 7.77 (dt, J=8.1, 1.0 Hz, 1H), 7.51-7.41 (m, 3H), 7.37 (dd, J=7.9, 1.8 Hz, 2H), 7.08 (d, J=1.5 Hz, 1H), 6.48 (d, J=1.5 Hz, 1H), 2.30 (s, 3H), 2.13 (s, 3H).

Example 150

6-(3,5-dimethylisoxazol-4-yl)-4-((3-ethylphenyl)(hydroxy)(pyridin-2-yl)methyl)-1H-benzo[d]imidazol-2(3H)-one

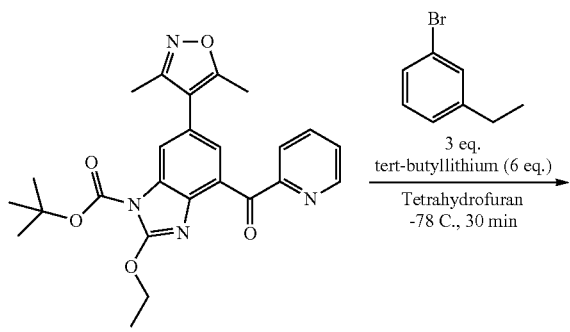

160

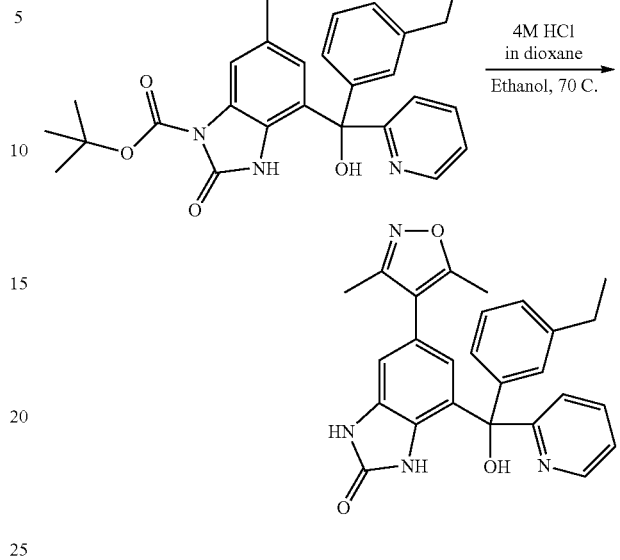

In a 2-neck, 50-mL round bottom flask, 1-bromo-3-ethylbenzene (43.2 mg, 0.233 mmol) was cooled to −78° C. in 2 mL of tetrahydrofuran while stirring under nitrogen. A 1.47 M solution of tert-butyllithium in pentane (310 μL, 0.456 mmol) was added dropwise and the reaction was allowed to stir for 15 minutes. In a solution of 1 mL of tetrahydrofuran, tert-butyl 6-(3,5-dimethylisoxazol-4-yl)-2-ethoxy-4-picolinoyl-1H-benzo[d]imidazole-1-carboxylate (35.0 mg, 0.0757 mmol) was added dropwise. The reaction mixture was warmed to room temperature while stirring under nitrogen for 15 minutes or until reaction completion. The reaction mixture was slowly quenched with brine and diluted with ethyl acetate. The organic layer was separated and saved and the aqueous layer was extracted with ethyl acetate three times. The organic layers were combined, dried over sodium sulfate, decanted and concentrated.

The crude intermediate was dissolved in 1 mL of ethanol and transferred to a microwave vial before 4M hydrochloric acid in dioxane (0.100 mL, 0.400 mmol) was added. The vial was sealed and heated at 70° C. for one hour or until reaction completion. The reaction mixture was concentrated and isolated by preparatory HPLC to yield the title compound.

C26H24N4O3. 441.1 (M+1). 1H NMR (400 MHz, Methanol-d4) δ 8.89-8.81 (m, 1H), 8.58 (td, J=8.0, 1.6 Hz, 1H), 8.08 (ddd, J=7.4, 5.8, 1.2 Hz, 1H), 7.92-7.83 (m, 1H), 7.40 (t, J=7.7 Hz, 1H), 7.36-7.29 (m, 2H), 7.14 (d, J=1.7 Hz, 1H), 7.11 (d, J=1.5 Hz, 1H), 6.47 (d, J=1.5 Hz, 1H), 2.69 (q, J=7.6 Hz, 2H), 2.31 (s, 3H), 2.13 (s, 3H), 1.23 (t, J=7.6 Hz, 3H).

Example 151

6-(3,5-dimethylisoxazol-4-yl)-4-(hydroxy(pyridin-2-yl)(m-tolyl)methyl)-1H-benzo[d]imidazol-2(3H)-one A procedure similar to that used for Example 165 was used to produce the intermediate ($C_{27}H_{26}N_4O_3$, 455.1 (M+1)) which was immediately taken forward to the deprotection step to yield a yellow solid (7.7 mg, 23%).

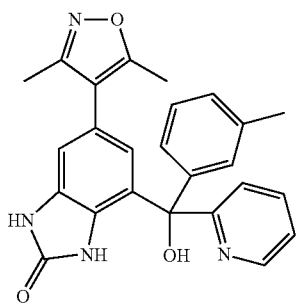 [SMILES: Cc1cccc(C(O)(c2ccccn2)c2cc(-c3c(C)noc3C)cc3[nH]c(=O)[nH]c23)c1]

$C_{25}H_{22}N_4O_3$. 427.1 (M+1). $^1$H NMR (400 MHz, Methanol-$d_4$) δ 8.87 (dd, J=6.0, 1.4 Hz, 1H), 8.61 (td, J=7.9, 1.5 Hz, 1H), 8.16-8.06 (m, 1H), 7.90 (d, J=8.1 Hz, 1H), 7.39 (t, J=7.7 Hz, 1H), 7.34-7.25 (m, 2H), 7.14 (d, J=7.8 Hz, 1H), 7.12 (d, J=1.5 Hz, 1H), 6.48 (d, J=1.5 Hz, 1H), 2.38 (s, 3H), 2.32 (s, 3H), 2.14 (s, 3H).

Example 152

6-(3,5-dimethylisoxazol-4-yl)-4-(hydroxy(3-methoxyphenyl)(pyridin-2-yl)methyl)-1H-benzo[d]imidazol-2(3H)-one A procedure similar to that used to synthesize the compound of Example 166 was used to produce the product as a white solid.

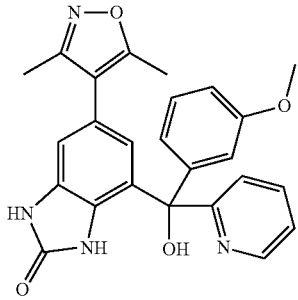 [SMILES: COc1cccc(C(O)(c2ccccn2)c2cc(-c3c(C)noc3C)cc3[nH]c(=O)[nH]c23)c1]

$C_{25}H_{22}N_4O_4$. 443.0 (M+1). $^1$H NMR (400 MHz, Chloroform-d) δ 8.67 (m, 1H), 8.56 (bs, 1H), 8.43 (bs, 1H), 7.72 (t, 2H), 7.34 (m, 1H), 7.10 (d, J=7.8 Hz, 1H), 6.86 (m, 3H), 6.78 (d, J=7.8 Hz, 1H), 6.25 (s, 1H), 3.75 (s, 3H), 2.25 (s, 3H), 2.10 (s, 3H).

Example 153

Preparation of 6-(3,5-dimethylisoxazol-4-yl)-4-((7-fluoroquinolin-2-yl)(hydroxy)(phenyl)methyl)-1H-benzo[d]imidazol-2(3H)-one

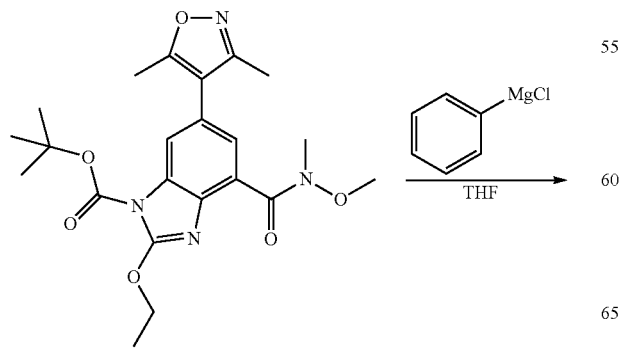

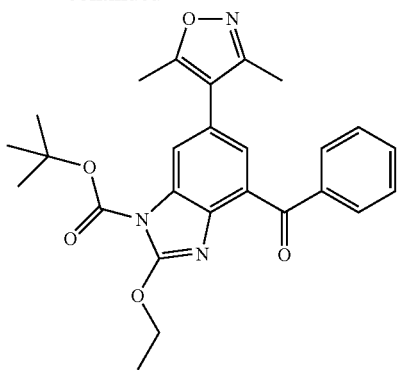

Text-butyl 6-(3,5-dimethylisoxazol-4-yl)-2-ethoxy-4-(methoxy(methyl)carbamoyl)-1H-benzo[d]imidazole-1-carboxylate was dissolved in THF (3 mL). To the solution was added a solution of phenyl magnesium chloride (2M in THF, 0.508 mmol, 0.254 mmol) at −78° C. after the addition, the reaction was allowed to warm up to room temperature. The reaction was stirred for 17 h at the same temperature. The reaction mixture was quenched with water (30 mL). The whole was extracted with AcOEt (30 mL×3). Organic layer was washed with brine (30 mL) and dried over $Na_2SO_4$. The solvent was removed under a reduced pressure to give the crude product. The crude product was purified by a silica gel column chromatography (hexane:EtOAc, 7:1 to 3:1) to give tert-butyl 4-benzoyl-6-(3,5-dimethylisoxazol-4-yl)-2-ethoxy-1H-benzo[d]imidazole-1-carboxylate.

$C_{26}H_{27}N_3O_5$. MS. m/z 462.2 (M+1).

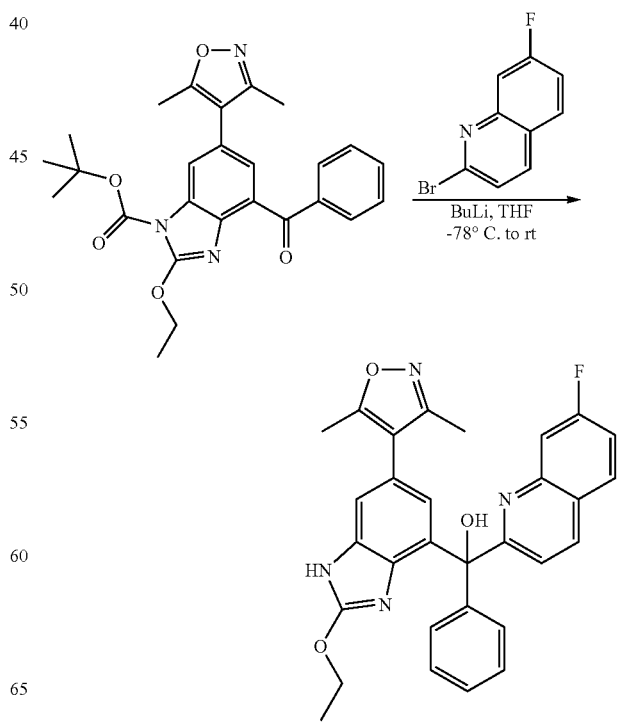

To a solution of 7-fluoro-2-bromoquinoline (54.1 mg) in THF (2 mL) was added BuLi (1.6 M, 0.25 mL) at −78° C. After 5 min, a solution of phenyl ketone (60.0 mg) in THF (1 mL) was added at −78° C. The reaction was immediately allowed to warm up to room temperature and stirred for 30 min. The reaction mixture was quenched with water (30 mL). The whole was extracted with AcOEt (30 mL×3). Organic layer was washed with brine (30 mL) and dried over $Na_2SO_4$. The solvent was removed under a reduced pressure to give the crude product. The crude product was treated with TFA to cleave the Boc group. The crude product was purified by a silica gel column chromatography (hexane:EtOAc, 7:1 to 3:1) to give tert-butyl 4-benzoyl-6-(3,5-dimethylisoxazol-4-yl)-2-ethoxy-1H-benzo[d]imidazole-1-carboxylate (18.0 mg). tert-butyl 4-benzoyl-6-(3,5-dimethylisoxazol-4-yl)-2-ethoxy-1H-benzo[d]imidazole-1-carboxylate. $C_{26}H_{27}N_3O_5$. MS. m/z 509.2 (M+1).

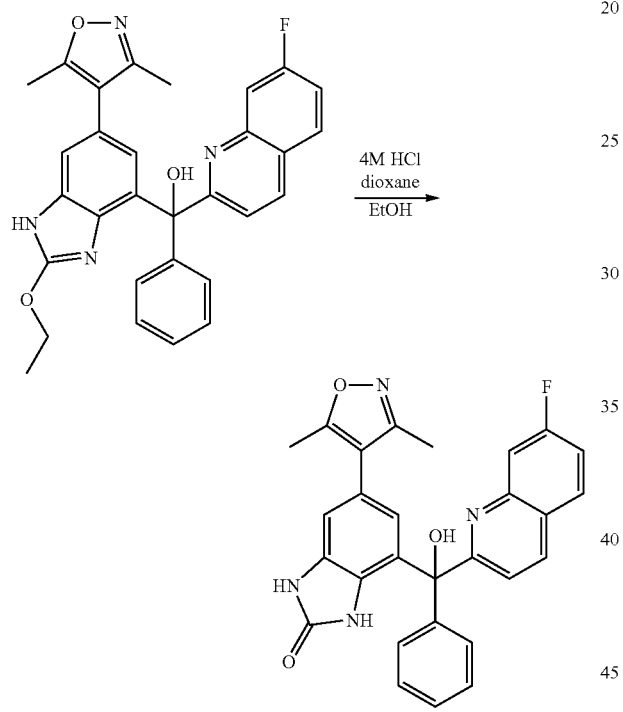

Tert-butyl 4-benzoyl-6-(3,5-dimethylisoxazol-4-yl)-2-ethoxy-1H-benzo[d]imidazole-1-carboxylate (18.0 mg) was dissolved into EtOH (2 mL) and 4M HCl/dioxane (2 mL). The solution was heated at 70° C. for 30 min. The reaction mixture was quenched with water (30 mL). The whole was extracted with EtOAc (30 mL×3). Combined organic layers were washed with brine (50 mL). The solvent was removed under a reduced pressure to give a crude product. The crude product was purified by a silica gel column chromatography (hexane:EtOAc, 7:1 to 3:1) to give tert-butyl 4-benzoyl-6-(3,5-dimethylisoxazol-4-yl)-2-ethoxy-1H-benzo[d]imidazole-1-carboxylate.

$C_{28}H_{21}FN_4O_3$. MS. m/z 481.1 (M+1). 1H NMR (400 MHz, Methanol-d4) δ 8.31 (1, J=8.7 Hz, 1H), 8.13 (dd, J=9.2, 5.3 Hz, 1H), 7.67-7.56 (m, 3H), 7.40-7.25 (m, 5H), 6.98 (d, J=1.6 Hz, 1H), 6.61 (d, J=1.6 Hz, 1H), 2.28 (s, 3H), 2.11 (s, 3H).

Example 154

6-(3,5-dimethylisoxazol-4-yl)-4-(hydroxy(phenyl)(quinolin-2-yl)methyl)-1H-benzo[d]imidazol-2(3H)-one

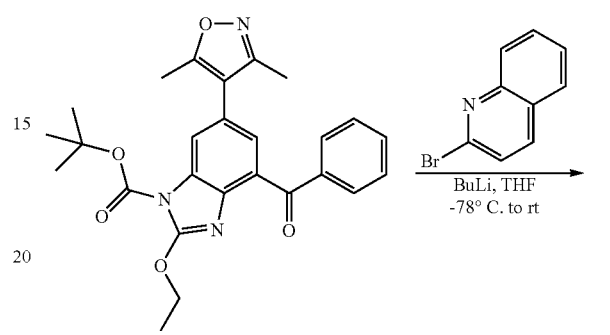

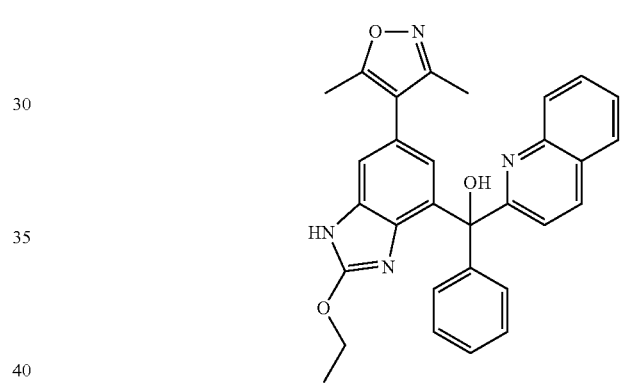

(6-(3,5-dimethylisoxazol-4-yl)-2-ethoxy-1H-benzo[d]imidazol-4-yl)(phenyl)(quinolin-2-yl)methanol was synthesized in the similar fashion with tert-butyl 4-benzoyl-6-(3,5-dimethylisoxazol-4-yl)-2-ethoxy-1H-benzo[d]imidazole-1-carboxylate.

$C_{30}H_{26}N_4O_3$. MS. m/z 491.2 (M+1).

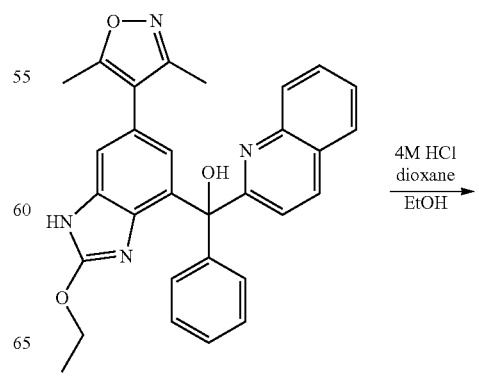

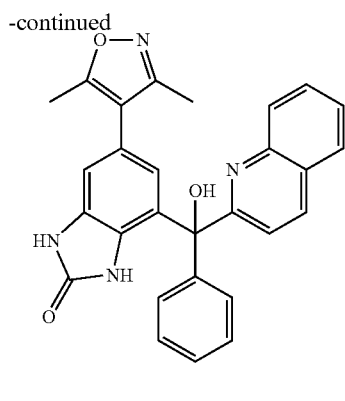

C$_{28}$H$_{22}$N$_4$O$_3$. MS. m/z 463.1 (M+1).). $^1$H NMR (400 MHz, Methanol-d$_4$) δ 8.30 (d, J=8.6 Hz, 1H), 8.09 (d, J=8.6 Hz, 1H), 7.93 (d, J=8.6 Hz, 1H), 7.77 (ddd, J=8.6, 7.0, 1.2 Hz, 1H), 7.61 (ddd, J=8.6, 7.0, 1.2 Hz, 1H), 7.54 (d, J=8.6 Hz, 1H), 7.40-7.26 (m, 5H), 6.98 (d, J=1.5 Hz, 1H), 6.61 (d, J=1.5 Hz, 1H), 2.27 (s, 3H), 2.10 (s, 3H).

Example 155

6-(3,5-dimethylisoxazol-4-yl)-4-(hydroxy(pyridin-2-yl)(quinolin-2-yl)methyl)-1H-benzo[d]imidazol-2(3H)-one

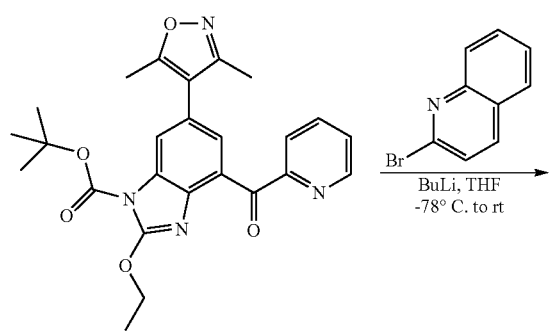

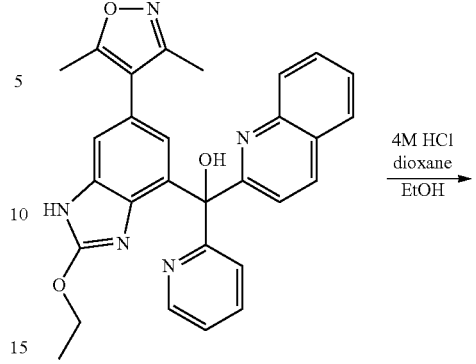

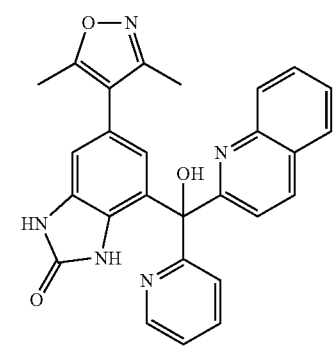

C$_{28}$H$_{22}$N$_4$O$_3$. MS. m/z 463.1 (M+1).). $^1$H NMR (400 MHz, Methanol-d$_4$) δ 8.78 (dd, J=6.6, 1.0 Hz, 1H), 8.66 (d, J=8.8 Hz, 1H), 8.47 (td, J=8.8, 1.0 Hz, 1H), 8.15-8.03 (m, 3H), 8.00-7.83 (m, 3H), 7.76 (t, J=8.0 Hz, 1H), 7.07 (d, J=1.0 Hz, 1H), 6.46 (d, J=1.0 Hz, 1H), 2.22 (s, 3H), 2.04 (s, 3H).

Example 156

1-tert-butyl 4-methyl 6-(3,5-dimethylisoxazol-4-yl)-3-methyl-2-oxo-2,3-dihydro-1H-benzo[d]imidazole-1,4-dicarboxylate

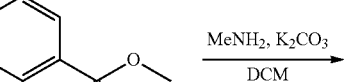

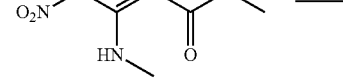

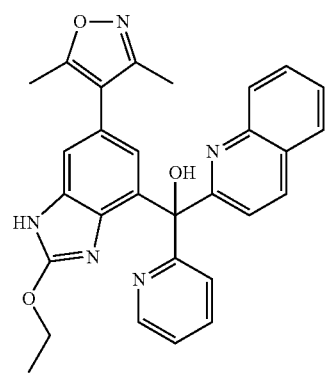

(6-(3,5-dimethylisoxazol-4-yl)-2-ethoxy-1H-benzo[d]imidazol-4-yl)(pyridin-2-yl)(quinolin-2-yl)methanol was synthesized in the similar fashion with tert-butyl 4-benzoyl-6-(3,5-dimethylisoxazol-4-yl)-2-ethoxy-1H-benzo[d]imidazole-1-carboxylate. C$_{29}$H$_{25}$N$_5$O$_3$. MS. m/z 492.2 (M+1).

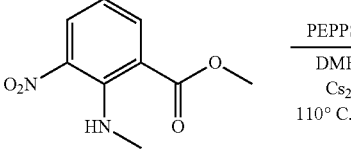

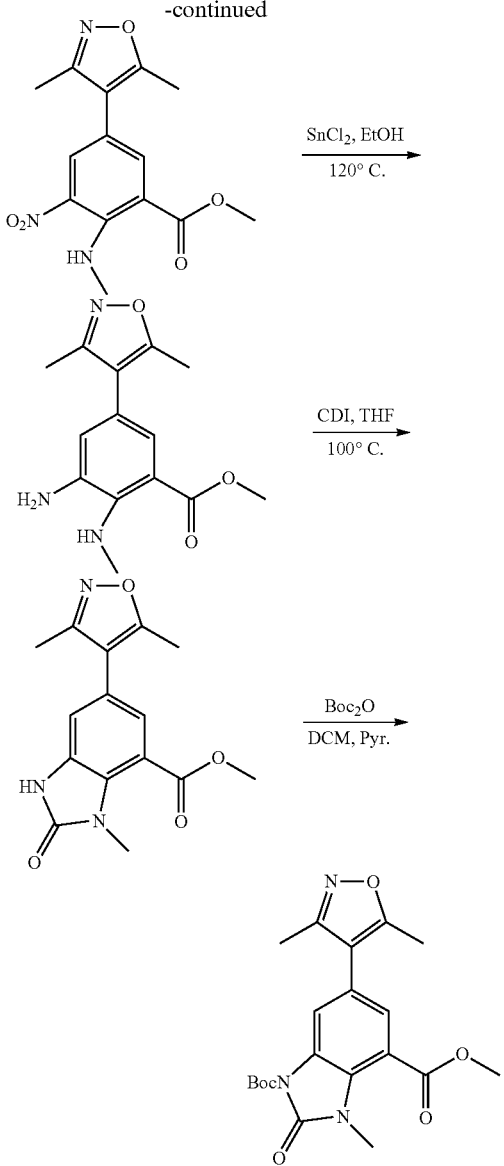

Methyl 2-fluoro-3-nitrobenzoate (25 g, 0.126 mol) was dissolved in DCM (400 ml) and to this was added Potassium carbonate (34.7 g, 0.25 mol) followed by Methylamine (20.63 ml, 0.5 mol). Reaction was stirred at room temperature under argon. Upon completion reaction was diluted with water and extracted with DCM (3×) then dried over magnesium sulfate. Solvents were removed under reduced pressure to afford methyl 2-(methylamino)-3-nitrobenzoate as a yellow solid.

Methyl 2-(methylamino)-3-nitrobenzoate (25.5 g, 0.121 mol) was dissolved in acetic acid (100 ml) and DCM (40 ml). In a separate flask bromine (7.46 ml, 0.15 mol) was dissolved in acetic acid (15 ml). The first solution was then slowly added to the bromine solution via an addition funnel and the reaction was stirred for 90 minutes. At this point the reaction was poured onto ice (200 g). After the ice had melted DCM was added and the reaction was extracted with DCM (3×), dried over magnesium sulfate then solvents removed under reduced pressure to methyl 5-bromo-2-(methylamino)-3-nitrobenzoate as a bright orange solid.

Methyl 5-bromo-2-(methylamino)-3-nitrobenzoate (20.1 g, 96.5 mmol), 3,5-dimethyl-4-(4,4,5,5-tetramethyl-1,3,2-dioxaborolan-2-yl)isoxazole (24.82 g, 111.25 mmol), PEPPSI"-IPr catalyst (2.63 g, 3.86 mmol), Cesium carbonate (67.96 g, 208.59 mmol), 1,2-Dimethoxyethane (100 ml) and Water (30 ml) were mixed together and the solution degassed for 5 minutes before heating to 110° C. for 1 hour. Reaction mixture was then cooled, diluted with EtAc and water and extracted EtAc (3×). Organics were washed with water then brine, dried over sodium sulfate and evaporated to dryness under reduced pressure. Crude material purified by silica gel chromatography using EtAc/Hex as the eluent to methyl 5-(3,5-dimethylisoxazol-4-yl)-2-(methylamino)-3-nitrobenzoate (20.5 g, 96%).

To methyl 5-(3,5-dimethylisoxazol-4-yl)-2-(methylamino)-3-nitrobenzoate (2000 mg, 6.55 mmol) was added stannous chloride (3726.66 mg, 19.65 mmol) and Ethanol (100 ml) in a pressure tube. The suspension was then heated in sealed vessel to 120° C. for 90 minutes at which point the reaction was cooled then stirred in a mixture of EtAc/1N NaOH for 1 hour or until precipitates form. Precipitates were filtered and crude mixture was diluted in EtAc and water and extracted 3× with EtAc. Organics were washed with water then brine, dried over sodium sulfate and evaporated to dryness under reduced pressure. Residue was purified by silica gel chromatography using MeOH/DCM as the eluent to afford methyl 3-amino-5-(3,5-dimethylisoxazol-4-yl)-2-(methylamino)benzoate as a dark form (1.1 g, 61%)

Methyl 3-amino-5-(3,5-dimethylisoxazol-4-yl)-2-(methylamino)benzoate (1.1 g, 4 mmol) and 1,1'-carbonyldiimidazole (1.3 g, 7.99 mmol) were stirred in Tetrahydrofuran (100 ml) in a sealed pressure vessel. Reaction was heated to 100° C. and allowed to react overnight. Next day solvents were removed under reduced pressure. Material was slurried in minimal DCM, sonicated and filtered. Solids were air dried to afford methyl 6-(3,5-dimethylisoxazol-4-yl)-3-methyl-2-oxo-2,3-dihydro-1H-benzo[d]imidazole-4-carboxylate as an off-white powder (417 mg, 35%).

Methyl 6-(3,5-dimethylisoxazol-4-yl)-3-methyl-2-oxo-2,3-dihydro-1H-benzo[d]imidazole-4-carboxylate (410 mg, 1.36 mmol) was dissolved in THF (10 ml) and to this was added Di-tert-butyl dicarbonate 97% (593.97 mg, 2.72 mmol) followed by 4-(Dimethylamino)pyridine (33.25 mg, 0.27 mmol) and finally Triethylamine (0.57 ml, 4.08 mmol). Reaction was allowed to stir at room temperature under argon for 3 hours, or until complete. Reaction was then diluted in EtAc and aqueous ammonium chloride and extracted with EtAc (3×). Organics were washed with ammonium chloride, water and brine and dried over sodium sulfate before evaporating to dryness. Crude material was purified by silica gel chromatography (EtAc/Hexanes as the eluent) to provide 1-tert-butyl 4-methyl 6-(3,5-dimethylisoxazol-4-yl)-3-methyl-2-oxo-2,3-dihydro-1H-benzo[d]imidazole-1,4-dicarboxylate as an opaque oil.

Example 157

5-(3,5-dimethylisoxazol-4-yl)-7-(hydroxydi(pyridin-2-yl)methyl)-1-methyl-1H-benzo[d]imidazol-2(3H)-one

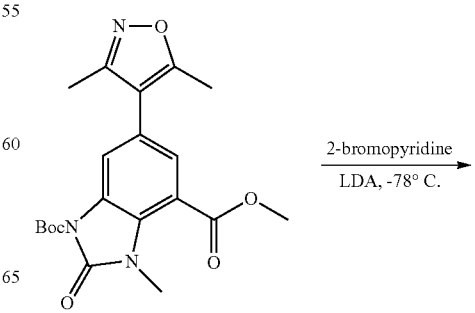

-continued

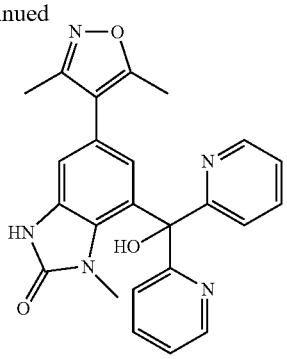

To a dry, argon purged flask was added 5 mL THF and 2-bromopyridine (0.06 ml, 0.62 mmol). Reaction was cooled to −78° C. under argon and then slowly was added 1.6M N-butyllithium in hexanes (0.43 ml) over 10 minutes. *Lithio* species was allowed to form for 30 minutes at which point 1-tert-butyl 4-methyl 6-(3,5-dimethylisoxazol-4-yl)-3-methyl-2-oxo-2,3-dihydro-1H-benzo[d]imidazole-1,4-dicarboxylate (50 mg, 0.12 mmol) in 0.5 mL THF was added slowly. Reaction stirred at −78° C. for 5 minutes then allowed to warm. When reaction vessel neared 0° C. was quenched with 1N HCl. Reaction was diluted with EtAc/H$_2$O and basified with 1N NaOH until neutral. Mixture was extracted with EtAc (3×) then organics were washed with water then brine and dried over sodium sulfate. Solvents were removed under reduced pressure and crude mixture was purified by preparative HPLC to afford GS-650721 (110 mg, 21%).

C$_{24}$H$_{21}$N$_5$O$_3$; 428.1 (M+1). 1H NMR (400 MHz, DMSO-d6) δ 11.09 (s, 1H), 8.57-8.50 (m, 2H), 7.89 (t, J=7.7 Hz, 2H), 7.55 (d, J=8.0 Hz, 2H), 7.39 (t, J=6.1 Hz, 2H), 6.97 (d, J=1.7 Hz, 1H), 5.86 (d, J=1.7 Hz, 1H), 2.76 (s, 3H), 2.18 (s, 3H), 1.97 (s, 3H).

Example 158

Example 159, and

Example 160 f 4-(cyclopentyl(hydroxy)methyl)-6-(3,5-dimethylisoxazol-4-yl)-1H-benzo[d]imidazol-2(3H)-one 4-(dicyclopentyl(hydroxy)methyl)-6-(3,5-dimethylisoxazol-4-yl)-1H-benzo[d]imidazol-2(3H)-one and 4-(cyclopentanecarbonyl)-6-(3,5-dimethylisoxazol-4-yl)-1H-benzo[d]imidazol-2(3H)-one

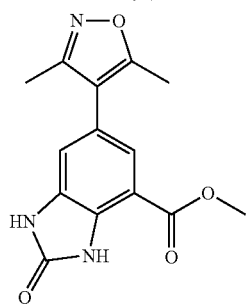

-continued

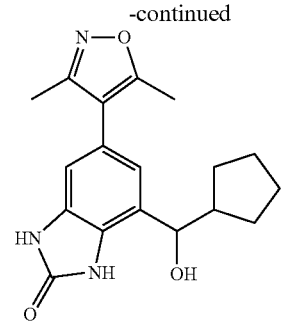

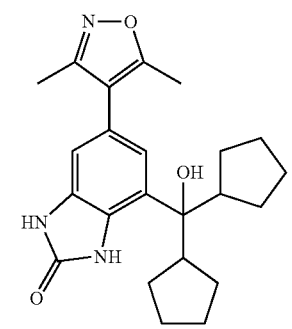

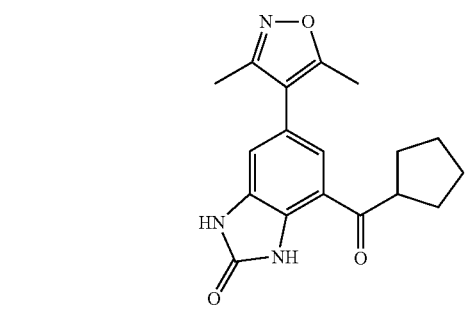

To a mixture containing methyl 6-(3,5-dimethylisoxazol-4-yl)-2-oxo-2,3-dihydro-1H-benzo[d]imidazole-4-carboxylate (60 mg, 0.21 mmol, 1 equiv.) and THF (3 mL) is added cyclopentyl magnesium chloride (0.88 mL, 1.46 mmol, 7 equiv.) at 0° C. for 5 min. After completion, the reaction was quenched and extracted with EtOAc and washed with water, saturated NH$_4$Cl. After drying with MgSO4, it was filtered and concentrated to dryness. Purification was carried out by reverse phase HPLC.

1H NMR (400 MHz, Methanol-d4) δ 6.96 (d, J=1.5 Hz, 1H), 6.88 (d, J=1.6 Hz, 1H), 4.66 (d, J=8.3 Hz, 1H), 2.39 (s, 3H), 2.24 (s, 3H), 1.93-1.80 (m, 1H), 1.76-1.43 (m, 3H), 1.40 (s, 0H), 1.28 (d, J=8.3 Hz, 1H). LCMS (m/z+1) 328.38

1H NMR (400 MHz, Methanol-d4) δ 6.94-6.68 (m, 1H), 2.53 (s, 0H), 2.53 (d, J=17.1 Hz, 1H), 2.38 (s, 2H), 2.23 (s, 2H), 1.84 (dd, J=12.4, 6.4 Hz, 1H), 1.59-1.43 (m, 6H), 1.43-1.31 (m, 2H). LCMS (m/z+1) 396.49

1H NMR (400 MHz, Methanol-d$_4$) δ 7.59 (d, J=1.5 Hz, 1H), 7.19 (d, J=1.5 Hz, 1H), 3.86 (t, J=7.8 Hz, 1H), 2.43 (s, 3H), 2.27 (s, 3H), 2.02-1.89 (m, 4H), 1.71 (td, J=5.4, 3.3 Hz, 4H). LCMS (m/z+1) 326.36

Example 161 and

Example 162

(6-(3,5-dimethylisoxazol-4-yl)-4-(3-hydroxypentan-3-yl)-1H-benzo[d]imidazol-2(3H)-one and methyl 6-(3,5-dimethylisoxazol-4-yl)-2-oxo-2,3-dihydro-1H-benzo[d]imidazole-4-carboxylate

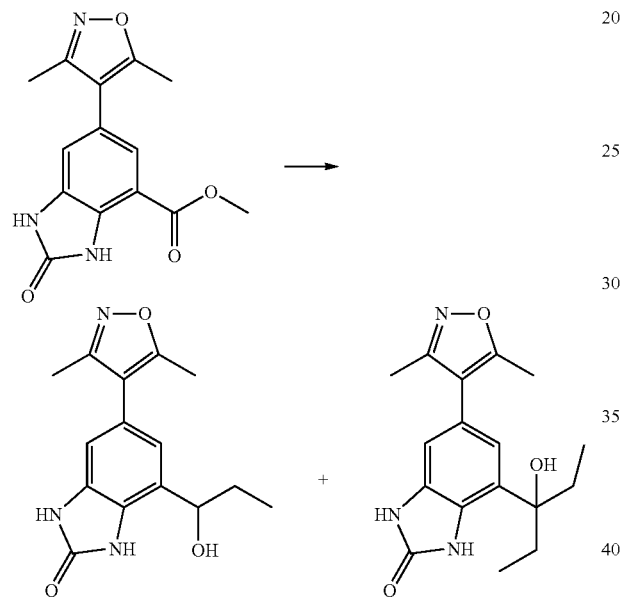

Into a flask containing methyl 6-(3,5-dimethylisoxazol-4-yl)-2-oxo-2,3-dihydro-1H-benzo[d]imidazole-4-carboxylate (60 mg, 0.21 mmol, 1 equiv.) is added cylopentylmagnesium chloride (0.88 mL, 1.46 mmol, 7 equiv., 1M Hexanes) at 0° C. for 5 min. After completion, the reaction was quenched and extracted with EtOAc and washed with water, saturated NH₄Cl. After drying with MgSO4, it was filtered and concentrated to dryness. Purification was carried out by reverse phase HPLC to GS-646013 and GS-646012. 1H NMR (400 MHz, Methanol-d4) δ 7.07-6.91 (m, 1H), 6.88 (d, J=1.6 Hz, 1H), 2.39 (s, 3H), 2.23 (s, 3H), 1.81 (td, J=7.0, 3.6 Hz, 2H), 0.95 (t, J=7.4 Hz, 3H). LCMS (m/z+1) 288.15

1H NMR (400 MHz, Methanol-d4) δ 7.55 (d, J=1.6 Hz, 1H), 7.18 (d, J=1.6 Hz, 1H), 3.97 (s, 3H), 2.40 (s, 3H), 2.24 (s, 3H). LCMS (m/z+1) 288.29

1H NMR (400 MHz, Methanol-d4) δ 6.86 (d, J=1.5 Hz, 1H), 6.74 (d, J=1.5 Hz, 1H), 2.39 (s, 3H), 2.23 (s, 3H), 1.94 (dd, J=14.3, 7.3 Hz, 2H), 1.90-1.74 (m, 2H), 0.82 (t, J=7.4 Hz, 7H). LCMS (m/z+1) 316.38

Example 163 and

Example 164

5-(3,5-dimethylisoxazol-4-yl)-1-methyl-7-(6-(trifluoromethyl)quinolin-7-yl)-1H-benzo[d]imidazol-2(3H)-one and 7-(6-(3,5-dimethylisoxazol-4-yl)-3-methyl-2-oxo-2,3-dihydro-1H-benzo[d]imidazol-4-yl)-6-(trifluoromethyl)quinoline 1-oxide

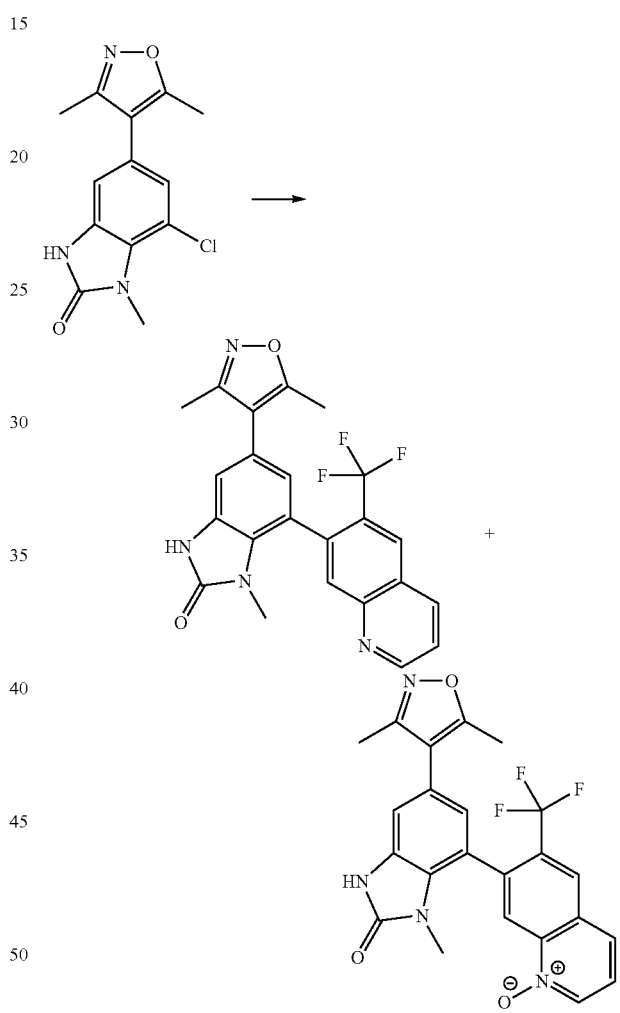

To a microwave vial containing 7-chloro-5-(3,5-dimethylisoxazol-4-yl)-1-methyl-1H-benzo[d]imidazol-2(3H)-one (100 mg, 0.36 mmol, 1 equiv.) was added 5-(4,4,5,5-tetramethyl-1,3,2-dioxaborolan-2-yl)-6-(trifluoromethyl)quinolone (350 mg, 1.08 mmol, 3 equiv.), Cs₂CO₃ (704 mg, 2.16 mmol, 6 equiv.) and PEPPSI™-IPr catalyst (98 mg, 0.14 mmol, 0.4 equiv.) and dissolved in DME-H2O (4 mL, 0.2 M, 2/1, v/v). The mixture was heated to 120° C. for 30 min in microwave. The reaction was concentrated in vacuo and purification was carried out by reverse phase HPLC.

1H NMR (400 MHz, Methanol-d4) δ 9.03 (dd, J=4.2, 1.6 Hz, 1H), 8.32 (d, J=9.1 Hz, 1H), 8.19 (d, J=9.0 Hz, 1H), 7.97-7.76 (m, 1H), 7.56 (dd, J=8.6, 4.3 Hz, 1H), 7.16 (d, J=1.5 Hz, 1H), 6.91 (d, J=1.4 Hz, 1H), 2.74 (s, 3H), 2.42 (s, 3H), 2.27 (s, 3H). LCMS (m/z+1) 439.4

1H NMR (400 MHz, Methanol-d4) δ 9.19 (s, 1H), 8.30-8.17 (m, 1H), 8.07-7.85 (m, 3H), 7.67 (ddd, J=8.3, 7.0, 1.2 Hz, 1H), 6.79 (d, J=1.3 Hz, 1H), 5.88 (d, J=1.3 Hz, 1H), 3.81 (s, 3H), 2.05 (s, 3H), 1.86 (s, 3H). LCMS (m/z+1) 455.26

Example 165

4-(1-cyclopentyl-1-hydroxypropyl)-6-(3,5-dimethyl-isoxazol-4-yl)-1H-benzo[d]imidazol-2(3H)-one

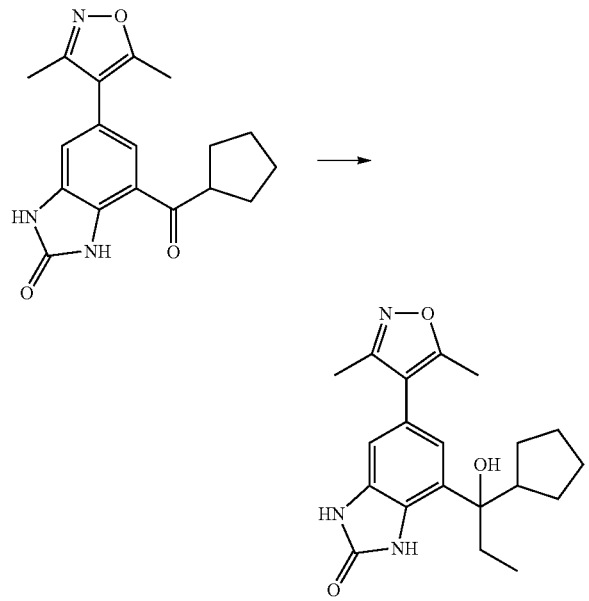

Into a flask containing the ketone (25 mg, 0.077 mmol, 1 equiv.) is added ethyl magnesium bromide (0.28 mL, 0.28 mmol, 4 equiv., 1M) at 0° C. for 5 min After completion, the reaction was quenched and extracted with EtOAc and washed with water, saturated NH₄Cl. After drying with MgSO₄, it was filtered and concentrated to dryness. Purification was carried out by reverse phase HPLC.

$^1$H NMR (400 MHz, Methanol-d₄) δ 6.85 (d, J=1.5 Hz, 1H), 6.78 (s, 1H), 2.41 (d, J=16.9 Hz, 4H), 2.25 (d, J=17.0 Hz, 4H), 2.03-1.68 (m, 4H), 1.50 (dtd, J=29.4, 15.0, 13.9, 7.8 Hz, 5H), 0.76 (t, J=7.4 Hz, 4H). $^{19}$F NMR (376 MHz, DMSO-d₆) δ −136.97 (d, J=6.5 Hz). LCMS (M+1) 355.96

Example 166

5-(3,5-dimethylisoxazol-4-yl)-4-fluoro-7-(6-methylquinolin-5-yl)-1H-benzo[d]imidazol-2(3H)-one

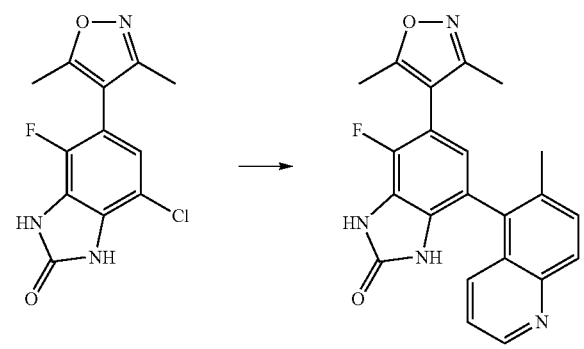 [SMILES: Cc1noc(C)c1-c1cc(Cl)c2[nH]c(=O)[nH]c2c1F ; Cc1ccc2ncccc2c1-c1cc(-c2c(C)noc2C)c(F)c2[nH]c(=O)[nH]c12]

To a microwave vial containing 7-chloro-5-(3,5-dimethyl-isoxazol-4-yl)-4-fluoro-1H-benzo[d]imidazol-2(3H)-one (16 mg, 0.057 mmol, 1 equiv.) was added 3,5-6-methylquinolin-5-ylboronic acid (53 mg, 0.28 mmol, 5 equiv.), Cs₂CO₃ (111 mg, 0.34 mmol, 6 equiv.) and PEPPSI™-IPr catalyst (7 mg, 0.0011 mmol, 0.2 equiv.) and dissolved in DME-H₂O (20 mL, 0.2 M, 2/1, v/v). The mixture was heated to 140° C. After 2 h, the reaction was complete. After cooling, the reaction was extracted with EtOAc and washed with water, saturated NH₄Cl. After drying with MgSO₄, it was filtered and concentrated to dryness. The resulting solid was washed with EtOAc. Purification was carried out by reverse phase HPLC to furnish 5-(3,5-dimethylisoxazol-4-yl)-4-fluoro-7-(6-methylquinolin-5-yl)-1H-benzo[d]imidazol-2(3H)-one.

1H NMR (400 MHz, DMSO-d6) δ 11.42 (d, J=1.8 Hz, 1H), 10.63 (s, 1H), 8.82 (dd, J=4.2, 1.6 Hz, 1H), 7.99 (d, J=8.6 Hz, 1H), 7.79-7.56 (m, 2H), 7.40 (dd, J=8.5, 4.2 Hz, 1H), 6.77 (d, J=6.6 Hz, 1H), 2.34 (d, J=0.9 Hz, 3H), 2.24 (s, 3H), 2.17 (d, J=0.9 Hz, 3H).
19F NMR (376 MHz, DMSO-d6) δ −136.97 (d, J=6.5 Hz). LCMS (m/z+1) 389.28

Example 167 and

Example 168

(7R and 7S)-5-(3,5-dimethylisoxazol-4-yl)-4-fluoro-7-(6-methylquinolin-5-yl)-1H-benzo[d]imidazol-2(3H)-one

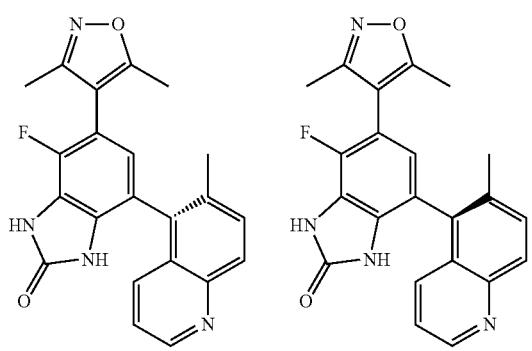

The racemate of Example 166 was separated with super critical column chromatography (JASCO SFC) using DAICEL AD-H (10 mm×250 mm, 20% MeOH, 15 mL/min, 40° C., 15 atm). RT 2.733 min, 1.9 mg (GS-649951). RT 3.742 min, 2.6 mg.

Example 169

5-(3,5-dimethylisoxazol-4-yl)-4-fluoro-7-(hydroxydi(pyridin-2-yl)methyl)-1H-benzo[d]imidazol-2(3H)-one Step 1: Methyl 2-amino-5-(3,5-dimethylisoxazol-4-yl)-4-fluorobenzoate

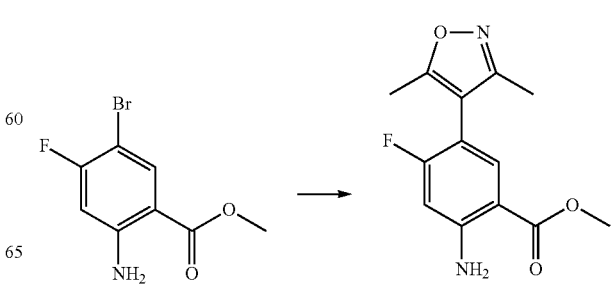

To methyl 2-amino-5-bromo-4-fluorobenzoate (20 g, 80.6 mol.) and 3,5-Dimethylisoxazole-4-boronic acid pinacol ester (24.2 g, 108.9 mol., 1.35 mmol) was added to a solvent mixture of 1,2-dimethoxymethane (120 ml) and water (60 ml). To the above mixture were added PEPPSI-Ipr (3120 mg, 4.2 mmol, 0.05 equiv.) and $Cs_2CO_3$ (78.8 g, 241 mol., 3 equiv.). The reaction mixture was heated at 120° C. for 2 h in a pressure tube. The reaction mixture was then diluted with EtOAc (100 ml), washed with bring (50 ml×2). The organic solvent was evaporated and the residue was dissolved in DCM and purified with combi-flash column chromatography (product came out at 50% EtOAc/Hexane) to afford methyl 2-amino-5-(3,5-dimethylisoxazol-4-yl)-4-fluorobenzoate.

¹HNMR (400 MHz, Chloroform-d) δ 7.79 (dd, J=8.1, 1.2 Hz, 1H), 6.80-6.60 (m, 1H), 3.90 (s, 4H), 2.34 (d, J=8.3 Hz, 4H), 2.20 (d, J=5.5 Hz, 4H). ¹⁹F NMR (377 MHz, Chloroform-d) δ −96.83--101.99 (m), −105.54 (d, J=13.8 Hz). LCMS (m/z+1) 265.32.

Step 2: Methyl 2-amino-5-(3,5-dimethylisoxazol-4-yl)-4-fluoro-3-nitrobenzoate

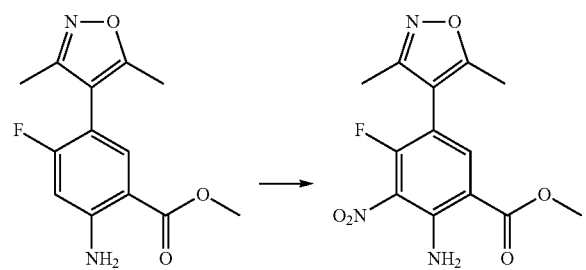 [SMILES: COC(=O)c1cc(-c2c(C)noc2C)c(F)cc1N ; COC(=O)c1cc(-c2c(C)noc2C)c(F)c([N+](=O)[O-])c1N]

To a mixture of methyl 2-amino-5-(3,5-dimethylisoxazol-4-yl)-4-fluorobenzoate (14 g, 53 mmol, 1 equiv.) and TFA (100 mL) is slowly added nitronium tetrafluoroborate (9.1 g, 68.9 mmol, 1.3 equiv.). After completion, the mixture was concentrated under reduced pressure. The residue was dissolved and then the residue was dissolved in EtOAc (200 ml) and washed with brine (30 ml×2). The organic solvent was evaporated. Methyl 2-amino-5-(3,5-dimethylisoxazol-4-yl)-4-fluoro-3-nitrobenzoate was used without further purification. ¹H NMR (400 MHz, Chloroform-d) δ 6.92 (d, J=5.8 Hz, 1H), 4.24 (s, 4H), 4.07-3.85 (m, 5H), 2.46-2.34 (m, 4H), 2.31-2.22 (m, 5H).

19F NMR (377 MHz, Chloroform-d) δ −76.44, −121.12 (d, J=5.7 Hz). LCMS (m/z+1) 310.2

Step 3: Methyl 2,3-diamino-5-(3,5-dimethylisoxazol-4-yl)-4-fluorobenzoate

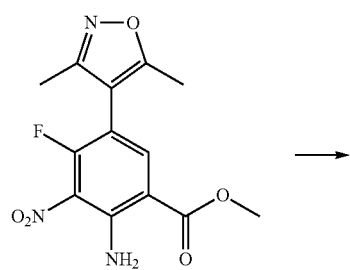

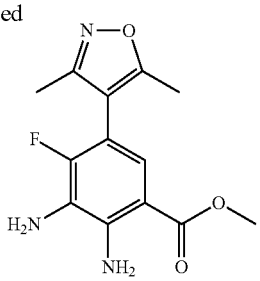

Into a pressure tube containing N-methyl 2-amino-5-(3,5-dimethylisoxazol-4-yl)-4-fluoro-3-nitrobenzoate (16.5 g, 53.2 mol., 1 equiv.) is added EtOH (200 mL) and tin (II) chloride (20.2 g, 107 mol., 2 equiv.). The reaction was heated for 3 h at 130° C. The reaction was then stirred in 2N NaOH solution for 20 minutes before being partitioned between water and ethyl acetate. The organic layer was washed with brine and dried over sodium sulfate. Purification was carried out by flash column chromatography to furnish methyl 2,3-diamino-5-(3,5-dimethylisoxazol-4-yl)-4-fluorobenzoate (5700 mg, 39%). LCMS (m/z+1) 270.2.

Step 4

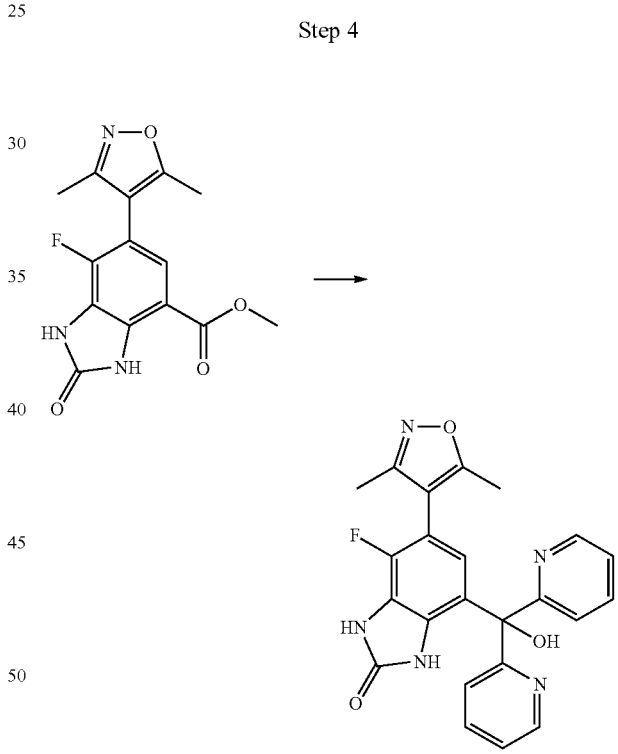

A flask containing 2-bromopyridine (135 μL, 1.37 mmol, 7 equiv.) and THF (3 mL) is cooled to −78° C. before BuLi (0.86 mL, 1.37 mmol, 7 equiv.) is added. After 30 min, methyl 6-(3,5-dimethylisoxazol-4-yl)-7-fluoro-2-oxo-2,3-dihydro-1H-benzo[d]imidazole-4-carboxylate (60 mg, 0.197 mmol, 1 equiv.) dissolved in THF (2 mL) is added to the reaction mixture. After completion, the reaction was quenched and extracted with EtOAc and washed with water, saturated $NH_4Cl$. After drying with $MgSO_4$, it was filtered and concentrated to dryness. Purification was carried out by reverse phase HPLC.

1H NMR (400 MHz, Methanol-d4) δ 8.62 (dd, J=5.3, 1.6 Hz, 2H), 8.13 (t, J=8.0 Hz, 2H), 7.84 (d, J=8.1 Hz, 2H), 7.60

(dd, J=7.6, 5.3 Hz, 2H), 6.43 (d, J=6.4 Hz, 1H), 2.24 (s, 3H), 2.07 (s, 3H). 19F NMR (377 MHz, Methanol-d4) δ −77.88, −137.06. LCMS (m/z+1) 431.92

Example 170

Example 171, and

Example 172

5-(3,5-dimethylisoxazol-4-yl)-4-fluoro-7-(hydroxydi(pyridin-2-yl)methyl)-1H-benzo[d]imidazol-2(3H)-one 7-((1H-imidazol-1-yl)di(pyridin-2-yl)methyl)-5-(3,5-dimethylisoxazol-4-yl)-4-fluoro-1H-benzo[d]imidazol-2(3H)-one and 7-(di(pyridin-2-yl)methyl)-5-(3,5-dimethylisoxazol-4-yl)-4-fluoro-1H-benzo[d]imidazol-2(3H)-one

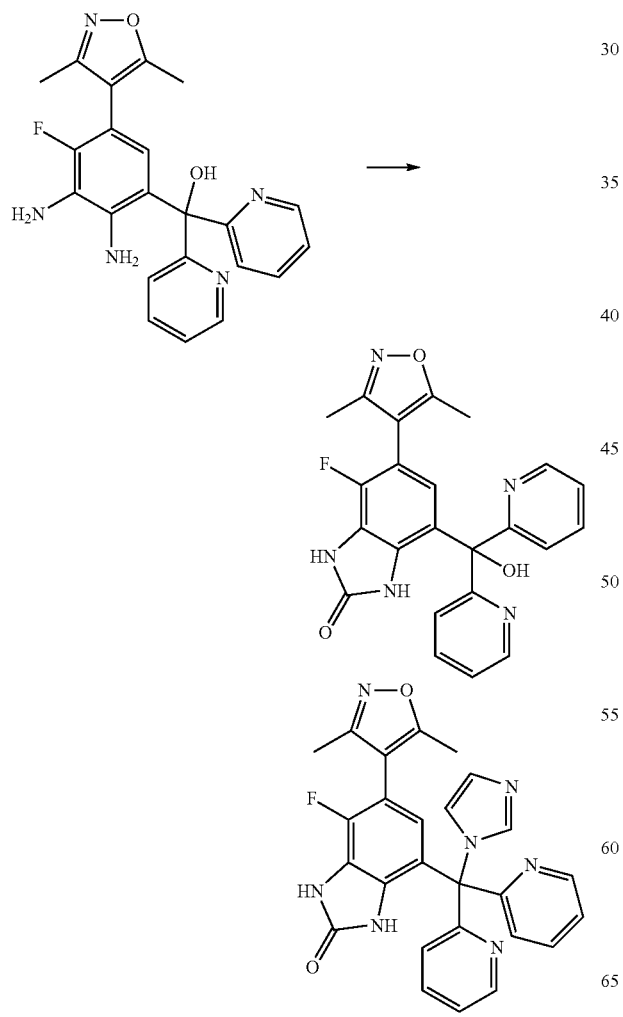

-continued

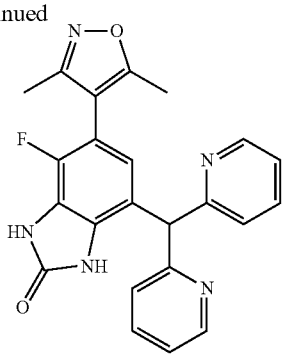

Alternatively, the title compound was made from (2,3-diamino-5-(3,5-dimethylisoxazol-4-yl)-4-fluorophenyl)di(pyridin-2-yl)methanol. Into a microwave vial containing (2,3-diamino-5-(3,5-dimethylisoxazol-4-yl)-4-fluorophenyl)di(pyridin-2-yl)methanol (50 mg, 0.12 mmol, 1 equiv.) is added THF (5 m) and CDI (30 mg, 0185 mmol, 1.5 equiv.). The mixture was heated to 120° C. for 30 minutes in a microwave reactor. The reaction was concentrated in vacuo and purified by HPLC.

1H NMR (400 MHz, Methanol-d4) δ 8.65 (ddt, J=5.4, 1.6, 0.7 Hz, 2H), 8.33-8.14 (m, 2H), 7.92 (dt, J=8.1, 0.9 Hz, 2H), 7.68 (ddt, J=7.3, 5.4, 0.9 Hz, 2H), 6.39 (d, J=6.4 Hz, 1H), 2.24 (s, 4H), 2.06 (s, 4H). 19F NMR (377 MHz, Methanol-d4) δ −77.95, −136.55 (d, J=6.2 Hz).

LCMS (m/z+1) 431.92

1H NMR (400 MHz, Methanol-d4) δ 9.50 (t, J=1.5 Hz, 0H), 8.67 (ddd, J=4.8, 1.8, 0.9 Hz, 1H), 7.96-7.79 (m, 1H), 7.54 (t, J=1.8 Hz, 0H), 7.47 (ddd, J=7.7, 4.7, 0.9 Hz, 1H), 7.03 (dd, J=8.1, 1.0 Hz, 1H), 5.92 (d, J=6.3 Hz, 0H), 2.23 (d, J=0.9 Hz, 1H), 2.05 (d, J=0.9 Hz, 1H).

19F NMR (377 MHz, Methanol-d4) δ −77.74, −134.19 (d, J=6.2 Hz). LCMS (m/z+1) 482.17

1H NMR (400 MHz, DMSO-d6) δ 7.70 (dt, J=4.8, 1.3 Hz, 1H), 6.98 (td, J=7.8, 1.9 Hz, 1H), 6.50 (ddd, J=7.6, 4.9, 1.1 Hz, 1H), 6.45 (d, J=7.9 Hz, 1H), 5.83 (d, J=6.5 Hz, 1H), 5.16 (s, 1H), 1.44 (d, J=0.9 Hz, 2H), 1.27 (d, J=0.8 Hz, 2H). ¹⁹F NMR (377 MHz, DMSO-d6) δ −78.29, −128.15, −140.19 (d, J=6.3 Hz). LCMS (m/z+1) 416.19.

Example 173 and

Example 174

6-(3,5-dimethylisoxazol-4-yl)-4-(3-hydroxy-2,4-dimethylpentan-3-yl)-1H-benzo[d]imidazol-2(3H)-one and 6-(3,5-dimethylisoxazol-4-yl)-4-isobutyryl-1H-benzo[d]imidazol-2(3H)-one

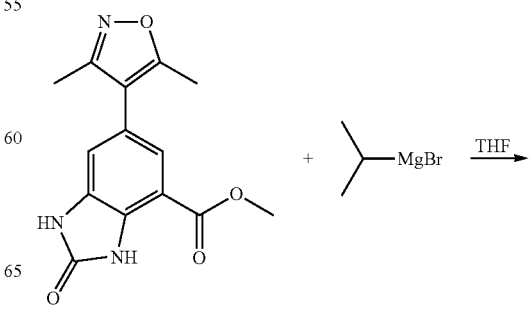

-continued

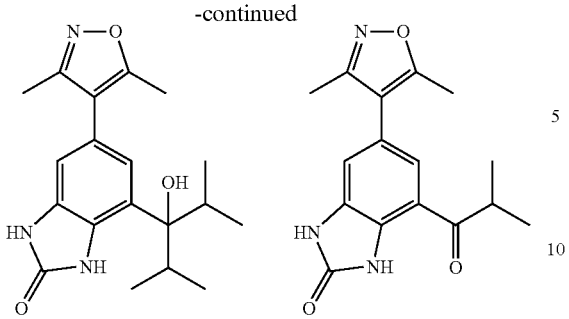

Methyl 6-(3,5-dimethylisoxazol-4-yl)-2-oxo-2,3-dihydro-1H-benzo[d]imidazole-4-carboxylate (100 mg, 0.35 mmol) was dissolved in 5 mL of THF and stirred at room temperature followed by the addition of isopropylmagnesium bromide (0.87 mL, 2.0 mmol). Addition Grignard was added in 1 hour intervals until the starting material was consumed. Once complete, the crude reaction mixture was quenched with DI water and extracted 3× with ethyl acetate. Combined organic layers were washed with brine, dried over sodium sulphate, filtered, concentrated in vacuo, and purified via HPLC.

C19H25N3O3; 344.2 (m/z+1). 1H NMR (400 MHz, cd3od) δ 6.88 (d, J=1.4 Hz, 1H), 6.70 (s, 1H), 2.39 (s, 3H), 2.34 (dd, J=13.4, 6.7 Hz, 2H), 2.23 (s, 3H), 0.91 (d, J=6.7 Hz, 6H), 0.85 (d, J=6.8 Hz, 6H).

C16H17N3O3; 300.1 (m/z+1). $^1$H NMR (400 MHz, cd$_3$od) δ 7.59 (s, 1H), 7.20 (d, J=1.3 Hz, 1H), 3.68 (dt, J=13.6, 6.8 Hz, 1H), 2.43 (s, 3H), 2.27 (s, 3H), 1.23 (d, J=6.8 Hz, 6H).

Example 175

6-(3,5-dimethylisoxazol-4-yl)-4-(1-hydroxy-1-(pyridin-2-yl)pentyl)-1H-benzo[d]imidazol-2(3H)-one

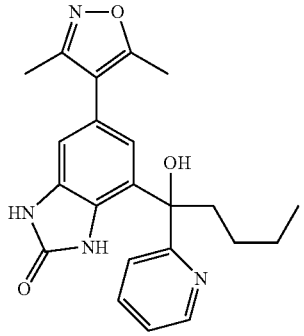 [SMILES: CCCCC(O)(c1ccccn1)c1cc(-c2c(C)noc2C)cc2[nH]c(=O)[nH]c12]

A solution of tert-butyl 6-(3,5-dimethylisoxazol-4-yl)-2-ethoxy-4-picolinoyl-1H-benzo[d]imidazole-1-carboxylate was treated with n-BuLi (1.5 equiv) at −78° C. The reaction was stirred for 15 minutes and quenched with 1M HCl, concentrated, dissolved in ethanol (1 mL) and 4M HCl in dioxane (0.5 mL) and heated to 80° C. for 1 h. The reaction mixture was concentrated and purified by reverse-phase HPLC to give the desired product.

C22H24N4O3. 393.1 (M+1). 1H NMR (400 MHz, DMSO-d6) δ 10.68 (s, 1H), 9.89 (d, J=1.9 Hz, 1H), 8.56 (d, J=4.9 Hz, 1H), 7.88 (d, J=7.7 Hz, 2H), 7.37 (s, 1H), 6.96 (d, J=1.6 Hz, 1H), 6.74 (d, J=1.5 Hz, 1H), 2.34 (m, 4H), 2.15 (s, 3H), 1.37-1.22 (m, 4H), 1.22-1.01 (m, 1H), 0.80 (t, J=7.0 Hz, 4H).

Example 176

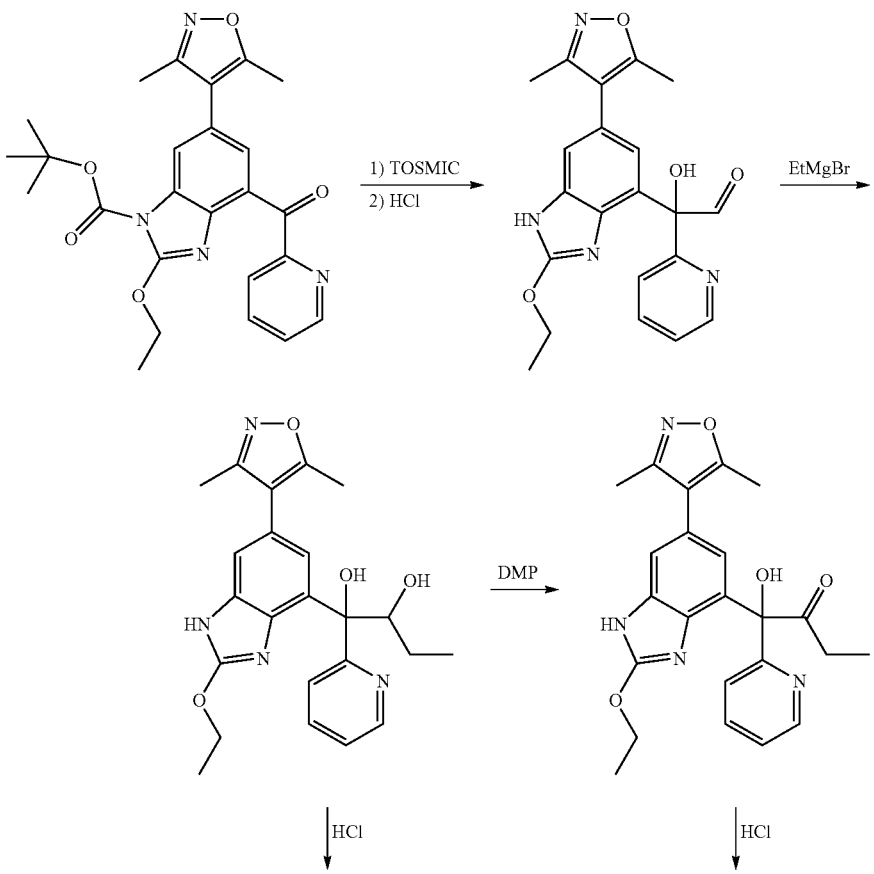

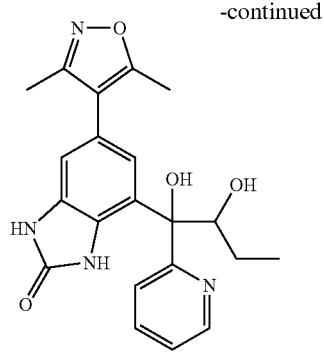
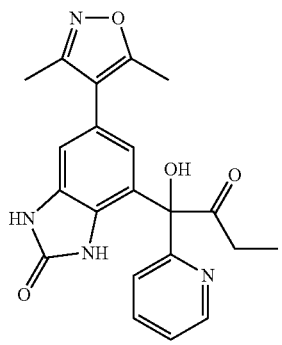

A solution of tert-butyl 6-(3,5-dimethylisoxazol-4-yl)-2-ethoxy-4-picolinoyl-1H-benzo[d]imidazole-1-carboxylate (360 mg, 0.79 mmol) and p-Toluenesulfonylmethyl isocyanide (183.95 mg, 0.94 mmol) in methanol (5 mL) was stirred at room temperature overnight. The reaction mixture was concentrated and 1M aqueous HCl (3 mL) and concentrated HCl (3 mL) was added. The reaction mixture was stirred for 30 minutes, concentrated and purified by reverse-phase HPLC to give 2-(6-(3,5-dimethylisoxazol-4-yl)-2-ethoxy-1H-benzo[d]imidazol-4-yl)-2-hydroxy-2-(pyridin-2-yl)acetaldehyde.

Ethyl magnesiumbromide (3M, 0.61 mL, 1.84 mmol) was added to a solution of 2-(6-(3,5-dimethylisoxazol-4-yl)-2-ethoxy-1H-benzo[d]imidazol-4-yl)-2-hydroxy-2-(pyridin-2-yl)acetaldehyde (120 mg, 0.31 mmol) in methyl-THF at 0° C. After 15 min, the reaction mixture was quenched with 1M HCl, concentrated and a portion of this material was purified by reverse-phase HPLC to give the major diastereomer 4-(1,2-dihydroxy-1-(pyridin-2-yl)butyl)-6-(3,5-dimethylisoxazol-4-yl)-1H-benzo[d]imidazol-2(3H)-one.

4-(1,2-dihydroxy-1-(pyridin-2-yl)butyl)-6-(3,5-dimethylisoxazol-4-yl)-1H-benzo[d]imidazol-2(3H)-one.

C21H22N4O4. 395.1 (M+1). 1H NMR (400 MHz, DMSO-d$_6$) δ 10.73-10.59 (m, 1H), 9.81 (s, 1H), 8.63 (d, J=4.7 Hz, 1H), 8.04 (s, 1H), 7.79 (d, J=7.9 Hz, 1H), 7.50 (s, 1H), 7.11 (d, J=1.7 Hz, 1H), 6.77 (s, 1H), 4.39 (d, J=9.6 Hz, 1H), 2.34 (s, 3H), 2.15 (s, 3H), 1.40-1.14 (m, 2H), 0.86 (t, J=7.3 Hz, 3H).

Dess-Martin Periodinane (90 mg, 0.24 mmol) was added to a solution of 4-(1,2-dihydroxy-1-(pyridin-2-yl)butyl)-6-(3,5-dimethylisoxazol-4-yl)-1H-benzo[d]imidazol-2(3H)-one (50 mg, 0.12 mmol) in a mixture of dichlormethane and THF. The reaction was stirred for 72 h at room temperature, concentrated and purified by reverse-phase HPLC. A portion of this product was dissolved in concentrated HCl (0.1 mL) and ethanol (1 mL), heated at 80° C. for 3 h and concentrated to give 6-(3,5-dimethylisoxazol-4-yl)-4-(1-hydroxy-2-oxo-1-(pyridin-2-yl)butyl)-1H-benzo[d]imidazol-2(3H)-one.

C21H20N4O4. 393.1 (M+1). 1H NMR (400 MHz, DMSO-d6) δ 10.73 (s, 1H), 9.87 (s, 1H), 8.62-8.39 (m, 1H), 7.89 (t, J=7.9 Hz, 1H), 7.61 (d, J=7.9 Hz, 1H), 7.50-7.27 (m, 1H), 6.83 (s, 1H), 6.40 (s, 1H), 2.83 (dd, J=18.2, 8.0 Hz, 2H), 2.27 (s, 3H), 2.07 (s, 3H), 0.91 (t, J=7.2 Hz, 3H).

Example 177

6-(3,5-dimethylisoxazol-4-yl)-4-(5,5,5-trifluoro-1,2-dihydroxy-1-(pyridin-2-yl)pentyl)-1H-benzo[d]imidazol-2(3H)-one

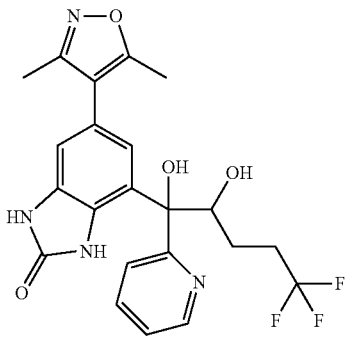 [SMILES: Cc1noc(C)c1-c1cc(C(O)(c2ccccn2)C(O)CCC(F)(F)F)c2[nH]c(=O)[nH]c2c1]

The following two diastereomers were likewise prepared using trifluoromethylethylmagnesium bromide in place of ethylmagnesium bromide.

Major diastereomer: C$_{22}$H$_{21}$F$_3$N$_4$O$_4$. 463.1 (M+1). $^1$H NMR (400 MHz, DMSO-d$_6$) δ 10.67 (s, 1H), 9.80 (d, J=6.8 Hz, 1H), 8.59 (s, 1H), 7.91 (s, 1H), 7.76 (s, 1H), 7.39 (s, 1H), 7.06 (s, 1H), 6.76 (s, 1H), 4.58 (d, J=9.9 Hz, 1H), 2.40-2.50 (m, 2H), 2.42-2.30 (m, 3H), 2.13 (s, 3H), 1.48 (m, 2H).

Minor diastereomer: C$_{22}$H$_{21}$F$_3$N$_4$O$_4$. 463.1 (M+1). $^1$H NMR (400 MHz, DMSO-d$_6$) δ 10.59 (s, 1H), 10.03 (s, 1H), 8.56 (dd, J=5.4, 1.7 Hz, 1H), 7.52 (s, 1H), 6.64 (d, J=1.6 Hz, 1H), 6.41 (s, 1H), 5.07 (s, 1H), 2.40 (m, 2H) 2.17 (s, 3H), 1.99 (s, 3H), 1.65 (d, J=15.9 Hz, 2H).

Example 178

6-(3,5-dimethylisoxazol-4-yl)-4-(2,2,3,3,3-pentafluoro-1-hydroxypropyl)-1H-benzo[d]imidazol-2(3H)-one

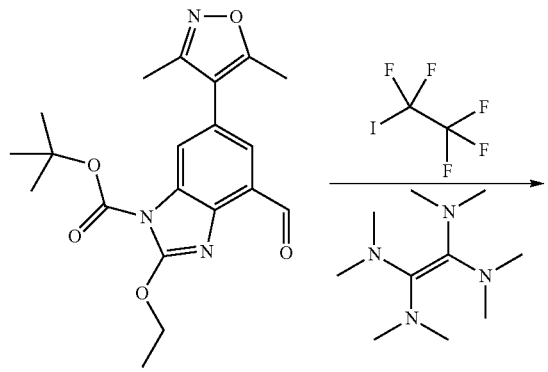

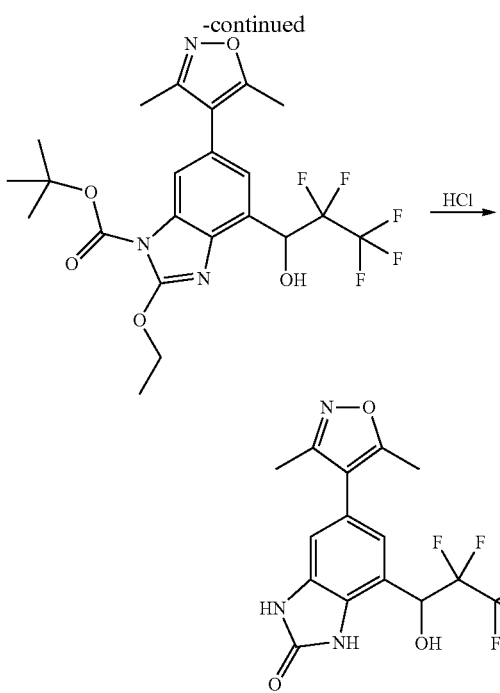

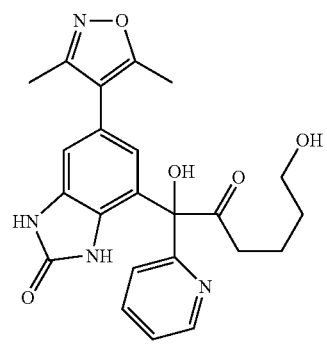

A solution of tert-butyl 6-(3,5-dimethylisoxazol-4-yl)-2-ethoxy-4-formyl-1H-benzo[d]imidazole-1-carboxylate (100 mg, 0.26 mmol), pentafluoroiodoethane (350 mg, 1.42 mmol) and DMF was cooled to −15° C. under nitrogen. Tetra (dimethlamino)ethylene was added (0.33 mL, 1.42 mmol) and the reaction mixture was irradiated with a sun lamp. A thick precipitate formed, and after 30 minutes, the reaction mixture was diluted with ethyl acetate filtered. The filtrate was washed with water and the organic layer was concentrated and dissolved in ethanol (3 mL) and 4M HCl in dioxane (1 mL) and heated to 70° C. for 1 h. The reaction mixture was concentrated and purified by reverse-phase HPLC to give the desired product as a white powder.

$C_{15}H_{12}F_5N_3O_3$. 378.1 (M+1). 1H NMR (400 MHz, DMSO-d6) δ 11.02 (d, J=2.0 Hz, 1H), 10.82 (s, 1H), 7.14-6.64 (m, 3H), 5.64-5.45 (m, 1H), 2.36 (s, 3H), 2.18 (s, 3H).

Example 179

6-(3,5-dimethylisoxazol-4-yl)-4-(2,2,2-trifluoro-1-hydroxyethyl)-1H-benzo[d]imidazol-2(3H)-one

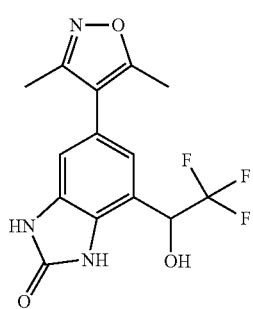 [SMILES: Cc1noc(C)c1-c1cc(C(O)C(F)(F)F)c2[nH]c(=O)[nH]c2c1]

The following compound was likewise prepared from trifluoroiodomethane to give 6-(3,5-dimethylisoxazol-4-yl)-4-(2,2,2-trifluoro-1-hydroxyethyl)-1H-benzo[d]imidazol-2 (3H)-one as a white powder.

$C_{14}H_{12}F_3N_3O_3$. 328.1 (M+1). 1H NMR (400 MHz, DMSO-d6) δ 10.95-10.85 (m, 1H), 10.82 (d, J=1.9 Hz, 1H), 7.11-7.00 (m, 1H), 6.90 (dd, J=13.1, 3.6 Hz, 2H), 5.43 (d, J=8.0 Hz, 1H), 2.35 (s, 3H), 2.17 (s, 3H).

Example 180

4-(1,6-dihydroxy-2-oxo-1-(pyridin-2-yl)hexyl)-6-(3,5-dimethylisoxazol-4-yl)-1H-benzo[d]imidazol-2 (3H)-one The following compound was isolated as a side product from the previous series of reactions:

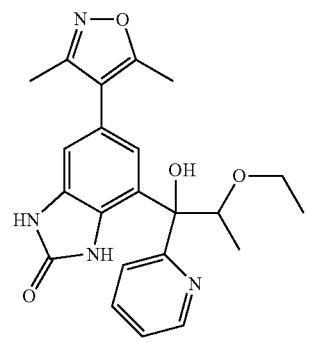 [SMILES: CCOC(C)C(O)(c1ccccn1)c1cc(-c2c(C)noc2C)cc2[nH]c(=O)[nH]c12]

$C_{23}H_{24}N_4O_5$. 437.1 (M+1). $^1$H NMR (400 MHz, DMSO-d$_6$) δ 10.74 (d, J=1.9 Hz, 1H), 9.89 (d, J=1.9 Hz, 1H), 8.53 (dd, J=5.0, 1.5 Hz, 1H), 7.87 (td, J=7.7, 1.7 Hz, 1H), 7.60 (d, J=8.0 Hz, 1H), 7.37 (dd, J=7.5, 4.8 Hz, 1H), 6.96 (s, 1H), 6.85-6.77 (m, 1H), 6.41 (d, J=1.5 Hz, 1H), 3.27 (t, J=6.5 Hz, 2H), 2.82 (ddd, J=17.9, 8.6, 6.2 Hz, 1H), 2.45-2.36 (m, 1H), 2.26 (s, 3H), 2.07 (s, 3H), 1.55-1.34 (m, 2H), 1.29 (td, J=8.8, 4.6 Hz, 2H).

Example 181

6-(3,5-dimethylisoxazol-4-yl)-4-(2-ethoxy-1-hydroxy-1-(pyridin-2-yl)propyl)-1H-benzo[d]imidazol-2(3H)-one Prepared analogously to give 6-(3,5-dimethylisoxazol-4-yl)-4-(hydroxy(pyridin-2-yl)(tetrahydro-2H-pyran-2-yl)methyl)-1H-benzo[d]imidazol-2(3H)-one using ethyl vinyl ether in place of 2,3-dihydro-2H-pyran.

$C_{22}H_{24}N_4O_4$. 409.1 (M+1). 1H NMR (400 MHz, DMSO-d6) δ 10.67 (d, J=2.1 Hz, 1H), 9.72 (s, 1H), 8.69-8.55 (m, 1H), 7.87 (t, J=7.6 Hz, 1H), 7.73 (d, J=8.1 Hz, 1H), 7.36 (d, J=7.2 Hz, 1H), 7.15 (d, J=1.5 Hz, 1H), 6.77 (d, J=1.5 Hz, 1H), 4.50 (q, J=6.1 Hz, 1H), 3.62-3.44 (m, 1H), 3.26-3.09 (m, 1H), 2.36 (s, 3H), 2.18 (s, 3H), 1.02-0.85 (m, 6H).

Example 182

1-(6-(2-(2-((6S)-4-(4-chlorophenyl)-2,3,9-trimethyl-6H-thieno[3,2-f][1,2,4]triazolo[4,3-a][1,4]diazepin-6-yl)acetyl)hydrazinyl)-6-oxohexyl)-3,3-dimethyl-2-((1E,3E,5E)-5-(1,3,3-trimethylindolin-2-ylidene)penta-1,3-dien-1-yl)-3H-indol-1-ium

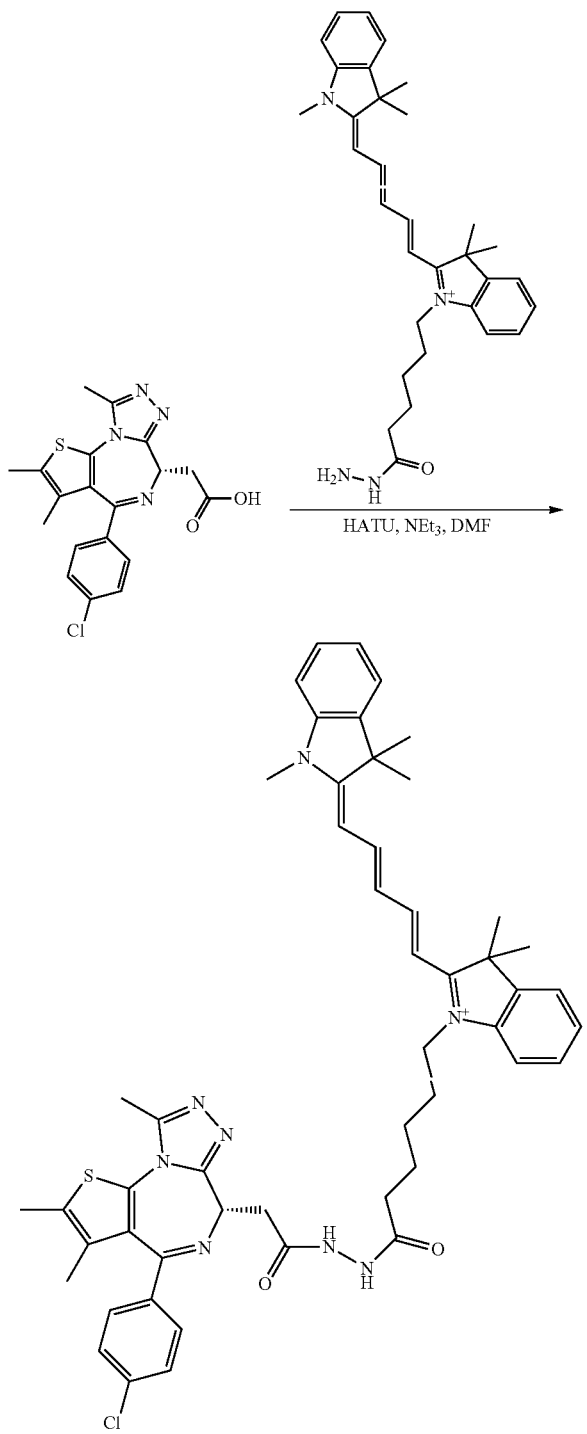

2-((6S)-4-(4-chlorophenyl)-2,3,9-trimethyl-6H-thieno[3,2-f][1,2,4]triazolo[4,3-a][1,4]diazepin-6-yl)acetic acid (7 mg, 0.018 mmol) was dissolved in 1 ml DMF, to the solution was added HATU (10 mg, 0.027 mmol) and the reaction mixture was stirred at RT for 30 mins, then to the reaction mixture was added 1-(6-hydrazinyl-6-oxohexyl)-3,3-dimethyl-2-((1E,3E,5E)-5-(1,3,3-trimethylindolin-2-ylidene)penta-1,3-dien-1-yl)-3H-indol-1-ium (5 mg, 0.009 mmol) at RT. The reaction was stirred at RT overnight. The solvent was then evaporated, the residue was purified with Prep HPLC to afford 3.6 mg product 1-(6-(2-(2-((6S)-4-(4-chlorophenyl)-2,3,9-trimethyl-6H-thieno[3,2-f][1,2,4]triazolo[4,3-a][1,4]diazepin-6-yl)acetyl)hydrazinyl)-6-oxohexyl)-3,3-dimethyl-2-((1E,3E,5E)-5-(1,3,3-trimethylindolin-2-ylidene)penta-1,3-dien-1-yl)-3H-indol-1-ium.

$C_{51}H_{56}ClN_8O_2S$. 879.4 (M−1). $^1$H NMR (400 MHz, $CD_3OD$) δ 7.18-7.10 (m, 2H), 6.44-6.38 (m, 4H), 6.35-6.28 (m, 4H), 6.22-6.17 (m, 5H), 5.58-5.45 (m, 1H), 5.23-5.17 (m, 2H), 3.62-3.58 (m, 1H), 3.08-2.97 (m, 2H), 2.58-2.52 (m, 1H), 2.48 (s, 3H), 2.22 (s, 3H), 1.60 (s, 3H), 1.38 (s, 3H), 1.23-1.20 (m, 2H), 0.82-0.65 (m, 4H), 0.62-0.60 (m, 12H), 0.54-0.48 (m, 2H).

Example 183

4-((6-(dimethylamino)pyridin-2-yl)(hydroxy)(pyridin-2-yl)methyl)-6-(3,5-dimethylisoxazol-4-yl)-1H-benzo[d]imidazol-2(3H)-one A procedure similar to that used for 6-(3,5-dimethylisoxazol-4-yl)-4-(hydroxy(6-methylpyridin-2-yl)(pyridin-2-yl)methyl)-1H-benzo[d]imidazol-2(3H)-one, using 6-bromo-2-N,N-dimethylaminopyridine as the starting material was used to produce the intermediate ($C_{32}H_{36}N_6O_5$, 585.2 (M+1)), which was taken directly to the deprotection step to yield the title compound as a yellow oil.

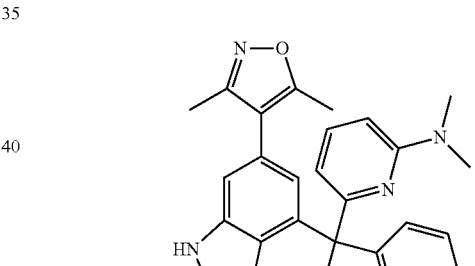

$C_{25}H_{24}N_6O_3$. 457.1 (M+1). $^1$H NMR (400 MHz, Chloroform-d) δ 8.78 (ddd, J=5.4, 1.7, 0.9 Hz, 1H), 8.30 (td, J=7.9, 1.7 Hz, 1H), 8.03 (dt, J=8.2, 1.0 Hz, 1H), 7.87 (dd, J=8.9, 7.4 Hz, 1H), 7.78 (ddd, J=7.7, 5.3, 1.2 Hz, 1H), 7.24 (t, J=7.5 Hz, 1H), 7.03 (d, J=1.5 Hz, 1H), 6.96 (dd, J=9.0, 0.8 Hz, 1H), 6.58 (d, J=1.5 Hz, 1H), 3.20 (s, 6H), 2.30 (s, 3H), 2.13 (s, 3H).

Example 184

6-(3,5-dimethylisoxazol-4-yl)-4-(hydroxy(pyridin-2-yl)(3-(trifluoromethyl)phenyl)methyl)-1H-benzo[d]imidazol-2(3H)-one A procedure analogous to 6-(3,5-dimethylisoxazol-4-yl)-4-(hydroxy(6-methylpyridin-2-yl)(pyridin-2-yl)methyl)-1H-benzo[d]imidazol-2(3H)-one was used to synthesize the intermediate ($C_{32}H_{31}F_3N_4O_5$, 609.2 (M+1)) which was immediately taken on to the deprotection step to yield a yellow solid.

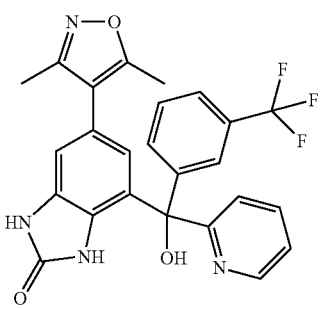 [SMILES: Cc1noc(C)c1-c1cc(C(O)(c2cccc(C(F)(F)F)c2)c2ccccn2)c2[nH]c(=O)[nH]c2c1]

C25H19F3N4O3. 481.1 (M+1). ¹H NMR (400 MHz, Methanol-$d_4$) δ 8.77-8.69 (m, 1H), 8.22 (td, J=7.9, 1.7 Hz, 1H), 7.76 (s, 1H), 7.72 (ddt, J=9.2, 6.6, 3.1 Hz, 3H), 7.59 (t, J=7.8 Hz, 1H), 7.51 (d, J=8.1 Hz, 1H), 7.05 (d, J=1.5 Hz, 1H), 6.43 (d, J=1.5 Hz, 1H), 2.27 (s, 3H), 2.10 (s, 3H).

Example 185

4-((4-chlorophenyl)(hydroxy)(pyridin-2-yl)methyl)-6-(3,5-dimethylisoxazol-4-yl)-1H-benzo[d]imidazol-2(3H)-one A procedure similar to 6-(3,5-dimethylisoxazol-4-yl)-4-(hydroxy(6-methylpyridin-2-yl)(pyridin-2-yl)methyl)-1H-benzo[d]imidazol-2(3H)-one was used to synthesize the intermediate (C$_{31}$H$_{31}$ClN$_4$O$_5$, 575.2 (M+1)) which was taken directly to the deprotection step to yield a yellow solid (9.8 mg).

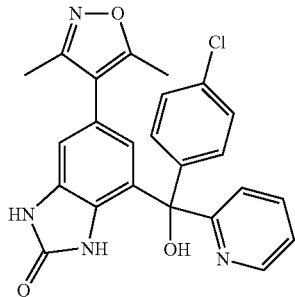 [SMILES: Cc1noc(C)c1-c1cc(C(O)(c2ccc(Cl)cc2)c2ccccn2)c2[nH]c(=O)[nH]c2c1]

C$_{24}$H$_{19}$ClN$_4$O$_3$. 447.1 (M+1). ¹H NMR (400 MHz, Methanol-$d_4$) δ 8.71 (ddd, J=5.3, 1.7, 0.9 Hz, 1H), 8.19 (td, J=7.9, 1.7 Hz, 1H), 7.74-7.66 (m, 2H), 7.44-7.38 (m, 2H), 7.33-7.28 (m, 2H), 7.03 (d, J=1.5 Hz, 1H), 6.48 (d, J=1.5 Hz, 1H), 2.29 (s, 3H), 2.12 (s, 3H).

Example 186

4-((6-aminopyridin-2-yl)(hydroxy)(pyridin-2-yl)methyl)-6-(3,5-dimethylisoxazol-4-yl)-1H-benzo[d]imidazol-2(3H)-one

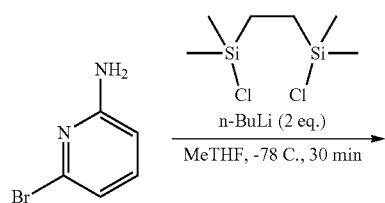

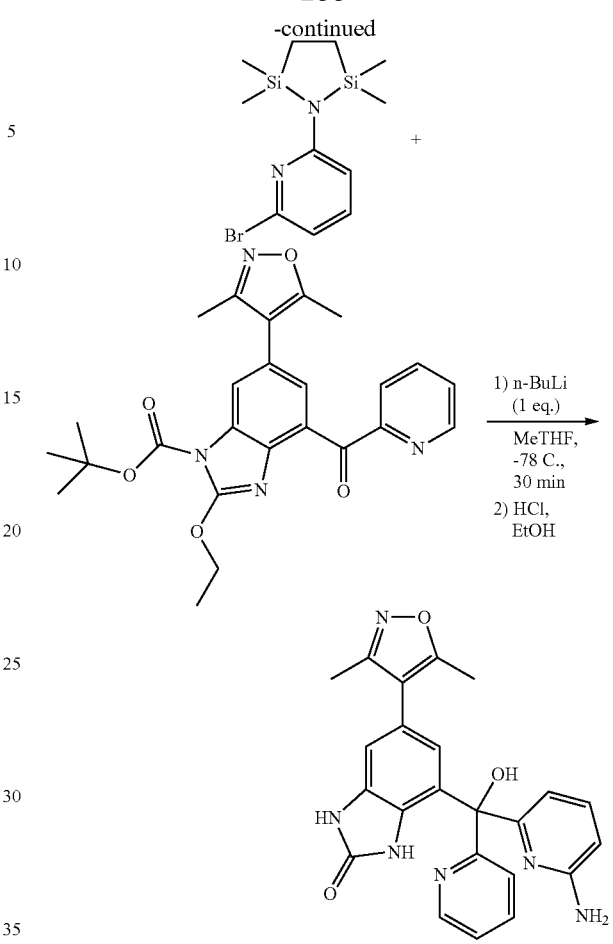

In a 2-neck, 50-mL round-bottom flask, a solution of 2-amino-6-bromopyridine (265.5 mg, 1.535 mmol) and 1,2-bis(chlorodimethylsilyl)ethane (329.9 mg, 1.532 mmol) in 2-methyltetrahydrofuran (12 mL) were cooled to −78° C. while stirring under a nitrogen atmosphere. A solution of n-butyllithium (1.42 M in hexanes, 3.26 mL, 2.30 mmol) was added dropwise in 4 equal fractions (waiting five minutes in between) and the reaction mixture was stirred for 30 minutes after the final addition. A solution of tert-butyl 6-(3,5-dimethylisoxazol-4-yl)-2-ethoxy-4-picolinoyl-1H-benzo[d]imidazole-1-carboxylate (300.8 mg, 0.6504 mmol) in 2-methyltetrahydrofuran (1.5 mL) was added dropwise. The reaction mixture was stirred for 45 minutes while warming to room temperature or until reaction completion. The reaction mixture was quenched with brine and diluted with ethyl acetate. The organic layer was separated and saved and the aqueous layer was extracted with ethyl acetate (three times, 40 mL each). The organic fractions were combined, dried over MgSO$_4$, filtered and concentrated. The crude product was taken directly to the deprotection step. C$_{25}$H$_{24}$N$_6$O$_3$. 457.2 (M+1).

The crude material was dissolved in ethanol (15 mL) and transferred to a microwave vial. Hydrochloric acid was added (4M in dioxane, 1.6 mL, 6.4 mmol) and the reaction vial was sealed and heated at 70° C. for 2 hours. The reaction mixture was cooled to room temperature and concentrated to yield a brown oil, which was triturated with dichloromethane. The remaining oil was taken up in acetonitrile and concentrated to yield a yellow-white solid, which was further purified by preparatory HPLC to yield a yellow oil.

189

$C_{23}H_{20}N_6O_3$. 429.1 (M+1). Rf=0.2 in 20% MeOH:DCM. $^1$H NMR (400 MHz, Methanol-$d_4$) δ 8.67 (ddd, J=5.0, 1.8, 0.9 Hz, 1H), 7.96 (td, J=7.8, 1.8 Hz, 1H), 7.85 (dd, J=9.0, 7.4 Hz, 1H), 7.70 (dt, J=8.0, 1.0 Hz, 1H), 7.47 (ddd, J=7.6, 4.8, 1.1 Hz, 1H), 7.04 (d, J=1.5 Hz, 1H), 6.97 (dd, J=9.0, 1.0 Hz, 1H), 6.66 (dd, J=7.4, 1.0 Hz, 1H), 6.42 (d, J=1.5 Hz, 1H), 2.28 (s, 3H), 2.11 (s, 3H).

Example 187

1-acetyl-4-((6-aminopyridin-2-yl)(hydroxy)(pyridin-2-yl)methyl)-6-(3,5-dimethylisoxazol-4-yl)-1H-benzo[d]imidazol-2(3H)-one

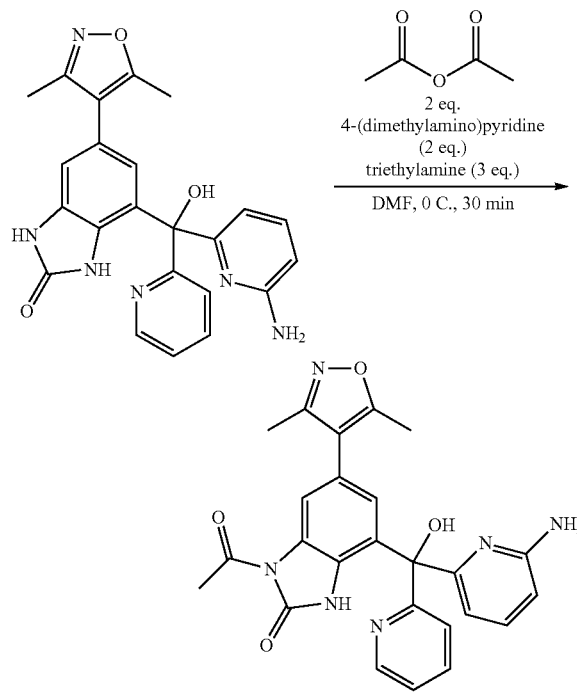

To a microwave vial capped with a septum, 4-(dimethylamino)pyridine (5.8 mg, 0.047 mmol) and triethylamine (9 µL, 0.07 mmol) in N,N-dimethylformamide (0.5 mL) were cooled to 0° C. in a nitrogen atmosphere. Acetic anhydride (4.4 µL, 0.047 mmol) was added and the reaction mixture was stirred for 15 minutes at 0° C. before a solution of 4-((6-aminopyridin-2-yl)(hydroxy)(pyridin-2-yl)methyl)-6-(3,5-dimethylisoxazol-4-yl)-1H-benzo[d]imidazol-2(3H)-one (10 mg, 0.023 mmol) in N,N-dimethylformamide (0.25 mL) was added dropwise to the reaction mixture. The reaction was allowed to warm to room temperature and stirred for thirty minutes (or until completion). The reaction was quenched with water and diluted with ethyl acetate. The organic layer was separated and saved and the organic layer was extracted with ethyl acetate (three times, 20 mL each). The organic fractions were collected, dried over $MgSO_4$, filtered and concentrated. The product was isolated by preparatory HPLC to yield a clear oil.

$C_{25}H_{22}N_6O_4$. 471.1 (M+1). $^1$H NMR (400 MHz, Methanol-$d_4$) δ 8.68 (d, J=4.8 Hz, 1H), 8.18 (d, J=1.6 Hz, 1H), 8.02-7.93 (m, 1H), 7.85 (dd, J=9.0, 7.4 Hz, 1H), 7.72-7.65 (m, 1H), 7.52-7.43 (m, 1H), 6.98 (dd, J=9.2, 1.0 Hz, 1H), 6.68-6.61 (m, 1H), 6.57 (d, J=1.6 Hz, 1H), 2.70 (s, 3H), 2.30 (s, 3H), 2.11 (s, 3H).

Example 188

4-((6-aminopyridin-2-yl)(hydroxy)(pyridin-2-yl)methyl)-1-(cyclopropanecarbonyl)-6-(3,5-dimethylisoxazol-4-yl)-1H-benzo[d]imidazol-2(3H)-one A procedure similar to 1-acetyl-4-((6-aminopyridin-2-yl)(hydroxy)(pyridin-2-yl)methyl)-6-(3,5-dimethylisoxazol-4-yl)-1H-benzo[d]imidazol-2(3H)-one was used.

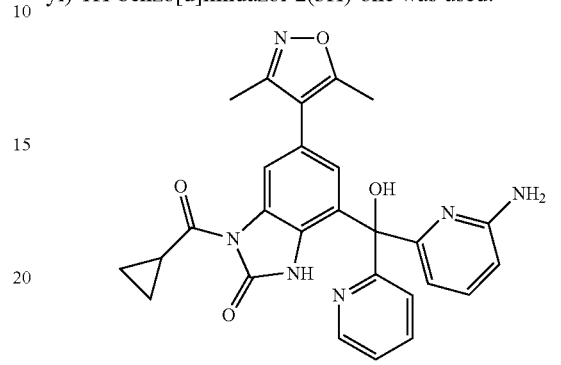

$C_{27}H_{24}N_6O_4$. 497.2 (M+1). $^1$H NMR (400 MHz, Methanol-$d_4$) δ 8.68 (ddd, J=4.9, 1.8, 0.9 Hz, 1H), 8.13 (d, J=1.6 Hz, 1H), 7.97 (td, J=7.8, 1.8 Hz, 1H), 7.85 (dd, J=9.0, 7.4 Hz, 1H), 7.69 (dt, J=8.0, 1.0 Hz, 1H), 7.48 (ddd, J=7.6, 4.8, 1.1 Hz, 1H), 7.25-7.08 (m, 2H), 6.98 (dd, J=8.9, 1.0 Hz, 1H), 6.65 (dd, J=7.4, 1.0 Hz, 1H), 6.56 (d, J=1.6 Hz, 1H), 3.48 (ddd, J=8.0, 4.6, 3.2 Hz, 1H), 2.29 (s, 3H), 2.10 (s, 3H), 1.21 (dt, J=5.2, 3.4 Hz, 2H), 1.15-1.06 (m, 2H).

Example 189

6-(3,5-dimethylisoxazol-4-yl)-4-(hydroxy(6-(methylamino)pyridin-2-yl)(pyridin-2-yl)methyl)-1H-benzo[d]imidazol-2(3H)-one

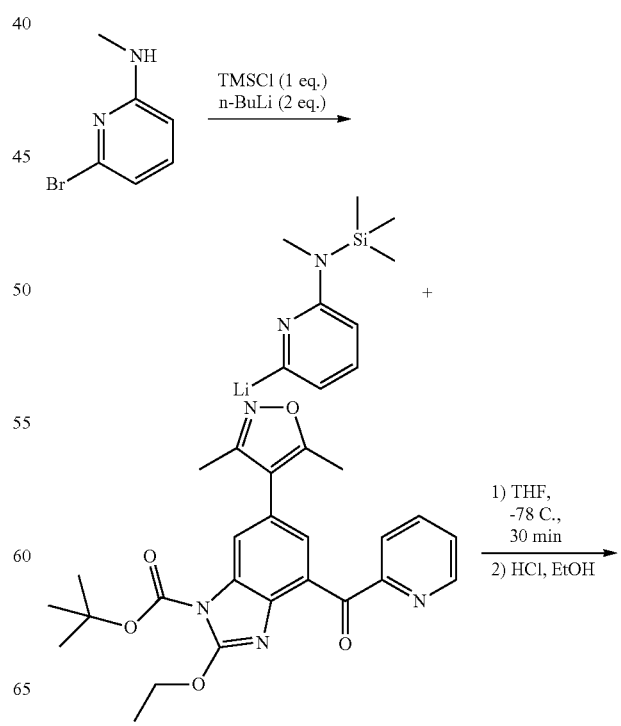

-continued

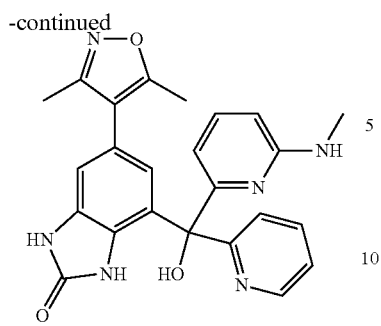

To a 50-mL, 2-neck round-bottom flask, 6-bromo-N-methylpyridin-2-amine (41.5 mg, 0.222 mmol) and chlorotrimethylsilane (29 µL, 0.23 mmol) were dissolved in tetrahydrofuran (2 mL). The cloudy white suspension was stirred under nitrogen for thirty minutes at room temperature. The reaction mixture was then cooled to −78° C. before a 1.6 M n-butyllithium solution in hexanes (0.23 mL, 0.37 mmol) was added dropwise and the solution was stirred for thirty minutes. A solution of tert-butyl 6-(3,5-dimethylisoxazol-4-yl)-2-ethoxy-4-picolinoyl-1H-benzo[d]imidazole-1-carboxylate in tetrahydrofuran (1 mL) was added dropwise and the reaction was warmed to ambient temperature and stirred for twenty minutes or until reaction completion. The reaction mixture was quenched with brine and diluted with ethyl acetate. The organic layer was separated and saved and the aqueous layer was neutralized and subsequently extracted with ethyl acetate twice. The combined organic fractions were dried over sodium sulfate, decanted and concentrated. The crude intermediate was taken directly to the deprotection step. $C_{31}H_{34}N_6O_5$. 611.3 (M+1).

In a microwave vial, the crude intermediate was dissolved in ethanol (3 mL) and 4M hydrochloric acid in dioxane (1 mL) was added. The vial was sealed and heated at 65° C. for 1 hour. The reaction mixture was concentrated, filtered and the title compounds was purified via preparatory HPLC to yield a yellow solid.

$C_{24}H_{22}N_6O_3$. 443.1 (M+1). $^1$H NMR (400 MHz, Methanol-$d_4$) δ 8.70 (ddd, J=5.0, 1.8, 0.9 Hz, 1H), 8.03 (td, J=7.8, 1.7 Hz, 1H), 7.90 (dd, J=9.0, 7.4 Hz, 1H), 7.81 (d, J=8.0 Hz, 1H), 7.53 (ddd, J=7.6, 4.9, 1.1 Hz, 1H), 7.02 (d, J=1.5 Hz, 1H), 7.00 (d, J=8.8 Hz, 1H), 6.87 (d, J=7.4 Hz, 1H), 6.48 (d, J=1.5 Hz, 1H), 3.06 (s, 3H), 2.28 (s, 3H), 2.10 (s, 3H).

Example 190

4-((6-bromo-3-fluoro-2-methylpyridin-4-yl)(hydroxy)(pyridin-2-yl)methyl)-6-(3,5-dimethylisoxazol-4-yl)-1H-benzo[d]imidazol-2(3H)-one

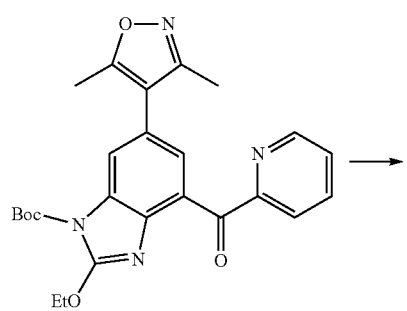

-continued

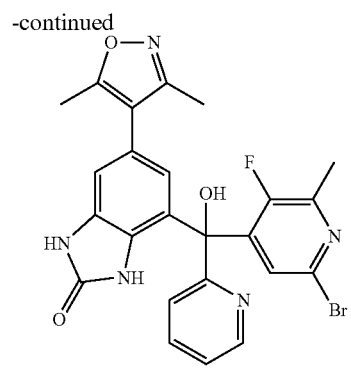

To a solution of 2-bromo-5-fluoro-6-methyl-2-pyridine (411 mg, 2.16 mmol) in THF (10 mL) was added BuLi (0.86 mL, 2.16 mmol, 2.5 M in THF) and the solution was stirred at −78° C. for 1 h. To the solution of tert-butyl 6-(3,5-dimethylisoxazol-4-yl)-2-ethoxy-4-picolinoyl-1H-benzo[d]imidazole-1-carboxylate (200 mg, 0.43 mmol) in THF (5 mL) was added the solution of the lithiate and the solution was stirred at −78° C. for 1 h. Aq NH$_4$Cl was added and the solution was extracted with EtOAc (200 mL). The organic solution was washed with brine and dried over Na$_2$OS$_4$. Solvent was removed and the residue was dissolved in EtOH (6 mL) with 0.8 mL of 4N HCl in dioxane. The solution was heated at microwave at 70° C. for 1 h. Solvent was removed and the residue was purified by HPLC to give 4-((6-bromo-3-fluoro-2-methylpyridin-4-yl)(hydroxy)(pyridin-2-yl)methyl)-6-(3,5-dimethylisoxazol-4-yl)-1H-benzo[d]imidazol-2(3H)-one $C_{24}H_{19}BrFN_5O_3$. MS m/z 523.9 (M+1).

Example 191

6-(3,5-dimethylisoxazol-4-yl)-4-((3-fluoro-2-methylpyridin-4-yl)(hydroxy)(pyridin-2-yl)methyl)-1H-benzo[d]imidazol-2(3H)-one

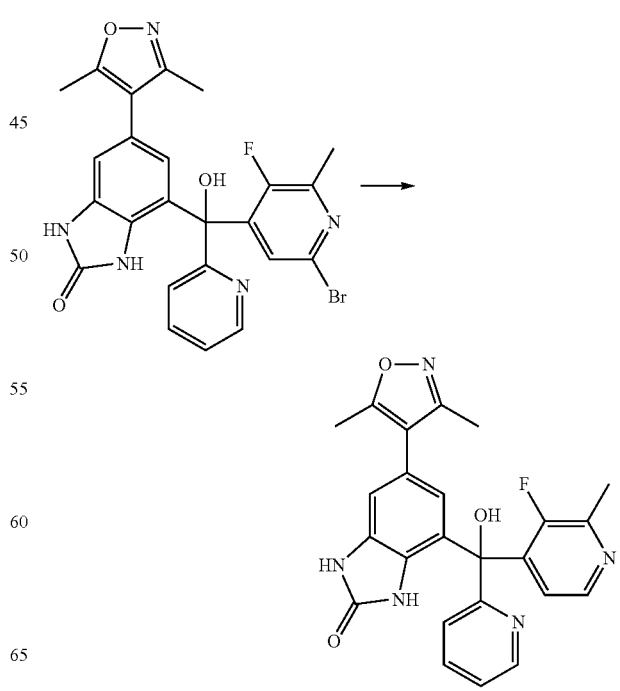

A mixture of 4-((6-bromo-3-fluoro-2-methylpyridin-4-yl)(hydroxy)(pyridin-2-yl)methyl)-6-(3,5-dimethylisoxazol-4-yl)-1H-benzo[d]imidazol-2(3H)-one obtained above and Pd/C (5% 100 mg) in MeOH (10 mL) was stirred under H$_2$ balloon for 1 h. Reaction mixture was filtered and the filtrate was concentrated to dryness. The residue was purified by HPLC to give 6-(3,5-dimethylisoxazol-4-yl)-4-((3-fluoro-2-methylpyridin-4-yl)(hydroxy)(pyridin-2-yl)methyl)-1H-benzo[d]imidazol-2(3H)-one.

$C_{24}H_{20}FN_5O_3$. MS m/z 446.02 (M+1). $^1$H NMR (400 MHz, Methanol-d$_4$) δ 8.56 (ddd, J=5.1, 1.8, 0.9 Hz, 1H), 8.42 (d, J=5.6 Hz, 1H), 8.00 (td, J=7.8, 1.7 Hz, 1H), 7.76-7.64 (m, 2H), 7.49 (ddd, J=7.6, 5.0, 1.1 Hz, 1H), 7.02 (d, J=1.5 Hz, 1H), 6.59 (t, J=1.8 Hz, 1H), 2.53 (d, J=3.0 Hz, 3H), 2.30 (s, 3H), 2.13 (s, 3H).

Example 192

4-(3,5-dimethylisoxazol-4-yl)-2-nitroaniline

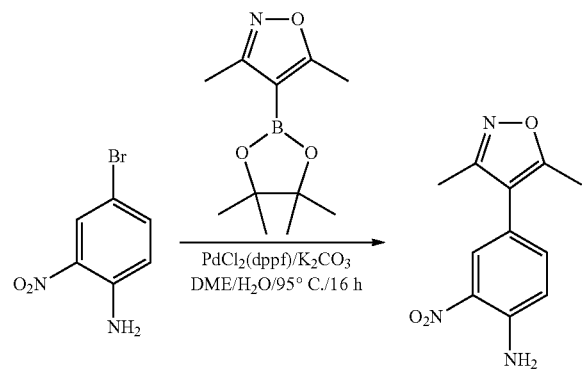

To a mixture of 4-bromo-2-nitro-phenylamine (150 g, 0.691 mol, 1.0 eq) and 3,5-dimethylisoxazole-4-boronic acid pinacol ester (169 g, 0.725 mol, 1.05 eq) in 1,2-dimethoxyethane (1.5 L) and water (700 mL) were added PdCl$_2$(dppf) (56 g, 69 mmol, 0.1 eq) and K$_2$CO$_3$ (190 g, 1.38 mol, 2.0 eq). The reaction mixture was heated at 95° C. overnight. The reaction mixture was diluted with EtOAc (3 L), washed with brine (2×500 mL). The organic solvent was evaporated and the residue was purified with flash chromatography on silica (PE/EA=10:1-1:1) to give 150 g 4-(3,5-dimethylisoxazol-4-yl)-2-nitroaniline as a red solid.

$C_{11}H_{11}N_3O_3$. 234.2 (M+1)

Example 193

4-(3,5-dimethylisoxazol-4-yl)-2-iodo-6-nitroaniline

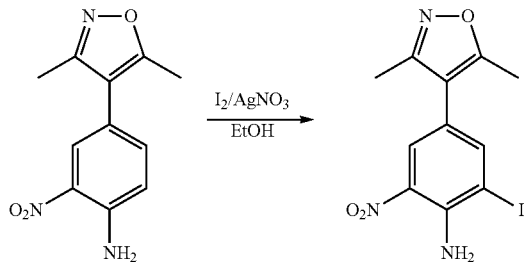 [SMILES: "EtOH" ; Cc1noc(C)c1-c1ccc(N)c([N+](=O)[O-])c1 ; Cc1noc(C)c1-c1cc(I)c(N)c([N+](=O)[O-])c1]

To a solution of compound 4-(3,5-dimethylisoxazol-4-yl)-2-nitroaniline (334 g, 1.43 mol, 1.0 eq) in ethanol (3.3 L) were added iodine (726 g, 2.8 mol, 2.0 eq) and silver nitrate (485 g, 2.8 mol, 2.0 eq). The reaction mixture was stirred at rt overnight, filtered, and the filtrate was evaporated to dryness. The residue was dissolved in EtOAc (5 L) and washed with water and brine, and dried over sodium sulfate. The organic solvent was evaporated to give a residue, which was purified by flash column chromatography on silica gel (PE/EA=4:1-3:1) to give compound 393 g of 4-(3,5-dimethylisoxazol-4-yl)-2-iodo-6-nitroaniline as an orange solid.

$C_{11}H_{10}IN_3O_3$. 360.1 (M+1)

Example 194

5-(3,5-dimethylisoxazol-4-yl)-3-iodobenzene-1,2-diamine

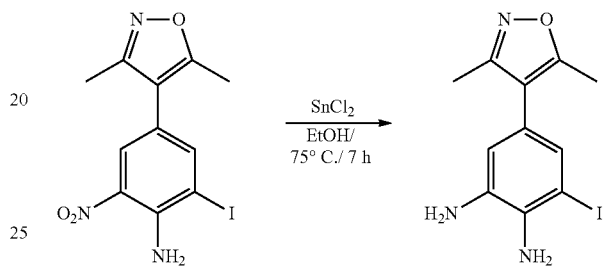

To a solution of 4-(3,5-dimethylisoxazol-4-yl)-2-iodo-6-nitroaniline (393 g, 1.09 mol, 1.0 eq) in ethanol (4 L) was added tin (II) chloride (1.03 kg, 5.46 mol, 5.0 eq). The reaction mixture was stirred at 75° C. for 10 h. The solvent was evaporated and the residue was dissolved in EtOAc (5 L), washed with 1 N sodium hydroxide (3×1 L) (the solid precipitated out should be filtered). The organic phase was dried over Na$_2$SO$_4$ and the solvent was removed to give a residue. The residue was purified by flash chromatography on silica (PE/EA=2:1-3:2) to give 253 g of 5-(3,5-dimethylisoxazol-4-yl)-3-iodobenzene-1,2-diamine as a slightly brown solid.

$C_{11}H_{12}IN_3O$. 330.1 (M+1)

Example 195

6-(3,5-dimethylisoxazol-4-yl)-4-iodo-1H-benzo[d]imidazol-2(3H)-one

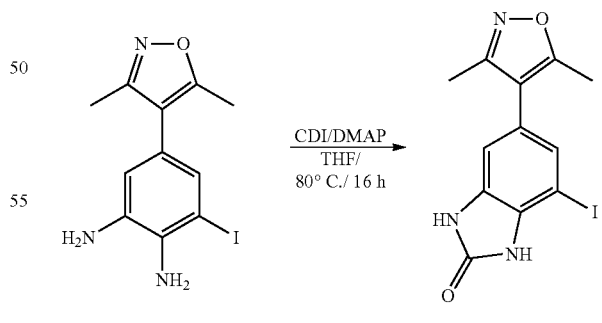

5-(3,5-dimethylisoxazol-4-yl)-3-iodobenzene-1,2-diamine (253 g, 0.77 mol, 1.0 eq) was treated with carbonyl diimidazole (187 g, 1.15 mol, 1.5 eq) and DMAP (47 g, 384 mmol, 0.5 eq) in THF (2.5 L) at 80° C. for 16 h. The precipitate was obtained by filtration. The solid was triturated with EA/PE (1/1) to give 197 g of 6-(3,5-dimethylisoxazol-4-yl)-4-iodo-1H-benzo[d]imidazol-2(3H)-one as a white solid.

$C_{12}H_{10}IN_3O_2$ 356.1 (M+1). $^1$H NMR (400 MHz, DMSO-$d_6$) δ 10.97 (s, 1H), 10.91 (s, 1H), 7.23 (s, 1H), 5.86 (s, 1H), 2.35 (s, 3H), 2.17 (s, 3H).

Example 196

6-(3,5-dimethylisoxazol-4-yl)-4-(4,4,5,5-tetramethyl-1,3,2-dioxaborolan-2-yl)-1H-benzo[d]imidazol-2(3H)-one

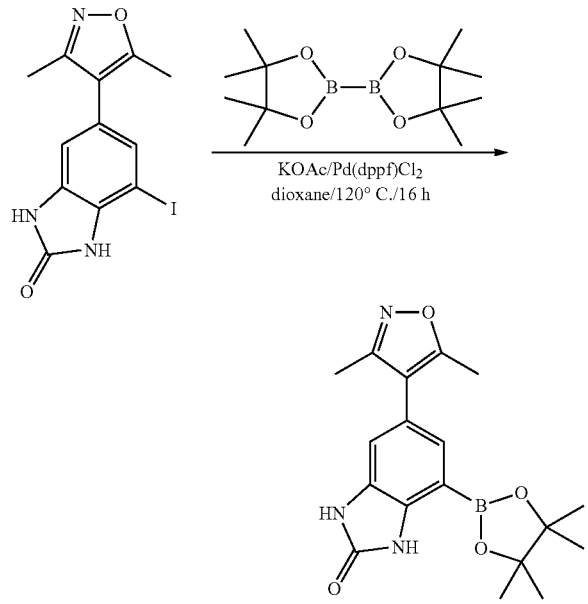

A mixture of 6-(3,5-dimethylisoxazol-4-yl)-4-iodo-1H-benzo[d]imidazol-2(3H)-one (166 g, 468 mmol 1.0 eq), Pd(dppf)Cl$_2$ (19 g, 5% mol), KOAc (92 g, 935 mmol, 2 eq) and bispinacolato diboron (237 g, 935 mmol, 2.0 eq) in degassed dioxane (3.5 L) was flushed with nitrogen. The reaction mixture was heated at 120° C. under N$_2$ overnight. Then the reaction mixture was concentrated and dry-loaded onto silica gel and purified by flash chromatography (PE/EA=10:1-3:1) to give 72 g of 6-(3,5-dimethylisoxazol-4-yl)-4-(4,4,5,5-tetramethyl-1,3,2-dioxaborolan-2-yl)-1H-benzo[d]imidazol-2(3H)-one.

$C_{18}H_{22}BN_3O_4$. 356.0 (M+1) $^1$H NMR (400 MHz, DMSO-$d_6$) δ 10.78 (s, 1H), 9.84 (s, 1H), 7.04 (s, 1H), 6.97 (s, 1H), 2.34 (s, 3H), 2.16 (s, 3H).

Example 197

4-(3,5-dimethylisoxazol-4-yl)-2-nitroaniline

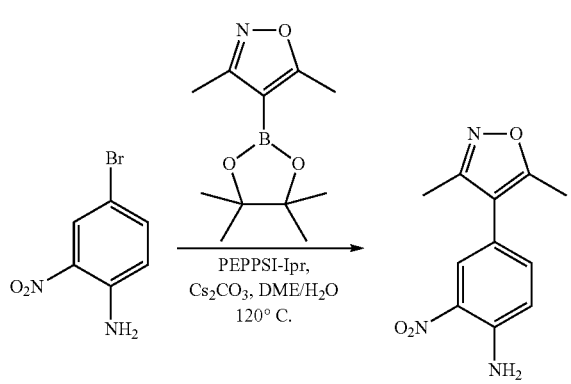

4-bromo-2-nitroaniline (1 g, 4.6 mmol) and 3,5-Dimethylisoxazole-4-boronic acid pinacol ester (2 g, 9.2 mmol) was added to a solvent mixture of 1,2-dimethoxymethane (12 ml) and water (6 ml). To the above mixture were added PEPPSI-Ipr (312 mg, 0.46 mmol) and CsCO$_3$ (4.5 g, 13.8 mmol). The reaction mixture was heated at 120° C. for 30 min. The reaction mixture was then diluted with EtOAc (100 ml), washed with bring (50 ml×2). The organic solvent was evaporated and the residue was dissolved in DCM and purified with flash column chromatography (50% EtOAc/Hexane) to afford 4-(3,5-dimethylisoxazol-4-yl)-2-nitroaniline.

Example 198

4-(3,5-dimethylisoxazol-4-yl)-2-iodo-6-nitroaniline

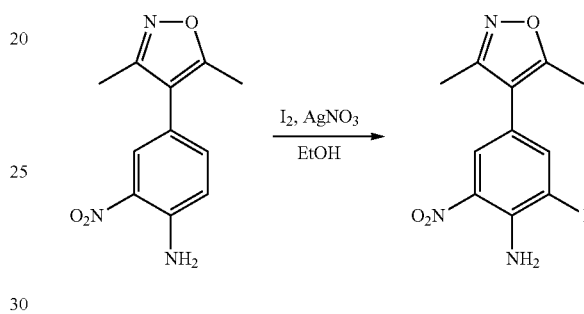

4-(3,5-dimethylisoxazol-4-yl)-2-nitroaniline (1 g, 4.6 mmol) was added to EtOH (50 ml), to the mixture was added 1, (1.4 g, 5.5 mmol) and AgNO$_3$ (0.94 g, 5.5 mmol). The reaction mixture was stirred at room temperature overnight. The solvent was evaporated and then the residue was dissolved in EtOAc (50 ml) and washed with brine (30 ml×2). The organic solvent was evaporated and the residue was dissolved in DCM and purified with flash column chromatography (product came out at 35% EtOAc/Hexane) to afford 4-(3,5-dimethylisoxazol-4-yl)-2-iodo-6-nitroaniline.

Example 199

5-(3,5-dimethylisoxazol-4-yl)-3-iodobenzene-1,2-diamine

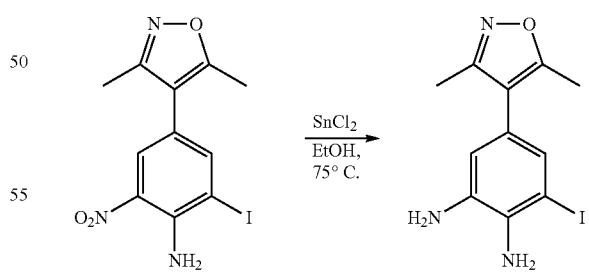

4-(3,5-dimethylisoxazol-4-yl)-2-iodo-6-nitroaniline (0.9 g, 2.5 mmol) was added to EtOH (50 ml), to the mixture were added SnCl$_2$ (2.4 g, 12.5 mmol). The reaction mixture was stirred at 75° C. for 7 h. The solvent was evaporated and then the residue was dissolved in EtOAc (100 ml) and washed with 1N NaOH (100 ml×3). The organic solvent was evaporated and the residue was dissolved in DCM and purified with combi-flash column chromatography (product came out at 60% EtOAc/Hexane) to afford 5-(3,5-dimethylisoxazol-4-yl)-3-iodobenzene-1,2-diamine. LCMS m/z [M+H]+ C11H12IN3O requires: 330.00. Found 330.03 ¹H NMR (400 MHz, CD₃OD) δ2.21 (s, 3H), 2.39 (s, 3H), 7.16 (d, 1H), 7.62 (d, 1H).

Example 200

6-(3,5-dimethylisoxazol-4-yl)-4-iodo-1H-benzo[d]imidazol-2(3H)-one

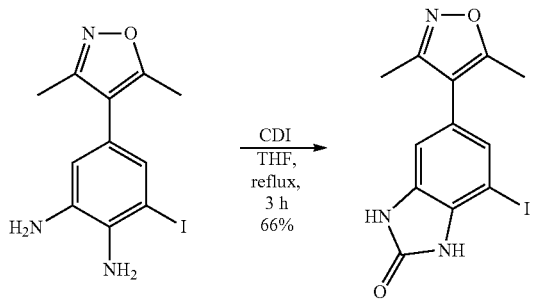

A mixture of 5-(3,5-dimethylisoxazol-4-yl)-3-iodobenzene-1,2-diamine (15 g, 45.6 mmol, 1.0 eq), DMAP (2.9 g, 22.7 mmol, 0.5 eq) and carbonyl diimidazole (11.0 g, 68.4 mmol, 1.5 eq) in THF (200 mL) was refluxed for 3 h. The reaction was cooled to room temperature, purified by flash column chromatography to give a solid, which contained some imidazole and DMAP. The solid was triturated with THF (2×) and filtered to afford 6-(3,5-dimethylisoxazol-4-yl)-4-iodo-1H-benzo[d]imidazol-2(3H)-one. LC-MS: 354.0 [M–H]⁻ ¹H NMR (400 MHz, DMSO-d6) δ 10.9 (br s, 2H), 7.24 (d, J=1.6 Hz, 1H), 6.97 (d, J=1.6 Hz, 1H), 2.37 (s, 3H), 1.78 (s, 3H).

Example 201

Biochemical Alpha Assay

Binding of the bromodomain BRD4_I to an acetylated histone H4 peptide was measured using a bead based Amplified Luminescent Proximity Homogeneous Assay (ALPHA). The synthetic peptide containing amino acids 1-18 of histone H4 was acetylated at lysine 5, 8, 12, 16 and conjugated to biotin (SGRGACKGGACKGLGACKGGAACKRH-GSGSK-biotin) was purchased from Millipore. BRD4_I was expressed and purified from *Escherichia coli* as an N-terminal His₆-tagged protein. Nickel-Chelate ALPHA acceptor beads (Perkin Elmer) were used to specifically bind BRD4__1 and ALPHA streptavidin donor beads (Perkin Elmer) were used because they specifically recognized the biotinylated H4 peptide. Binding of BRD4__1 to the peptide resulted in proximity of the donor and acceptor beads which leads to an increase in ALPHA signal whereas disruption of this protein-peptide interaction with a small molecule inhibitor resulted in a decrease in ALPHA signal. Assays were performed in 50 mM Hepes (pH 7.5), 150 mM NaCl, 0.1 mg/ml BSA, 0.01% (v/v) Brij, 0.5% (v/v) DMSO, 200 nM H4 peptide and 15 nM of BRD4__1 protein. After an assay reaction time of 60 minutes at 25° C., binding was measured with 20 μg/ml streptavidin donor beads and 20 μg/ml nickle-chelate acceptor beads. ALPHA signal was detected on an Envision plate reader (Ex: 320 nm; Em: 570 nm; Ex time: 180 ms). Data were normalized based on a positive (2 μM I-BET) and negative (DMSO) controls and IC₅₀ values were calculated from the fit of the dose-response curves to a four-parameter equation. All IC₅₀ values represent geometric mean values of a minimum of four determinations. These assays generally produced results within 3-fold of the reported mean.

Biochemical HTRF Assay

Binding of the two tandem bromodomains, BRD4_I and BRD4__2, to an acetylated histone H4 peptide were measured using a homogeneous time resolved fluorescence resonance energy transfer (TR-FRET) assay. The synthetic peptide containing amino acids 1-18 of histone H4 was acetylated at lysine 5, 8, 12, 16 and conjugated to biotin (SGRGACKG-GACKGLGACKGGAACKRH-GSGSK-biotin) was purchased from Millipore. BRD4_I and BRD4__2 were expressed and purified from *Escherichia coli* as N-terminal His₆-tagged proteins. An XL665 labeled anti-His antibody (Cisbio) was used to specifically bind BRD4 and a cryptate labeled streptavidin protein was used because it specifically recognized the biotinylated H4 peptide. Binding of BRD4 to the peptide resulted in an increase in FRET signal whereas disruption of this protein-peptide interaction with a small molecule inhibitor resulted in a decrease in FRET signal. Assays were performed in 50 mM Hepes (pH 7.5), 150 mM NaCl, 0.1 mg/ml BSA, 0.01% (v/v) Brij, 0.5% (v/v) DMSO and 200 nM H4 peptide at the following concentrations for each BRD4 isoform: 60 nM BRD4__1 and 120 nM BRD4__2. After an assay reaction time of 60 minutes at 25° C., binding was measured with 2 nM cryptate labeled streptavidin and 10 nM anti-His-XL665 antibody. TR-FRET signal was detected on an Envision plate reader (Ex: 320 nm; Em: 615/665 nm; 100 μs delay and 200 μs read window). Data were normalized based on a positive (2 μM I-BET) and negative (DMSO) controls and IC₅₀ values were calculated from the fit of the dose-response curves to a four-parameter equation. All IC₅₀ values represent geometric mean values of a minimum of four determinations. These assays generally produced results within 3-fold of the reported mean.

BRD4-1 Ligand KI and BRD4-2 Ligand KI Assays:

Binding of the two tandem bromodomains, BRD4-I and BRD4-2, to a Cy5 labeled probe/ligand (Compound 201-A) were measured using a homogeneous time resolved fluorescence resonance energy transfer (TR-FRET) assay.

(201-A)

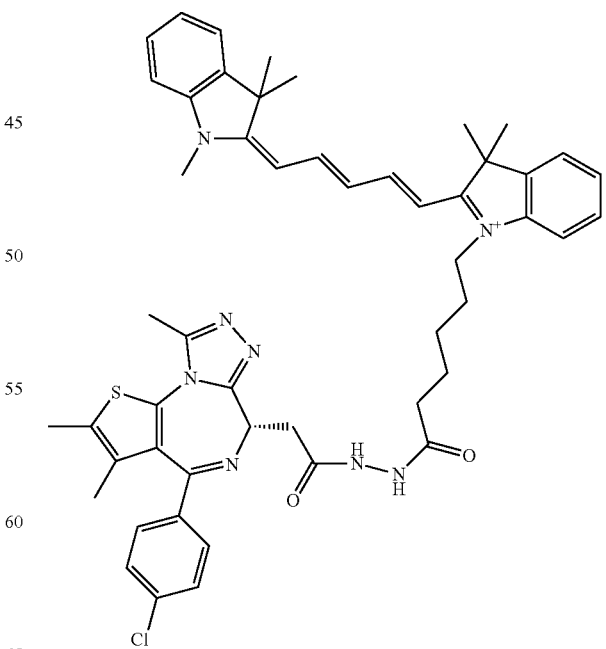

The labeled ligand specifically binds BRD4-1 and BRD4-2 and can be displaced by a small molecule inhibitor that shares a similar or overlapping binding site. BRD4-I and BRD4-2 were expressed and purified from *Escherichia coli* as N-terminal His$_6$-tagged proteins. A Eu-cryptate labeled anti-His antibody (Perkin Elmer) was used to specifically bind BRD4. Binding of BRD4 to the labeled probe/ligand resulted in an increase in FRET signal whereas displacement of this labeled ligand from BRD4 with a small molecule inhibitor resulted in a decrease in FRET signal. Assays were performed in 50 mM Hepes (pH 7.5), 150 mM NaCl, 0.1 mg/ml BSA, 0.01% (v/v) Brij, 0.5% (v/v) DMSO and 10 nM labeled ligand at the following concentrations for each BRD4 isoform: 2 nM BRD4-1 and 0.5 nM BRD4-2. After an assay reaction time of 60 minutes at 25° C., binding was measured with 2 nM Eu-cryptate labeled anti-H is antibody. TR-FRET signal was detected on an Envision plate reader (Ex: 320 nm; Em: 615/665 nm; 100 μs delay and 200 μs read window). Data were normalized based on a positive (2 μM I-BET) and negative (DMSO) controls and IC50 values were calculated from the fit of the dose-response curves to a four-parameter equation. All IC50 values represent geometric mean values of a minimum of four determinations. The IC50 values were converted to Ki values (dissociation constant for BRD4-inhibitor complex) using the Cheng and Prusoff equation for a competitive inhibitor mode of action. These assays generally produced results within 3-fold of the reported mean.

MT-4 Proliferation Assay in 384-Well Format

Compounds were tested in a standardized high-throughput 384-well assay format. Each compound was serially diluted 3-fold in 100% DMSO in polypropylene 384-well plates using a Biomek FX Workstation, and 0.4 μL compound added to an assay plate containing 40 μL RPMI media. Compounds were arranged in a horizontal pattern, with 10 concentrations per compound, and 8 compounds added per plate. Due to low DMSO tolerability, the final DMSO concentration never exceeded 0.5% (v/v). Each assay plate contained 10 μM Puromycin and 0.5% DMSO in RPMI-1640 as positive and negative controls respectively. MT-4 cells (HTLV-1 transformed, human T lymphoblastoid cells, NIH Aids Reagent program) were added in volumes of 35 μL per well and 2,000 cells per well using a Biotek uFlow Workstation (Biotek, Winooski, Vt.), and the plates subsequently incubated for 5 days at 37° C. in an incubator set at 5% CO2 and 90% humidity.

After 5 days, 22 μL Cell Titer Glo (Promega) was added to the assay plates with a Biotek uFlow Workstation. Plates were subsequently placed on a Perkin Elmer Envision Plate Reader for 5 minutes before the luminescence signal was read. $CC_{50}$ values were calculated from the compound concentration that caused a 50% decrease in luminescence signal, a measure of toxicity, and calculated by non-linear regression using Pipeline Pilot software (Accelrys, San Diego, Calif.).

c-Myc Down Regulation and Viability Assays

An enzyme linked immunosorbent assay using the Meso Scale Diagnostic (MSD) technology was used to detect levels of c-Myc produced in MM1S cells (ATCC). MM1S cells were cultured in RPMI-1640 media (Corning), supplemented with 10% FBS (Hyclone), 1% penicillin-streptomycin (Cellgro), 2-mercaptoethanol (Gibco) and seeded onto 384-tissue culture treated filter binding plates (Millipore) at a density of 40K cells/well containing titrations of small molecule inhibitors or DMSO (0.4%) in a volume of 100 μl of media. After an incubation time of 24 hrs, cells were lysed (1× lysis buffer (Thermo) supplemented with protease and phosophatase inhibitor cocktail (Thermo)) and the plates centrifuged (1000 rpm, 1 min) to capture c-Myc on MSD plates coated with a monoclonal c-Myc antibody (Origene). Assay wells were washed (3× Invitrogen wash buffer) and probed with a polyclonal c-Myc antibody (Abcam) and MSD detection antibody solution in order to detect levels of c-Myc on the MSD platform. c-Myc capture was reported in pg/ml based on a standard curve using recombinant c-Myc protein (Prosci). EC50 values were calculated from the fit of the dose-response curves to a four-parameter equation. All EC50 values represent geometric mean values of a minimum of four determinations. These assays generally produced results within 3-fold of the reported mean.

For cell viability in the MM1S cell line, cells were seeded onto 384-tissue culture treated plates (Greiner) at a density of 60K cells/well containing titrations of small molecule inhibitors or DMSO (0.2%). After 72 hr incubation cells were analyzed for cell viability by addition of CellTiter Glo (Promega) to the assay plates. After 15 min incubation at room temperature the signal from the viable cells was analyzed on an Envision plate reader (Perkin Elmer). EC50 values were calculated from the fit of the dose-response curves to a four-parameter equation. All EC50 values represent geometric mean values of a minimum of four determinations. These assays generally produced results within 3-fold of the reported mean.

Results are shown in Tables 1 and 2. An 'n/a" indicates that assay was not performed for that compound.

TABLE 1

| Compound of Example No. | Structure | BRD4_1- ALPHA [nM] | IC$_{50}$ HTBS BRD4-1 HTRF [nM] | IC$_{50}$ HTBS BRD4-2 HTRF [nM] | CC$_{50}$ MT4 384 [nM] |
|---|---|---|---|---|---|
| 1 | 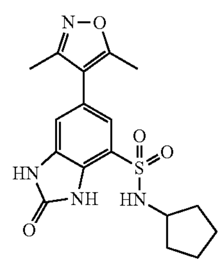 [SMILES: Cc1noc(C)c1-c1cc(S(=O)(=O)NC2CCCC2)c2[nH]c(=O)[nH]c2c1] | n/a | 1412 | 1068 | 1123.8 |
| 2 | 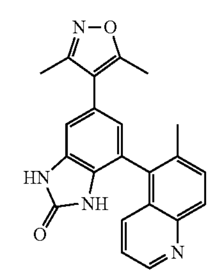 [SMILES: Cc1ccc2ncccc2c1-c1cc(-c2c(C)noc2C)cc2[nH]c(=O)[nH]c12] | 30.8 | 135 | 119 | 18.951 |
| 3 | 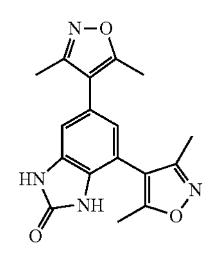 [SMILES: Cc1noc(C)c1-c1cc(-c2c(C)noc2C)c2[nH]c(=O)[nH]c2c1] | 119.4 | 295 | n/a | 196.26 |

TABLE 1-continued

| Compound of Example No. | Structure | BRD4_1-ALPHA [nM] | IC$_{50}$ HTBS BRD4-1 HTRF [nM] | IC$_{50}$ HTBS BRD4-2 HTRF [nM] | CC$_{50}$ MT4 384 [nM] |
|---|---|---|---|---|---|
| 4 | 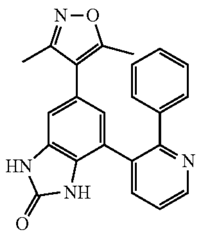 [SMILES: Cc1noc(C)c1-c1cc(-c2cccnc2-c2ccccc2)c2[nH]c(=O)[nH]c2c1] | 37.2 | 119 | 141 | 102.76 |
| 5 | 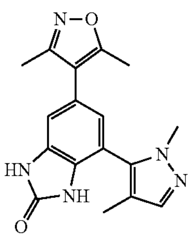 [SMILES: Cc1cnn(C)c1-c1cc(-c2c(C)noc2C)cc2[nH]c(=O)[nH]c12] | 233.5 | 350 | 144 | 232.94 |
| 6 | 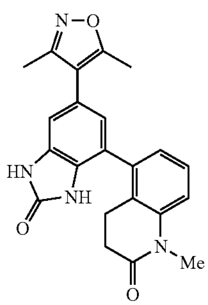 [SMILES: Cc1noc(C)c1-c1cc(-c2cccc3c2CCC(=O)N3C)c2[nH]c(=O)[nH]c2c1] | 46.8 | 132 | 108 | 53.911 |
| 7 | 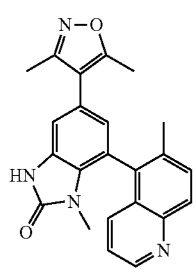 [SMILES: Cc1ccc2ncccc2c1-c1cc(-c2c(C)noc2C)cc2[nH]c(=O)n(C)c12] | 37.3 | 121 | 101 | 17.543 |
| 8 | 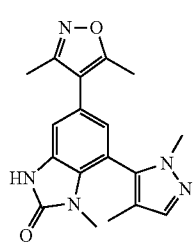 [SMILES: Cc1cnn(C)c1-c1cc(-c2c(C)noc2C)cc2[nH]c(=O)n(C)c12] | 240.6 | 511 | 168 | 116.58 |
| 9 | | 270.3 | 497 | 227 | 203.9 |
| 10 | | 196.5 | 313 | 396 | 1027.6 |
| 11 | | 222 | 438 | 174 | 420.62 |
| 12 | | 232.7 | 316 | 314 | 761.13 |
| 13 | | 45.2 | n/a | n/a | 51.551 |

TABLE 1-continued
| Compound of Example No. | Structure | BRD4_1-ALPHA [nM] | IC₅₀ HTBS BRD4-1 HTRF [nM] | IC₅₀ HTBS BRD4-2 HTRF [nM] | CC₅₀ MT4 384 [nM] |
|---|---|---|---|---|---|
| 14 | 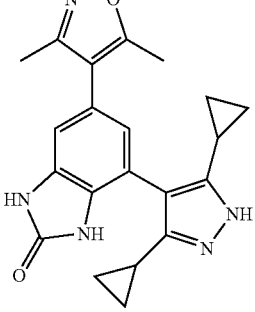 | 14 | n/a | n/a | 9.543 |
TABLE 2
| Compound of Example No. | Structure | BRD4-1 Ligand K1 [nM] | BRD4-1 Ligand K2 [nM] | CC₅₀ MT4 384 [nM] | cMYC EC₅₀ [nM] |
|---|---|---|---|---|---|
| 23 | 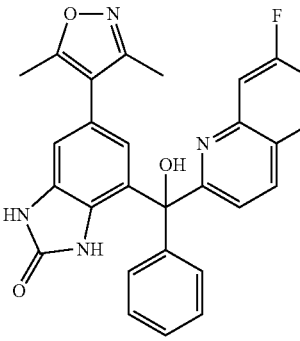 | 12.9 | 3.0 | 9.1 | 13.2 |
| 33 | 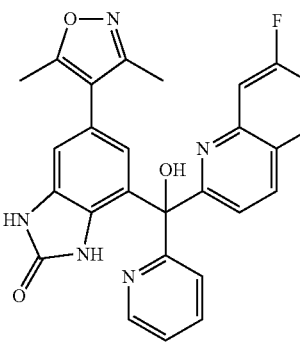 | 14.1 | 5.3 | 29.1 | 176.5 |
| 36 | 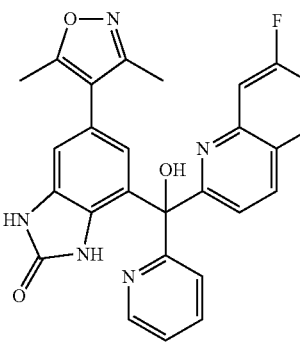 | 14.1 | 5.3 | 29.1 | 176.5 |

TABLE 2-continued

| Compound of Example No. | Structure | BRD4-1 Ligand K1 [nM] | BRD4-1 Ligand K2 [nM] | CC$_{50}$ MT4 384 [nM] | cMYC EC$_{50}$ [nM] |
| --- | --- | --- | --- | --- | --- |
| 38 | 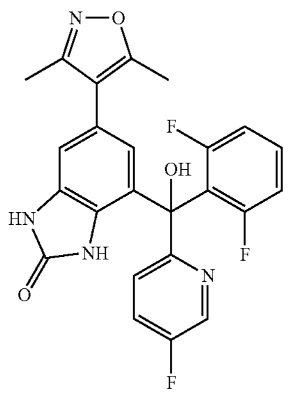 [SMILES: Cc1noc(C)c1-c1cc(C(O)(c2ccc(F)cn2)c2c(F)cccc2F)c2[nH]c(=O)[nH]c2c1] | 7.8 | 4.4 | 29.7 | 84.7 |
| 39 | 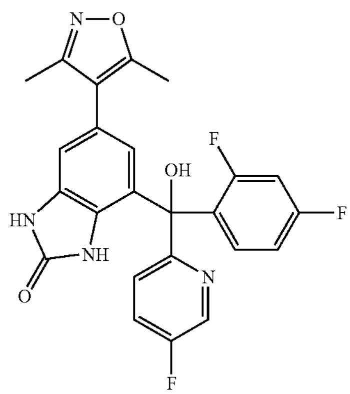 [SMILES: Cc1noc(C)c1-c1cc(C(O)(c2ccc(F)cn2)c2ccc(F)cc2F)c2[nH]c(=O)[nH]c2c1] | 11.8 | 5.9 | 42.1 | 127.7 |
| 41 | 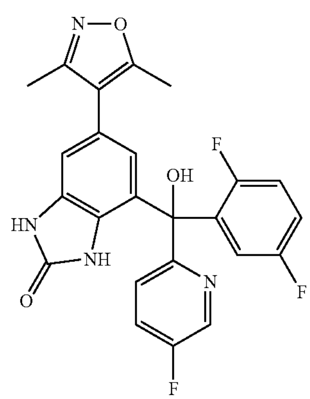 [SMILES: Cc1noc(C)c1-c1cc(C(O)(c2ccc(F)cn2)c2cc(F)ccc2F)c2[nH]c(=O)[nH]c2c1] | 12.8 | 5.0 | 47.3 | 104.0 |
| 49 | 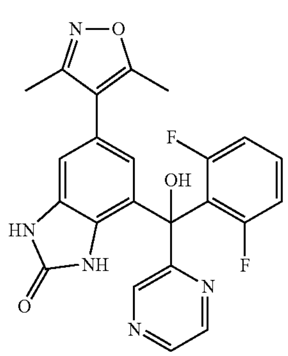 [SMILES: Cc1noc(C)c1-c1cc(C(O)(c2cnccn2)c2c(F)cccc2F)c2[nH]c(=O)[nH]c2c1] | 8.1 | 2.7 | 9.7 | n/a |

TABLE 2-continued

| Compound of Example No. | Structure | BRD4-1 Ligand K1 [nM] | BRD4-1 Ligand K2 [nM] | CC₅₀ MT4 384 [nM] | cMYC EC₅₀ [nM] |
| --- | --- | --- | --- | --- | --- |
| 50 | 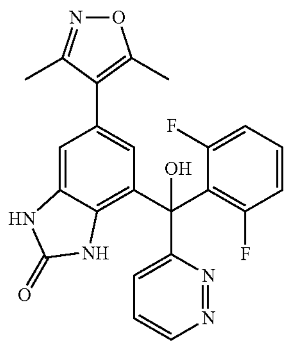 [SMILES: Cc1noc(C)c1-c1cc(C(O)(c2cccnn2)c2c(F)cccc2F)c2[nH]c(=O)[nH]c2c1] | 8.7 | 5.9 | 16.0 | n/a |
| 52 | 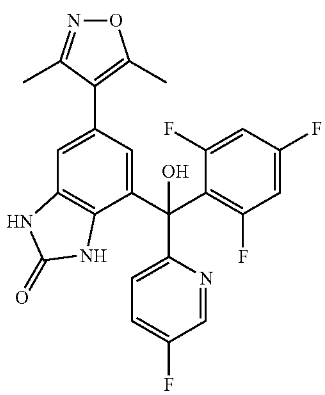 [SMILES: Cc1noc(C)c1-c1cc(C(O)(c2ccc(F)cn2)c2c(F)cc(F)cc2F)c2[nH]c(=O)[nH]c2c1] | 8.9 | 6.4 | 36.1 | 134.9 |
| 53 | 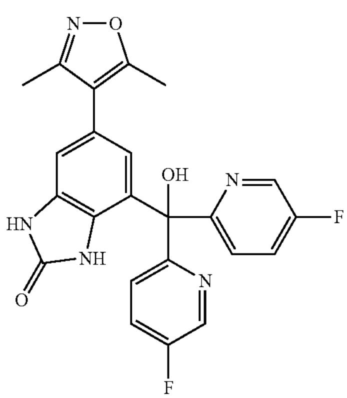 [SMILES: Cc1noc(C)c1-c1cc(C(O)(c2ccc(F)cn2)c2ccc(F)cn2)c2[nH]c(=O)[nH]c2c1] | 26.6 | 24.1 | 28.6 | 171.7 |
| 54 | 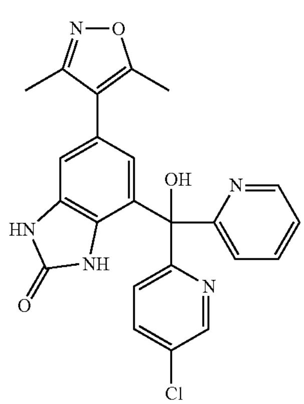 [SMILES: Cc1noc(C)c1-c1cc(C(O)(c2ccccn2)c2ccc(Cl)cn2)c2[nH]c(=O)[nH]c2c1] | 22.7 | 14.1 | 27.1 | 111.2 |

TABLE 2-continued

| Compound of Example No. | Structure | BRD4-1 Ligand K1 [nM] | BRD4-1 Ligand K2 [nM] | CC$_{50}$ MT4 384 [nM] | cMYC EC$_{50}$ [nM] |
|---|---|---|---|---|---|
| 55 | 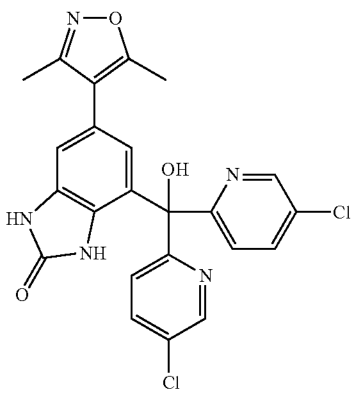 [SMILES: Cc1noc(C)c1-c1cc(C(O)(c2ccc(Cl)cn2)c2ccc(Cl)cn2)c2[nH]c(=O)[nH]c2c1] | 14.5 | 18.2 | 41.0 | 141.2 |
| 56 | 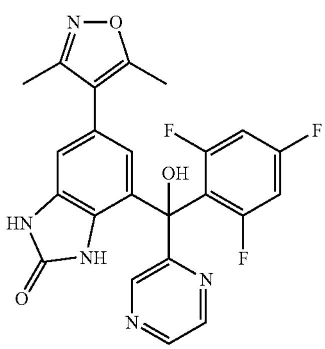 [SMILES: Cc1noc(C)c1-c1cc(C(O)(c2cnccn2)c2c(F)cc(F)cc2F)c2[nH]c(=O)[nH]c2c1] | 6.0 | 3.6 | 24.8 | 40.9 |
| 73 | 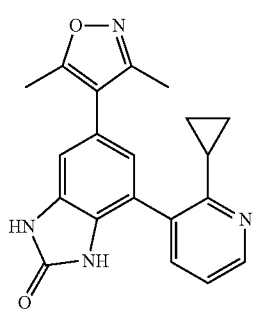 [SMILES: Cc1noc(C)c1-c1cc(-c2cccnc2C2CC2)c2[nH]c(=O)[nH]c2c1] | 34.2 | 24.0 | 61.0 | 153.6 |
| 133 | 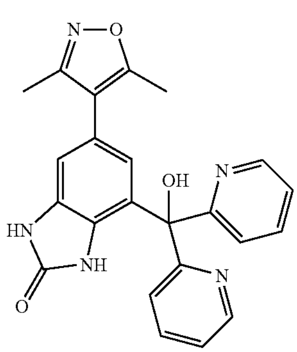 [SMILES: Cc1noc(C)c1-c1cc(C(O)(c2ccccn2)c2ccccn2)c2[nH]c(=O)[nH]c2c1] | 40.3 | 15.8 | 25.5 | 44.3 |

TABLE 2-continued

| Compound of Example No. | Structure | BRD4-1 Ligand K1 [nM] | BRD4-1 Ligand K2 [nM] | CC$_{50}$ MT4 384 [nM] | cMYC EC$_{50}$ [nM] |
|---|---|---|---|---|---|
| 134 | 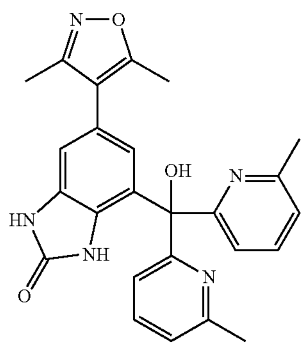 [SMILES: Cc1cccc(C(O)(c2cccc(C)n2)c2cc(-c3c(C)noc3C)cc3[nH]c(=O)[nH]c23)n1] | 69.9 | 5.3 | 19.1 | 74.4 |
| 140 | 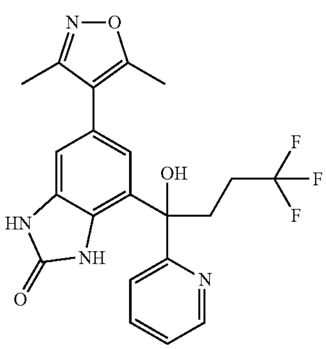 [SMILES: Cc1noc(C)c1-c1cc(C(O)(CCC(F)(F)F)c2ccccn2)c2[nH]c(=O)[nH]c2c1] | 35.2 | 43.8 | 78.3 | 216.7 |
| 143 | 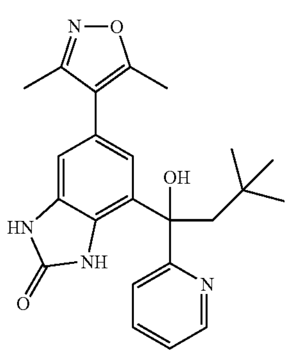 [SMILES: Cc1noc(C)c1-c1cc(C(O)(CC(C)(C)C)c2ccccn2)c2[nH]c(=O)[nH]c2c1] | 29.3 | 8.0 | 20.4 | 118.2 |
| 144 | 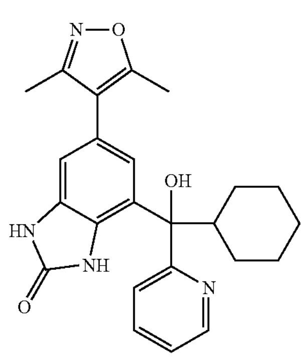 [SMILES: Cc1noc(C)c1-c1cc(C(O)(c2ccccn2)C2CCCCC2)c2[nH]c(=O)[nH]c2c1] | 7.7 | 2.7 | n/a | n/a |

TABLE 2-continued

| Compound of Example No. | Structure | BRD4-1 Ligand K1 [nM] | BRD4-1 Ligand K2 [nM] | CC$_{50}$ MT4 384 [nM] | cMYC EC$_{50}$ [nM] |
|---|---|---|---|---|---|
| 147 | 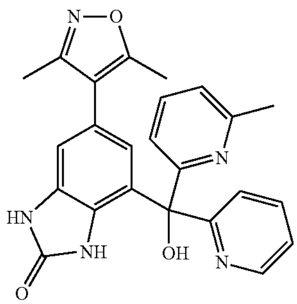 [SMILES: Cc1cccc(C(O)(c2ccccn2)c2cc(-c3c(C)noc3C)cc3[nH]c(=O)[nH]c23)n1] | 81.6 | 16.0 | 56.5 | 107.3 |
| 149 | 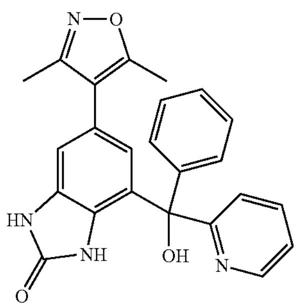 [SMILES: Cc1noc(C)c1-c1cc(C(O)(c2ccccc2)c2ccccn2)c2[nH]c(=O)[nH]c2c1] | 17.3 | 4.6 | 17.5 | 73.8 |
| 169 | 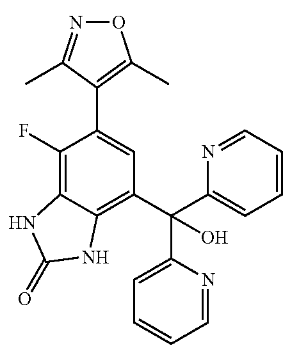 [SMILES: Cc1noc(C)c1-c1cc(C(O)(c2ccccn2)c2ccccn2)c2[nH]c(=O)[nH]c2c1F] | 62.0 | 33.5 | 41.4 | 128.2 |

While the foregoing description describes specific embodiments and aspects, those with ordinary skill in the art will appreciate that various modifications and alternatives can be developed. Accordingly, the particular embodiments and aspects described above are meant to be illustrative only, and not to limit the scope of the invention, which is to be given the full breadth of the appended claims, and any and all equivalents thereof.

We claim:

1. A compound of Formula (I)

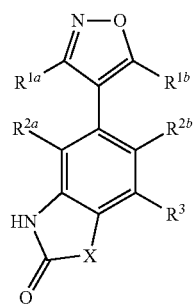

(I)

wherein
$R^{1a}$ and $R^{1b}$ are each independently $C_1$-$C_6$ alkyl, $C_1$-$C_6$ alkoxy, $C_1$-$C_6$ haloalkyl, $C_1$-$C_6$ haloalkoxy, $C_1$-$C_6$ hydroxyalkyl, $C_3$-$C_6$ cycloalkyl, or $CH_2$—$C_3$-$C_6$ cycloalkyl;
$R^{2a}$ and $R^{2b}$ are each independently H or halogen;
$R^3$ is
  $C_5$-$C_{10}$ aryl, $C_5$-$C_{10}$ heteroaryl, or $C_5$-$C_{10}$ heteroarylalkyl, each of which is optionally substituted with from 1 to 5 $R^{20}$ groups; or
  —$S(O)_2NHR^4$,
    wherein $R^4$ is $C_1$-$C_6$ alkyl or $C_3$-$C_7$ cycloalkyl, each of which is optionally substituted with from 1 to 5 $R^{20}$ groups; or
  a moiety of the formula

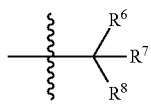

wherein
$R^6$ is H, OH, or halogen; and $R^7$ and $R^8$ are each independently $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, $C_5$-$C_{12}$ aryl, $C_5$-$C_{12}$ heteroaryl, or $C_5$-$C_{12}$ heteroarylalkyl, each of which is optionally substituted with from 1 to 5 $R^{20}$ groups; or $R^6$ is H, $C_1$-$C_6$ alkyl, $C_2$-$C_6$ alkenyl, $C_2$-$C_6$ alkynyl, $C_3$-$C_6$ cycloalkyl, phenyl, naphthyl, or $C_3$-$C_{12}$ heteroaryl; and $R^7$ and $R^8$ together form a $C_1$-$C_6$ alkylidene group having a double bond with the carbon to which each of $R^6$, $R^7$, and $R^8$ are bound wherein each of the $C_1$-$C_6$ alkyl, $C_2$-$C_6$ alkenyl, $C_2$-$C_6$ alkynyl, —$C_3$-$C_6$ cycloalkyl, phenyl, naphthyl, or $C_3$-$C_{12}$ heteroaryl groups is optionally substituted with from 1 to 5 $R^{20}$ groups;

X is N-Q, or O;

Q is H, $C_1$-$C_3$ alkyl, $C_1$-$C_3$ haloalkyl, benzyl or substituted benzyl;

each $R^{20}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, wherein each $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$;

each $R^a$ and $R^b$ is independently H; or $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, each of which is optionally substituted with from one to five $R^{21}$; or $R^a$ and $R^b$ together with the atoms to which they are attached form a heterocycle, and;

each $R^{21}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, or halogen;

or a pharmaceutically acceptable salt thereof.

2. A compound of claim 1, of Formula (Ia)

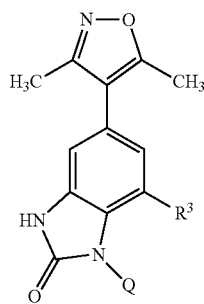

(Ia)

wherein $R^3$ is
 $C_5$-$C_{10}$ aryl, $C_5$-$C_{10}$ heteroaryl, or $C_5$-$C_{10}$ heteroarylalkyl, each of which is optionally substituted with from 1 to 5 $R^{20}$ groups; or
 —$S(O)_2NHR^4$,
  wherein $R^4$ is $C_1$-$C_6$ alkyl or $C_3$-$C_7$ cycloalkyl, each of which is optionally substituted with from 1 to 5 $R^{20}$ groups; or a moiety of the formula

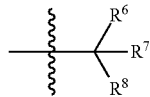

wherein $R^6$ is H, OH, or halogen; and $R^7$ and $R^8$ are each independently $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, $C_5$-$C_{12}$ aryl, $C_5$-$C_{12}$ heteroaryl, or $C_5$-$C_{12}$ heteroarylalkyl, each of which is optionally substituted with from 1 to 5 $R^{20}$ groups; or $R^6$ is H, $C_1$-$C_6$ alkyl, $C_2$-$C_6$ alkenyl, $C_2$-$C_6$ alkynyl, $C_3$-$C_6$ cycloalkyl, phenyl, naphthyl, or $C_3$-$C_{12}$ heteroaryl; and $R^7$ and $R^8$ together form a $C_1$-$C_6$ alkylidene group having a double bond with the carbon to which each of $R^6$, $R^7$, and $R^8$ are bound wherein each of the $C_1$-$C_6$ alkyl, $C_2$-$C_6$ alkenyl, $C_2$-$C_6$ alkynyl, —$C_3$-$C_6$ cycloalkyl, phenyl, naphthyl, or $C_3$-$C_{12}$ heteroaryl groups is optionally substituted with from 1 to 5 $R^{20}$ groups;

Q is H, $C_1$-$C_3$ alkyl, $C_1$-$C_3$ haloalkyl, benzyl or substituted benzyl;

each $R^{20}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, wherein each $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$;

each $R^a$ and $R^b$ is independently H; or $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, each of which is optionally substituted with from one to five $R^{21}$; or $R^a$ and $R^b$ together with the atoms to which they are attached form a heterocycle, and;

each $R^{21}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, or halogen;

or a pharmaceutically acceptable salt thereof.

3. A compound of claim 1, of Formula (Ib)

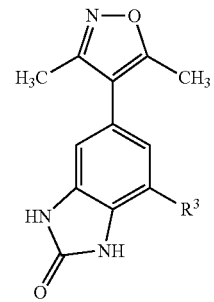

(Ib)

wherein $R^3$ is
 $C_5$-$C_{10}$ aryl, $C_5$-$C_{10}$ heteroaryl, or $C_5$-$C_{10}$ heteroarylalkyl, each of which is optionally substituted with from 1 to 5 $R^{20}$ groups; or
 —$S(O)_2NHR^4$, wherein $R^4$ is $C_1$-$C_6$ alkyl or $C_3$-$C_7$ cycloalkyl, each of which is optionally substituted with from 1 to 5 $R^{20}$ groups; or a moiety of the formula

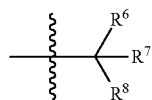

wherein
- $R^6$ is H, OH, or halogen; and $R^7$ and $R^8$ are each independently $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, $C_5$-$C_{12}$ aryl, $C_5$-$C_{12}$ heteroaryl, or $C_5$-$C_{12}$ heteroarylalkyl, each of which is optionally substituted with from 1 to 5 $R^{20}$ groups; or
- $R^6$ is H, $C_1$-$C_6$ alkyl, $C_2$-$C_6$ alkenyl, $C_2$-$C_6$ alkynyl, $C_3$-$C_6$ cycloalkyl, phenyl, naphthyl, or $C_3$-$C_{12}$ heteroaryl; and $R^7$ and $R^8$ together form a $C_1$-$C_6$ alkylidene group having a double bond with the carbon to which each of $R^6$, $R^7$, and $R^8$ are bound wherein each of the $C_1$-$C_6$ alkyl, $C_2$-$C_6$ alkenyl, $C_2$-$C_6$ alkynyl, $C_3$-$C_6$ cycloalkyl, phenyl, naphthyl, or $C_3$-$C_{12}$ heteroaryl groups is optionally substituted with from 1 to 5 $R^{20}$ groups;

each $R^{20}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, wherein each $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$;

each $R^a$ and $R^b$ is independently H; or $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, each of which is optionally substituted with from one to five $R^{21}$; or $R^a$ and $R^b$ together with the atoms to which they are attached form a heterocycle, and;

each $R^{21}$ is independently $C_1$-$C_6$ alkyl, $C_3$-$C_6$ cycloalkyl, $C_1$-$C_6$ heteroalkyl, $C_3$-$C_6$ heterocyclic, $C_5$-$C_{12}$ aryl, $C_5$-$C_{12}$ heteroaryl, or halogen;

or a pharmaceutically acceptable salt thereof.

4. A compound of claim 1, wherein $R^3$ is $C_5$-$C_{10}$ aryl, $C_5$-$C_{10}$ heteroaryl, or $C_5$-$C_{10}$ heteroarylalkyl, each of which is optionally substituted with from 1 to 5 $R^{20}$ groups.

5. A compound of claim 1, wherein $R^3$ is a moiety of the formula

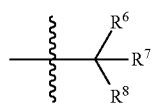

wherein $R^6$ is H, OH, or halogen; and
$R^7$ and $R^8$ are each independently $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, $C_5$-$C_{12}$ aryl, $C_5$-$C_{12}$ heteroaryl, or $C_5$-$C_{12}$ heteroarylalkyl, each of which is optionally substituted with from 1 to 5 $R^{20}$ groups.

6. A compound of claim 1, wherein $R^6$ is OH.

7. A compound of claim 5, wherein $R^7$ and $R^8$ are each independently $C_1$-$C_6$ alkyl, $C_3$-$C_6$ cycloalkyl, $C_1$-$C_6$ heteroalkyl, $C_5$-$C_{12}$ aryl, $C_5$-$C_{12}$ heteroaryl, or $C_5$-$C_{12}$ heteroarylalkyl, each of which is optionally substituted with from 1 to 5 $R^{20}$ groups.

8. A compound of claim 5, wherein $R^7$ and $R^8$ are each independently $C_1$-$C_6$ alkyl, $C_6$ aryl or $C_6$ heteroaryl, each of which is optionally substituted with from 1 to 5 $R^{20}$ groups.

9. A compound of claim 5, wherein $R^7$ and $R^8$ are each independently $C_6$ aryl or $C_6$ heteroaryl, each of which is optionally substituted with from 1 to 5 $R^{20}$ groups.

10. A compound of claim 5, wherein $R^7$ and $R^8$ are each independently $C_1$-$C_6$ alkyl, each of which is optionally substituted with from 1 to 5 $R^{20}$ groups.

11. A compound chosen from the following list:

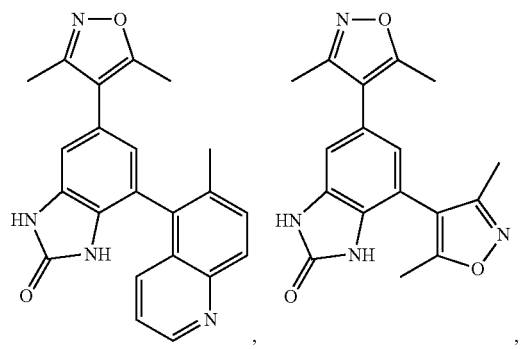

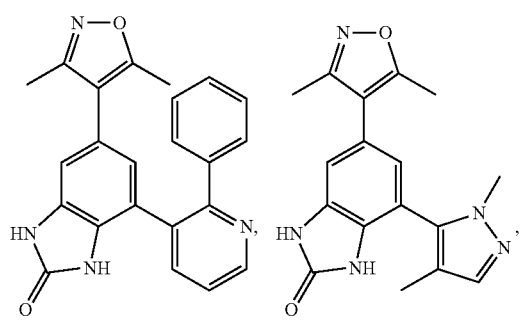

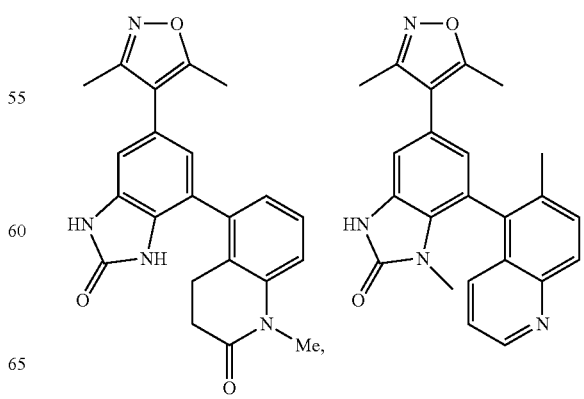

-continued
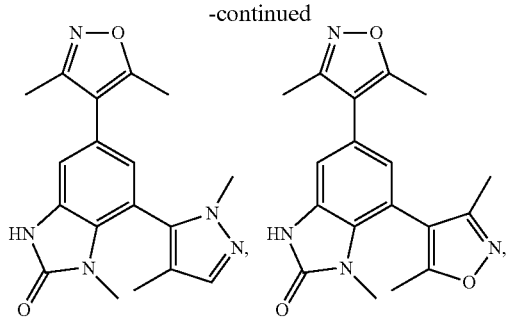
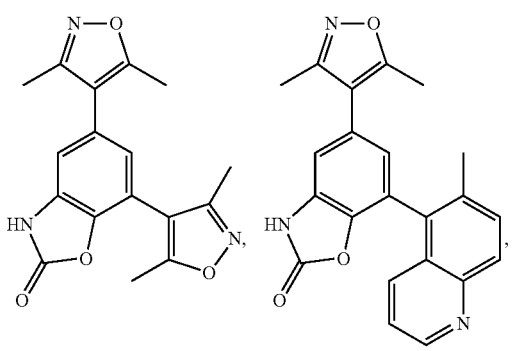
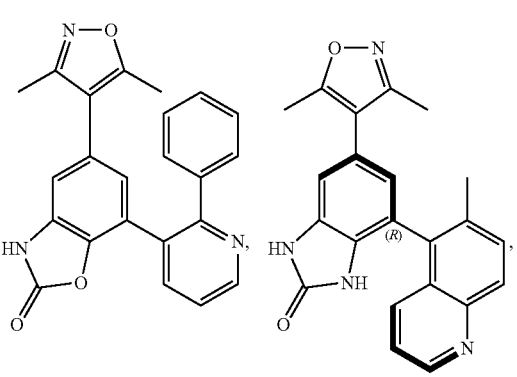
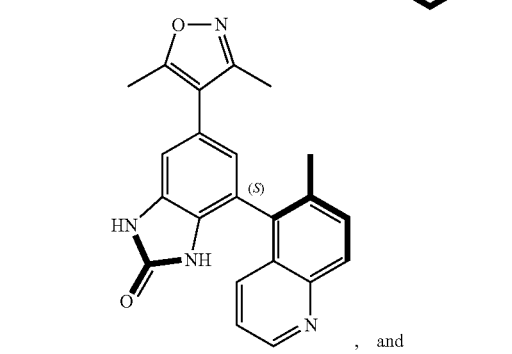
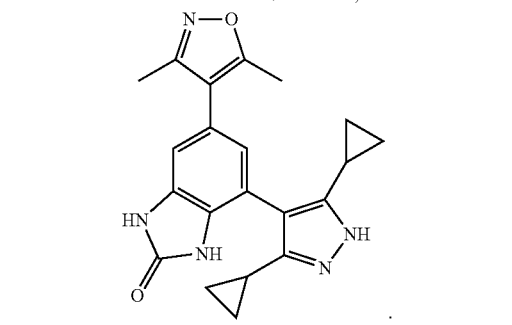
, and
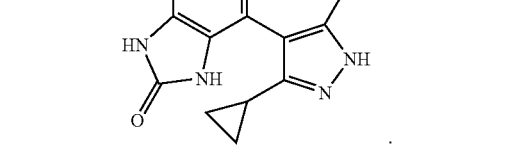
.
12. A compound chosen from the following list:
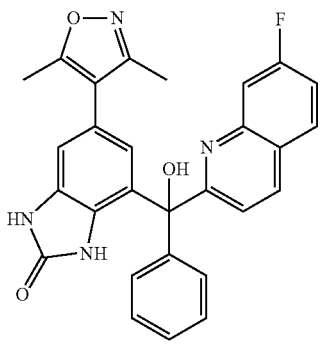
,
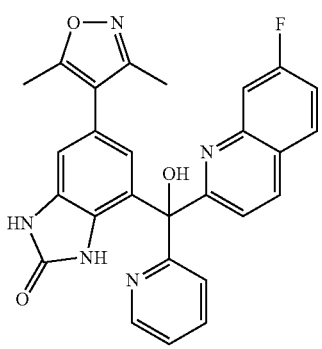
,
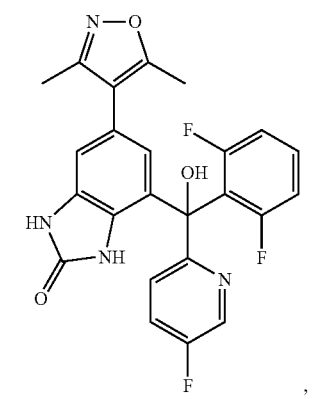
,
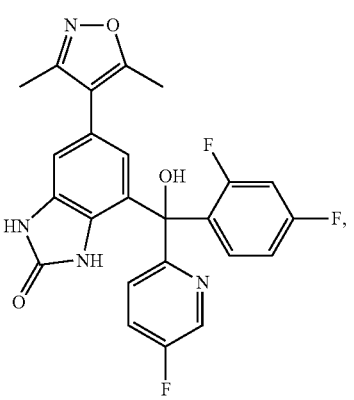
, 221
-continued
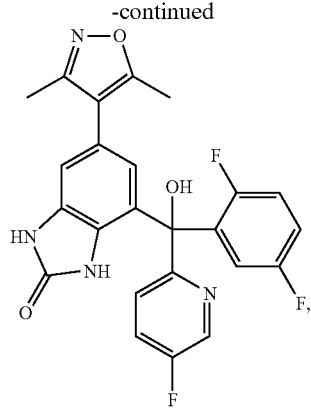
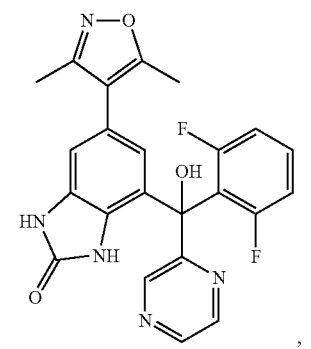
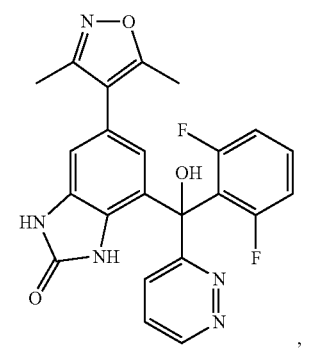
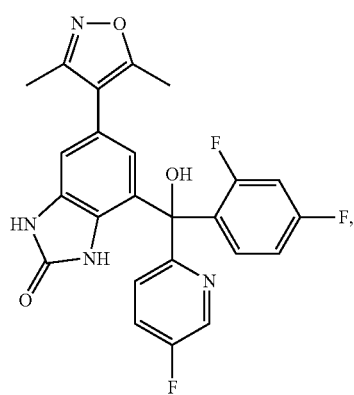
222
-continued
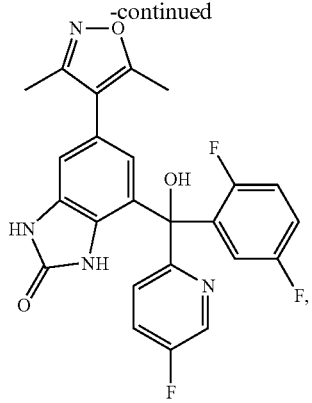
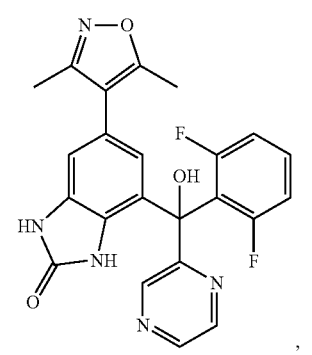
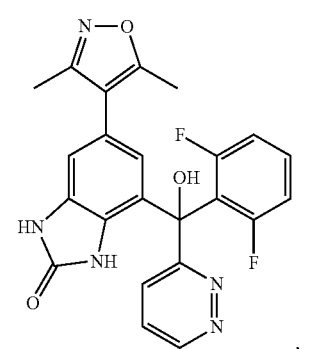
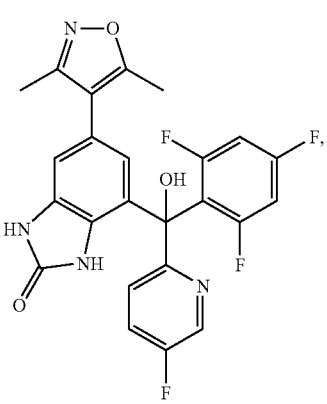

-continued

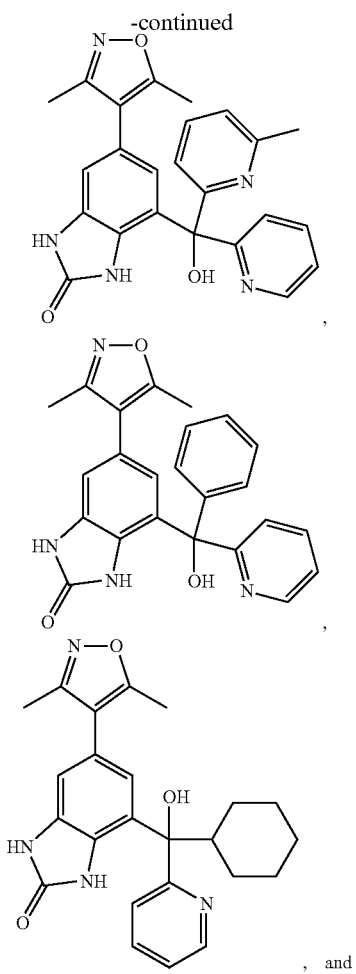

, and

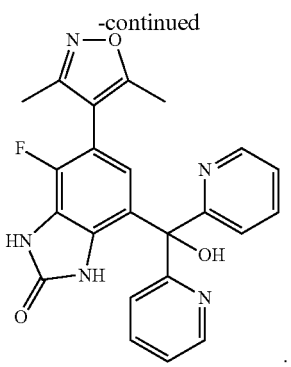

13. A pharmaceutical composition comprising a compound of claim 1, or a pharmaceutically acceptable salt thereof, and a pharmaceutically acceptable carrier.

14. A method of treating a human having a disease or condition responsive to the inhibition of a bromodomain-containing protein, comprising administering to the subject a therapeutically effective amount of a compound of claim 1, or a pharmaceutically acceptable salt thereof.

15. The method of claim 14, wherein the bromodomain-containing protein is BRD4.

16. The method of claim 14, wherein the disease or condition is a solid tumor of the colon, rectum, prostate, lung, pancreas, liver, kidney, cervix, stomach, ovaries, breast, skin, brain, meninges, or central nervous system.

17. The method of claim 14, wherein the disease or condition is multiple myeloma.

18. The method of claim 14, wherein the disease or condition is a B-cell lymphoma.

19. The method of claim 14, wherein the disease or condition is diffuse large B-cell lymphoma or Burkitt's lymphoma.

* * * * *